(12) United States Patent
Kumamoto et al.

(10) Patent No.: US 8,309,589 B2
(45) Date of Patent: Nov. 13, 2012

(54) FLUORINE-CONTAINING ORGANOSULFUR COMPOUND AND PESTICIDAL COMPOSITION COMPRISING THE SAME

(75) Inventors: Koji Kumamoto, Toyonaka (JP); Hiroyuki Miyazaki, Takarazuka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 88 days.

(21) Appl. No.: 12/675,703

(22) PCT Filed: Aug. 28, 2008

(86) PCT No.: PCT/JP2008/065926
§ 371 (c)(1),
(2), (4) Date: Apr. 20, 2010

(87) PCT Pub. No.: WO2009/028727
PCT Pub. Date: Mar. 5, 2009

(65) Prior Publication Data
US 2010/0240722 A1    Sep. 23, 2010

(30) Foreign Application Priority Data

Aug. 31, 2007 (JP) ................................ 2007-225593

(51) Int. Cl.
*A01N 43/80* (2006.01)
*A61K 31/42* (2006.01)

(52) U.S. Cl. ........ 514/378; 514/399; 514/438; 548/247; 548/342.1; 549/78

(58) Field of Classification Search .................. 514/378, 514/399, 438; 548/247, 342; 549/78
See application file for complete search history.

(56) References Cited

FOREIGN PATENT DOCUMENTS

| | | | |
|---|---|---|---|
| DE | 198 58 193 A1 | 6/2000 | |
| JP | 2005-179321 A | 7/2005 | |
| JP | 2006-056812 A | 3/2006 | |
| WO | WO-2007/060839 A1 | 5/2007 | |
| WO | WO 2009/025397 A1 | 2/2009 | |

OTHER PUBLICATIONS

Chemical Abstract registry RN: 904565-84-0 (entered on Aug. 25, 2006), and RN: 904565-82-8 (entered on Aug. 25, 2006).*
Scientific Exchange Product List, Database CHEMCATS 2044176491, RN 904565-84-0, Jun. 4, 2008, XP002507721 abstract.
Egyptian Office Action dated Dec. 1, 2011 for Egyptian Application No. PCT2010020336.
Chinese Office Action issued Aug. 3, 2011 in corresponding Chinese Patent Application No. 200880114577.8.
International Preliminary Report on Patentability (Form PCT/IB/373) and Written Opinion of the INternational Searching Authority (Form PCT/ISA/237) issued on Mar. 2, 2010 in PCT/JP2008/065926.
Russian Office Action for Russian Application No. 2010112404 dated Apr. 24, 2012, with English translation.

* cited by examiner

*Primary Examiner* — Yong Chu
*Assistant Examiner* — Valerie Rodriguez-Garcia
(74) *Attorney, Agent, or Firm* — Birch, Stewart, Kolasch & Birch, LLP

(57) ABSTRACT

There is provided a fluorine-containing organosulfur compound having an excellent controlling effect on arthropod pests represented by the formula (I): wherein m represents 0 or 1; n represents 0, 1 or 2; A represents an optionally substituted 5-membered aromatic heterocyclic group; $R^1$ and $R^3$ are independently represent an optionally substituted C1-C4 chain hydrocarbon group, $-C(=G)R^5$, cyano, halogen or hydrogen; $R^2$ and $R^4$ independently represent an optionally substituted C1-C4 chain hydrocarbon group, halogen or hydrogen; Q represents a C1-C5 haloalkyl group containing at least one fluorine, or fluorine; G represents oxygen or sulfur; and $R^5$ represents optionally substituted C1-C4 alkyl, hydroxyl, optionally substituted C1-C4 alkoxy, optionally substituted C3-C6 alkenyloxy, optionally substituted C3-C6 alkynyloxy, amino, optionally substituted C1-C4 alkylamino, optionally substituted di(C1-C4 alkyl)amino, C2-C5 cyclic amino or hydrogen.

(I)

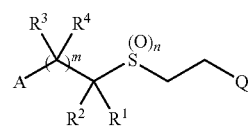

8 Claims, No Drawings

FLUORINE-CONTAINING ORGANOSULFUR COMPOUND AND PESTICIDAL COMPOSITION COMPRISING THE SAME

TECHNICAL FIELD

The present invention relates to a fluorine-containing organosulfur compound and a pesticidal composition comprising, the compound.

BACKGROUND ART

Hitherto, many pesticidal compositions for controlling arthropod pests have been developed and used practically. Further, JP-A 2005-179321 discloses a certain halogen-containing organosulfur compound.

DISCLOSURE OF INVENTION

An object of the present invention is to provide a novel compound having an excellent controlling effect on arthropod pests and its use.

The present inventors have intensively studied to find out a compound having an excellent controlling effect on arthropod pests. As a result, they have found that a fluorine-containing organosulfur compound represented by the following formula (I) has an excellent controlling effect on arthropod pests such as harmful insects or harmful mites. Thus, the present invention has been completed.

That is, the present invention provides:
(1) A fluorine-containing organosulfur compound represented by the formula (I):

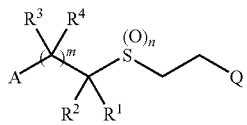

wherein m represents 0 or 1; n represents 0, 1 or 2;

A represents a 5-membered aromatic heterocyclic group optionally substituted with a group selected from the group E1 and the group E2;

$R^1$ and $R^3$ are the same as or different from each other, and represent a C1-C4 chain hydrocarbon group optionally substituted with a halogen atom, —C(=G)$R^5$, a cyano group, a halogen atom, or a hydrogen atom;

$R^2$ and $R^4$ are the same as or different from each other, and represent a C1-C4 chain hydrocarbon group optionally substituted with a halogen atom, a halogen atom, or a hydrogen atom;

Q represents a C1-C5 haloalkyl group containing at least one fluorine atom, or a fluorine atom;

G represents an oxygen atom or a sulfur atom;

$R^5$ represents a C1-C4 alkyl group optionally substituted with a halogen atom, a hydroxyl group, a C1-C4 alkoxy group optionally substituted with a halogen atom, a C3-C6 alkenyloxy group optionally substituted with a halogen atom, a C3-C6 alkynyloxy group optionally substituted with a halogen atom, an amino group, a C1-C4 alkylamino group optionally substituted with a halogen atom, a di(C1-C4 alkyl)amino group optionally substituted with a halogen atom, a C2-C5 cyclic amino group, or a hydrogen atom;

the group E1 is a group of monovalent substituents consisting of a C1-C6 chain hydrocarbon group optionally substituted with a group of the group L, a C3-C6 cycloalkyl group optionally substituted with a halogen atom, —O$R^6$, —S$R^6$, —S(=O)$R^6$, —S(=O)$_2R^6$, —C(=O)$R^7$, —OC(=O)$R^8$, a halogen atom, a cyano group, a nitro group, and a hydroxyl group;

the group E2 is a group of bivalent substituents consisting of a C2-C6 alkanediyl group optionally substituted with a group of the group L, a 1,3-butadiene-1,4-diyl group optionally substituted with a group of the group L, -G-T-G-, and -T-G-T-;

T represents a methylene group or an ethylene group;

$R^6$ represents a C1-C4 chain hydrocarbon group optionally substituted with a halogen atom or a C3-C6 cycloalkyl group optionally substituted with a halogen atom;

$R^7$ represents a hydroxyl group, a C1-C4 alkoxy group optionally substituted with a halogen atom, a C3-C6 alkenyloxy group optionally substituted with a halogen atom, a C3-C6 alkynyloxy group optionally substituted with a halogen atom, an amino group, a C1-C4 alkylamino group optionally substituted with a halogen atom, a di(C1-C4 alkyl)amino group optionally substituted with a halogen atom, a C2-C5 cyclic amino group, a C1-C4 alkyl group optionally substituted with a halogen atom, or a hydrogen atom;

$R^8$ represents a C1-C4 alkoxy group optionally substituted with a halogen atom, a C3-C6 alkenyloxy group optionally substituted with a halogen atom, a C3-C6 alkynyloxy, group optionally substituted with a halogen atom, an amino group, a C1-C4 alkylamino group optionally substituted with a halogen atom, a di(C1-C4 alkyl)amino group optionally substituted with a halogen atom, a C2-C5 cyclic amino group, a C1-C4 alkyl group optionally substituted with a halogen atom, or a hydrogen atom; and the group L is a group of monovalent substituents consisting of —O$R^6$, —S$R^6$, —S(=O)$R^6$, —S(=O)$_2R^6$, —C(=O)$R^7$, —OC(=O)$R^8$, a cyano group, a nitro group, and a halogen atom (hereinafter, referred to as "the compound of the present invention");

(2) The fluorine-containing organosulfur compound according to the above (1), wherein m is 0;

(3) The fluorine-containing organosulfur compound according to the above (1), wherein m is 1;

(4) The fluorine-containing organosulfur compound according to any one of the above (1) to (3), wherein n is 0;

(5) The fluorine-containing organosulfur compound according to any one of the above (1) to (3), wherein n is 1 or 2;

(6) The fluorine-containing organosulfur compound according to any one of the above (1) to (5), wherein A represents a pyrrolyl group, a furanyl group, a thienyl group, a pyrazolyl group, an isoxazolyl group, an isothiazolyl group, an imidazolyl group, an oxazolyl group, a thiazolyl group, a 1,2,4-triazolyl group, a 1,3,4-oxadiazolyl group, a 1,3,4-thiadiazolyl group, a 1,2,4-oxadiazolyl group or a 1,2,4-thiadiazolyl group, which is optionally substituted with a group selected from the group. E1 and the group E2;

(7) The fluorine-containing organosulfur compound according to any one of the above (1) to (5), wherein A represents a pyrrolyl group optionally substituted with a group selected from the group E3, a furanyl group optionally substituted with a group selected from the group E3, a thienyl group optionally substituted with a group selected from a group E3, a pyrazolyl group optionally substituted with the group E3, an isoxazolyl group optionally substituted with a group selected from the group E3, an isothiazolyl group optionally substituted with a group selected from the group E3, an imidazolyl group optionally substituted with a group selected from the group E3, an oxazolyl group optionally substituted with a group selected from the group E3, a thiazolyl group optionally substituted with a group selected from the group E3, a 1,2,4-triazolyl group optionally substituted with a group selected from the group E3, a 1,3,4-oxadiazolyl group optionally substituted with a group selected from the group E3, a 1,3,4-thiadiazolyl group optionally substituted with a group selected from the group E3, a 1,2,4-oxadiazolyl group optionally substituted with a group selected from the group E3, or a 1,2,4-thiadiazolyl group optionally substituted with a group selected from the group E3, and the group E3 is a group of monovalent substituents consisting of a halogen atom, a tert-butyl group, a trifluoromethyl group, a pentafluoroethyl group, an ethynyl group, a propargyl group, a propargyloxy group, a cyano group, a trifluoromethylthio group, a trifluoromethanesulfinyl group and a trifluoromethanesulfonyl group;

(8) A pesticidal composition which comprises the fluorine-containing organosulfur compound according to any one of the above (1) to (7) as an active ingredient; and (9) A method of controlling an arthropod pest which comprises applying an effective amount of the fluorine-containing organosulfur compound according to any one of the above (1) to (7) to the arthropod pest or a place where the arthropod pest inhabits.

ILLUSTRATIVE EMBODIMENT FOR CARRYING OUT THE INVENTION

The expression "C1-C4" or the like, as used herein, means the total number of carbon atoms constituting each substituent group.

Examples of the "halogen atom" include a fluorine atom, a chlorine atom and a bromine atom.

Examples of the 5-membered aromatic heterocyclic group include a pyrrolyl group such as a 1-pyrrolyl group, a 2-pyrrolyl group or a 3-pyrrolyl group; a furanyl group such as a 2-furanyl group or a 3-furanyl group; a thienyl group such as a 2-thienyl group or a 3-thienyl group; a pyrazolyl group such as a 1-pyrazolyl group, a 3-pyrazolyl group or a 4-pyrazolyl group; an isoxazolyl group such as a 3-isoxazolyl group, a 4-isoxazolyl group or a 5-isoxazolyl group; an isothiazolyl group such as a 3-isothiazolyl group, a 4-isothiazolyl group or a 5-isothiazolyl group; an imidazolyl group such as a 1-imidazolyl group, a 2-imidazolyl group or a 4-imidazolyl group; an oxazolyl group such as a 2-oxazolyl group, a 4-oxazolyl group or a 5-oxazolyl group; a thiazolyl group such as a 2-thiazolyl group, a 4-thiazolyl group or a 5-thiazolyl group; a 1,2,4-triazolyl group such as a 1,2,4-triazol-1-yl group or a 1,2,4-triazol-3-yl group; an oxadiazolyl group such as a 1,3,4-oxadiazol-2-yl group; a 1,3,4-thiadiazolyl group such as a 1,3,4-thiadiazol-2-yl group; a 1,2,4-oxadiazolyl group such as a 1,2,4-oxadiazol-3-yl group or a 1,2,4-oxadiazol-5-yl group; and a 1,2,4-thiadiazolyl group such as a 1,2,4-thiadiazol-3-yl group or a 1,2,4-thiadiazol-5-yl group.

Examples of the "5-membered aromatic heterocyclic group optionally substituted with a group selected from the group E1 and the group E2" include a 5-trifluoro-2-thienyl group, a 5-cyano-2-thienyl group, a 5-trifluoromethylsulfinyl-2-thienyl group, a 5-chloro-2-thienyl group, a 5-trifluoro-3-thienyl group, a 5-cyano-3-thienyl group, a 5-trifluoromethylsulfinyl-3-thienyl group, a 5-chloro-3-thienyl group, a 2-trifluoro-4-thiazolyl group, a 2-cyano-4-thiazolyl group, a 2-trifluoromethylsulfinyl-4-thiazolyl group, a 2-chloro-4-thiazolyl group, a 4-trifluoro-2-oxazolyl group, a 4-cyano-2-oxazolyl group, a 4-trifluoromethylsulfinyl-2-oxazolyl group, a 4-chloro-2-oxazolyl group, a 4-trifluoro-1-imidazolyl group, a 4-cyano-1-imidazolyl group, a 4-trifluoromethylsulfinyl-1-imidazolyl group, a 4-chloro-1-imidazolyl group, a 5-trifluoro-1,2,4-thiadiazol-3-yl group, a 5-cyano-1,2,4-thiadiazol-3-yl group, a 5-trifluoromethylsulfinyl-1,2,4-thiadiazol-3-yl group, a 5-chloro-1,2,4-thiadiazol-3-yl group, a 5-trifluoro-1,2,4-oxadiazol-3-yl group, a 5-cyano-1,2,4-oxadiazol-3-yl group, a 5-trifluoromethylsulfinyl-1,2,4-oxadiazol-3-yl group, a 5-chloro-1,2,4-oxadiazol-3-yl group, a 5-trifluoro-1,3,4-oxadiazol-2-yl group, a 5-cyano-1,3,4-oxadiazol-2-yl group, a 5-trifluoromethylsulfinyl-1,3,4-oxadiazol-2-yl group, a 5-chloro-1,3,4-oxadiazol-2-yl group, a 1-methyl-3-trifluoromethylpyrazol-5-yl group, a 5-trifluoromethyl-3-isoxazolyl group, a 5-(tert-butyl)-3-isoxazolyl group, a 1-trifluoromethylpyrazol-4-yl group and a 1-(tert-butyl)pyrazol-4-yl group.

Examples of the "C1-C4 chain hydrocarbon group optionally substituted with a halogen atom" include a C1-C4 alkyl group optionally substituted with a halogen atom, such as a methyl group, an ethyl group, a propyl group, a 1-methylethyl group (hereinafter sometimes referred to as an i-propyl group), a 1,1-dimethylethyl group (hereinafter sometimes referred to as a t-butyl group), a chloromethyl group, a fluoromethyl group, a difluoromethyl group, a trifluoromethyl group, a 2,2,2-trifluoroethyl group, a 1,1,2,2-tetrafluoroethyl group or a 1,1,2,2,2-pentafluoroethyl group; a C2-C4 alkenyl group optionally substituted with a halogen atom, such as a vinyl group, a 2,2-difluorovinyl group, a 1,2,2-trifluorovinyl group, a 1-propenyl group, a 2-propenyl group, a 3,3-difluoro-2-propenyl group, a 1-methyl-2-propenyl group, a 2-methyl-2-propenyl group, a 1-butenyl group or a 2-butenyl group; and a C2-C4 alkynyl group optionally substituted with a halogen atom, such as an ethynyl group, a 1-propynyl group, a 3,3,3-trifluoro-1-propynyl group, a 2-propynyl group, a 1-methyl-2-propynyl group, a 1-butynyl group, a 2-butynyl group or 3-butynyl group.

Examples of the "C1-C5 haloalkyl group containing at least one fluorine atom" include a fluoromethyl group, a difluoromethyl group, a trifluoromethyl group, a 1-fluoroethyl group, a 2-fluoroethyl group, a 1,1-difluoroethyl group, a 2,2-difluoroethyl group, a 2,2,2-trifluoroethyl group, a 1,1,2,2,2-pentafluoroethyl group, a 1-fluoropropyl group, a 1,1-difluoropropyl group, a 2-fluoropropyl group, a 2,2-difluoropropyl group, a 3-fluoropropyl group, a 3,3-difluoropropyl group, a 3,3,3-trifluoropropyl group, a 1,1,2,2,3,3,3-heptafluoropropyl group, a 2,2,3,3,3-pentafluoropropyl group, a 2,2,2-trifluoro-(1-trifluoromethyl)ethyl group, a 1,2,2,2-tetrafluoro-trifluoro-(1-trifluoromethyl)ethyl group, a 2,2,3,3-tetrafluoropropyl group, a 1-fluorobutyl group, a 1,1-difluorobutyl group, a 2-fluorobutyl group, a 2,2-difluorobutyl group, a 3-fluorobutyl group, a 3,3-difluorobutyl group, a 4-fluorobutyl group, a 4,4-difluorobutyl group, a 4,4,4-trifluorobutyl group, a 3,3,4,4,4-pentafluorobutyl group, a 2,2,3,4,4-pentafluorobutyl group, a 2,2,3,3,4,4,4-heptafluorobutyl group, a 1-fluoropentyl group, 1,1-difluoropentyl group, a 2-fluoropentyl group, 2,2-difluoropentyl group, a 3-fluoropentyl group, 3,3-difluoropentyl group, a 4-fluoropentyl group, 4,4-difluoropentyl group, a 5-fluoropentyl group, a 5,5-difluoropentyl group, a 5,5,5-trifluoropentyl group, a 4,4,5,5,5-pentafluoropentyl group, a 3,3,4,4,5,5,5-heptafluoropentyl group, a 2,2,3,3,4,4,5,5-octafluoropentyl group and a 2,2,3,3,4,4,5,5,5-nonafluoropentyl group.

Examples of the "C1-C4 alkyl group optionally substituted with a halogen atom" include a methyl group, an ethyl group, a 1-methylethyl group, a 1-ethylethyl group, a 1,1-dimethylethyl group, a propyl group, a 1-methylpropyl group, a butyl group, a fluoromethyl group, a chloromethyl group, a bromomethyl group, an iodomethyl group, a difluoromethyl group, a chlorodifluoromethyl group, a bromodifluoromethyl group, a trifluoromethyl group, a dichloromethyl group, a trichloromethyl group, a 1-chloroethyl group, a 1-bromoethyl group, a 1-fluoroethyl group, a 2-chloroethyl group, a 2-bromoethyl group, a 2-fluoroethyl group, a 2,2-difluoroethyl group, a 2,2,2-trifluoroethyl group, a 2,2,2-trichloroethyl group, a pentafluoroethyl group, a 2,2,2-trifluoro-1-chloroethyl group, a 3-fluoropropyl group, a 3-chloropropyl group, a 1-fluoro-1-methylethyl group, a 1-chloro-1-methylethyl group, a 2-chloro-1,1-dimethylethyl group, a 2-fluoro-1,1-dimethylethyl group, a heptafluoropropyl group, a 1,1,2,2,3,3-hexafluoropropyl group, a 4-chlorobutyl group and a 4-fluorobutyl group.

Examples of the "C1-C4 alkoxy group optionally substituted with a halogen atom" include a methoxy group, an ethoxy group, a propoxy group, a trifluoromethoxy group, a bromodifluoromethoxy group, a difluoromethoxy group, a chlorodifluoromethoxy group, a pentafluoroethoxy group, a 2,2,2-trifluoroethoxy group and a 1,1,2,2-tetrafluoroethoxy group.

Examples of the "C3-C6 alkenyloxy group optionally substituted with a halogen atom" include a 1-propenyloxy group, a 2-propenyloxy group, a 1-methyl-2-propenyloxy group, a 1,1-dimethyl-2-propenyloxy group and a 2,2-difluoro-2-propenyloxy group.

Examples of the "C3-C6 alkynyloxy group optionally substituted with a halogen atom" include a 2-propynyloxy group, a 1-methyl-2-propynyloxy group, a 1,1-dimethyl-2-propynyloxy group, a 2-butynyloxy group, a 1-methyl-2-butynyloxy group, a 1,1-dimethyl-2-butynyloxy group and a 3,3,3-trifluoro-1-propynyloxy group.

Examples of the "C1-C4 alkylamino group optionally substituted with a halogen atom" include an N-methylamino group, an N-ethylamino group, an N-propylamino group, an N-(1-methylethyl)amino group and an N-(2,2,2-trifluoroethyl)amino group.

Examples of the "di(C1-C4 alkyl)amino group optionally substituted with a halogen atom" include an N,N-dimethylamino group, an N-ethyl-N-methylamino group, an N,N-diethylamino group, an N-methyl-N-propylamino group, an N-ethyl-N-propylamino group, an N,N-dipropylamino group, an N-methyl-N-(1-methylethyl)amino group, an N-ethyl-N-(1-methylethyl)amino group, an N,N-di(1-methylethyl)amino group, an N-methyl-N-(2,2,2-trifluoroethyl)amino group and an N-methyl-N-ethyl-N-(2,2,2-trifluoroethyl)amino group.

Examples of the "C2-C5 cyclic amino group" include a 1-aziridino group, a 1-azetidinyl group, a 1-pyrrolidinyl group, a piperidino group and a morpholino group.

Examples of the "C1-C6 chain hydrocarbon group optionally substituted with a group of the group L" include a C1-C6 alkyl group optionally substituted with a group of the group L, a C2-C6 alkenyl group optionally substituted with a group of the group L, and a C2-C6 alkynyl group optionally substituted with a group of the group L.

Examples of the "C1-C6 alkyl group optionally substituted with a group of the group L" include a C1-C6 alkyl group optionally substituted with a halogen atom, such as a methyl group, an ethyl group, a propyl group, a 1-methylethyl group, a 2,2-dimethylpropyl group, a chloromethyl group, a fluoromethyl group, a difluoromethyl group, a trifluoromethyl group, a 2,2,2-trifluoroethyl group, a 1,1,2,2-tetrafluoroethyl group, a 1,1,2,2,2-pentafluoroethyl group or a 1,1-dimethylethyl group; a (C1-C4 alkoxy)C1-C4 alkyl group optionally substituted with a halogen atom, such as a methoxymethyl group, an ethoxymethyl group, a 1-methoxyethyl group, a 1-ethoxyethyl or a trifluoromethoxymethyl group; a (C3-C6 alkenyloxy)C1-C4 alkyl group optionally substituted with a halogen atom, such as a (1-propenyloxy)methyl group, a (2-propenyloxy)methyl group, a (1-methyl-2-propenyloxy)methyl group, a (1,1-dimethyl-2-propenyloxy)methyl group, a (2,2-difluoro-2-propenyloxy)methyl group, a 1-(1-propenyloxy)ethyl group, a 1-(2-propenyloxy)ethyl group, a 1-(1-methyl-2-propenyloxy)ethyl group, a 1-(1,1-dimethyl-2-propenyloxy)ethyl group, a 1-(2,2-difluoro-2-propenyloxy)ethyl group, a 2-(1-propenyloxy)ethyl group, 2-(2-propenyloxy)ethyl group, a 2-(1-methyl-2-propenyloxy)ethyl group, a 2-(1,1-dimethyl-2-propenyloxy)ethyl group or a 2-(2,2-difluoro-2-propenyloxy)ethyl group; a (C3-C6 alkynyloxy)C1-C4 alkyl group optionally substituted with a halogen atom, such as a (2-propynyloxy)methyl group, a (1-methyl-2-propynyloxy)methyl group, a (1,1-dimethyl-2-propynyloxy)methyl group, a (2-butynyloxy)methyl group, a (1-methyl-2-butynyloxy)methyl group, a (1,1-dimethyl-2-butynyloxy) methyl group, a (3,3,3-trifluoro-1-propynyloxy)methyl group, a 1-(2-propynyloxy)ethyl group, a 1-(1-methyl-2-propynyloxy)ethyl group, a 1-(1,1-dimethyl-2-propynyloxy)ethyl group, a 1-(2-butynyloxy)ethyl group, a 1-(1-methyl-2-butynyloxy)ethyl group, a 1-(1,1-dimethyl-2-butynyloxy)ethyl group, a 1-(3,3,3-trifluoro-1-propynyloxy)ethyl group, a 2-(2-propynyloxy)ethyl group, a 2-(1-methyl-2-propynyloxy)ethyl group, a 2-(1,1-dimethyl-2-propynyloxy)ethyl group, a 2-(2-butynyloxy)ethyl group, a 2-(1-methyl-2-butynyloxy)ethyl group, a 2-(1,1-dimethyl-2-butynyloxy)ethyl group or a 2-(3,3,3-trifluoro-1-propynyloxy)ethyl group; and a (hydroxy)C1-C4 alkyl group optionally substituted with a halogen atom, such as a hydroxymethyl group, a 1-hydroxyethyl group, a 1-hydroxy-1-methylethyl group, a 2-hydroxyethyl group or a 2-hydroxy-1-methylethyl group.

Examples of the "C2-C6 alkenyl group optionally substituted with a group of the group L" include a C2-C6 alkenyl group optionally substituted with a halogen atom, such as a vinyl group, a 2,2-difluorovinyl group, a 1,2,2-trifluorovinyl group, a 1-propenyl group, a 2-propenyl group, a 3,3-difluoro-2-propenyl group or a 1-methyl-2-propenyl group.

Examples of the "C2-C6 alkynyl group optionally substituted with a group of the group L" include an ethynyl group such as a 1-ethynyl group, a 2-bromoethynyl group, a 2-iodoethynyl group or a 2-(methoxycarbonyl)ethynyl group; a 1-propynyl group or a substituted 1-propynyl group such as a 3-fluoro-1-propynyl group, a 3,3-difluoro-1-propynyl group, a 3-(dimethylamino)-1-propynyl group, a 3,3,3-trifluoro-1-propynyl group, a 3-methoxy-1-propynyl group or a 3-(methoxycarbonyl)-1-propynyl group;

a 2-propynyl group or a substituted 2-propynyl group such as a 1-fluoro-2-propynyl or a 1,1-difluoro-2-propynyl group;

a 1-butynyl group or a substituted 1-butynyl group such as a 4-fluoro-1-butynyl group, a 4-methoxy-1-butynyl group, a 4-(dimethylamino)-1-butynyl group or a 4-(methoxycarbonyl)-1-butynyl group;

a 2-butynyl group or a substituted 2-butynyl group such as a 4-fluoro-2-butynyl group, a 4-methoxy-2-butynyl group, a 4-(dimethylamino)-2-butynyl group or a 4-(methoxycarbonyl)-2-butynyl group;

a 3-butynyl group or a substituted 3-butynyl group such as a 1,1-difluoro-3-butynyl group;

a 1-pentynyl group or a substituted 1-pentynyl group such as a 5-fluoro-1-pentynyl group, a 5-methoxy-1-pentynyl group, a 5-(dimethylamino)-1-pentynyl group or a 5-(methoxycarbonyl)-1-pentynyl group; and a 2-pentynyl group or a substituted 2-pentynyl group such as a 5-fluoro-2-pentynyl group, a 5-methoxy-2-pentynyl group, a 5-(dimethylamino)-2-pentynyl group or a 5-(methoxycarbonyl)-2-pentynyl group.

Examples of the "C3-C6 cycloalkyl group optionally substituted with a halogen atom" include a cyclopropyl group, a 1-methylcyclopropyl group, a 2,2-dichlorocyclopropyl group, a 2,2-dichloro-1-methylcyclopropyl group, a 2,2-difluorocyclopropyl group, a 2,2-difluoro-1-methylcyclopropyl group, a cyclobutyl group, a cyclopentyl group and a cyclohexyl group.

Examples of the "C2-C6 alkanediyl group optionally substituted with a group of the group L" include an ethane-1,2-diyl group, a propane-1,2-diyl group, a propane-1,3-diyl group, a butane-1,4-diyl group, a 2,3-dichlorobutane-1,4-diyl group and a pentane-1,5-diyl group.

Examples of the "1,3-butadiene-1,4-diyl group optionally substituted with a group of the group L" include a 1,3-butadiene-1,4-diyl group, a 2,2-dimethyl-1,3-butadiene-1,4-diyl group, a 1-chloro-1,3-butadiene-1,4-diyl group, a 2-chloro-1,3-butadiene-1,4-diyl group, a 2,2-dichloro-1,3-butadiene-1,4-diyl group and a 1,4-dichloro-1,3-butadiene-1,4-diyl group.

Specific examples of the compound of the present invention include:

a fluorine-containing organosulfur compound represented by the formula (I), wherein A is a pyrrolyl, a furanyl group, a thienyl group, a pyrazolyl group, an isoxazolyl group, an isothiazolyl group, an imidazolyl group, an oxazolyl group, a thiazolyl group, a 1,2,4-triazolyl group, a 1,3,4-oxadiazolyl group, a 1,3,4-thiadiazolyl group, a 1,2,4-oxadiazolyl group or a 1,2,4-thiadiazolyl group, which is optionally substituted with a group selected from the group E1 and the group E2;

a fluorine-containing organosulfur compound represented by the formula (I), wherein A is a pyrrolyl group optionally substituted with a group selected from the group E1 and the group E2;

a fluorine-containing organosulfur compound represented by the formula (I), wherein A is a furanyl group optionally substituted with a group selected from the group E1 and the group E2;

a fluorine-containing organosulfur compound represented by the formula (I), wherein A is a thienyl group optionally substituted with a group selected from the group E1 and the group E2;

a fluorine-containing organosulfur compound represented by the formula (I), wherein A is an isoxazolyl group optionally substituted with a group selected from the group E1 and the group E2;

a fluorine-containing organosulfur compound represented by the formula (I), wherein A is an isothiazolyl group optionally substituted with a group selected from the group E1 and the group E2;

a fluorine-containing organosulfur compound represented by the formula (I), wherein A is an imidazolyl group optionally substituted with a group selected from the group E1 and the group E2;

a fluorine-containing organosulfur compound represented by the formula (I), wherein A is an oxazolyl group optionally substituted with a group selected from the group E1 and the group E2;

a fluorine-containing organosulfur compound represented by the formula (I), wherein A is a thiazolyl group optionally substituted with a group selected from the group E1 and the group E2;

a fluorine-containing organosulfur compound represented by the formula (I), wherein A is a 1,2,4-triazolyl group optionally substituted with a group selected from the group E1 and the group E2;

a fluorine-containing organosulfur compound represented by the formula (I), wherein A is a 1,3,4-oxadiazolyl group optionally substituted with a group selected from the group E1 and the group E2;

a fluorine-containing organosulfur compound represented by the formula (I), wherein A is a 1,3,4-thiadiazolyl group optionally substituted with a group selected from the group E1 and the group E2;

a fluorine-containing organosulfur compound represented by the formula (I), wherein A is a 1,2,4-oxadiazolyl group optionally substituted with a group selected from the group E1 and the group E2;

a fluorine-containing organosulfur compound represented by the formula (I), wherein A is a 1,2,4-thiadiazolyl group optionally substituted with a group selected from the group E1 and the group E2;

a fluorine-containing organosulfur compound represented by the formula (I), wherein A is a 5-membered aromatic heterocyclic group optionally substituted with a group selected from the group E1;

a fluorine-containing organosulfur compound represented by the formula (I), wherein A is a 5-membered aromatic heterocyclic group optionally substituted with a monovalent group selected from the group E3 consisting of: a halogen atom, a tert-butyl group, a trifluoromethyl group, a pentafluoroethyl group, an ethynyl group, a propargyl group, a propargyloxy group, a cyano group, trifluoromethylthio group, a trifluoromethanesulfinyl group and a trifluoromethanesulfonyl group;

a fluorine-containing organosulfur compound represented by the formula (I), wherein A is a pyrrolyl group, a furanyl group, a thienyl group, a pyrazolyl group, an isoxazolyl group, an isothiazolyl group, an imidazolyl group, an oxazolyl group, a thiazolyl group, a 1,2,4-triazolyl group, a 1,3,4-oxadiazolyl group, a 1,3,4-thiadiazolyl group, a 1,2,4-oxadiazolyl group or a 1,2,4-thiadiazolyl group, which is optionally substituted with a group selected from the group E3;

a fluorine-containing organosulfur compound represented by the formula (I), wherein $R^1$ and $R^2$ are hydrogen atoms; a fluorine-containing organosulfur compound represented by the formula (I), wherein $R^1$ is a C1-C4 chain hydrocarbon group optionally substituted with a halogen atom and $R^2$ is a hydrogen atom;

a fluorine-containing organosulfur compound represented by the formula (I), wherein $R^1$ is a C1-C4 alkyl group optionally substituted with a halogen atom and $R^2$ is a hydrogen atom;

a fluorine-containing organosulfur compound represented by the formula (I), wherein $R^1$ is a methyl group and $R^2$ is a hydrogen atom;

a fluorine-containing organosulfur compound represented by the formula (I), wherein $R^1$ is a C1-C4 chain hydrocarbon group optionally substituted with a halogen atom and $R^2$ is a halogen atom;

a fluorine-containing organosulfur compound represented by the formula (I), wherein $R^1$ is a C1-C4 alkyl group optionally substituted with a halogen atom and $R^2$ is a halogen atom;

a fluorine-containing organosulfur compound represented by the formula (I), wherein $R^1$ is a methyl group and $R^2$ is a halogen atom;

a fluorine-containing organosulfur compound represented by the formula (I), wherein $R^1$ is a C1-C4 chain hydrocarbon group optionally substituted with a halogen atom and $R^2$ is a methyl group;

a fluorine-containing organosulfur compound represented by the formula (I), wherein $R^1$ is a C1-C4 alkyl group optionally substituted with a halogen atom and $R^2$ is a methyl group;

a fluorine-containing organosulfur compound represented by the formula (I), wherein $R^1$ and $R^2$ are methyl groups;

a fluorine-containing organosulfur compound represented by the formula (I), wherein $R^1$ is —C(=G)$R^5$ and $R^2$ is a hydrogen atom;

a fluorine-containing organosulfur compound represented by the formula (I), wherein $R^1$ is —C(=G)$R^5$, G is an oxygen atom, and $R^2$ is a hydrogen atom;

a fluorine-containing organosulfur compound represented by the formula (I), wherein $R^1$ is —C(=G)$R^5$, G is an oxygen atom, $R^5$ is a C1-C4 alkoxy group optionally substituted with a halogen atom, and $R^2$ is a hydrogen atom;

a fluorine-containing organosulfur compound represented by the formula (I), wherein $R^1$ is —C(=G)$R^5$, G is an oxygen atom, $R^5$ is a methoxy group, and $R^2$ is a hydrogen atom;

a fluorine-containing organosulfur compound represented by the formula (I), wherein $R^1$ is —C(=G)$R^5$, G is an oxygen atom, $R^5$ is an amino group, and $R^2$ is a hydrogen atom;

a fluorine-containing organosulfur compound represented by the formula (I), wherein $R^1$ is a cyano group and $R^2$ is a hydrogen atom;

a fluorine-containing organosulfur compound represented by the formula (I), wherein $R^1$ is —C(=G)$R^5$ and $R^2$ is a halogen atom;

a fluorine-containing organosulfur compound represented by the formula (I), wherein $R^1$ is —C(=G)$R^5$, G is an oxygen atom, and $R^2$ is a halogen atom;

a fluorine-containing organosulfur compound represented by the formula (I), wherein $R^1$ is —C(=G)$R^5$, G is an oxygen atom, $R^5$ is a C1-C4 alkoxy group optionally substituted with a halogen atom, and $R^2$ is a halogen atom;

a fluorine-containing organosulfur compound represented by the formula (I), wherein $R^1$ is —C(=G)$R^5$, G is an oxygen atom, $R^5$ is a methoxy group, and $R^2$ is a halogen atom;

a fluorine-containing organosulfur compound represented by the formula (I), wherein $R^1$ is —C(=G)$R^5$, G is an oxygen atom, $R^5$ is an amino group, and $R^2$ is a halogen atom;

a fluorine-containing organosulfur compound represented by the formula (I), wherein $R^1$ is a cyano group and $R^2$ is a halogen atom;

a fluorine-containing organosulfur compound represented by the formula (I), wherein $R^1$ is —C(=G)$R^5$ and $R^2$ is a methyl group;

a fluorine-containing organosulfur compound represented by the formula (I), wherein $R^1$ is —C(=G)$R^5$, G is an oxygen atom, and $R^2$ is a methyl group;

a fluorine-containing organosulfur compound represented by the formula (I), wherein $R^1$ is —C(=G)$R^5$, G is an oxygen atom, $R^5$ is a C1-C4 alkoxy group optionally substituted with a halogen atom, and $R^2$ is a methyl group;

a fluorine-containing organosulfur compound represented by the formula (I), wherein $R^1$ is —C(=G)$R^5$, G is an oxygen atom, $R^5$ is a methoxy group, and $R^2$ is a methyl group;

a fluorine-containing organosulfur compound represented by the formula (I), wherein $R^1$ is —C(=G)$R^5$, G is an oxygen atom, $R^5$ is an amino group, and $R^2$ is a methyl group;

a fluorine-containing organosulfur compound represented by the formula (I), wherein $R^1$ is a cyano group and $R^2$ is a methyl group;

a fluorine-containing organosulfur compound represented by the formula (I), wherein $R^1$ is a halogen atom and $R^2$ is a hydrogen atom;

a fluorine-containing organosulfur compound represented by the formula (I), wherein $R^1$ and $R^2$ are halogen atoms;

a fluorine-containing organosulfur compound represented by the formula (I), wherein m is 0;

a fluorine-containing organosulfur compound represented by the formula (I), wherein m is 1, and $R^3$ and $R^4$ are hydrogen atoms;

a fluorine-containing organosulfur compound represented by the formula (I), wherein m is 1, $R^3$ is a C1-C4 chain hydrocarbon group, and $R^4$ is a hydrogen atom;

a fluorine-containing organosulfur compound represented by the formula (I), wherein m is 1, $R^3$ is a C1-C4 alkyl group, and $R^4$ is a hydrogen atom;

a fluorine-containing organosulfur compound represented by the formula (I), wherein m is 1, $R^3$ is a methyl group, and $R^4$ is a hydrogen atom;

a fluorine-containing organosulfur compound represented by the formula (I), wherein m is 1, and $R^3$ and $R^4$ are methyl groups;

a fluorine-containing organosulfur compound represented by the formula (I), wherein $R^1$ and $R^2$ are hydrogen atoms, and m is 0;

a fluorine-containing organosulfur compound represented by the formula (I), wherein $R^1$ is a C1-C4 chain hydrocarbon group optionally substituted with a halogen atom, $R^2$ is a hydrogen atom, and m is 0;

a fluorine-containing organosulfur compound represented by the formula (I), wherein $R^1$ is a C1-C4 alkyl group optionally substituted with a halogen atom, $R^2$ is a hydrogen atom, and m is 0;

a fluorine-containing organosulfur compound represented by the formula (I), wherein $R^1$ is a methyl group, $R^2$ is a hydrogen atom, and m is 0;

a fluorine-containing organosulfur compound represented by the formula (I), wherein $R^1$ is a C1-C4 chain hydrocarbon group optionally substituted with a halogen atom, $R^2$ is a halogen atom, and m is 0;

a fluorine-containing organosulfur compound represented by the formula (I), wherein $R^1$ is a C1-C4 alkyl group optionally substituted with a halogen atom, $R^2$ is a halogen atom, and m is 0;

a fluorine-containing organosulfur compound represented by the formula (I), wherein $R^1$ is a methyl group, $R^2$ is halogen atom, and m is 0;

a fluorine-containing organosulfur compound represented by the formula (I), wherein $R^1$ is a C1-C4 chain hydrocarbon group optionally substituted with a halogen atom, $R^2$ is a methyl group, and m is 0;

a fluorine-containing organosulfur compound represented by the formula (I), wherein $R^1$ is a C1-C4 alkyl group optionally substituted with a halogen atom, $R^2$ is a methyl group, and m is 0;

a fluorine-containing organosulfur compound represented by the formula (I), wherein $R^1$ and $R^2$ are methyl groups, and m is 0;

a fluorine-containing organosulfur compound represented by the formula (I), wherein $R^1$ is —C(=G)$R^5$, $R^2$ is a hydrogen atom, and m is 0;

a fluorine-containing organosulfur compound represented by the formula (I), wherein $R^1$ is —C(=G)$R^5$, G is an oxygen atom, $R^2$ is a hydrogen atom, and m is 0;

a fluorine-containing organosulfur compound represented by the formula (I), wherein $R^1$ is —C(=G)$R^5$, G is an oxygen atom, $R^5$ is a C1-C4 alkoxy group optionally substituted with a halogen atom, $R^2$ is a hydrogen atom, and m is 0;

a fluorine-containing organosulfur compound represented by the formula (I), wherein $R^1$ is —C(=G)$R^5$, G is an oxygen atom, $R^5$ is a methoxy group, $R^2$ is a hydrogen atom, and m is 0;

a fluorine-containing organosulfur compound represented by the formula (I), wherein $R^1$ is —C(=G)$R^5$, G is an oxygen atom, $R^5$ is an amino group, $R^2$ is a hydrogen atom, and m is 0;

a fluorine-containing organosulfur compound represented by the formula (I), wherein $R^1$ is a cyano group, $R^2$ is a hydrogen atom, and m is 0;

a fluorine-containing organosulfur compound represented by the formula (I), wherein $R^1$ is —C(=G)$R^5$, $R^2$ is a halogen atom, and m is 0;

a fluorine-containing organosulfur compound represented by the formula (I), wherein $R^1$ is —C(=G)$R^5$, G is an oxygen atom, $R^2$ is a halogen atom, and m is 0;

a fluorine-containing organosulfur compound represented by the formula (I), wherein $R^1$ is —C(=G)$R^5$, G is an oxygen atom, $R^5$ is a C1-C4 alkoxy group optionally substituted with a halogen atom, $R^2$ is a halogen atom, and m is 0;

a fluorine-containing organosulfur compound represented by the formula (I), wherein $R^1$ is —C(=G)$R^5$, G is an oxygen atom, $R^5$ is a methoxy group, $R^2$ is a halogen atom, and m is 0;

a fluorine-containing organosulfur compound represented by the formula (I), wherein $R^1$ is —C(=G)$R^5$, G is an oxygen atom, $R^5$ is an amino group, $R^2$ is a halogen atom, and m is 0;

a fluorine-containing organosulfur compound represented by the formula (I), wherein $R^1$ is a cyano group, $R^2$ is a halogen atom, and m is 0;

a fluorine-containing organosulfur compound represented by the formula (I), wherein $R^1$ is —C(=G)$R^5$, $R^2$ is a methyl group, and m is 0;

a fluorine-containing organosulfur compound represented by the formula (I), wherein $R^1$ is —C(=G)$R^5$, G is an oxygen atom, $R^2$ is a methyl group, and m is 0;

a fluorine-containing organosulfur compound represented by the formula (I), wherein $R^1$ is —C(=G)$R^5$, G is an oxygen atom, $R^5$ is a C1-C4 alkoxy group optionally substituted with a halogen atom, $R^2$ is a methyl group, and m is 0;

a fluorine-containing organosulfur compound represented by the formula (I), wherein $R^1$ is —C(=G)$R^5$, G is an oxygen atom, $R^5$ is a methoxy group, $R^2$ is a methyl group, and m is 0;

a fluorine-containing organosulfur compound represented by the formula (I), wherein $R^1$ is —C(=G)$R^5$, G is an oxygen atom, $R^5$ is an amino group, $R^2$ is a methyl group, and m is 0;

a fluorine-containing organosulfur compound represented by the formula (I), wherein $R^1$ is a cyano group, $R^2$ is a methyl group, and m is 0;

a fluorine-containing organosulfur compound represented by the formula (I), wherein $R^1$ is a halogen atom, $R^2$ is a hydrogen atom, and m is 0;

a fluorine-containing organosulfur compound represented by the formula (I), wherein $R^1$ and $R^2$ are halogen atoms, and m is 0;

a fluorine-containing organosulfur compound represented by the formula (I), wherein $R^1$ and $R^2$ are hydrogen atoms, m is 1, and $R^3$ and $R^4$ are independently a C1-C4 chain hydrocarbon group or a hydrogen atom;

a fluorine-containing organosulfur compound represented by the formula (I), wherein $R^1$ is a C1-C4 chain hydrocarbon group optionally substituted with a halogen atom, $R^2$ is a hydrogen atom, m is 1, and $R^3$ and $R^4$ are independently a C1-C4 chain hydrocarbon group or a hydrogen atom;

a fluorine-containing organosulfur compound represented by the formula (I), wherein $R^1$ is a C1-C4 alkyl group optionally substituted with a halogen atom, $R^2$ is a hydrogen atom, m is 1, and $R^3$ and $R^4$ are independently a C1-C4 chain hydrocarbon group or a hydrogen atom;

a fluorine-containing organosulfur compound represented by the formula (I), wherein $R^1$ is a methyl group, $R^2$ is a hydrogen atom, m is 1, and $R^3$ and $R^4$ are independently a C1-C4 chain hydrocarbon group or a hydrogen atom; a fluorine-containing organosulfur compound represented by the formula (I), wherein $R^1$ is a C1-C4 chain hydrocarbon group optionally substituted with a halogen atom, $R^2$ is a halogen atom, m is 1, and $R^3$ and $R^4$ are independently a C1-C4 chain hydrocarbon group or a hydrogen atom;

a fluorine-containing organosulfur compound represented by the formula (I), wherein $R^1$ is a C1-C4 alkyl group optionally substituted with a halogen atom, $R^2$ is a hydrogen atom, m is 1, and $R^3$ and $R^4$ are independently a C1-C4 chain hydrocarbon group or hydrogen atom;

a fluorine-containing organosulfur compound represented by the formula (I), wherein $R^1$ is a methyl group, $R^2$ is a halogen atom, m is 1, and $R^3$ and $R^4$ are independently a C1-C4 chain hydrocarbon group or hydrogen atom;

a fluorine-containing organosulfur compound represented by the formula (I), wherein $R^1$ is a C1-C4 chain hydrocarbon group optionally substituted with a halogen atom, $R^2$ is a methyl group, m is 1, and $R^3$ and $R^4$ are independently a C1-C4 chain hydrocarbon group or hydrogen atom;

a fluorine-containing organosulfur compound represented by the formula (I), wherein $R^1$ is a C1-C4 alkyl group optionally substituted with a halogen atom, $R^2$ is a methyl group, m is 1, and $R^3$ and $R^4$ are independently a C1-C4 chain hydrocarbon group or hydrogen atom;

a fluorine-containing organosulfur compound represented by the formula (I), wherein $R^1$ and $R^2$ are methyl groups, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, $R^2$ is a hydrogen atom, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, G is an oxygen atom, $R^2$ is a hydrogen atom, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, G is an oxygen atom, $R^5$ is a C1-C4 alkoxy group optionally substituted with a halogen atom, $R^2$ is a hydrogen atom, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, G is an oxygen atom, $R^5$ is a methoxy group, $R^2$ is a hydrogen atom, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, G is an oxygen atom, $R^5$ is an amino group, $R^2$ is a hydrogen atom, m is 1, and $R^3$ and $R^4$ are independently a C1-C4 chain hydrocarbon group or hydrogen atom;

a fluorine-containing organosulfur compound represented by the formula (I), wherein $R^1$ is a cyano group, $R^2$ is a hydrogen atom, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, $R^2$ is a halogen atom, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, G is an oxygen atom, $R^2$ is a halogen atom, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, G is an oxygen atom, $R^5$ is a C1-C4 alkoxy group optionally substituted with a halogen atom, $R^2$ is a halogen atom, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, G is an oxygen atom, $R^5$ is a methoxy group, $R^2$ is a halogen atom, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, G is an oxygen atom, $R^5$ is an amino group, $R^2$ is a halogen atom, m is 1, and $R^3$ and $R^4$ are independently a C1-C4 chain hydrocarbon group or hydrogen atom;

a fluorine-containing organosulfur compound represented by the formula (I), wherein $R^1$ is a cyano group, $R^2$ is a halogen atom, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, $R^2$ is a methyl group, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, G is an oxygen atom, $R^2$ is a methyl group, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, G is an oxygen atom, $R^5$ is a C1-C4 alkoxy group optionally substituted with a halogen atom, $R^2$ is a methyl group, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, G is an oxygen atom, $R^5$ is a methoxy group, $R^2$ is a methyl group, m is 1, and $R^3$ and $R^4$ are independently a C1-C4 chain hydrocarbon group or hydrogen atom;

a fluorine-containing organosulfur compound represented by the formula (I), wherein $R^1$ is —C(=G)$R^5$, G is an oxygen atom, $R^5$ is an amino group, $R^2$ is a methyl group, m is 1, and $R^3$ and $R^4$ are independently a C1-C4 chain hydrocarbon group or hydrogen atom;

a fluorine-containing organosulfur compound represented by the formula (I), wherein $R^1$ is a cyano group, $R^2$ is a methyl group, m is 1, and $R^3$ and $R^4$ are independently a C1-C4 chain hydrocarbon group or hydrogen atom;

a fluorine-containing organosulfur compound represented by the formula (I), wherein $R^1$ is a halogen atom, $R^2$ is a hydrogen atom, m is 1, and $R^3$ and $R^4$ are independently a C1-C4 hydrocarbon group or hydrogen atom;

a fluorine-containing organosulfur compound represented by the formula (I), wherein $R^1$ and $R^2$ are halogen atoms, m is 1, and $R^3$ and $R^4$ are independently a C1-C4 chain hydrocarbon group or hydrogen atom;

a fluorine-containing organosulfur compound represented by the formula (I), wherein Q is a fluorine atom;

a fluorine-containing organosulfur compound represented by the formula (I), wherein Q is a C1-C5 haloalkyl group containing at least one fluorine atom;

a fluorine-containing organosulfur compound represented by the formula (I), wherein Q is a fluoromethyl group;

a fluorine-containing organosulfur compound represented by the formula (I), wherein Q is a trifluoromethyl group;

a fluorine-containing organosulfur compound represented by the formula (I), wherein Q is a 1,1,2,2,2-pentafluoroethyl group;

a fluorine-containing organosulfur compound represented by the formula (I), wherein Q is a 1,1,2,2,3,3,3-heptafluoropropyl group;

a fluorine-containing organosulfur compound represented by the formula (I), wherein n is 0;

a fluorine-containing organosulfur compound represented by the formula (I), wherein n is 1; and a fluorine-containing organosulfur compound represented by the formula (I), wherein n is 2.

Then, a process for producing the compound of the present compound is explained.

A compound represented by the formula (I-a), which is a compound of the present invention represented by the formula (I) wherein n is 0, can be produced, for example, by the following Production Process 1 to Production Process 4.

Production Process 1

A compound represented by the formula (I-a) can be produced, for example, by reacting the following compound (a) and the following compound (b):

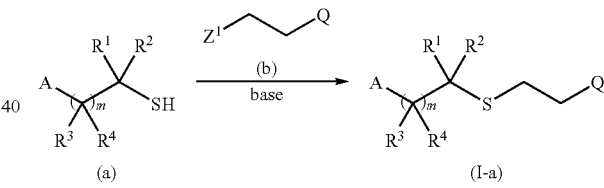

wherein A, Q, $R^1$, $R^2$, $R^3$ and m are as defined above, and $Z^1$ represents a leaving group such as a chlorine atom, a bromine atom, an iodine atom, or a methanesulfonyl group.

The reaction is generally performed in a solvent in the presence of a conventional base.

Examples of the solvent used in the reaction include ethers such as diethylether, tetrahydrofuran and dimethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydride, sodium hydroxide, potassium hydroxide and potassium carbonate, alkali metal alkoxides such as sodium methoxide and potassium tert-butoxide, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (a).

The amount of the compound (b) used in the reaction is usually 1 to 10 mol per 1 mol of the compound (a).

The reaction temperature is usually in a range of −50 to 100° C., and the reaction time is usually 1 to 24 hours.

After completion of the reaction, the compound (I-a) can be isolated, for example, by pouring a reaction mixture into water and extracting the resulting mixture with an organic solvent, followed by concentration. The isolated compound (I-a) can be further purified by chromatography, recrystallization or the like, if necessary.

Production Process 2

A compound represented by the formula (I-a) can be also produced, for example, by reacting the following compound (c) and compound (d):

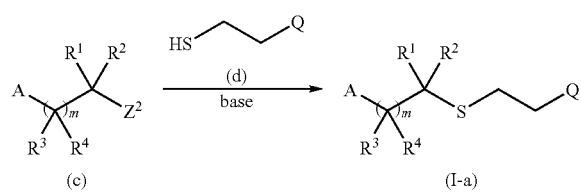

wherein A, Q, $R^1$, $R^2$, $R^3$, $R^4$ and m are as defined above, and $Z^2$ represents a leaving group such as a chlorine atom, a bromine atom, an iodine atom or a methanesulfonyl group.

The reaction is generally performed in a solvent in the presence of a conventional base.

Examples of the solvent used in the reaction include ethers such as diethylether, tetrahydrofuran and dimethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydride, sodium hydroxide, potassium hydroxide and potassium carbonate, alkali metal alkoxides such as sodium methoxide and potassium tert-butoxide, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (d).

The amount of the compound (c) used in the reaction is usually 1 to 10 mol per 1 mol of the compound (d).

The reaction temperature is usually in a range of −50 to 100° C., and the reaction time is usually 1 to 24 hours.

After completion of the reaction, the compound (I-a) can be isolated, for example, by pouring a reaction mixture into water and extracting the resulting mixture with an organic solvent, followed by concentration. The isolated compound (I-a) can be further purified by chromatography, recrystallization or the like, if necessary.

Production Process 3

A compound represented by the formula (I-a) can be also produced from the compound (c) according to the following method:

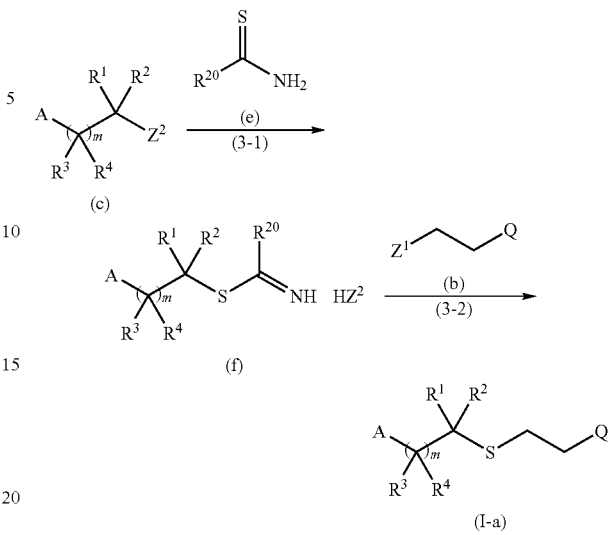

wherein A, Q, $R^1$, $R^2$, $R^3$, $R^4$, m, $Z^1$ and $Z^2$ are as defined above, and $R^{20}$ represents a methyl group or an amino group.

Step (3-1):

The compound (f) can be produced by reacting the compound (c) with the compound (e).

The reaction is generally performed in a solvent.

Examples of the solvent used in the reaction include halogenated hydrocarbons such as dichloromethane and chloroform, alcohols such as methanol and ethanol, and a mixture thereof.

The amount of the compound (e) used in the reaction is usually 1 to 3 mol per 1 mol of the compound (c).

The reaction temperature is usually in a range of 20 to 200° C., and the reaction time is usually 0.5 to 24 hours.

After completion of the reaction, the compound (f) can be isolated, for example, by concentrating a reaction mixture. The isolated compound (f) can be used as it is in the step (3-2) or, if necessary, can be further purified by recrystallization or the like.

Step (3-2):

A compound represented by the formula (I-a) can be produced by reacting the compound (f) and the compound (b) in the presence of a base.

The reaction is generally performed in a solvent in the presence of a base.

Examples of the solvent used in the reaction include ethers such as diethylether, tetrahydrofuran and dimethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydroxide and potassium hydroxide, and alkali metal alkoxides such as sodium methoxide and potassium tert-butoxide.

The amount of the base used in the reaction is usually 1 to 50 mol per 1 mol of the compound (f).

The amount of the compound (b) used in the reaction is usually 1 to 10 mol per 1 mol of the compound (f).

The reaction can be performed using a phase transfer catalyst such as tetra n-butylammonium bromide, if necessary.

The amount of the phase transfer catalyst used is usually 0.05 to 1.0 mol per 1 mol of the compound (f).

The reaction temperature is usually in a range of −50 to 100° C., and the reaction time is usually 1 to 24 hours.

After completion of the reaction, the compound (I-a) can be isolated, for example, by pouring a reaction mixture into water and extracting the resulting mixture with an organic solvent, followed by concentration. The isolated compound (I-a) can be further purified by chromatography, recrystallization or the like, if necessary.

Production Process 4

A compound represented by the formula (I-a) can be also produced from the compound (c) according to the following method:

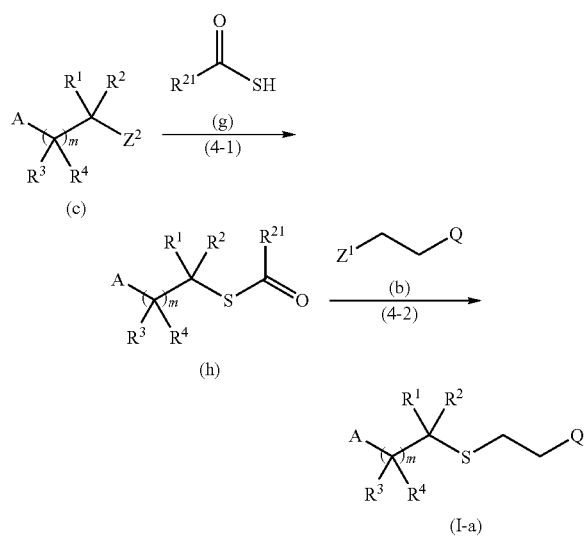

wherein A, Q, $R^1$, $R^2$, $R^3$, $R^4$, m, $Z^1$ and $Z^2$ are as defined above, and $R^{21}$ represents a methyl group or a phenyl group.

Step (4-1):

The compound (h) can be produced by reacting the compound (c) with the compound (g) in the presence of a base.

The reaction is generally performed in a solvent in the presence of a base.

Examples of the solvent used in the reaction include ethers such as diethylether, tetrahydrofuran and dimethoxyethane, acid amides such as N,N-dimethylformaide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, and a mixture thereof.

Examples of the base used in the reaction include inorganic bases such as sodium hydride and potassium carbonate, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (c).

The amount of the compound (g) used in the reaction is usually 1 to 5 mol per 1 mol of the compound (c).

The reaction temperature is usually in a range of −20 to 80° C., and the reaction time is usually 1 to 24 hours.

After completion of the reaction, the compound (h) can be isolated, for example, by pouring a reaction mixture into acidic water (e.g. diluted hydrochloric acid etc.) and extracting the resulting mixture with an organic solvent, followed by concentration. The isolated compound (h) can be further purified by chromatography, recrystallization or the like, if necessary.

Step (4-2):

A compound represented by the formula (I-a) can be produced by reacting the compound (b) and the compound (h) in the presence of a base.

The reaction is performed in a conventional solvent in the presence of a conventional base.

Examples of the solvent used in the reaction include ethers such as diethylether, tetrahydrofuran and dimethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydroxide and potassium hydroxide, and alkali methal alkoxides such as sodium methoxide, sodium ethoxide and potassium tert-butoxide.

The amount of the base used in the reaction is usually 1 to 10 mol per 1 mol of the compound (h).

The amount of the compound (b) used in the reaction is usually 1 to 10 mol per 1 mol of the compound (h). The reaction temperature is usually in a range of −50 to 100° C., and the reaction time is usually 1 to 24 hours.

After completion of the reaction, the compound (I-a) can be isolated, for example, by pouring a reaction mixture into water and extracting the resulting mixture with an organic solvent, followed by concentration. The isolated compound (I-a) can be further purified by chromatography, recrystallization or the like, if necessary.

Production Process 5

A compound represented by the formula (I-a) can be also produced from the compound (b) according to the following method:

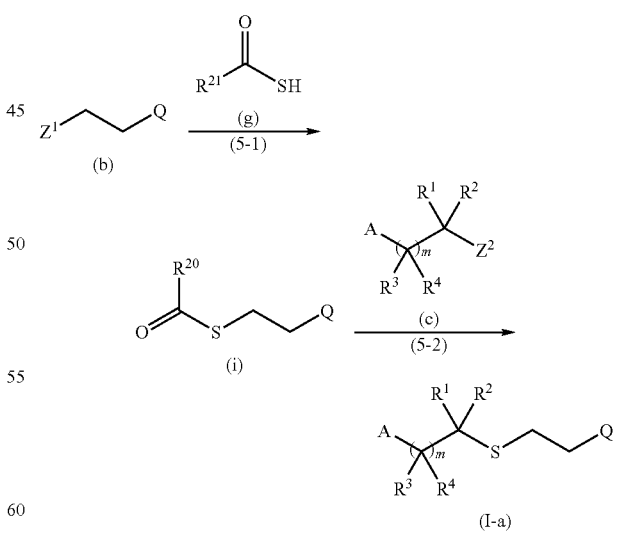

wherein A, Q, $R^1$, $R^2$, $R^3$, $R^4$, $R^{20}$, $Z^1$ and $Z^2$ are as defined above.

Step (5-1):

The compound (i) can be produced by reacting the compound (b) with the compound (g) in the presence of a base.

The reaction is generally performed in a solvent in the presence of a base.

Examples of the solvent used in the reaction include ethers such as diethylether, tetrahydrofuran and dimethoxyethane, acid amides such as N,N-dimethylformaide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, and a mixture thereof.

Examples of the base used in the reaction include inorganic bases such as sodium hydride and potassium carbonate, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (b).

The amount of the compound (g) used in the reaction is usually 1 to 5 mol per 1 mol of the compound (b).

The reaction temperature is usually in a range of −20 to 80° C., and the reaction time is usually 1 to 24 hours.

After completion of the reaction, the compound (i) can be isolated, for example, by pouring a reaction mixture into acidic water (e.g. diluted hydrochloric acid etc.) and extracting the resulting mixture with an organic solvent, followed by concentration. The isolated compound (i) can be further purified by chromatography, recrystallization or the like, if necessary.

Step (5-2):

A compound represented by the formula (I-a) can be produced by reacting the compound (c) with the compound (i) in the presence of a base.

The reaction is generally performed in a solvent in the presence of a base.

Examples of the solvent used in the reaction include ethers such as diethylether, tetrahydrofuran and dimethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydroxide and potassium hydroxide, and alkali metal alkoxides such as sodium methoxide, sodium ethoxide and potassium tert-butoxide.

The amount of the base used in the reaction is usually 1 to 10 mol per 1 mol of the compound (i).

The amount of the compound (c) used in the reaction is usually 1 to 10 mol per 1 mol of the compound (i).

The reaction temperature is usually in a range of −50 to 100° C., and the reaction time is usually 1 to 24 hours.

After completion of the reaction, the compound (I-a) can be isolated, for example, by pouring a reaction mixture into water and extracting the resulting mixture with an organic solvent, followed by concentration. The isolated compound (I-a) can be further purified by chromatography, recrystallization or the like, if necessary.

Production Process 6

A compound represented by the formula (I-b), which is a compound of the present invention represented by the formula (I) wherein $R^1$ is —C(=O)$R^5$ or a cyano group and $R^2$ is a hydrogen atom, or a compound represented by the formula (I-c), which is a compound of the present invention represented by the formula (I) wherein $R^1$ is —C(=O)$R^5$ or a cyano group and $R^2$ is a C1-C4 chain hydrocarbon group optionally substituted with a halogen atom, can be produced from the compound (j) according to the following method:

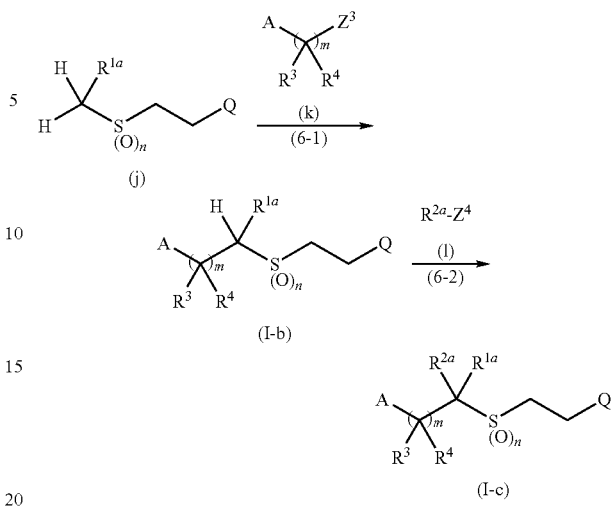

wherein A, Q, $R^3$, $R^4$, n and m are as defined above, $Z^3$ represents a leaving group such as a fluorine atom, a chlorine atom, a bromine atom, an iodine atom or a methanesulfonyl group, $Z^4$ represents a leaving group such as a chlorine atom, a bromine atom, an iodine atom or a methanesulfonyl group, $R^{1a}$ represents —C(=O)$R^5$ or a cyano group, and $R^{2a}$ represents a C1-C4 chain hydrocarbon group optionally substituted with a halogen atom.

Step (6-1):

A compound represented by the formula (I-b) can be produced by reacting the compound (k) with the compound (j) in the presence of a base.

The reaction is performed in a conventional solvent in the presence of a base.

Examples of the solvent used in the reaction include ethers such as diethylether, tetrahydrofuran and dimethoxyethane, acid amides such as N,N-dimethylformaide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydride, sodium hydroxide, potassium hydroxide and potassium carbonate, alkali metal alkoxides such as sodium methoxide and potassium tert-butoxide, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (j).

The amount of the compound (k) used in the reaction is usually 1 to 10 mol per 1 mol of the compound (j).

The reaction temperature is usually in a range of −50 to 100° C., and the reaction time is usually 1 to 24 hours. After completion of the reaction, the compound (I-b) can be isolated, for example, by pouring a reaction mixture into water and extracting the resulting mixture with an organic solvent, followed by concentration. The isolated compound (I-b) can be further purified by chromatography, recrystallization or the like, if necessary.

Step (6-2):

A compound represented by the formula (I-c) can be produced by reacting the compound (l) with the compound (I-b) in the presence of a base.

The reaction is performed in a conventional solvent in the presence of a conventional base.

Examples of the solvent used in the reaction include ethers such as diethylether, tetrahydrofuran and dimethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydride, sodium hydroxide, potassium hydroxide and potassium carbonate, alkali metal alkoxides such as sodium methoxide and potassium tert-butoxide, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (I-b).

The amount of the compound (l) used in the reaction is usually 1 to 10 mol per 1 mol of the compound (I-b).

The reaction temperature is usually in a range of −50 to 100° C., and the reaction time is usually 1 to 24 hours.

After completion of the reaction, the compound (I-c) can be isolated, for example, by pouring a reaction mixture into water and extracting the resulting mixture with an organic solvent, followed by concentration. The isolated compound (I-c) can be further purified by chromatography, recrystallization or the like, if necessary.

Production Process 7

A compound (I-c), which is a compound of the present invention represented by the formula (I) wherein $R^1$ is $-C(=O)R^5$ or a cyano group and $R^2$ is a C1-C4 chain hydrocarbon group optionally substituted with a halogen atom, can be also produced from the compound (j) according to the following method:

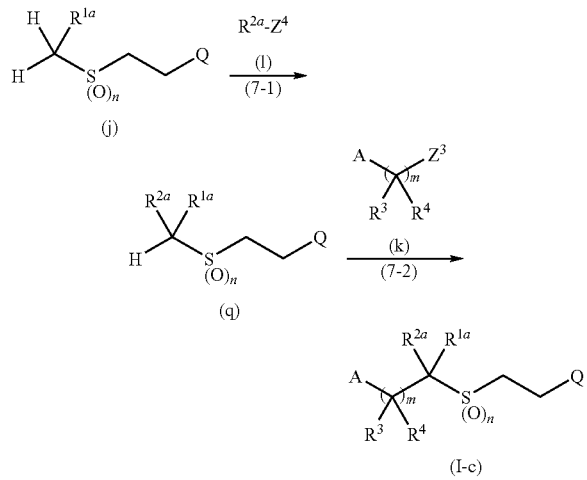

wherein A, Q, $R^{1a}$, $R^{2a}$, $R^3$, $R^4$, n, m, $Z^3$ and $Z^4$ are as defined above.

Step (7-1):

The compound (q) can be produced by reacting the compound (l) with the compound (j) in the presence of a base.

The reaction is performed in a conventional solvent in the presence of a conventional base.

Examples of the solvent used in the reaction include ethers such as diethylether, tetrahydrofuran and dimethoxyethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, halogenated hydrocarbons such as 1,2-dichloroethane and chlorobenzene, water, and a mixture thereof.

Examples of the base used in the reaction include inorganic bases such as sodium hydride, sodium hydroxide, potassium hydroxide and potassium carbonate, alkali metal alkoxides such as sodium methoxide, and potassium tert-butoxide, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (j).

The amount of the compound (l) used in the reaction is usually 1 to 10 mol per 1 mol of the compound (j).

The reaction temperature is usually in a range of −50 to 100° C., and the reaction time is usually 1 to 24 hours.

After completion of the reaction, the compound (q) can be isolated, for example, by pouring a reaction mixture into water and extracting the resulting mixture with an organic solvent, followed by concentration. The isolated compound (q) can be further purified by chromatography, recrystallization or the like, if necessary.

Step (7-2):

A compound represented by the formula (I-c) can be produced by reacting the compound (k) with the compound (q) in the presence of a base.

The reaction is performed in a conventional solvent in the presence of a conventional base.

Examples of the solvent used in the reaction include ethers such as diethylether, tetrahydrofuran and dimethoxymethane, acid amides such as N,N-dimethylformamide, organic sulfurs such as dimethyl sulfoxide and sulfolane, aliphatic hydrocarbons such as hexane and heptane, aromatic hydrocarbons such as toluene and xylene, and halogenated hydrocarbons such as 1,2-dichloroethane and chlorobenzene, water, and a mixture thereof.

Examples of the base used in the reaction include inorganic bases such as sodium hydride, sodium hydroxide, potassium hydroxide and potassium carbonate, alkali metal alkoxides such as sodium methoxide and potassium tert-butoxide, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (q).

The amount of the compound (k) used in the reaction is usually 1 to 10 mol per 1 mol of the compound (q). The reaction temperature is usually in a range of −50 to 100° C., and the reaction time is usually 1 to 24 hours.

After completion of the reaction, the compound (I-c) can be isolated, for example, by pouring a reaction mixture into water and extracting the resulting mixture with an organic solvent, followed by concentration. The isolated compound (I-c) can be further purified by chromatography, recrystallization or the like, if necessary.

Production Process 8

A compound represented by the formula (I-d), which is a compound of the present invention represented by the formula (I) wherein $R^1$ is $-C(=O)R^5$ or a cyano group and $R^2$ is a halogen atom, can be produced from the compound (I-b) according to the following method:

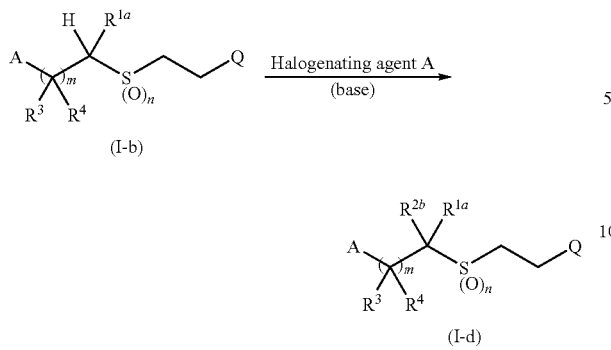

(I-b)

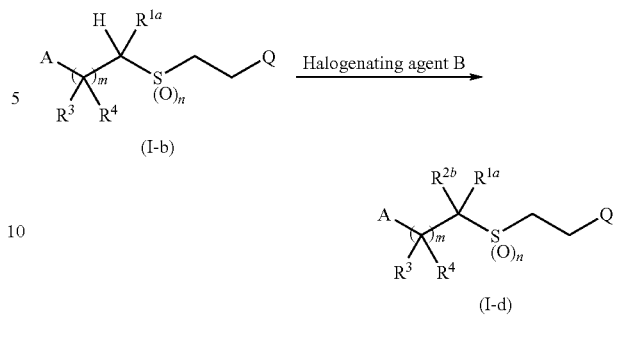

(I-b)

(I-d)

wherein, A, Q, $R^{1a}$, $R^3$, $R^4$, n and m are as defined above, and $R^{2b}$ represents a halogen atom.

The reaction is performed in a conventional solvent in the presence of a conventional base.

Examples of the solvent used in the reaction include acid amides such as N,N-dimethylformamide, ethers such as diethylether and tetrahydrofuran, organic sulfurs such as dimethyl sulfoxide and sulfolane, halogenated hydrocarbons such as chloroform, carbon tetrachloride, 1,2-dichloroethane, dichloromethane and dichlorobenzene, aliphatic nitriles such as acetonitrile and propionitrile, aromatic hydrocarbons such as toluene and xylene, water, and a mixture thereof.

Examples of the base used in the reaction include inorganic bases such as sodium hydride, sodium hydroxide, potassium hydroxide and potassium carbonate, alkali metal alkoxides such as sodium methoxide and potassium tert-butoxide, alkali metal amides such as lithium diisopropylamide, and organic bases such as triethylamine, 1,4-diazabicyclo[2.2.2]octane and 1,8-diazabicyclo[5.4.0]-7-undecene.

The amount of the base used in the reaction is usually 1 to 10 mol per 1 mol of the compound (I-b).

Examples of the halogenating agent A used in the reaction include halogenated hydrocarbons such as carbon tetrachloride and hexachloroethane, halogens such as fluorine, chlorine, bromine and iodine, N-halogenated succinimide such as N-chlorosuccinimide, N-bromosuccinimide and N-iodosuccinimide, N-fluoropyridinium salts such as 1-fluoro-2,4,6-trimethylpyridinium trifluoromethanesulfonate and 1,1'-difluoro-2,2'-bipyridinium bistetrafluoroborate, and inorganic salts such as copper (II) chloride and copper (II) bromide.

The amount of the halogenating agent used in the reaction is usually 1 to 10 mol per 1 mol of the compound (I-b).

The reaction temperature is usually in a range of −100 to 100° C., and the reaction time is usually 1 to 24 hours.

After completion of the reaction, the compound (I-d) can be isolated, for example, by pouring a reaction mixture into water and extracting the resulting mixture with an organic solvent, followed by concentration. The isolated compound (I-d) can be further purified by chromatography, recrystallization or the like, if necessary.

Production Process 9

A compound represented by the formula (I-d), which is a compound of the present invention represented by the formula (I) wherein $R^1$ is —C(=O)$R^5$ or a cyano group and $R^2$ is a halogen atom, can be produced from the compound (I-b) according to the following method:

wherein A, Q, $R^{1a}$, $R^{2b}$, $R^3$, $R^4$, n and m are as defined above.

The reaction is performed in a conventional solvent.

Examples of the solvent used in the reaction include halogenated hydrocarbons such as chloroform, carbon tetrachloride, 1,2-dichloroethane, dichloromethane and dichlorobenzene, aliphatic nitriles such as acetonitrile, and propionitrile, aromatic hydrocarbons such as toluene and xylene, aliphatic carboxylic acids such as acetic acid, carbon disulfide, water, and a mixture thereof.

Examples of the halogenating agent B used in the reaction include halogens such as fluorine, chlorine, bromine and iodine, hydrogen halide such as hydrogen fluoride, hydrogen chloride, hydrogen bromide and hydrogen iodide, sulfur halide compounds such as thionyl chloride, thionyl bromide and sulfuryl chloride, and phosphorus halide compounds such as phosphorus trichloride, phosphorus tribromide, phosphorus pentachloride and phosphorus oxychloride.

The amount of the halogenating agent used in the reaction is usually 1 to 10 mol per 1 mol of the compound (1-b).

The reaction temperature is usually in a range of −100 to 200° C., and the reaction time is usually 1 to 24 hours.

After completion of the reaction, the compound (I-d) can be isolated, for example, by pouring a reaction mixture into water and extracting the resulting mixture with an organic solvent, followed by concentration. The isolated compound (I-d) can be further purified by chromatography, recrystallization or the like, if necessary.

Production Process 10

A compound represented by the formula (I-e), which is a compound of the present invention represented by the formula (I) wherein n is 1 or 2, can be produced by oxidizing a compound represented by the formula (I-a):

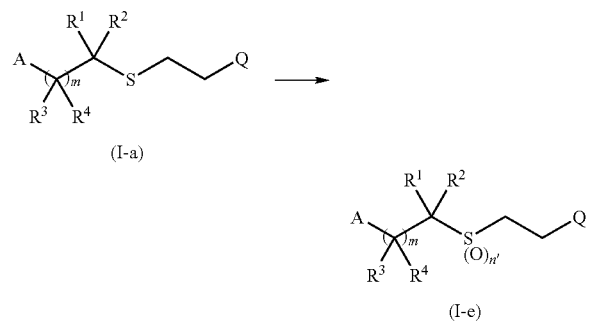

wherein A, Q, $R^1$, $R^2$, $R^3$, $R^4$ and m are as defined above, and n' represents 1 or 2.

The reaction is performed in a conventional solvent.

Examples of the solvent used in the reaction include alcohols such as methanol and ethanol, halogenated hydrocarbons such as dichloromethane and chloroform, aromatic hydrocarbons such as toluene and xylene, aliphatic carboxylic acids such as acetic acid and trifluoroacetic acid, water, and a mixture thereof.

Examples of the oxidizing agent used in the reaction include organic peroxides such as peracetic acid, trifluoroperacetic acid and m-chloroperbenzoic acid, halogen molecules such as chlorine and bromine, halogen-containing imides, such as N-chlorosuccinimide, halogenated compounds such as perchloric acid (or a salt thereof) and periodic acid (or a salt thereof), permanganates such as potassium permanganate, chromates such as potassium chromate, peroxysulfates such as potassium persulfate, and hydrogen peroxide.

The amount of the oxidizing agent used in the reaction is usually 1 to 10 mol per 1 mol of the compound (I-a).

The reaction temperature is usually in a range of −50 to 200° C., and the reaction time is usually 1 to 72 hours.

After completion of the reaction, the compound (I-e) can be isolated as a sulfide derivative, for example, by pouring a reaction mixture into water and extracting the resulting mixture with an organic solvent, followed by concentration. The isolated sulfide derivative (1-e) can be further purified by chromatography, recrystallization or the like, if necessary.

The compound (a), the compound (b), the compound (d), the compound (e), the compound (g), the compound (j), the compound (k) and the compound (l) are known compounds, or can be produced by a known method.

The compound (c) is a known compound, or can be produced by a known method.

Examples of arthropod pests on which the compound of the present invention exhibits a controlling effect include harmful insects and harmful mites, and more specifically, the following arthropods.

Hemiptera:

Planthoppers (Delphacidae) such as small brown planthopper (*Laodelphax striatellus*), brown rice planthopper (*Nilaparvata lugens*), and white-backed rice planthopper (*Sogatella furcifera*); leafhoppers (Deltocephalidae) such as green rice leafhopper (*Nephotettix cincticeps*), green rice leafhopper (*Nephotettix virescens*), and tea green leafhopper (*Empoasca onukii*); aphids (Aphididae) such as cotton aphid (*Aphis gossypii*), green peach aphid (*Myzus persicae*), cabbage aphid (*Brevicoryne brassicae*), spiraea aphid (*Aphis spiraecola*), potato aphid (*Macrosiphum euphorbiae*), foxglove aphid (*Aulacorthum solani*), oat bird-cherry aphid (*Rhopalosiphum padi*), tropical citrus aphid (*Toxoptera citricidus*), and mealy plum aphid (*Hyalopterus pruni*); stink bugs (Pentatomidae) such as green stink bug (*Nezara antennata*), bean bug (*Riptortus clavetus*), rice bug (*Leptocorisa chinensis*), white spotted spined bug (*Eysarcoris parvus*), and stink bug (*Halyomorpha mista*); whiteflies (Aleyrodidae) such as greenhouse whitefly (*Trialeurodes vaporariorum*), sweetpotato whitefly (*Bemisia tabaci*), citrus whitefly (*Dialeurodes citri*), and citrus spiny white fly (*Aleurocanthus spiniferus*); scales (Coccidae) such as Calformia red scale (*Aonidiella aurantii*), San Jose scale (*Comstockaspis perniciosa*), citrus north scale (*Unaspis citri*), red wax scale (*Ceroplastes rubens*), cottonycushion scale (*Icerya purchasi*), Japanese mealybug (*Planococcus kraunhiae*), Cosmstock mealybug (*Pseudococcus longispinis*), and white peach scale (*Pseudaulacaspis pentagona*); lace bugs (Tingidae); cimices such as *Cimex lectularius*; psyllids (Psyllidae), etc.;

Lepidoptera:

Pyralid moths (Pyralidae) such as rice stem borer (*Chilo suppressalis*), yellow rice borer (*Tryporyza incertulas*), rice leafroller (*Cnaphalocrocis medinalis*), cotton leafroller (*Notarcha derogata*), Indian meal moth (*Plodia interpunctella*), *Ostrinia furnacalis*, cabbage webworm (*Hellula undalis*), and bluegrass webworm (*Pediasia teterrellus*); owlet moths (Noctuidae) such as common cutworm (*Spodoptera litura*), beet armyworm (*Spodoptera exigua*), armyworm (*Pseudaletia separata*), cabbage armyworm (*Mamestra brassicae*), black cutworm (*Agrotis ipsilon*), beet semi-looper (*Plasia nigrisigna*), *Thoricoplusia* spp., *Heliothis* spp., and *Helicoverpa* spp.; white butterflies (Pieridae) such as common white (*Pieris rapae*); tortricid moths (Tortricidae) such as *Adoxophyes* spp., oriental fruit moth (*Grapholita molesta*), soybean pod borer (*Leguminivora glycinivorella*), azuki bean podworm (*Matsumuraeses azukivora*), summer fruit tortrix (*Adoxophyes orana* fasciata), smaller tea tortrix (*Adoxophyes* sp.), oriental tea tortrix (*Homona magnanima*), apple tortrix (*Archips fuscocupreanus*), and codling moth (*Cydia pomonella*); leafblotch miners (Gracillariidae) such as tea leafroller (*Caloptilia theivora*), and apple leafminer (*Phyllonorycter ringoneella*); Carposimidae such as peach fruit moth (*Carposina niponensis*); lyonetiid moths (Lyonetiidae) such as *Lyonetia* spp.; tussock moths (Lymantriidae) such as *Lymantria* spp., and *Euproctis* spp.; yponomeutid moths (Yponomeutidae) such as diamondback (*Plutella xylostella*); gelechiid moths (Gelechiidae) such as pink bollworm (*Pectinophora gossypiella*), and potato tubeworm (*Phthorimaea operculella*); tiger moths and allies (Arctiidae) such as fall webworm (*Hyphantria cunea*); tineid moths (Tineidae) such as casemaking clothes mothATinea translucens), and webbing clothes moth (*Tineola bisselliella*), etc.;

Thysanoptera:

Yellow citrus thrips (*Frankliniella occidentalis*), melon thrips (*Thrips palmi*), yellow tea thrips (*Scirtothrips dorsalis*), onion thrips (*Thrips tabaci*), flower thrips (*Frankliniella intonsa*), etc.;

Diptera:

Culices (Calicidae) such as common mosquito (*Culex pipiens pallens*), *Culex tritaeniorhynchus*, and Southern house mosquito (*Culex quinquefasciatus*); *Aedes* spp. such as yellow fever mosquito (*Aedes aegypti*), and Asian tiger mosquito (*Aedes albopictus*); *Anopheles*spp. such as *Anopheles sinensis*; Chironomidae; Houseflies (Muscidae) such as housefly (*Musca domestica*), and false stable fly (*Muscina stabulans*); blow flies (Calliphoridae); flesh flies (Sarcophagidae); little house flies (Fanniidae); anthomyiid flies (Anthomyiidae) such as seedcorn maggot (*Delia platura*), and onion maggot (*Delia antiqua*); leafminer flies (Agromyzidae) such as rice leafminer (*Agromyza oryzae*), rice leafminer (*Hydrellia griseola*), tomato leafminer (*Liriomyza sativae*), legume leafminer (*Liriomyza trifolii*), and garden pea leafminer (*Chromatomyia horticola*); gout flies (Chloropidae) such as rice stem maggot (*Chlorops oryzae*); fruit flies (Tephritidae) such as melon fly (*Dacus cucurbitae*), and Mediteranean fruit fly (*Ceratitis capitata*); drosophila flies (Drosophilidae); humpbacked flies (Phoridae) such as *Megaselia spiracularis*; Psychodidae such as *Clogmia albipunctata*; Simuliidae; Tabanidae such as horsefly (*Tabanus trigonus*); stable flies (*Stomoxys calcitrans*), etc.;

Coleoptera:

Corn root worms (*Diabrotica* spp.) such as Western corn root worm (*Diabrotica virgifera virgifera*), and Southern corn root worm (*Diabrotica undecimpunctata* howardi); scarabs (Scarabaeidae) such as cupreous chafer (*Anomala cuprea*), soybean beetle (*Anomala rufocuprea*), and Japanese beetle (*Popillia japonica*); weevils (Curculionidae) such as maize weevil (*Sitophilus zeamais*), rice water weevil (*Lissorhoptrus oryzophilus*), azuki bean weevil (*Callosobruchus chinensis*), rice curculio (*Echinocnemus squameus*), boll weevil (*Anthonomus grandis*), and hunting billbug (*Sphenophorus vena-

*tus*); darkling beetles (Tenebrionidae) such as yellow mealworm (*Tenebrio molitor*), and red flour beetle (*Tribolium castaneum*); leaf beetles (Chrysomelidae) such as rice leaf beetle (*Oulema oryzae*), cucurbit leaf beetle (*Aulacophora femoralis*), striped flea beetle (*Phyllotreta striolata*), and Colorado beetle (*Leptinotarsa decemlineata*); dermestid beetles (Dermestidae) such as varied carper beetle (*Anthrenus verbasci*), and hide beetle (*Dermestes maculates*); deathwatch beetles (Anobiidae) such as cigarette beetle (*Lasioderma serricorne*); *Epilachna* such as twenty-eight-spotted ladybird (*Epilachna vigintioctopunctata*); bark beetles (Scolytidae) such as powder post beetle (*Lyctus brunneus*), and pine shoot beetle (*Tomicus piniperda*); false powderpost beetles (Bostrichidae); spider beetles (Ptimidae); longhorn beetles (Cerambycidae) such as white-spotted longicorn beetle (*Anoplophora malasiaca*); click beetles (*Agriotes* spp.); Paederus fuscipes, etc.;

Orthoptera:

Asiatic locust (*Locusta migratoria*), African mole cricket (*Gryllotalpa africana*), rice grasshopper (*Oxya yezoensis*), rice grasshopper (*Oxya japonica*), Grylloidea, etc.;

Shiphonaptera:

Cat flea (*Ctenocephalides felis*), dog flea (*Ctenocephalides canis*), human flea (*Pulex irritans*), oriental rat flea (*Xenopsylla cheopis*), etc.;

Anoplura:

Human body louse (*Pediculus humanus corporis*), crab louse (*Phthirus pubis*), short-nosed cattle louse (*Haematopinus eurysternus*), sheep louse (*Dalmalinia ovis*), hog louse (*Haematopinus suis*), etc.;

Hymenoptera:

Ants (Formicidae) such as *Monomorium pharaosis, Formica fusca japonica*, black house ant (*Ochetellus glaber*), *Pristomyrmex pungens, Pheidole noda*, leaf-cutting ant (*Acromyrmex* spp.), and fire ant (*Solenopsis* spp.); hornets (Vespidae); bethylid wasps (Bethylidae); sawflies (Tenthredimidae) such as Cabbage sawfly (*Athalia rosae*), and *Athalia japonica*, etc.;

Blattodea:

Cockroaches (Blattariae) such as German cockroach (*Blattella germanica*), smokybrown cockroach (*Periplaneta fuliginosa*), American cockroach (*Periplaneta americana*), *Periplaneta* brunnea, and oriental cockroach (*Blatta orientalis*);

Isoptera:

Termites (Termitidae) such as subterranean termites such as Japanese subterranean termite (*Reticulitermes speratus*), Formosan subterranean termite (*Coptotermes formosanus*), western drywood termite (*Incisitermes minor*), Daikoku drywood termite (*Cryptotermes domesticus*), *Odontotermes formosanus, Neotermes koshunesis, Glyptotermes satsumesis, Glyptotermes nakajimai, Glyptotermes fuscus, Glyptotermes kodamai, Glyptotermes kushimensis*, Japanese dampwood termite (*Hodotermopsis japonica*), *Coptotermes guangzhoensis, Reticulitermes miyatakei, Reticulitermes flavipes amamianus, Reticulitermes kanmonensis* (*Reticulitermes* sp.), *Nasutitermes takasagoensis, Pericapritermes nitobei, Sinocapritermes mushae*, etc.;

Acarina:

Spider mites (Tetranychidae) such as two-spotted spider mite (*Tetranychus urticae*), Kanzawa spider mite (*Tetranychus kanzawai*), citrus red mite (*Panonychus citri*), European red mite (*Panonychus ulmi*), and *Oligonychus* spp.; eriophyid mites (Eriophyidae) such as pink citrus rust mite (*Aculops pelekassi*), *Phyllocoptruta citri*, tomato rust mite (*Aculops lycopersici*), purple tea mite (*Calacarus carinatus*), pink tea rust mite (*Acaphylla theavagran*), *Eriophyes chibaensis*, and apple rust mite (*Aculus schlechtendali*); tarosonemid mites (Tarsonemidae) such as broad mite (*Polyphagotarsonemus latus*); false spider mites (Tenuipalpidae) such as *Brevipalpus phoenicis*; Tuckerellidae; ticks (Ixodidae) such as Haemaphysalis longicornis, American dog tick (*Dermacentor variabilis*), *Haemaphysalis flava, Dermacentor taiwanicus*, American dog tick (*Dermacentor variabilis*), *Ixodes ovatus, Ixodes persulcatus*, black legged tick (*Ixodes scapularis*), lone star tick (*Amblyomma americanum*), *Boophilus microplus*, and *Rhipicephalus sanguineus*; Psoroptidae such as ear mite (*Otodectes cynotis*); itch mites (Sarcoptidae) such as Sarcoptes scabiei; folicle mites (Demodicidae) such as dog folicle mite (*Demodex canis*); acarid mites (Acaridae) such as mold mite (*Tyrophagus putrescentiae*), and *Tyrophagus similis*; house dust mites (Pyroglyphidae) such as *Dermatophagoides farinae*, and *Dermatophagoides ptrenyssnus*; cheyletide mites (Cheyletidae) such as *Cheyletus eruditus, Cheyletus malaccensis*, and *Cheyletus moorei*; parasitoid mites (Dermanyssidae) such as tropical rat mite (*Ornithonyssus bacoti*), northern fowl mite (*Ornithonyssus sylviarum*), and poultry red mite (*Dermanyssus gallinae*); chiggers (Trombiculidae) such as *Leptotrombidium akamushi*; spiders (Araneae) such as Japanese foliage spider (*Chiracanthium japonicum*), redback spider (*Latrodectus hasseltii*), etc.;

Chilopoda: *Thereuonema hilgendorfi, Scolopendra subspinipes*, etc.;

Diplopoda: garden millipede (*Oxidus gracilis*), *Nedyopus tambanus*, etc.;

Isopoda: common pill bug (*Armadillidium vulgare*), etc.;

Gastropoda: *Limax marginatus, Limax flavus*, etc.

Although the pesticidal composition of the present invention may be the compound of the present invention itself, the pesticidal composition of the present invention usually comprises the compound of the present invention in combination with a solid carrier, a liquid carrier and/or a gaseous carrier, and if necessary, a surfactant or other pharmaceutical additives and takes the form of an emulsifiable concentrate, an oil solution, a shampoo formulation, a flowable formulation, a dust, a wettable powder, a granule, a paste formulation, a microcapsule formulation, a foam formulation, an aerosol formulation, a carbon dioxide gas formulation, a tablet, a resin formulation or the like. The pesticidal composition of the present invention may be processed into a poison bait, a mosquito coil, an electric mosquito mat, a smoking pesticide, a fumigant or a sheet, and then be used.

The pesticidal composition of the present invention usually contains 0.1 to 95% by weight of the compound of the present invention.

Examples of the solid carrier include finely-divided powder and granules of clay (e.g., kaolin clay, diatomaceous earth, bentonite, Fubasami clay, acid clay, etc.), synthetic hydrated silicon oxide, talc, ceramics, other inorganic minerals (e.g., sericite, quartz, sulfur, activated carbon, calcium carbonate, hydrated silica, etc.), chemical fertilizers (e.g., ammonium sulfate, ammonium phosphate, ammonium nitrate, ammonium chloride, urea, etc.) and the like.

Examples of the liquid carrier include aromatic or aliphatic hydrocarbons (e.g., xylene, toluene, alkylnaphthalene, phenylxylylethane, kerosene, light oil, hexane, cyclohexane, etc.), halogenated hydrocarbons (e.g., chlorobenzene, dichloromethane, dichloroethane, trichloroethane, etc.), alcohols (e.g., methanol, ethanol, isopropyl alcohol, butanol, hexanol, ethylene glycol, etc.), ethers (e.g., diethylether, ethylene glycol dimethyl ether, diethylene glycol monomethyl ether, diethylene glycol monoethyl ether, propylene glycol monomethyl ether, tetrahydrofuran, dioxane, etc.), esters (e.g., ethyl acetate, butyl acetate, etc.), ketones (e.g., acetone, methyl ethyl ketone, methyl isobutyl ketone, cyclohexanone etc.), nitriles (e.g., acetonitrile, isobutyronitrile etc.), sulfoxides (e.g., dimethyl sulfoxide etc.), acid amides (e.g., N,N-dimethylformamide, N,N-dimethylacetamide etc.), vegetable oils (e.g., soybean oil, cottonseed oil etc.), vegetable essential oils (e.g., orange oil, hyssop oil, lemon oil, etc.), water and the like.

Examples of the gaseous carrier include butane gas, chlorofluorocarbon, LPG (liquefied petroleum gas), dimethyl ether, carbon dioxide gas and the like.

Examples of the surfactant include alkyl sulfate salts, alkyl sulfonate salts, alkylaryl sulfonate salts, alkyl aryl ethers and their polyoxyethylated derivatives, polyethylene glycol ethers, polyhydric alcohol esters, and sugar alcohol derivatives.

Examples of other formulation additives include a binder, a dispersant, a stabilizer and the like, and specific examples thereof include casein, gelatin, polysaccharides (e.g., starch, gum arabic, cellulose derivatives, alginic acid, etc.), lignin derivatives, bentonite, saccharides, synthetic water-soluble polymers (e.g., polyvinyl alcohol, polyvinylpyrrolidone, polyacrylic acid, etc.), PAP (isopropyl acid phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids, and fatty acid esters.

Examples of a base material for a resin formulation include vinyl chloride polymers, polyurethane and the like. To the base material, if necessary, a plasticizer such as phthalate (e.g., dimethyl phthalate, dioctyl phthalate, etc.), adipate, stearic acid or the like may be added. The resin formulation is obtained by kneading the compound of the present invention into the base material using a conventional kneading apparatus, followed by molding such as injection molding, extrusion molding, press molding or the like. The resulting resin formulation may be formed into the shape of a plate, a film, a tape, a net, a string or the like via a further step of molding, cutting, or the like, if necessary. These resin formulations may be used, for example, in the form of an animal collar, an animal ear tag, a sheet formulation, a lead, or a horticultural post.

Examples of a base material of a poison bait includes cereal powder, vegetable oil, sugar, crystalline cellulose and the like. To the base material, if necessary, an antioxidant such as dibutylhydroxytoluene or nordihydroguaiaretic acid, a preservative such as dehydroacetic acid, an agent for preventing children or pets from eating the poison bait by mistake such as hot pepper powder, a pest-attractive perfume such as cheese perfume, onion perfume or peanut oil or the like may be added.

The pesticidal composition of the present invention can be applied, for example, to arthropod pests directly and/or a place where arthropod pests inhabit (e.g., plants, animals, soil, etc.).

The pesticidal composition of the present invention can be used in crop lands such as cultivated lands, paddy fields, lawns and orchards. The pesticidal composition of the present invention may control harmful arthropods in a crop land without causing drug damage to crop plants cultivated in the crop land.

Examples of such crop plants include

Agricultural crops: corn, rice, wheat, barley, rye, oat, sorghum, cotton, soybean, peanut, sarrazin, sugar beet, rapeseed, sunflower, sugar cane, tobacco etc.;

Vegetables: Solanaceae vegetables (eggplant, tomato, green pepper, hot pepper, potato etc.), Cucurbitaceae vegetables (cucumber, pumpkin, zucchini, watermelon, melon etc.), Cruciferae vegetables (Japanese radish, turnip, horseradish, kohlrabi, Chinese cabbage, cabbage, brown mustard, broccoli, cauliflower etc.), Compositae vegetables (burdock, garland chrysanthemum, artichoke, lettuce etc.), Liliaceae vegetables (Welsh onion, onion, garlic, asparagus etc.), Umbelliferae vegetables (carrot, parsley, celery, parsnip etc.), Chenopodiaceae vegetables (spinach, Swiss chard etc.), Labiatae vegetables (Japanese basil, mint, basil etc.), strawberry, sweat potato, yam, aroid etc.;

Flowers and ornamental plants;

Foliage plant;

Fruit trees: pomaceous fruits (apple, common pear, Japanese pear, Chinese quince, quince etc.), stone fleshy fruits (peach, plum, nectarine, Japanese plum, cherry, apricot, prune etc.), citrus plants (Satsuma mandarin, orange, lemon, lime, grapefruit etc.), nuts (chestnut, walnut, hazel nut, almond, pistachio, cashew nut, *macadamia* nut etc.), berry fruits (blueberry, cranberry, blackberry, raspberry etc.), grape, persimmon, olive, loquat, banana, coffee, date, coconut etc.;

Trees other than fruit trees: tea, mulberry, flowering trees and shrubs, street trees (ash tree, birch, dogwood, eucalyptus, ginkgo, lilac, maple tree, oak, poplar, cercis, Chinese sweet gum, plane tree, zelkova, Japanese arborvitae, fir tree, Japanese hemlock, needle juniper, pine, spruce, yew) etc.

The aforementioned crop plants include those having herbicide resistance imparted by a classical breeding method, a genetic engineering technique or the like. Examples of the herbicide to be resisted include an HPPD inhibitor such as isoxaflutole; an ALS inhibitor such as imazethapyr or thifensulfuron-methyl; an EPSP synthesizing enzyme inhibitor; a glutamine synthesizing enzyme inhibitor; an acetyl CoA carboxylase inhibitor such as trioxime or aryloxyphenoxypropionic acid herbicide; and bromoxynil.

Examples of the crop plant having herbicide resistance imparted by a classical breeding method include Clearfield (registered trademark) canola resistant to an imidazolinone herbicide such as imazethapyr, STS soybean resistant to a sulfonylurea ALS inhibitor herbicide such as thifensulfuron-methyl, and the like. Examples of the crop plant having resistance to an acetyl CoA carboxylase inhibitor include SR corn and the like. For example, crop plants having resistance to acetyl CoA carboxylase inhibitors are found in Proc. Natl. Acad. Sci. USA 1990, 87, p. 7175-7179. In addition, a mutant acetyl CoA carboxylase resistant to an acetyl CoA carboxylase inhibitor is known, for example, in Weed Science 53: p. 728-746, 2005. When a gene encoding the mutant acetyl CoA carboxylase is introduced into a crop plant by a genetic engineering technique or when a mutation related to impartation of resistance is introduced into a gene encoding acetyl CoA carboxylase of a crop plant, a crop plant having the resistance to an acetyl CoA carboxylase inhibitor can be produced. Further, nucleic acids for introduction of a base substitution mutation can be introduced into the cell of a crop plant by chimeraplasty (see, Gura T. 1999, Repairing the Genome's Spelling Mistakes, Science 285: 316-318) to induce a site-directed amino acid mutation in the gene which is targeted by an acetyl CoA carboxylase inhibitor or herbicide of the crop plant, and thereby a crop plant resistant to an acetyl CoA carboxylase inhibitor or herbicide can be produced.

Examples of the crop plant having herbicide resistance imparted by a genetic engineering technique include corn cultivars having resistance to glyphosate or glufosinate. Some of such corn cultivars are sold under the trade name of RoundupReady (registered trademark), LibertyLink (registered trademark), and the like.

The aforementioned crop plants include those having an ability to produce an insecticidal toxin, for example a selective toxin originated from *Bacillus* which ability has been imparted by a genetic engineering technique.

Examples of the insecticidal toxin which is produced by such a genetically engineered plant include insecticidal proteins derived from *Bacillus cereus* and *Bacillus popilliae*; δ-endotoxins derived from *Bacillus thuringiensis*, such as Cry1Ab, Cry1Ac, Cry1F, Cry1Fa2, Cry2Ab, Cry3A, Cry3Bb1 and Cry9C; insecticidal proteins derived from *Bacillus thuringiensis*, such as VIP 1, VIP 2, VIP 3 and VIP 3A; insecticidal proteins derived from nematodes; toxins produced by animals such as scorpion toxins, spider toxins, bee toxins and insect-specific nerve toxins; fungal toxins; plant lectin; agglutinin; protease inhibitors such as trypsin inhibitors, serine protease inhibitors, patatin, cystatin, and papain inhibitors; ribosome-inactivating proteins (RIP) such as ricin, corn-RIP, abrin, saporin, and briodin; steroid metabolizing enzymes such as 3-hydroxysteroid oxidase, ecdysteroid-UDP-glucosyltransferase, and cholesterol oxidase; ecdysone inhibitors; HMG-CoA reductase; ion channel inhibitors such as sodium channel inhibitors and calcium channel inhibitors; juvenile hormone esterase; diuretic hormone receptors; stilbene synthase; bibenzyl synthase; chitinase; and glucanase.

The insecticidal toxin produced by such a genetically engineered plant also includes hybrid toxins of different insecticidal proteins, for example, δ-endotoxins such as Cry1Ab, Cry1Ac, Cry1F, Cry1Fa2, Cry2Ab, Cry3A, Cry3Bb1 and Cry9C and insecticidal proteins such as VIP 1, VIP 2, VIP 3 and VIP 3A, and toxins in which a part of amino acids constituting an insecticidal protein is deleted or modified. The hybrid toxin is made by combining different domains of the insecticidal proteins by a genetic engineering technique. An example of the toxin in which a part of amino acids constituting an insecticidal protein is deleted includes Cry1Ab in which a part of amino acids is deleted. An example of the toxin in which a part of amino acids constituting an insecticidal protein is modified includes a toxin in which one or more of amino acids of a naturally occurring toxin are substituted.

The insecticidal toxin and the genetically engineered crop plant having the ability to produce the insecticidal toxin are described, for example, in EP-A-0 374 753, WO 93/07278, WO 95/34656, EP-A-0 427 529, EP-A-451878, WO 03/052073, and the like. The genetically engineered crop plant having the ability to produce the insecticidal toxin particularly has resistance to attack by a coleopteran pest, dipteran pest or a lepidopteran pest.

Genetically engineered plants which have one or more pest-resistance genes and thereby produce one or more insecticidal toxins are also known, and some of them are commercially available. Examples of such genetically engineered plants include YieldGard (registered trademark) (a corn cultivar expressing Cry1Ab toxin), YieldGard Rootworm (registered trademark) (a corn cultivar expressing Cry3Bb1 toxin), YieldGard Plus (registered trademark) (a corn cultivar expressing Cry1Ab and Cry3Bb1 toxins), Heculex I (registered trademark) (a corn cultivar expressing Cry1Fa2 toxin and phosphinothricin N-acetyltransferase (PAT) for imparting resistance to gluphosinate), NuCOTN33B (registered trademark) (a cotton cultivar expressing Cry1Ac toxin), Bollgard I (registered trademark) (a cotton cultivar expressing Cry1Ac toxin), Bollgard II (registered trademark) (a cotton cultivar expressing Cry1Ac and Cry2Ab toxins), VIPCOT (registered trademark) (a cotton cultivar expressing VIP toxin), NewLeaf (registered trademark) (a potato cultivar expressing Cry3A toxin), NatureGard Agrisure GT Advantage (registered trademark) (GA21 glyphosate-resistance character), Agrisure CB Advantage (registered trademark) (Bt11 corn borer (CB) character), Protecta (registered trademark), and the like.

The aforementioned crop plants include those having an ability to produce an anti-pathogen substance which ability has been imparted by a genetic engineering technique.

Examples of the anti-pathogen substance includes PR proteins (PRPs described in EP-A-0 392 225); ion channel inhibitors such as sodium channel inhibitors, and calcium channel inhibitors (e.g. KP1, KP4, KP6 toxins etc. produced by viruses); stilbene synthase; bibenzyl synthase; chitinase; glucanase; substances produced by microorganisms such as peptide antibiotics, heterocycle-containing antibiotics, and protein factors involved in plant disease-resistance (described in WO 03/000906); and the like. Such anti-pathogen substances and genetically engineered plants which produce the anti-pathogen substances are described in EP-A-0 392 225, WO 05/33818, EP-A-0 353 191, and the like.

When the pesticidal composition of the present invention is used for controlling pests in agriculture and forestry, the application amount is usually 1 to 10,000 g/ha, preferably 10 to 500 g/ha of the compound of the present invention as the active ingredient. When the pesticidal composition of the present invention is the form of an emulsifiable concentrate, a wettable powder, a flowable formulation or a microcapsule formulation, it is usually used after dilution with water so as to contain 0.01 to 1,000 ppm of the compound of the present invention. When the pesticidal composition of the present invention is the form of a dust or a granule, it is usually used as it is. The pesticidal composition of the present invention may be sprayed directly to plants to be protected from arthropod pests. Soil can be treated with the pesticidal composition of the present invention to control arthropod pests living in the soil. Seedbeds before planting or planting holes or plant feet in planting can be also treated with the pesticidal composition of the present invention. Further, a sheet formulation of the pesticidal composition of the present invention may be applied by winding around plants, disposing in the vicinity of plants, laying on the soil surface at the plant feet, or the like.

When the pesticidal composition of the present invention is used for control of epidemic, the application amount is usually 0.001 to 10 mg/m$^3$ of the compound of the present invention as the active ingredient for application to space, and 0.001 to 100 mg/m$^2$ of the compound of the present invention as the active ingredient for application to a plane. The pesticidal composition in the form of an emulsifiable concentrate, a wettable powder or a flowable formulation is usually applied after dilution with water so as to contain usually 0.001 to 10,000 ppm of the compound of the present invention. The pesticidal composition in the form of an oil solution, an aerosol formulation, a smoking pesticide or a poison bait is usually applied as it is.

When the pesticidal composition of the present invention is used for controlling external parasites of livestock such as a cow, a horse, a pig, a sheep, a goat and a chicken, or small animals such as a dog, a cat, a rat and a mouse, it can be applied to said animals by a known method in the veterinary field. Specifically, when systemic control is intended, the pesticidal composition of the present invention is administered, for example, as a tablet, a mixture with feed, a suppository or an injection (e.g., intramuscularly, subcutaneously, intravenously, intraperitoneally, etc.). When non-systemic control is intended, the pesticidal composition of the present invention is applied to an animal by spraying, pour-on treatment or a spot-on treatment with the pesticidal composition in the form of an oil solution or an aqueous liquid, washing the animal with the pesticidal composition in the form of a shampoo formulation, and attaching a collar or a ear tag made of the pesticidal composition in the form of a resin formulation to the animal. When administered to an animal, the amount of the compound of the present invention is usually in the range of 0.1 to 1,000 mg per 1 kg body weight of the animal.

The pesticidal composition of the present invention may be used in admixture or combination with other insecticides, nematocides, acaricides, fungicides, herbicides, plant growth regulators, synergists, fertilizers, soil conditioners, animal feed, and the like. Examples of an active ingredient of such insecticide include (1) Organic Phosphorus Compounds:
acephate, aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos, and the like;

(2) Carbamate Compounds:
alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb, and the like;

(3) Synthetic Pyrethroid Compounds:
acrinathrin, allethrin, beta-cyfluthrin, bifenthrin, cyclopro-thrin, cyfluthrin, cyhalothrin, cypermethrin, empenthrin, deltamethrin, esfenvalerate, ethofenprox, fenpropathrin, fenvalerate, flucythrinate, flufenoprox, flumethrin, fluvalinate, halfenprox, imiprothrin, permethrin, prallethrin, pyrethrins, resmethrin, sigma-cypermethrin, silafluofen, tefluthrin, tralomethrin, transfluthrin, tetramethrin, phenothrin, cyphenothrin, alpha-cypermethrin, zeta-cypermethrin, lambda-cyhalothrin, gamma-cyhalothrin, furamethrin, tau-fluvalinate, metofluthrin, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate, and the like;

(4) Nereistoxin Compounds:
cartap, bensultap, thiocyclam, monosultap, bisultap, and the like;

(5) Neonicotinoid Compounds:
imidacloprid, nitenpyram, acetamiprid, thiamethoxam, thiacloprid, dinotefuran, clothianidin, and the like;

(6) Benzoylurea Compounds:
chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, triazuron, and the like;

(7) Phenylpyrazole Compounds:
acetoprole, ethiprole, fipronil, vaniliprole, pyriprole, pyrafluprole, and the like;

(8) Bt Toxin Insecticides:
live spores or crystal toxins originated from *Bacillus* thuringiesis and a mixture thereof;

(9) Hydrazine Compounds:
chromafenozide, halofenozide, methoxyfenozide, tebufenozide, and the like;

(10) Organic Chlorine Compounds:
aldrin, dieldrin, dienochlor, endosulfan, methoxychlor, and the like;

(11) Natural Insecticides:
machine oil, nicotine sulfate, and the like;

(12) Other Insecticides:
avermectin-B, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, pyriproxyfen, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metham-ammonium, metham-sodium, methyl bromide, potassium oleate, protrifenbute, spiromesifen, sulfur, metaflumizone, spirotetramat, pyrifluquinazone, spinetoram, chlorantraniliproie, tralopyril, a compound represented by the following formula (A):

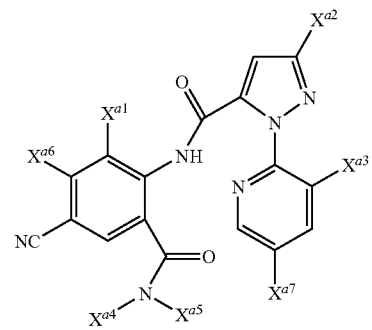

(A)

wherein $X^{a1}$ represents methyl, chlorine, bromine or fluorine, $X^{a2}$ represents fluorine, chlorine, bromine, C1-C4 haloalkyl or C1-C4 haloalkoxy, $X^{a3}$ represents fluorine, chlorine or bromine, $X^{a4}$ represents optionally substituted C1-C4 alkyl, optionally substituted C3-C4 alkenyl, optionally substituted C3-C4 alkynyl, optionally substituted C3-C5 cycloalkyl or hydrogen, $X^{a5}$ represents hydrogen or methyl, $X^{a6}$ represents hydrogen, fluorine or chlorine, and $X^{a7}$ represents hydrogen, fluorine or chlorine;

a compound represented by the following formula (B):

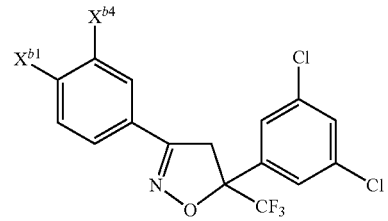

(B)

wherein $X^{b1}$ represents $X^{b2}$—NH—C(=O), $X^{b2}$—C(=O)—NH—CH$_2$, $X^{b3}$—S(O), optionally substituted pyrrol-1-yl, optionally substituted imidazol-1-yl, optionally substituted pyrazol-1-yl, or optionally substituted 1,2,4-triazol-1-yl, $X^{b2}$ represents optionally substituted C1-C4 haloalkyl such as 2,2,2-trifluoroethyl or optionally substituted C3-C6 cycloalkyl such as cyclopropyl, $X^{b3}$ represents optionally substituted C1-C4 alkyl such as methyl, and $X^{b4}$ represents hydrogen, chlorine, cyano or methyl;

a compound represented by the following formula (C):

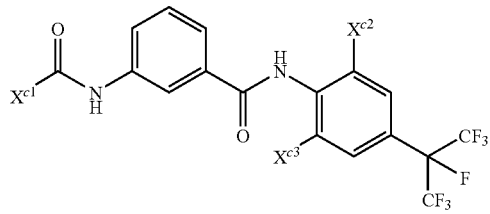

(C)

wherein $X^{c1}$ represents optionally substituted C1-C4 alkyl such as 3,3,3-trifluoropropyl, optionally substituted C1-C4 alkoxy such as 2,2,2-trichloroethoxy or optionally substituted phenyl such as 4-cyanophenyl or optionally substituted pyridyl such as 2-chloro-3-pyridyl, $X^{c2}$ represents methyl or trifluoromethylthio, and $X^{c3}$ represents methyl or halogen; and the like.

Examples of an active ingredient of the acaricide include acequinocyl, amitraz, benzoximate, bifenate, bromopropylate, chinomethionat, chlorobenzilate, CPCBS (chlorfenson), clofentezine, cyflumetofen, kelthane (dicofol), etoxazole, fenbutatin oxide, fenothiocarb, fenpyroximate, fluacrypyrim, fluproxyfen, hexythiazox, propargite (BPPS), polynactins, pyridaben, pyrimidifen, tebufenpyrad, tetradifon, spirodiclofen, spiromesifen, spirotetramat, amidoflumet, cyenopyrafen, and the like.

Examples of the nematicide include DCIP, fosthiazate, levamisol hydrochloride, methylisothiocyanate, morantel tartarate, imicyafos, and the like.

Examples of an active ingredient of such fungicide include strobilurin compounds such as azoxystrobin; organophosphate compounds such as tolclofos-methyl; azole compounds such as triflumizole, pefurazoate and difenoconazole; fthalide, flutolanil, validamycin, probenazole, diclomezine, pencycuron, dazomet, kasugamycin, IBP, pyroquilon, oxolinic acid, tricyclazole, ferimzone, mepronil, EDDP, isoprothiolane, carpropamid, diclocymet, furametpyr, fludioxonil, procymidone and diethofencarb.

EXAMPLES

Hereinafter, the present invention will be described in more detail by way of Production Examples, Formulation Examples and Test Examples. However, the present invention is not limited thereto.

First, Production Examples of the compound of the present invention are shown.

Production Example 1

To a solution of 236 mg of sodium borohydride in 20 mL of methanol was added 1.00 g of 2-acetyl-5-chlorothiophene at room temperature. The mixture was stirred at the same temperature for 0.5 hours. To the reaction mixture was added 10% hydrochloric acid, followed by extraction with chloroform. The organic layer was dried over anhydrous magnesium sulfate and then concentrated under reduced pressure. The resultant residue was dissolved in 20 mL of chloroform, and 0.9 mL of thionyl chloride was added to the solution at room temperature. The mixture was stirred at the same temperature for one hour and then concentrated under reduced pressure. The resultant residue was dissolved in 20 mL of tetrahydrofuran, and 1.46 g of S-(3,3,3-trifluoropropyl)benzenethioate was added to the solution at room temperature. To the solution, 1.2 mL of a 28% solution of sodium methoxide in methanol was added dropwise at room temperature. After stirring at the same temperature for one hour, to the reaction mixture was added 10% hydrochloric acid, followed by extraction with ethyl acetate. The organic layer was dried over anhydrous magnesium sulfate and then concentrated under reduced pressure. The resultant residue was subjected to column chromatography to obtain 300 mg of 2-chloro-5-[1-(3,3,3-trifluoropropylsulfanyl)ethyl]thiophene (hereinafter referred to as the present compound (1)).

The Present Compound (1):

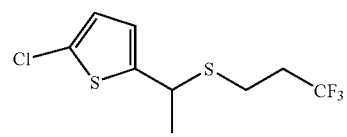

(1)

$^1$H-NMR (CDCl$_3$,TMS): δ (ppm) 6.69-6.72 (2H, m), 4.13 (1H, q), 2.57-2.64 (2H, m), 2.26-2.38 (2H, m), 1.62 (3H, d).

Production Example 2

To a solution of 500 mg of 3-chloromethyl-5-tert-butylisoxazole and 537 mg of S-(3,3,3-trifluoropropyl)benzenethioate in 20 mL of methanol was added dropwise 0.5 mL of a 28% solution of sodium methoxide in methanol at room temperature. After stirring at the same temperature for 2 hours, to the reaction mixture was added 10% hydrochloric acid, followed by extraction with ethyl acetate. The organic layer was dried over anhydrous magnesium sulfate and then concentrated under reduced pressure. The resultant residue was subjected to column chromatography to obtain 440 mg of 5-tert-butyl-3-[(3,3,3-trifluoropropylsulfanyl)methyl]isoxazole (hereinafter referred to as the present compound (2)).

The Present Compound (2):

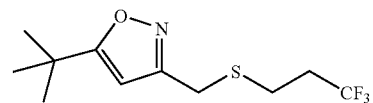

(2)

$^1$H-NMR (CDCl$_3$, TMS): δ (ppm) 5.96 (1H, s), 3.70 (2H, s), 2.63-2.67 (2H, m), 2.29-2.41 (2H, m), 1.34 (9H, d).

Production Example 3

Ten (10) mL of a 36% aqueous solution of formaldehyde was added to a solution containing 1.00 g of 4-trifluoromethylimidazole and 0.4 mL of a 10% tetra-n-butylammonium hydroxide solution in 10 mL of tetrahydrofuranat room temperature. The mixture was stirred at the same temperature for 14 hours and then concentrated under reduced pressure. The resultant residue was subjected to column chromatography to obtain crude 4-trifluoromethylimidazol-1-ylmethanol. The crude product was dissolved in 20 mL of chloroform and thereto 0.8 mL of thionyl chloride was added at room temperature. The mixture was stirred under reflux conditions for 16 hours, allowed to be cooled to room temperature, and then concentrated under reduced pressure. The resultant residue was dissolved in 20 mL of tetrahydrofuran and thereto 940 mg of S-(3,3,3-trifluoropropyl)benzenethioate was added. To the solution, 2.4 mL of a 28% solution of sodium methoxide in methanol was added dropwise at room temperature. After stirring at the same temperature for 10 hours, to the reaction mixture was added 10% hydrochloric acid, followed by extraction with ethyl acetate. The organic layer was dried over anhydrous magnesium sulfate and then concentrated under reduced pressure. The resultant residue was subjected to column chromatography to obtain 800 mg of 4-trifluoromethyl-1-[(3,3,3-trifluoropropylsulfanyl)methyl]-1H-imidazole (hereinafter referred to as the present compound (3)).
The Present Compound (3):

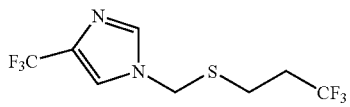

(3)

$^1$H-NMR (CDCl$_3$, TMS): δ (ppm) 7.65 (1H, s), 7.43 (1H, s), 5.01 (2H, s), 2.67-2.71 (2H, m), 2.27-2.381 (2H, m).

Production Example 4

To 26 ml of methanol were added 1.68 g of potassium thioacetate and 2.32 g of 1-tert-butyl-4-(chloromethyl)-1H-pyrazole, and the mixture was heated at 50° C. for 4 hours. The reaction mixture was cooled to room temperature, and thereto were added 2.78 g of a 28% solution of sodium methoxide in methanol and 3.54 g of 1-iodo-3,3,3-trifluoropropane. The mixture was heated at 50° C. for 4 hours. The reaction mixture was cooled to room temperature, and thereto was added 50 ml of water, followed by concentration under reduced pressure until a whole volume of 50 ml. After extraction with ethyl acetate, the organic layer was washed with an aqueous saturated sodium chloride solution. The organic layer was dried over anhydrous sodium sulfate, filtered and then concentrated under reduced pressure. The resultant residue was subjected to column chromatography to obtain 2.73 g of 1-tert-butyl-4-[(3,3,3-trifluoropropylsulfanyl)methyl]-1H-pyrazole (hereinafter referred to as the present compound (4)).
The Present Compound (4):

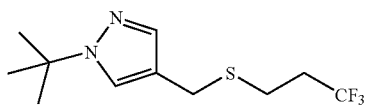

(4)

$^1$H-NMR (CDCl$_3$, TMS): δ (ppm) 7.46 (1H, s), 7.45 (1H, s), 3.65 (2H, s), 2.61-2.65 (2H, m), 2.26-2.38 (2H, m), 1.54 (9H, s).

Production Example 5

To a solution of 24.59 g of potassium hydrogen monopersulfate (Oxone (registered trade mark), produced by Du Pont Kabushiki Kaisha) in 40 mL of water was added a solution of 2.40 g of the present compound (4) in 40 mL of methanol. The mixture was heated to 50° C., stirred for 5 hours, and then cooled to room temperature. Thereto was added a 10% sodium sulfite aqueous solution, followed by extraction with ethyl acetate. The organic layer was dried over anhydrous sodium sulfate, filtered and then concentrated under reduced pressure. The resultant residue was subjected to column chromatography to obtain 2.61 g of 1-tert-butyl-4-[(3,3,3-trifluoropropylsulfonyl)methyl]-1H-pyrazole (hereinafter referred to as the present compound (5)).
The Present Compound (5):

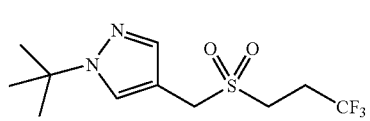

(5)

$^1$H-NMR (CDCl$_3$, TMS): δ (ppm) 7.66 (1H, s), 7.56 (1H, s), 4.20 (2H, s), 3.05-3.09 (2H, m), 2.51-2.63 (2H, m), 1.60 (9H, s).

Specific examples of the compound of the present invention are shown below.
A compound represented by the formula (I$^1$):

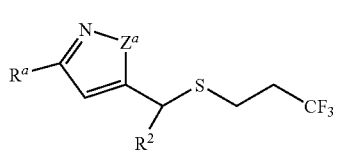

(I$^1$)

wherein R$^2$, R$^a$ and Z$^a$ represent any one of combinations shown below.

A compound represented by the formula (I$^2$):

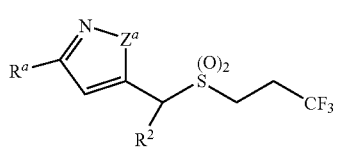

(I$^2$)

wherein R$^2$, R$^a$ and Z$^a$ represent any one of combinations shown below.

A compound represented by the formula (I$^3$):

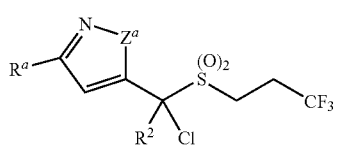

(I$^3$)

wherein R$^2$, R$^a$ and Z$^a$ represent any one of combinations shown below.

A compound represented by the formula (I⁴):

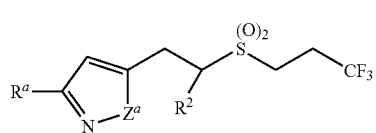

wherein R², Rᵃ and Zᵃ represent any one of combinations shown below.

A compound represented by the formula (I⁵):

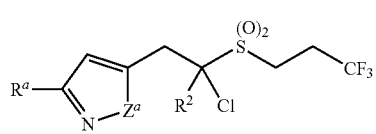

wherein R², Rᵃ and Zᵃ represent any one of combinations shown below.

A compound represented by the formula (I⁶):

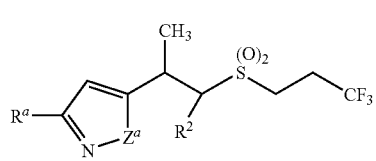

wherein R², Rᵃ and Zᵃ represent any one of combinations shown below.

A compound represented by the formula (I⁷):

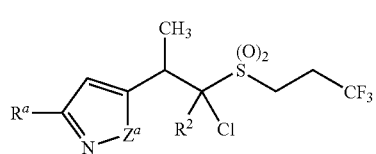

wherein R², Rᵃ and Zᵃ represent any one of combinations shown below.

A compound represented by the formula (I⁸):

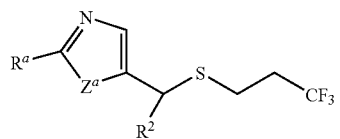

wherein R², Rᵃ and Zᵃ represent any one of combinations shown below.

A compound represented by the formula (I⁹):

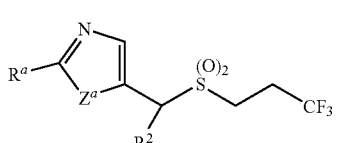

wherein R², Rᵃ and Zᵃ represent any one of combinations shown below.

A compound represented by the formula (I¹⁰):

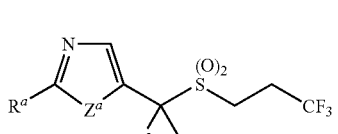

wherein R², Rᵃ and Zᵃ represent any one of combinations shown below.

A compound represented by the formula (I¹¹):

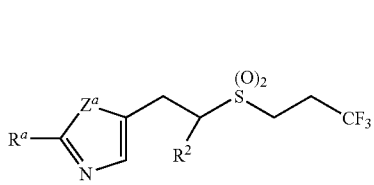

wherein R², Rᵃ and Zᵃ represent any one of combinations shown below.

A compound represented by the formula (I¹²):

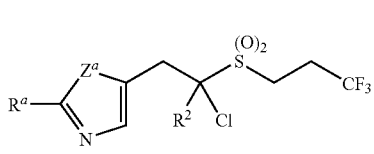

wherein R², Rᵃ and Zᵃ represent any one of combinations shown below.

A compound represented by the formula (I¹³):

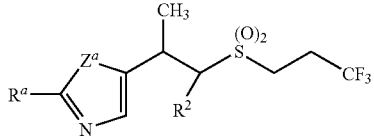

wherein R², Rᵃ and Zᵃ represent any one of combinations shown below.

A compound represented by the formula ($I^{14}$):

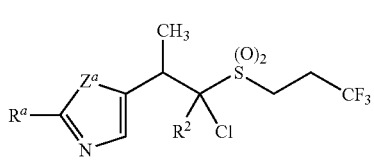

wherein $R^2$, $R^a$ and $Z^a$ represent any one of combinations shown below.

A compound represented by the formula ($I^{15}$):

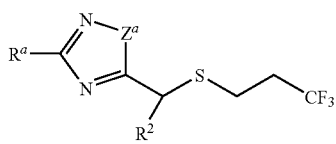

wherein $R^2$, $R^a$ and $Z^a$ represent any one of combinations shown below.

A compound represented by the formula ($I^{16}$):

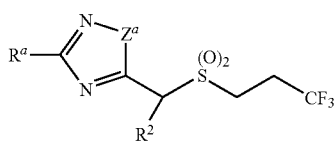

wherein $R^2$, $R^a$ and $Z^a$ represent any one of combinations shown below.

A compound represented by the formula ($I^{17}$):

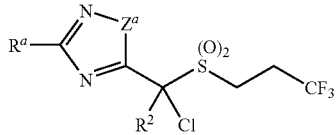

wherein $R^2$, $R^a$ and $Z^a$ represent any one of combinations shown below.

A compound represented by the formula ($I^{18}$):

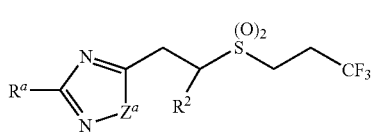

wherein $R^2$, $R^a$ and $Z^a$ represent any one of combinations shown below.

A compound represented by the formula ($I^{19}$):

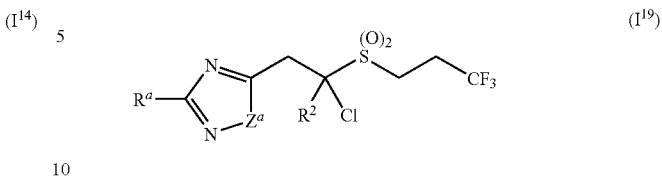

wherein $R^2$, $R^a$ and $Z^a$ represent any one of combinations shown below.

A compound represented by the formula ($I^{20}$):

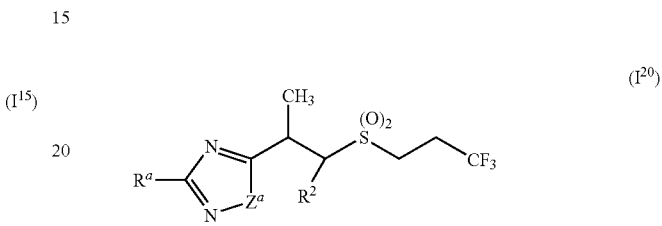

wherein $R^2$, $R^a$ and $Z^a$ represent any one of combinations shown below.

A compound represented by the formula ($I^{21}$):

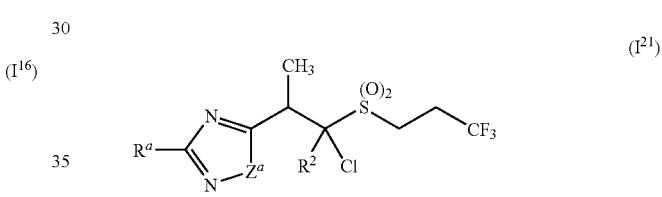

wherein $R^2$, $R^a$ and $Z^a$ represent any one of combinations shown below.

A compound represented by the formula ($I^{22}$):

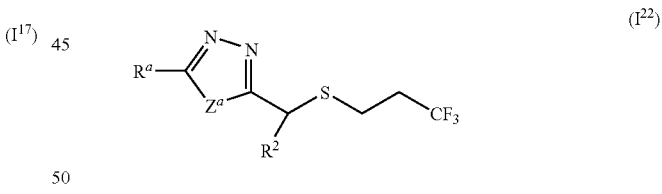

wherein $R^2$, $R^a$ and $Z^a$ represent any one of combinations shown below.

A compound represented by the formula ($I^{23}$):

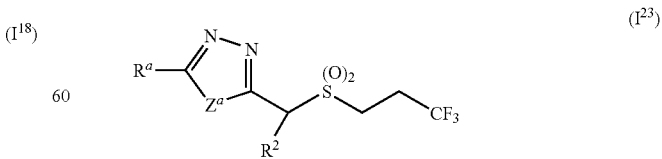

wherein $R^2$, $R^a$ and $Z^a$ represent any one of combinations shown below.

A compound represented by the formula (I$^{24}$):

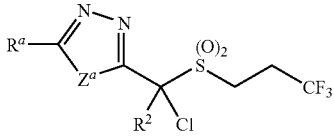

wherein R$^2$, R$^a$ and Z$^a$ represent any one of combinations shown below.

A compound represented by the formula (I$^{25}$):

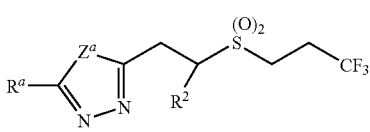

wherein R$^2$, R$^a$ and Z$^a$ represent any one of combinations shown below.

A compound represented by the formula (I$^{26}$):

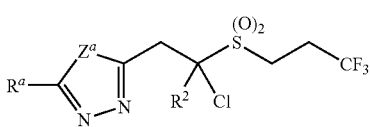

wherein R$^2$, R$^a$ and Z$^a$ represent any one of combinations shown below.

A compound represented by the formula (I$^{27}$):

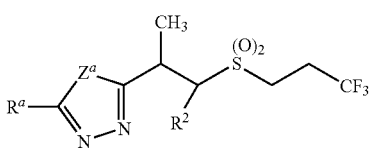

wherein R$^2$, R$^a$ and Z$^a$ represent any one of combinations shown below.

A compound represented by the formula (I$^{28}$):

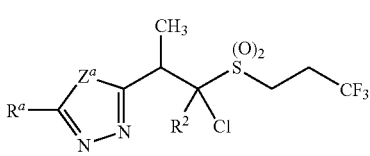

wherein R$^2$, R$^a$ and Z$^a$ represent any one of combinations shown below.

Combinations of R$^2$, R$^a$ and Z$^a$ for the compounds represented by the formulas (I$^1$) to (I$^{28}$) are shown below. In brackets, a combination number, a group represented by R$^2$, a group represented by R$^a$, and a group represented by Z$^a$ are shown in this order. Herein, symbols J1 to J10 represent the following groups.

J1: C(=O)—OCH$_3$
J2: C(=O)O—C(CH$_3$)$_3$
J3: C(=O)—NH$_2$
J4: C(=O)—NH(CH$_3$)
J5: C(=O)—NH(CH$_2$CH$_3$)
J6: C(=O)—N(CH$_3$)$_2$
J7: C(=S)—OCH$_3$
J8: C(=S)—NH$_2$
J9: C(=S)—NH(CH$_3$)
J10: C(=S)—N(CH$_3$)$_2$

[Combination number: R$^2$, R$^a$, Z$^a$]=[1: H, C(CH$_3$)$_3$, NH], [2 C(CH$_3$)$_3$, NH], [3: Cl, C(CH$_3$)$_3$, NH], [4: Br, C(CH$_3$)$_3$, NH], [5: CH$_3$, C(CH$_3$)$_3$, NH], [6: CN, C(CH$_3$)$_3$, NH], [7: J1, C(CH$_3$)$_3$, NH], [8: J2, C(CH$_3$)$_3$, NH], [9: J3, C(CH$_3$)$_3$, NH], [10: J4, C(CH$_3$)$_3$, NH], [11: J5, C(CH$_3$)$_3$, NH], [12: J6, C(CH$_3$)$_3$, NH], [13: J7, C(CH$_3$)$_3$, NH], [14: J8, C(CH$_3$)$_3$, NH], [15: J9, C(CH$_3$)$_3$, NH], [16: J10, C(CH$_3$)$_3$, NH], [17 CF$_3$, NH], [18: CF$_3$, NH], [19: Cl, CF$_3$, NH], [20: Br, CF$_3$, NH], [21: CH$_3$, CF$_3$, NH], [22: CN, CF$_3$, NH], [23: J1, CF$_3$, NH], [24: J2, CF$_3$, NH], [25: J3, CF$_3$, NH], [26: J4, CF$_3$, NH], [27: J5, CF$_3$, NH], [28: J6, CF$_3$, NH], [29: J7, CF$_3$, NH], [30: J8, CF$_3$, NH], [31: J9, CF$_3$, NH], [32: J10, CF$_3$, NH], [33 CF$_2$CF$_3$, NH], [34: F, CF$_2$CF$_3$, NH], [35: Cl, CF$_2$CF$_3$, NH], [36: Br, CF$_2$CF$_3$, NH][37: CH$_3$, CF$_2$CF$_3$, NH], [38: CN, CF$_2$CF$_3$, NH], [39: J1, CF$_2$CF$_3$, NH], [40: J2, CF$_2$CF$_3$, NH], [41: J3, CF$_2$CF$_3$, NH], [42: J4, CF$_2$CF$_3$, NH], [43: J5, CF$_2$CF$_3$, NH], [44: J6, CF$_2$CF$_3$, NH], [45: J7, CF$_2$CF$_3$, NH], [46: J8, CF$_2$CF$_3$, NH], [47: J9, CF$_2$CF$_3$, NH], [48: J10, CF$_2$CF$_3$, NH][49: H, SCF$_3$, NH], [50: F, SCF$_3$, NH], [51: Cl, SCF$_3$, NH], [52: Br, SCF$_3$, NH], [53: CH$_3$, SCF$_3$, NH], [54: CN, SCF$_3$, NH], [55: J1, SCF$_3$, NH], [56: J2, SCF$_3$, NH], [57: J3, SCF$_3$, NH], [58: J4, SCF$_3$, NH], [59: J5, SCF$_3$, NH], [60: J6, SCF$_3$, NH], [61: J7, SCF$_3$, NH], [62: J8, SCF$_3$, NH], [63: J9, SCF$_3$, NH], [64: J10, SCF$_3$, NH], [65: H, SOCF$_3$, NH], [66: F, SOCF$_3$, NH], [67: Cl, SOCF$_3$, NH], [68: Br, SOCF$_3$, NH], [69: CH$_3$, SOCF$_3$, NH], [70: CN, SOCF$_3$, NH], [71: J1, SOCF$_3$, NH], [72: J2, SOCF$_3$, NH], [73: J3, SOCF$_3$, NH], [74: J4, SOCF$_3$, NH], [75: J5, SOCF$_3$, NH], [76: J6, SOCF$_3$, NH], [77: J7, SOCF$_3$, NH], [78: J8, SOCF$_3$, NH], [79: J9, SOCF$_3$, NH], [80: J10, SOCF$_3$, NH], [81: H, SO$_2$CF$_3$, NH], [82: F, SO$_2$CF$_3$, NH], [83: Cl, SO$_2$CF$_3$, NH], [84: Br, SO$_2$CF$_3$, NH], [85: CH$_3$, SO$_2$CF$_3$, NH], [86: CN, SO$_2$CF$_3$, NH], [87: J1, SO$_2$CF$_3$, NH], [88: J2, SO$_2$CF$_3$, NH], [89: J3, SO$_2$CF$_3$, NH], [90: J4, SO$_2$CF$_3$, NH], [91: J5, SO$_2$CF$_3$, NH], [92: J6, SO$_2$CF$_3$, NH], [93: J7, SO$_2$CF$_3$, NH], [94: J8, SO$_2$CF$_3$, NH], [95: J9, SO$_2$CF$_3$, NH], [96: J10, SO$_2$CF$_3$, NH], [97: H, CH$_2$C=CH, NH], [98: F, CH$_2$C=CH, NH], [99: Cl, CH$_2$C=CH, NH], [100: Br, CH$_2$C=CH, NH], [101: CH$_3$, CH$_2$C=CH, NH], [102: CN, CH$_2$C=CH, NH], [103: J1, CH$_2$C=CH, NH], [104: J2, CH$_2$C=CH, NH], [105: J3, CH$_2$C=CH, NH], [106: J4, CH$_2$C=CH, NH], [107: J5, CH$_2$C=CH, NH], [108: J6, CH$_2$C=CH, NH], [109: J7, CH$_2$C=CH, NH], [110: J8, CH$_2$C=CH, NH], [1111: J9, CH$_2$C=CH, NH], [112: J10, CH$_2$C=CH, NH], [113: H, OCH$_2$C=CH, NH], [114: F, OCH$_2$C=CH, NH], [115: Cl, OCH$_2$C=CH, NH], [116: Br, OCH$_2$C=CH, NH], [117: CH$_3$, OCH$_2$C=CH, NH][118: CN, OCH$_2$C=CH, NH], [119: J1, OCH$_2$C=CH, NH], [120: J2, OCH$_2$C=CH, NH], [121: J3, OCH$_2$C=CH, NH], [112: J4, OCH$_2$C=CH, NH], [123: J5, OCH$_2$C=CH, NH], [124: J6, OCH$_2$C=CH, NH], [125: J7, OCH$_2$C=CH, NH], [128: J8, OCH$_2$C=CH, NH], [127: J9, OCH$_2$C=CH, NH], [128: J10, OCH$_2$C=CH, NH], [129: H, Cl, NH], [130: F, Cl, NH], [131: Cl, Cl, NH], [132: Br, Cl, NH], [133: CH$_3$, Cl, NH], [134: CN, Cl, NH], [135: J1, Cl, NH], [136: J2, Cl, NH], [137: J3, Cl, NH], [138: J4, Cl, NH], [139: J5, Cl, NH], [140: J6, Cl, NH], [141: J7, Cl, NH], [142: J8, Cl, NH], [143: J9, Cl, NH], [144: J10, Cl, NH], [145:

H, CN, NH], [146: F, CN, NH], [147: Cl, CN, NH], [148: Br, CN, NH], [149: CH$_3$, CN, NH], [150: CN, CN, NH], [151: J1, CN, NH], [152: J2, CN, NH], [153: J3, CN, NH], [154: J4, CN, NH], [155: J5, CN, NH], [156: J6, CN, NH], [157: J7, CN, NH], [158: J8, CN, NH], [159: J9, CN, NH], [160: J10, CN, NH], [161: H, C≡CH, NH], [162: F, C≡CH, NH], [163: Cl, C≡CH, NH], [164: Br, C≡CH, NH], [165: CH$_3$, C≡CH, NH], [166: CN, C≡CH, NH], [167: J1, C≡CH, NH], [168: J2, C≡CH, NH], [169: J3, C≡CH, NH], [170: J4, C≡CH, NH], [171: J5, C≡CH, NH], [172: J6, C≡CH, NH], [173: J7, C≡CH, NH], [174: J8, C≡CH, NH], [175: J9, C≡CH, NH], [176: J10, C≡CH, NH], [177: H, C(CH$_3$)$_3$, NCH$_3$], [178: F, C(CH$_3$)$_3$, NCH$_3$], [179: Cl, C(CH$_3$)$_3$, NCH$_3$], [180: Br, C(CH$_3$)$_3$, NCH$_3$], [181: CH$_3$, C(CH$_3$)$_3$, NCH$_3$], [182: CN, C(CH$_3$)$_3$, NCH$_3$], [183: J1, C(CH$_3$)$_3$, NCH$_3$], [184: J2, C(CH$_3$)$_3$, NCH$_3$], [185: J3, C(CH$_3$)$_3$, NCH$_3$], [186: J4, C(CH$_3$)$_3$, NCH$_3$], [187: J5, C(CH$_3$)$_3$, NCH$_3$], [188: J6, C(CH$_3$)$_3$, NCH$_3$], [189: J7, C(CH$_3$)$_3$, NCH$_3$], [190: J8, C(CH$_3$)$_3$, NCH$_3$], [191: J9, C(CH$_3$)$_3$, NCH$_3$], [192: J10, C(CH$_3$)$_3$, NCH$_3$], [193: H, CF$_3$, NCH$_3$], [194: F, CF$_3$, NCH$_3$], [195: Cl, CF$_3$, NCH$_3$], [196: Br, CF$_3$, NCH$_3$], [197: CH$_3$, CF$_3$, NCH$_3$], [198: CN, CF$_3$, NCH$_3$], [199: J1, CF$_3$, NCH$_3$], [200: J2, CF$_3$, NCH$_3$], [201: J3, CF$_3$, NCH$_3$], [202: J4, CF$_3$, NCH$_3$], [203: J5, CF$_3$, NCH$_3$], [204: J6, CF$_3$, NCH$_3$], [205: J7, CF$_3$, NCH$_3$], [206: J8, CF$_3$, NCH$_3$], [207: J9, CF$_3$, NCH$_3$], [208: J10, CF$_3$, NCH$_3$], [209: H, CF$_2$CF$_3$, NCH$_3$], [210: F, CF$_2$CF$_3$, NCH$_3$], [211: Cl, CF$_2$CF$_3$, NCH$_3$], [212: Br, CF$_2$CF$_3$, NCH$_3$], [213: CH$_3$, CF$_2$CF$_3$, NCH$_3$], [214: CN, CF$_2$CF$_3$, NCH$_3$], [215: J1, CF$_2$CF$_3$, NCH$_3$], [216: J2, CF$_2$CF$_3$, NCH$_3$], [217: J3, CF$_2$CF$_3$, NCH$_3$], [218: J4, CF$_2$CF$_3$, NCH$_3$], [219: J5, CF$_2$CF$_3$, NCH$_3$], [220: J6, CF$_2$CF$_3$, NCH$_3$], [221: J7, CF$_2$CF$_3$, NCH$_3$], [222: J8, CF$_2$CF$_3$, NCH$_3$], [223: J9, CF$_2$CF$_3$, NCH$_3$], [224: J10, CF$_2$CF$_3$, NCH$_3$], [225: H, SCF$_3$, NCH$_3$], [226: F, SCF$_3$, NCH$_3$], [227: Cl, SCF$_3$, NCH$_3$], [228: Br, SCF$_3$, NCH$_3$], [229: CH$_3$, SCF$_3$, NCH$_3$], [230: CN, SCF$_3$, NCH$_3$], [231: J1, SCF$_3$, NCH$_3$], [232: J2, SCF$_3$, NCH$_3$], [233: J3, SCF$_3$, NCH$_3$], [234: J4, SCF$_3$, NCH$_3$], [235: J5, SCF$_3$, NCH$_3$], [236: J6, SCF$_3$, NCH$_3$], [237: J7, SCF$_3$, NCH$_3$], [238: J8, SCF$_3$, NCH$_3$], [239: J9, SCF$_3$, NCH$_3$], [240: J10, SCF$_3$, NCH$_3$], [241: H, SOCF$_3$, NCH$_3$], [242: F, SOCF$_3$, NCH$_3$], [243: Cl, SOCF$_3$, NCH$_3$], [244: Br, SOCF$_3$, NCH$_3$], [245: CH$_3$, SOCF$_3$, NCH$_3$], [246: CN, SOCF$_3$, NCH$_3$], [247: J1, SOCF$_3$, NCH$_3$], [248: J2, SOCF$_3$, NCH$_3$], [249: J3, SOCF$_3$, NCH$_3$], [250: J4, SOCF$_3$, NCH$_3$], [251: J5, SOCF$_3$, NCH$_3$], [252: J6, SOCF$_3$, NCH$_3$], [253: J7, SOCF$_3$, NCH$_3$], [254: J8, SOCF$_3$, NCH$_3$], [255: J9, SOCF$_3$, NCH$_3$], [256: J10, SOCF$_3$, NCH$_3$], [257: H, SO$_2$CF$_3$, NCH$_3$], [258: F, SO$_2$CF$_3$, NCH$_3$], [259: Cl, SO$_2$CF$_3$, NCH$_3$], [260: Br, SO$_2$CF$_3$, NCH$_3$], [261: CH$_3$, SO$_2$CF$_3$, NCH$_3$], [262: CN, SO$_2$CF$_3$, NCH$_3$], [263: J1, SO$_2$CF$_3$, NCH$_3$], [264: J2, SO$_2$CF$_3$, NCH$_3$], [265: J3, SO$_2$CF$_3$, NCH$_3$], [266: J4, SO$_2$CF$_3$, NCH$_3$], [267: J5, SO$_2$CF$_3$, NCH$_3$], [268: J6, SO$_2$CF$_3$, NCH$_3$], [269: J7, SO$_2$CF$_3$, NCH$_3$], [270: J8, SO$_2$CF$_3$, NCH$_3$], [271: J9, SO$_2$CF$_3$, NCH$_3$], [272: J10, SO$_2$CF$_3$, NCH$_3$], [273: H, CH$_2$C≡CH, NCH$_3$], [274: F, CH$_2$C≡CH, NCH$_3$], [275: Cl, CH$_2$C≡CH, NCH$_3$], [276: Br, CH$_2$C≡CH, NCH$_3$], [277: CH$_3$, CH$_2$C≡CH, NCH$_3$], [278: CN, CH$_2$C≡CH, NCH$_3$], [279: J1, CH$_2$C≡CH, NCH$_3$], [280: J2, CH$_2$C≡CH, NCH$_3$], [281: J3, CH$_2$C≡CH, NCH$_3$], [282: J4, CH$_2$C≡CH, NCH$_3$], [283: J5, CH$_2$C≡CH, NCH$_3$], [284: J6, CH$_2$C≡CH, NCH$_3$], [285: J7, CH$_2$C≡CH, NCH$_3$], [286: J8, CH$_2$C≡CH, NCH$_3$], [287: J9, CH$_2$C≡CH, NCH$_3$], [288: J10, CH$_2$C≡CH, NCH$_3$], [289: H, OCH$_2$C≡CH, NCH$_3$], [290: F, OCH$_2$C≡CH, NCH$_3$], [291: Cl, OCH$_2$C≡CH, NCH$_3$], [292: Br, OCH$_2$C≡CH, NCH$_3$], [293: CH$_3$, OCH$_2$C≡CH, NCH$_3$], [294: CN, NCH$_3$], [295: J1, OCH$_2$C≡CH, NCH$_3$], [296: J2, OCH$_2$C≡CH, NCH$_3$], [297: J3, OCH$_2$C≡CH, NCH$_3$], [298: J4, OCH$_2$C≡CH, NCH$_3$], [299: J5, OCH$_2$C≡CH, NCH$_3$], [300: J6, OCH$_2$C≡CH, NCH$_3$], [301: J7, OCH$_2$C≡CH, NCH$_3$], [302: J8, OCH$_2$C≡CH, NCH$_3$], [303: J9, OCH$_2$C≡CH, NCH$_3$], [304: J10, OCH$_2$C≡CH, NCH$_3$], [305: H, Cl, NCH$_3$], [306: F, Cl, NCH$_3$], [307: Cl, Cl, NCH$_3$], [308: Br, Cl, NCH$_3$], [309: CH$_3$, Cl, NCH$_3$], [310: CN, Cl, NCH$_3$], [311: J1, Cl, NCH$_3$], [312: J2, Cl, NCH$_3$], [313: J3, Cl, NCH$_3$], [314: J4, Cl, NCH$_3$], [315: J5, Cl, NCH$_3$], [316: J6, Cl, NCH$_3$], [317: J7, Cl, NCH$_3$], [318: J8, Cl, NCH$_3$], [319: J9, Cl, NCH$_3$], [320: J10, Cl, NCH$_3$], [321: H, CN, NCH$_3$], [322: F, CN, NCH$_3$], [323: Cl, CN, NCH$_3$], [324: Br, CN, NCH$_3$], [325: CH$_3$, CN, NCH$_3$], [326: CN, CN, NCH$_3$], [327: J1, CN, NCH$_3$], [328: J2, CN, NCH$_3$], [329: J3, CN, NCH$_3$], [330: J4, CN, NCH$_3$], [331: J5, CN, NCH$_3$], [332: J6, CN, NCH$_3$], [333: J7, CN, NCH$_3$], [334: J8, CN, NCH$_3$], [335: J9, CN, NCH$_3$], [336: J10, CN, NCH$_3$], [337: H, C≡CH, NCH$_3$], [338: F, C≡CH, NCH$_3$], [339: Cl, C≡CH, NCH$_3$], [340: Br, C≡CH, NCH$_3$], [341: CH$_3$, C≡CH, NCH$_3$], [342: CN, C≡CH, NCH$_3$], [343: J1, C≡CH, NCH$_3$], [344: J2, C≡CH, NCH$_3$], [345: J3, C≡CH, NCH$_3$], [346: J4, C≡CH, NCH$_3$], [347: J5, C≡CH, NCH$_3$], [348: J6, C≡CH, NCH$_3$], [349: J7, C≡CH, NCH$_3$], [350: J8, C≡CH, NCH$_3$], [351: J9, C≡CH, NCH$_3$], [352: J10, C≡CH, NCH$_3$], [353: H, C(CH$_3$)$_3$, S], [354: F, C(CH$_3$)$_3$, S][355: Cl, C(CH$_3$)$_3$, S], [356: Br, C(CH$_3$)$_3$, S], [357: CH$_3$, C(CH$_3$)$_3$, S], [358: CN, C(CH$_3$)$_3$, S], [359: J1, C(CH$_3$)$_3$, S], [360: J2, C(CH$_3$)$_3$, S], [361: J3, C(CH$_3$)$_3$, S], [362: J4, C(CH$_3$)$_3$, S], [363: J5, C(CH$_3$)$_3$, S], [364: J6, C(CH$_3$)$_3$, S], [365: J7, C(CH$_3$)$_3$, S], [366: J8, C(CH$_3$)$_3$, S], [367: J9, C(CH$_3$)$_3$, S], [368: J10, C(CH$_3$)$_3$, S], [369: H, CF$_3$, S], [370: F, CF$_3$, S], [371: Cl, CF$_3$, S], [372: Br, CF$_3$, S], [373: CH$_3$, CF$_3$, S], [374: CN, CF$_3$, S], [375: J1, CF$_3$, S], [376: J2, CF$_3$, S], [377: J3, CF$_3$, S], [378: J4, CF$_3$, S], [379: J5, CF$_3$, S], [380: J6, CF$_3$, S], [381: J7, CF$_3$, S], [382: J8, CF$_3$, S], [383: J9, CF$_3$, S], [384: J10, CF$_3$, S][385: H, CF$_2$CF$_3$, S], [386: F, CF$_2$CF$_3$, S], [387: Cl, CF$_2$CF$_3$, S], [388: Br, CF$_2$CF$_3$, S], [389: CH$_3$, CF$_2$CF$_3$, S], [390: CN, CF$_2$CF$_3$, S], [391: J1, CF$_2$CF$_3$, S], [392: J2, CF$_2$CF$_3$, S], [393: J3, CF$_2$CF$_3$, S], [394: J4, CF$_2$CF$_3$, S], [395: J5, CF$_2$CF$_3$, S], [396: J6, CF$_2$CF$_3$, S], [397: J7, CF$_2$CF$_3$, S], [398: J8, CF$_2$CF$_3$, S], [399: J9, CF$_2$CF$_3$, S][400: J10, CF$_2$CF$_3$, S], [401: H, SCF$_3$, S], [402: F, SCF$_3$, S], [403: Cl, SCF$_3$, S], [404: Br, SCF$_3$, S], [405: CH$_3$, SCF$_3$, S], [406: CN, SCF$_3$, S], [407: J1, SCF$_3$, S], [408: J2, SCF$_3$, S], [409: J3, SCF$_3$, S], [410: J4, SCF$_3$, S], [411: J5, SCF$_3$, S], [412: J6, SCF$_3$, S], [413: J7, SCF$_3$, S], [414: J8, SCF$_3$, S], [415: J9, SCF$_3$, S], [416: J10, SCF$_3$, S], [417: H, SOCF$_3$, S][418: F, SOCF$_3$, S], [419: Cl, SOCF$_3$, S], [420: Br, SOCF$_3$, S], [421: CH$_3$, SOCF$_3$, S], [422: CN, SOCF$_3$, S], [423: J1, SOCF$_3$, S], [424: J2, SOCF$_3$, S], [425: J3, SOCF$_3$, S], [426: J4, SOCF$_3$, S], [427: J5, SOCF$_3$, S], [428: J6, SOCF$_3$, S], [429: J7, SOCF$_3$, S], [430: J8, SOCF$_3$, S], [431: J9, SOCF$_3$, S], [432: J10, SOCF$_3$, S], [433: H, SO$_2$CF$_3$, S], [434: F, SO$_2$CF$_3$, S], [435: Cl, SO$_2$CF$_3$, S][436: Br, SO$_2$CF$_3$, S], [437: CH$_3$, SO$_2$CF$_3$, S], [438: CN, SO$_2$CF$_3$, S][439: J1, SO$_2$CF$_3$, S], [440: J2, SO$_2$CF$_3$, S], [441: J3, SO$_2$CF$_3$, S][442: J4, SO$_2$CF$_3$, S], [443: J5, SO$_2$CF$_3$, S], [444: J6, SO$_2$CF$_3$, S][445: J7, SO$_2$CF$_3$, S], [446: J8, SO$_2$CF$_3$, S], [447: J9, SO$_2$CF$_3$, S], [448: J10, SO$_2$CF$_3$, S], [449: H, CH$_2$C≡CH, S], [450: F, CH$_2$C≡CH, S][451: Cl, CH$_2$C≡CH, S], [452: Br, CH$_2$C≡CH, S], [453: CH$_3$, CH$_2$C≡CH, S][454: CN, CH$_2$C≡CH, S], [455: J1, CH$_2$C≡CH, S], [456: J2, CH$_2$C≡CH, S], [457: J3, CH$_2$C≡CH, S], [458: J4, CH$_2$C≡CH, S], [459: J5, CH$_2$C≡CH, S], [460: J6, CH$_2$C≡CH, S], [461: J7, CH$_2$C≡CH, S], [462: J8, CH$_2$C≡CH, S], [463: J9, CH$_2$C≡CH, S], [464: J10, CH$_2$C≡CH, S], [465: H, OCH$_2$C≡CH, S], [466: F,

OCH₂C≡CH, S], [467: Cl, OCH₂C≡CH, S], [468: Br, OCH₂C≡CH, S], [469: CH₃, OCH₂C≡CH, S], [470: CN, OCH₂C≡CH, S], [471: J1, OCH₂C≡CH, S], [472: J2, OCH₂C≡CH, S], [473: J3, OCH₂C≡CH, S], [474: J4, OCH₂C≡CH, S], [475: J5, OCH₂C≡CH, S], [476: J6, OCH₂C≡CH, S], [477: J7, OCH₂C≡CH, S], [478: J8, OCH₂C≡CH, S], [479: J9, OCH₂C≡CH, S], [480: J10, OCH₂C≡CH, S], [481: H, Cl, S], [482: F, Cl, S], [483: Cl, Cl, S], [484: Br, Cl, S], [485: CH₃, Cl, S], [486: CN, Cl, S], [487: J1, Cl, S], [488: J2, Cl, S], [489: J3, Cl, S], [490: J4, Cl, S], [491: J5, Cl, S], [492: J6, Cl, S], [493: J7, Cl, S], [494: J8, Cl, S], [495: J9, Cl, S], [496: J10, Cl, S], [497: H, CN, S], [498: F, CN, S], [499: Cl, CN, S], [500: Br, CN, S], [501: CH₃, CN, S], [502: CN, CN, S], [503: J1, CN, S], [504: J2, CN, S], [505: J3, CN, S], [506: J4, CN, S], [507: J5, CN, S], [508: J6, CN, S], [509: J7, CN, S], [510: J8, CN, S], [511: J9, CN, S], [512: J10, CN, S], [513: H, C≡CH, S], [514: F, C≡CH, S], [515: Cl, C≡CH, S], [516: Br, C≡CH, S], [517: CH₃, C≡CH, S], [518: CN, C≡CH, S], [519: J1, C≡CH, S], [520: J2, C≡CH, S], [521: J3, C≡CH, S], [522: J4, C≡CH, S], [523: J5, C≡CH, S], [524: J6, C≡CH, S], [525: J7, C≡CH, S], [526: J8, C≡CH, S], [527: J9, C≡CH, S], [528: J10, C≡CH, S], [529: H, C(CH₃)₃, O], [530: F, C(CH₃)₃, O], [531: Cl, C(CH₃)₃, O], [532: Br, C(CH₃)₃, O], [533: CH₃, C(CH₃)₃, O], [534: CN, C(CH₃)₃, O], [535: J1, C(CH₃)₃, O], [536: J2, C(CH₃)₃, O], [537: J3, C(CH₃)₃, O], [538: J4, C(CH₃)₃, O], [539: J5, C(CH₃)₃, O], [540: J6, C(CH₃)₃, O], [541: J7, C(CH₃)₃, O], [542: J8, C(CH₃)₃, O], [543: J9, C(CH₃)₃, O], [544: J10, C(CH₃)₃, O], [545: H, CF₃, O], [546: F, CF₃, O], [547: Cl, CF₃, O], [548: Br, CF₃, O], [549: CH₃, CF₃, O], [550: CN, CF₃, O], [551: J1, CF₃, O], [552: J2, CF₃, O], [553: J3, CF₃, O], [554: J4, CF₃, O], [555: J5, CF₃, O], [556: J6, CF₃, O], [557: J7, CF₃, O], [558: J8, CF₃, O], [559: J9, CF₃, O], [560: J10, CF₃, O], [561: H, CF₂CF₃, O], [562: F, CF₂CF₃, O], [563: Cl, CF₂CF₃, O], [564: Br, CF₂CF₃, O], [565: CH₃, CF₂CF₃, O], [566: CN, CF₂CF₃, O], [567: J1, CF₂CF₃, O], [568: J2, CF₂CF₃, O], [569: J3, CF₂CF₃, O], [570: J4, CF₂CF₃, O], [571: J5, CF₂CF₃, O], [572: J6, CF₂CF₃, O], [573: J7, CF₂CF₃, O], [574: J8, CF₂CF₃, O], [575: J9, CF₂CF₃, O], [576: J10, CF₂CF₃, O], [577: H, SCF₃, O], [578: F, SCF₃, O], [579: Cl, SCF₃, O], [580: Br, SCF₃, O], [581: CH₃, SCF₃, O], [582: CN, SCF₃, O], [583: J1, SCF₃, O], [584: J2, SCF₃, O], [585: J3, SCF₃, O], [586: J4, SCF₃, O], [587: J5, SCF₃, O], [588: J6, SCF₃, O], [589: J7, SCF₃, O], [590: J8, SCF₃, O], [591: J9, SCF₃, O], [592: J10, SCF₃, O], [593: H, SOCF₃, O], [594: F, SOCF₃, O], [595: Cl, SOCF₃, O], [596: Br, SOCF₃, O], [597: CH₃, SOCF₃, O], [598: CN, SOCF₃, O], [599: J1, SOCF₃, O], [600: J2, SOCF₃, O], [601: J3, SOCF₃, O], [602: J4, SOCF₃, O], [603: J5, SOCF₃, O], [604: J6, SOCF₃, O], [605: J7, SOCF₃, O], [606: J8, SOCF₃, O], [607: J9, SOCF₃, O], [608: J10, SOCF₃, O], [609: H, SO2CF₃, O], [610: F, SO2CF₃, O], [611: Cl, SO2CF₃, O], [612: Br, SO2CF₃, O], [613: CH₃, SO2CF₃, O], [614: CN, SO2CF₃, O], [615: J1, SO2CF₃, O], [616: J2, SO2CF₃, O], [617: J3, SO2CF₃, O], [618: J4, SO2CF₃, O], [619: J5, SO2CF₃, O], [620: J6, SO2CF₃, O], [621: J7, SO2CF₃, O], [622: J8, SO2CF₃, O], [623: J9, SO2CF₃, O], [624: J10, SO2CF₃, O], [625: H, CH₂C≡CH, O], [626: F, CH₂C≡CH, O], [627: Cl, CH₂C≡CH, O], [628: Br, CH₂C≡CH, O], [629: CH₃, CH₂C≡CH, O], [630: CN, CH₂C≡CH, O], [631: J1, CH₂C≡CH, O], [632: J2, CH₂C≡CH, O], [633: J3, CH₂C≡CH, O], [634: J4, CH₂C≡CH, O], [635: J5, CH₂C≡CH, O], [636: J6, CH₂C≡CH, O], [637: J7, CH₂C≡CH, O], [638: J8, CH₂C≡CH, O], [639: J9, CH₂C≡CH, O], [640: J10, CH₂C≡CH, O], [641: H, OCH₂C≡CH, O], [642: F, OCH₂C≡CH, O], [643: Cl, OCH₂C≡CH, O], [644: Br, OCH₂C≡CH, O], [645: CH₃, OCH₂C≡CH, O], [646: CN, OCH₂C≡CH, O], [647: J1, OCH₂C≡CH, O], [648: J2, OCH₂C≡CH, O], [649: J3, OCH₂C≡CH, O], [650: J4, OCH₂C≡CH, O], [651: J5, OCH₂C≡CH, O], [652: J6, OCH₂C≡CH, O], [653: J7, OCH₂C≡CH, O], [654: J8, OCH₂C≡CH, O], [655: J9, OCH₂C≡CH, O], [656: J10, OCH₂C≡CH, O], [657: H, Cl, O], [658: F, Cl, O], [659: Cl, Cl, O], [660: Br, Cl, O], [661: CH₃, Cl, O], [662: CN, Cl, O], [663: J1, Cl, O], [664: J2, Cl, O], [665: J3, Cl, O], [666: J4, Cl, O], [667: J5, Cl, O], [668: J6, Cl, O], [669: J7, Cl, O], [670: J8, Cl, O], [671: J9, Cl, O], [672: J10, Cl, O], [673: H, CN, O], [674: F, CN, O], [675: Cl, CN, O], [676: Br, CN, O], [677: CH₃, CN, O], [678: CN, CN, O], [679: J1, CN, O], [680: J2, CN, O], [681: J3, CN, O], [682: J4, CN, O], [683: J5, CN, O], [684: J6, CN, O], [685: J7, CN, O], [686: J8, CN, O], [687: J9, CN, O], [688: J10, CN, O], [689: H, C≡CH, O], [690: F, C≡CH, O], [691: Cl, C≡CH, O], [692: Br, C≡CH, O], [693: CH₃, C≡CH, O], [694: CN, C≡CH, O], [695: J1, C≡CH, O], [696: J2, C≡CH, O], [697: J3, C≡CH, O], [698: J4, C≡CH, O], [699: J5, C≡CH, O], [700: J6, C≡CH, O], [701: J7, C≡CH, O], [702: J8, C≡CH, O], [703: J9, C≡CH, O], [704: J10, C≡CH, O].

A compound represented by the formula ($I^{29}$):

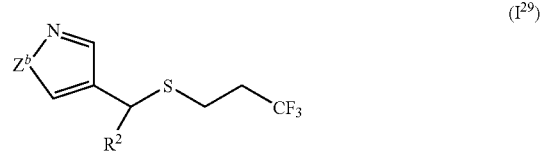

wherein $R^2$ and $Z^b$ represent any one of combinations shown below.

A compound represented by the formula ($I^{30}$):

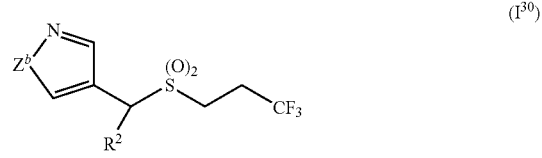

wherein $R^2$ and $Z^b$ represent any one of combinations shown below.

A compound represented by the formula ($I^{31}$):

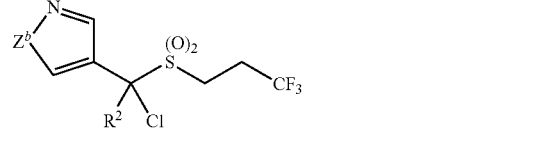

wherein $R^2$ and $Z^b$ represent any one of combinations shown below.

A compound represented by the formula ($I^{32}$):

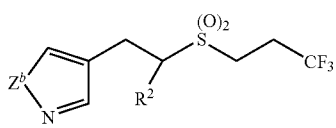

($I^{32}$)

wherein $R^2$ and $Z^b$ represent any one of combinations shown below.

A compound represented by the formula ($I^{33}$):

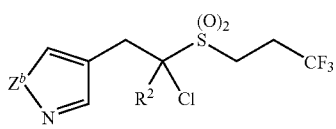

($I^{33}$)

wherein $R^2$ and $Z^b$ represent any one of combinations shown below.

A compound represented by the formula ($I^{34}$):

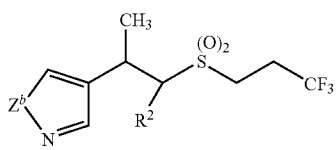

($I^{34}$)

wherein $R^2$ and $Z^b$ represent any one of combinations shown below.

A compound represented by the formula ($I^{35}$):

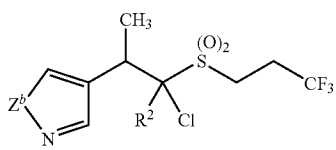

($I^{35}$)

wherein $R^2$ and $Z^b$ represent any one of combinations shown below.

Combinations of $R^2$ and $Z^b$ for the compounds represented by the formulas ($I^{29}$) to ($I^{35}$) are shown below. In brackets, a combination number, a group represented by $R^2$ and a group represented by $Z^b$ are shown in this order. Herein, symbols J1 to J10 are as defined above. [Combination number: $R^2$, $Z^b$]= [1: H, NC(CH$_3$)$_3$], [2: F, NC(CH$_3$)$_3$], [3: Cl, NC(CH$_3$)$_3$], [4: Br, NC(CH$_3$)$_3$], [5: CH$_3$, NC(CH$_3$)$_3$], [6: CN, NC(CH$_3$)$_3$], [7: J1, NC(CH$_3$)$_3$], [8: J2, NC(CH$_3$)$_3$], [9: J3, NC(CH$_3$)$_3$], [10: J4, NC(CH$_3$)$_3$], [11: J5, NC(CH$_3$)$_3$], [12: J6, NC(CH$_3$)$_3$], [13: J7, NC(CH$_3$)$_3$], [14: J8, NC(CH$_3$)$_3$], [15: J9, NC(CH$_3$)$_3$], [16: J10, NC(CH$_3$)$_3$], [17: H, NCH$_2$CF$_3$], [18: F, NCH$_2$CF$_3$], [19: Cl, NCH$_2$CF$_3$], [20: Br, NCH$_2$CF$_3$], [21: CH$_3$, NCH$_2$CF$_3$], [22: CN, NCH$_2$CF$_3$], [23: J1, NCH$_2$CF$_3$], [24: J2, NCH$_2$CF$_3$], [25: J3, NCH$_2$CF$_3$], [26: J4, NCH$_2$CF$_3$], [27: J5, NCH$_2$CF$_3$], [28: J6, NCH$_2$CF$_3$], [29: J7, NCH$_2$CF$_3$], [30: J8, NCH$_2$CF$_3$], [31: J9, NCH$_2$CF$_3$], [32: J10, NCH$_2$CF$_3$], [33: H, NCH$_2$C≡CH], [34: F, NCH$_2$C≡CH], [35: Cl, NCH$_2$C≡CH], [36: Br, NCH$_2$C≡CH], [37: CH$_3$, NCH$_2$C≡CH], [38: CN, NCH$_2$C≡CH], [39: J1, NCH$_2$C≡CH], [40: J2, NCH$_2$C≡CH], [41: J3, NCH$_2$C≡CH], [42: J4, NCH$_2$C≡CH], [43: J5, NCH$_2$C≡CH], [44: NCH$_2$C≡CH], [45: J7, NCH$_2$C≡CH], [46: J8, NCH$_2$C≡CH], [47: J9, NCH$_2$C≡CH], [48: J10, NCH$_2$C≡CH].

A compound represented by the formula ($I^{36}$):

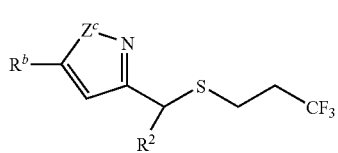

($I^{36}$)

wherein $R^2$, $R^b$ and $Z^c$ represent any one of combinations shown below.

A compound represented by the formula ($I^{37}$):

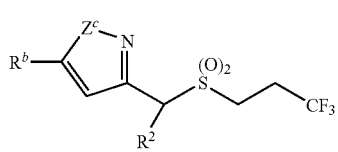

($I^{37}$)

wherein $R^2$, $R^b$ and $Z^c$ represent any one of combinations shown below.

A compound represented by the formula ($I^{38}$):

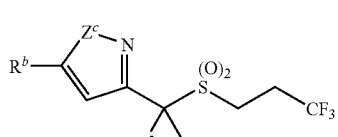

($I^{38}$)

wherein $R^2$, $R^b$ and $Z^c$ represent any one of combinations shown below.

A compound represented by the formula ($I^{39}$):

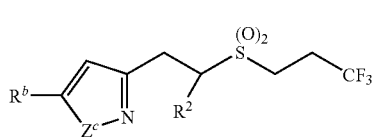

($I^{39}$)

wherein $R^2$, $R^b$ and $Z^c$ represent any one of combinations shown below.

A compound represented by the formula ($I^{40}$):

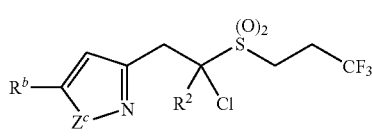

($I^{40}$)

wherein $R^2$, $R^b$ and $Z^c$ represent any one of combinations shown below.

51

A compound represented by the formula (I⁴¹):

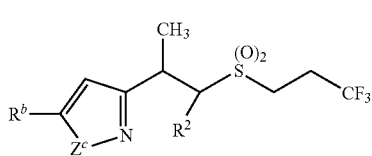
(I⁴¹)

wherein R², Rᵇ and Zᶜ represent any one of combinations shown below.

A compound represented by the formula (I⁴²):

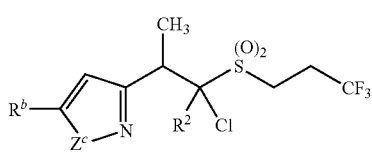
(I⁴²)

wherein R², Rᵇ and Zᶜ represent any one of combinations shown below.

A compound represented by the formula (I⁴³):

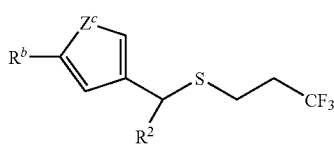
(I⁴³)

wherein R², Rᵇ, and Zᶜ represent any one of combinations shown below.

A compound represented by the formula (I⁴⁴):

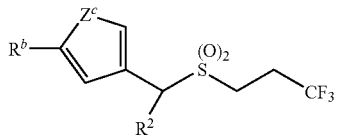
(I⁴⁴)

wherein R², Rᵇ and Zᶜ represent any one of combinations shown below.

A compound represented by the formula (I⁴⁵):

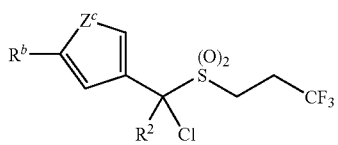
(I⁴⁵)

wherein R², Rᵇ and Zᶜ represent any one of combinations shown below.

52

A compound represented by the formula (I⁴⁶):

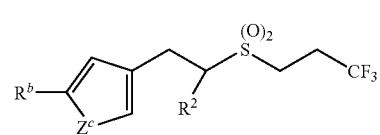
(I⁴⁶)

wherein R², Rᵇ and Zᶜ represent any one of combinations shown below.

A compound represented by the formula (I⁴⁷):

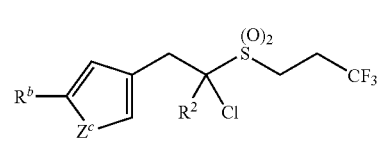
(I⁴⁷)

wherein R², Rᵇ and Zᶜ represent any one of combinations shown below.

A compound represented by the formula (I⁴⁸):

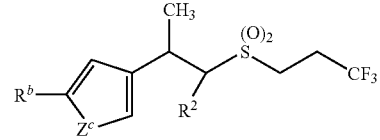
(I⁴⁸)

wherein R², Rᵇ and Zᶜ represent any one of combinations shown below.

A compound represented by the formula (I⁴⁹):

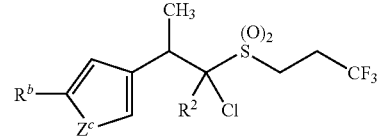
(I⁴⁹)

wherein R², Rᵇ and Zᶜ represent any one of combinations shown below.

A compound represented by the formula (I⁵⁰):

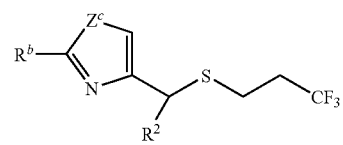
(I⁵⁰)

wherein R², Rᵇ and Zᶜ represent any one of combinations shown below.

53

A compound represented by the formula (I$^{51}$):

(I$^{51}$)

wherein R$^2$, R$^b$ and Z$^c$ represent any one of combinations shown below.

A compound represented by the formula (I$^{52}$):

(I$^{52}$)

wherein R$^2$, R$^b$ and Z$^c$ represent any one of combinations shown below.

A compound represented by the formula (I$^{53}$):

(I$^{53}$)

wherein R$^2$, R$^b$ and Z$^c$ represent any one of combinations shown below.

A compound represented by the formula (I$^{54}$):

(I$^{54}$)

wherein R$^2$, R$^b$ and Z$^c$ represent any one of combinations shown below.

A compound represented by the formula (I$^{55}$):

(I$^{55}$)

wherein R$^2$, R$^b$ and Z$^c$ represent any one of combinations shown below.

54

A compound represented by the formula (I$^{56}$):

(I$^{56}$)

wherein R$^2$, R$^b$ and Z$^c$ represent any one of combinations shown below.

A compound represented by the formula (I$^{57}$):

(I$^{57}$)

wherein R$^2$, R$^b$ and Z$^c$ represent any one of combinations shown below.

A compound represented by the formula (I$^{58}$):

(I$^{58}$)

wherein R$^2$, R$^b$ and Z$^c$ represent any one of combinations shown below.

A compound represented by the formula (I$^{59}$):

(I$^{59}$)

wherein R$^2$, R$^b$ and Z$^c$ represent any one of combinations shown below.

A compound represented by the formula (I$^{60}$):

(I$^{60}$)

wherein R$^2$, R$^b$ and Z$^c$ represent any one of combinations shown below.

A compound represented by the formula (I⁶¹):

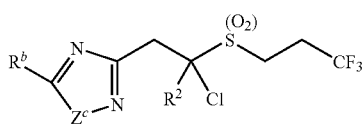

wherein R², R^b and Z^c represent any one of combinations shown below.

A compound represented by the formula (I⁶²):

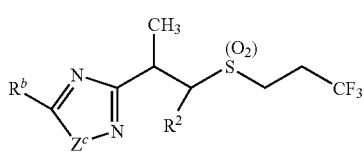

wherein R², R^b and Z^c represent any one of combinations shown below.

A compound represented by the formula (I⁶³):

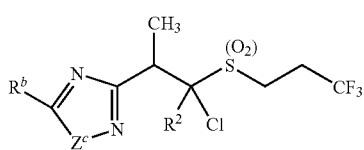

wherein R², R^b and Z^c represent any one of combinations shown below.

Combinations of R², R^b and Z^c for the compounds represented by the formulas (I³⁶) to (I⁶³) are shown below. In brackets, a combination number, a group represented by R², a group represented by R^b, and a group represented by Z^c are shown in this order. Herein, symbols J1 to J10 are as defined above. [Combination number: R², R^b, Z^c]=[1: H, C(CH₃)₃, NH], [2: F, C(CH₃)₃, NH], [3: Cl, C(CH₃)₃, NH], [4: Br, C(CH₃)₃, NH], [5: CH₃, C(CH₃)₃, NH], [6: CN, C(CH₃)₃, NH], [7: J1, C(CH₃)₃, NH], [8: J2, C(CH₃)₃, NH], [9: J3, C(CH₃)₃, NH], [10: J4, C(CH₃)₃, NH], [11: J5, C(CH₃)₃, NH], [12: J6, C(CH₃)₃, NH], [13: J7, C(CH₃)₃, NH], [14: J8, C(CH₃)₃, NH], [15: J9, C(CH₃)₃, NH], [16: J10, C(CH₃)₃, NH], [17: H, CF₃, NH], [18: F, CF₃, NH], [19: Cl, CF₃, NH], [20: Br, CF₃, NH], [21: CH₃, CF₃, NH], [22: CN, CF₃, NH], [23: J1, CF₃, NH], [24: J2, CF₃, NH], [25: J3, CF₃, NH], [26: J4, CF₃, NH], [27: J5, CF₃, NH], [28: J6, CF₃, NH], [29: J7, CF₃, NH], [30: J8, CF₃, NH], [31: J9, CF₃, NH], [32: J10, CF₃, NH], [33: H, CF₂CF₃, NH], [34: F, CF₂CF₃, NH], [35: Cl, CF₂CF₃, NH], [36: Br, CF₂CF₃, NH], [37: CH₃, CF₂CF₃, NH], [38: CN, CF₂CF₃, NH], [39: J1, CF₂CF₃, NH], [40: J2, CF₂CF₃, NH], [41: J3, CF₂CF₃, NH], [42: J4, CF₂CF₃, NH], [43: J5, CF₂CF₃, NH], [44: J6, CF₂CF₃, NH], [45: J7, CF₂CF₃, NH], [46: J8, CF₂CF₃, NH], [47: J9, CF₂CF₃, NH], [48: J10, CF₂CF₃, NH][49: H, SCF₃, NH], [50: F, SCF₃, NH], [51: Cl, SCF₃, NH], [52: Br, SCF₃, NH], [53: CH₃, SCF₃, NH], [54: CN, SCF₃, NH], [55: J1, SCF₃, NH], [56: J2, SCF₃, NH], [57: J3, SCF₃, NH], [58: J4, SCF₃, NH], [59: J5, SCF₃, NH], [60: J6, SCF₃, NH], [61: J7, SCF₃, NH], [62: J8, SCF₃, NH], [63: J9, SCF₃, NH], [64: J10, SCF₃, NH], [65: H, SOCF₃, NH], [66: F, SOCF₃, NH], [67: Cl, SOCF₃, NH], [68: Br, SOCF₃, NH], [69: CH₃, SOCF₃, NH], [70: CN, SOCF₃, NH], [71: J1, SOCF₃, NH], [72: J2, SOCF₃, NH], [73: J3, SOCF₃, NH], [74: J4, SOCF₃, NH], [75: J5, SOCF₃, NH], [76: J6, SOCF₃, NH], [77: J7, SOCF₃, NH], [78: J8, SOCF₃, NH], [79: J9, SOCF₃, NH], [80: J10, SOCF₃, NH], [81: H, SO₂CF₃, NH], [82: F, SO₂CF₃, NH], [83: Cl, SO₂CF₃, NH], [84: Br, SO₂CF₃, NH], [85: CH₃, SO₂CF₃, NH], [86: CN, SO₂CF₃, NH], [87: J1, SO₂CF₃, NH], [88: J2, SO₂CF₃, NH], [89: J3, SO₂CF₃, NH], [90: J4, SO₂CF₃, NH], [91: J5, SO₂CF₃, NH], [92: J6, SO₂CF₃, NH], [93: J7, SO₂CF₃, NH], [94: J8, SO₂CF₃, NH], [95: J9, SO₂CF₃, NH], [96: J10, SO₂CF₃, NH], [97: H, CH₂C=CH, NH], [98: F, CH₂C=CH, NH], [99: Cl, CH₂C=CH, NH], [100: Br, CH₂C=CH, NH], [101: CH₃, CH₂C=CH, NH], [102: CN, CH₂C=CH, NH], [103: J1, CH₂C=CH, NH], [104: J2, CH₂C=CH, NH], [105: J3, CH₂C=CH, NH], [106: J4, CH₂C=CH, NH], [107: J5, CH₂C=CH, NH][108: J6, CH₂C=CH, NH], [109: J7, CH₂C=CH, NH], [110: J8, CH₂C=CH, NH], [111: J9, CH₂C=CH, NH], [112: J10, CH₂C=CH, NH], [113: H, OCH₂C=CH, NH], [114: F, OCH₂C=CH, NH], [115: Cl, OCH₂C=CH, NH], [116: Br, OCH₂C=CH, NH], [117: CH₃, OCH₂C=CH, NH], [118: CN, OCH₂C=CH, NH], [119: J1, OCH₂C=CH, NH], [120: J2, OCH₂C=CH, NH], [121: J3, OCH₂C=CH, NH], [122: J4, OCH₂C=CH, NH], [123: J5, OCH₂C=CH, NH], [124: J6, OCH₂C=CH, NH], [125: J7, OCH₂C=CH, NH], [126: J8, OCH₂C=CH, NH], [127: J9, OCH₂C=CH, NH], [128: J10, OCH₂C=CH, NH], [129: H, Cl, NH], [130: F, Cl, NH], [131: Cl, Cl, NH], [132: Br, Cl, NH], [133: CH₃, Cl, NH], [134: CN, Cl, NH], [135: J1, Cl, NH], [136: J2, Cl, NH], [137: J3, Cl, NH], [138: J4, Cl, NH], [139: J5, Cl, NH], [140: J6, Cl, NH], [141: J7, Cl, NH], [142: J8, Cl, NH], [143: J9, Cl, NH], [144: J10, Cl, NH], [145: H, CN, NH], [146: F, CN, NH], [147: Cl, CN, NH], [148: Br, CN, NH], [149: CH₃, CN, NH], [150: CN, CN, NH], [151: J1, CN, NH], [152: J2, CN, NH], [153: J3, CN, NH], [154: J4, CN, NH], [155: J5, CN, NH], [156: J6, CN, NH], [157: J7, CN, NH], [158: J8, CN, NH], [159: J9, CN, NH], [160: J10, CN, NH], [161: H, C=CH, NH], [162: F, C=CH, NH], [163: Cl, C=CH, NH], [164: Br, C=CH, NH], [165: CH₃, C=CH, NH], [166: CN, C=CH, NH], [167: J1, C=CH, NH], [168: J2, C=CH, NH], [169: J3, C=CH, NH], [170: J4, C=CH, NH], [171: J5, C=CH, NH], [172: J6, C=CH, NH], [173: J7, C=CH, NH], [174: J8, C=CH, NH], [175: J9, C=CH, NH], [176: J10, C=CH, NH], [177: H, C(CH₃)₃, NCH₃], [178: F, C(CH₃)₃, NCH₃], [179: Cl, C(CH₃)₃, NCH₃], [180: Br, C(CH₃)₃, NCH₃], [181: CH₃, C(CH₃)₃, NCH₃], [182: CN, C(CH₃)₃, NCH₃], [183: J1, C(CH₃)₃, NCH₃], [184: J2, C(CH₃)₃, NCH₃], [185: J3, C(CH₃)₃, NCH₃], [186: J4, C(CH₃)₃, NCH₃], [187: J5, C(CH₃)₃, NCH₃], [188: J6, C(CH₃)₃, NCH₃], [189: J7, C(CH₃)₃, NCH₃], [190: J8, C(CH₃)₃, NCH₃], [191: J9, C(CH₃)₃, NCH₃], [192: J10, C(CH₃)₃, NCH₃], [193: H, CF₃, NCH₃], [194: F, CF₃, NCH₃], [195: Cl, CF₃, NCH₃], [196: Br, CF₃, NCH₃], [197: CH₃, CF₃, NCH₃], [198: CN, CF₃, NCH₃], [199: J₁, CF₃, NCH₃], [200: J2, CF₃, NCH₃], [201: J3, CF₃, NCH₃], [202: J4, CF₃, NCH₃], [203: J5, CF₃, NCH₃], [204: J6, CF₃, NCH₃], [205: J7, CF₃, NCH₃], [206: J8, CF₃, NCH₃], [207: J9, CF₃, NCH₃], [208': J10, CF₃, NCH₃], [209: H, CF₂CF₃, NCH₃], [210: F, CF₂CF₃, NCH₃], [211: Cl, CF₂CF₃, NCH₃], [212: Br, CF₂CF₃, NCH₃], [213: CH₃, CF₂CF₃, NCH₃], [214: CN, CF₂CF₃, NCH₃], [215: J1, CF₂CF₃, NCH₃], [216: J2, CF₂CF₃, NCH₃], [217: J3, CF₂CF₃, NCH₃], [218: J4, CF₂CF₃, NCH₃], [219: J5, CF₂CF₃, NCH₃], [220: J6, CF₂CF₃, NCH₃], [221: J7, CF₂CF₃, NCH₃], [222: J8, CF₂CF₃, NCH₃], [223: J9, CF₂CF₃, NCH₃], [224: J10, CF₂CF₃, NCH₃], [225: H, SCF₃, NCH₃], [226: F, SCF₃, NCH₃], [227: Cl, SCF₃, NCH₃], [228: Br, SCF₃, NCH₃],

[229: CH₃, SCF₃, NCH₃], [230: CN, SCF₃, NCH₃], [231: J1, SCF₃, NCH₃], [232: J2, SCF₃, NCH₃], [233: J3, SCF₃, NCH₃], [234: J4, SCF₃, NCH₃], [235: J5, SCF₃, NCH₃], [236: J6, SCF₃, NCH₃], [237: J7, SCF₃, NCH₃], [238: J8, SCF₃, NCH₃], [239: J9, SCF₃, NCH₃], [240: J10, SCF₃, NCH₃], [241: H, SOCF₃, NCH₃], [242: F, SOCF₃, NCH₃], [243: Cl, SOCF₃, NCH₃], [244: Br, SOCF₃, NCH₃], [245: CH₃, SOCF₃, NCH₃], [246: CN, SOCF₃, NCH₃], [247: J1, SOCF₃, NCH₃], [248: J2, SOCF₃, NCH₃], [249: J3, SOCF₃, NCH₃], [250: J4, SOCF₃, NCH₃], [251: J5, SOCF₃, NCH₃], [252: J6, SOCF₃, NCH₃], [253: J7, SOCF₃, NCH₃], [254: J8, SOCF₃, NCH₃], [255: J9, SOCF₃, NCH₃], [256: J10, SOCF₃, NCH₃], [257: H, SO2CF₃, NCH₃], [258: F, SO2CF₃, NCH₃], [259: Cl, SO2CF₃, NCH₃], [260: Br, SO2CF₃, NCH₃], [261: CH₃, SO2CF₃, NCH₃], [262: CN, SO2CF₃, NCH₃], [263: J1, SO2CF₃, NCH₃], [264: J2, SO2CF₃, NCH₃], [265: J3, SO2CF₃, NCH₃], [266: J4, SO2CF₃, NCH₃], [267: J5, SO2CF₃, NCH₃], [268: J6, SO2CF₃, NCH₃], [269: J7, SO2CF₃, NCH₃], [270: J8, SO2CF₃, NCH₃], [271: J9, SO2CF₃, NCH₃], [272: J10, SO2CF₃, NCH₃], [273: H, CH₂C≡CH, NCH₃], [274: F, CH₂C≡CH, NCH₃], [275: Cl, CH₂C≡CH, NCH₃], [276: Br, CH₂C≡CH, NCH₃], [277: CH₃, CH₂C≡CH, NCH₃], [278: CN, CH₂C≡CH, NCH₃], [279: J1, CH₂C≡CH, NCH₃], [280: J2, CH₂C≡CH, NCH₃], [281: J3, CH₂C≡CH, NCH₃], [282: J4, CH₂C≡CH, NCH₃], [283: J5, CH₂C≡CH, NCH₃], [284: J6, CH₂C≡CH, NCH₃], [285: J7, CH₂C≡CH, NCH₃], [286: J8, CH₂C≡CH, NCH₃], [287: J9, CH₂C≡CH, NCH₃], [288: J10, CH₂ClCH, NCH₃], [289: H, OCH₂C≡CH, NCH₃], [290: F, OCH₂C≡CH, NCH₃], [291: Cl, OCH₂C≡CH, NCH₃], [292: Br, OCH₂C≡CH, NCH₃], [293: CH₃, OCH₂C≡CH, NCH₃], [294: CN, OCH₂C≡CH, NCH₃], [295: J1, OCH₂C≡CH, NCH₃], [296: J2, OCH₂C≡CH, NCH₃], [297: J3, OCH₂C≡CH, NCH₃], [298: J4, OCH₂C≡CH, NCH₃], [299: J5, OCH₂C≡CH, NCH₃], [300: J6, OCH₂C≡CH, NCH₃], [301: J7, OCH₂C≡CH, NCH₃], [302: J8, OCH₂C≡CH, NCH₃], [303: J9, OCH₂C≡CH, NCH₃], [304: J10, OCH₂C≡CH, NCH₃], [305: H, Cl, NCH₃], [306: F, Cl, NCH₃], [307: Cl, Cl, NCH₃], [308: Br, Cl, NCH₃], [309: CH₃, Cl, NCH₃], [310: CN, Cl, NCH₃], [311: J1, Cl, NCH₃], [312: J2, Cl, NCH₃], [313: J3, Cl, NCH₃], [314: J4, Cl, NCH₃], [315: J5, Cl, NCH₃], [316: J6, Cl, NCH₃], [317: J7, Cl, NCH₃], [318: J8, Cl, NCH₃], [319: J9, Cl, NCH₃], [320: J10, Cl, NCH₃], [321: H, CN, NCH₃], [322: F, CN, NCH₃], [323: Cl, CN, NCH₃], [324: Br, CN, NCH₃], [325: CH₃, CN, NCH₃], [326: CN, CN, NCH₃], [327: J1, CN, NCH₃], [328: J2, CN, NCH₃], [329: J3, CN, NCH₃], [330: J4, CN, NCH₃], [331: J5, CN, NCH₃], [332: J6, CN, NCH₃], [333: J7, CN, NCH₃], [334: J8, CN, NCH₃], [335: J9, CN, NCH₃], [336: J10, CN, NCH₃], [337: H, C≡CH, NCH₃], [338: F, C≡CH, NCH₃], [339: Cl, C≡CH, NCH₃], [340: Br, C≡CH, NCH₃], [341: CH₃, C≡CH, NCH₃], [342: CN, C≡CH, NCH₃], [343: J1, C≡CH, NCH₃], [344: J2, C≡CH, NCH₃], [345: J3, C≡CH, NCH₃], [346: J4, C≡CH, NCH₃], [347: J5, C≡CH, NCH₃], [348: J6, C≡CH, NCH₃], [349: J7, C≡CH, NCH₃], [350: J8, C≡CH, NCH₃], [351: J9, C≡CH, NCH₃], [352: J10, C≡CH, NCH₃], [353: H, C(CH₃)₃, S], [354: F, C(CH₃)₃, S][355: Cl, C(CH₃)₃, S], [356: Br, C(CH₃)₃, S], [357: CH₃, C(CH₃)₃, S], [358: CN, C(CH₃)₃, S], [359: J1, C(CH₃)₃, S], [360: J2, C(CH₃)₃, S], [361: J3, C(CH₃)₃, S], [362: J4, C(CH₃)₃, S], [363: J5, C(CH₃)₃, S], [364: J6, C(CH₃)₃, S], [365: J7, C(CH₃)₃, S], [366: J8, C(CH₃)₃, S], [367: J9, C(CH₃)₃, S], [368: J10, C(CH₃)₃, S], [369: H, CF₃, S], [370: F, CF₃, S], [371: Cl, CF₃, S], [372: Br, CF₃, S], [373: CH₃, CF₃, S], [374: CN, CF₃, S], [375: J1, CF₃, S], [376: J2, CF₃, S], [377: J3, CF₃, S], [378: J4, CF₃, S], [379: J5, CF₃, S], [380: J6, CF₃, S], [381: J7, CF₃, S], [382: J8, CF₃, S], [383: J9, CF₃, S], [384: J10, CF₃, S], [385: H, CF₂CF₃, S], [386: F, CF₂CF₃, S], [387: Cl, CF₂CF₃, S], [388: Br, CF₂CF₃, S], [389: CH₃, CF₂CF₃, S], [390: CN, CF₂CF₃, S], [391: J1, CF₂CF₃, S], [392: J2, CF₂CF₃, S], [393: J3, CF₂CF₃, S], [394: J4, CF₂CF₃, S], [395: J5, CF₂CF₃, S], [396: J6, CF₂CF₃, S], [397: J7, CF₂CF₃, S], [398: J8, CF₂CF₃, S], [399: J9, CF₂CF₃, S], [400: J10, CF₂CF₃, S], [401: SCF₃, S], [402: F, SCF₃, S][403: Cl, SCF₃, S], [404: Br, SCF₃, S], [405: CH₃, SCF₃, S], [406: CN, SCF₃, S], [407: J1, SCF₃, S], [408: J2, SCF₃, S], [409: J3, SCF₃, S], [410: J4, SCF₃, S], [411: J5, SCF₃, S], [412: J6, SCF₃, S], [413: J7, SCF₃, S], [414: J8, SCF₃, S], [415: J9, SCF₃, S], [416: J10, SCF₃, S], [417: H, SOCF₃, S], [418: F, SOCF₃, S], [419: Cl, SOCF₃, S], [420: Br, SOCF₃, S], [421: CH₃, SOCF₃, S], [422: CN, SOCF₃, S], [423: J1, SOCF₃, S], [424: J2, SOCF₃, S], [425: J3, SOCF₃, S], [426: J4, SOCF₃, S], [427: J5, SOCF₃, S], [428: J6, SOCF₃, S], [429: J7, SOCF₃, S], [430: J8, SOCF₃, S], [431: J9, SOCF₃, S], [432: J10, SOCF₃, S], [433: H, SO₂CF₃, S], [434: F, SO₂CF₃, S], [435: Cl, SO₂CF₃, S][436: Br, SO₂CF₃, S], [437: CH₃, SO₂CF₃, S], [438: CN, SO₂CF₃, S], [439: J1, SO₂CF₃, S], [440: J2, SO₂CF₃, S], [441: J3, SO₂CF₃, S], [442: J4, SO₂CF₃, S], [443: J5, SO₂CF₃, S], [444: J6, SO₂CF₃, S], [445: J7, SO₂CF₃, S], [446: J8, SO₂CF₃, S], [447: J9, SO₂CF₃, S], [448: J10, SO₂CF₃, S], [449: H, CH₂C≡CH, S], [450: F, CH₂C≡CH, S], [451: Cl, CH₂C≡CH, S], [452: Br, CH₂C≡CH, S], [453: CH₃, CH₂C≡CH, S], [454: CN, CH₂C≡CH, S], [455: J1, CH₂C≡CH, S], [456: J2, CH₂C≡CH, S], [457: J3, CH₂C≡CH, S], [458: J4, CH₂C≡CH, S], [459: J5, CH₂C≡CH, S], [460: J6, CH₂C≡CH, S], [461: J7, CH₂C≡CH, S], [462: J8, CH₂C≡CH, S], [463: J9, CH₂C≡CH, S], [464: J10, CH₂C≡CH, S], [465: H, OCH₂C≡CH, S], [466: F, OCH₂C≡CH, S], [467: Cl, OCH₂C≡CH, S], [468: Br, OCH₂C≡CH, S], [469: CH₃, OCH₂C≡CH, S], [470: CN, OCH₂C≡CH, S], [471: J1, OCH₂C≡CH, S], [472: J2, OCH₂C≡CH, S], [473: J3, OCH₂C≡CH, S], [474: J4, OCH₂C≡CH, S], [475: J5, OCH₂C≡CH, S], [476: J6, OCH₂C≡CH, S], [477: J7, OCH₂C≡CH, S], [478: J8, OCH₂C≡CH, S], [479: J9, OCH₂C≡CH, S], [480: J10, OCH₂C≡CH, S], [481: H, Cl, S], [482: F, Cl, S], [483: Cl, Cl, S], [484: Br, Cl, S], [485: CH₃, Cl, S], [486: CN, Cl, S], [487: J1, Cl, S], [488: J2, Cl, S], [489: J3, Cl, S], [490: J4, Cl, S], [491: J5, Cl, S], [492: J6, Cl, S], [493: J7, Cl, S], [494: J8, Cl, S], [495: J9, Cl, S], [496: J10, Cl, S], [497: H, CN, S], [498: F, CN, S], [499: Cl, CN, S], [500: Br, CN, S], [501: CH₃, CN, S], [502: CN, CN, S], [503: J1, CN, S], [504: J2, CN, S], [505: J3, CN, S], [506: J4, CN, S], [507: J5, CN, S], [508: J6, CN, S], [509: J7, CN, S], [510: J8, CN, S], [511: J9, CN, S], [512: J10, CN, S], [513: H, C≡CH, S], [514: F, C≡CH, S], [515: Cl, C≡CH, S], [516: Br, C≡CH, S], [517: CH₃, C≡CH, S], [518: CN, C≡CH, S], [519: J1, C≡CH, S], [520: J2, C≡CH, S], [521: J3, C≡CH, S], [522: J4, C≡CH, S], [523: J5, C≡CH, S], [524: J6, C≡CH, S], [525: J7, C≡CH, S], [526: J8, C≡CH, S], [527: J9, C≡CH, S], [528: J10, C≡CH, S], [529: H, C(CH₃)₃, O], [530: F, C(CH₃)₃, O], [531: Cl, C(CH₃)₃, O], [532: Br, C(CH₃)₃, O], [533: CH₃, C(CH₃)₃, O], [534: CN, C(CH₃)₃, O], [535: J1, C(CH₃)₃, O], [536: J2, C(CH₃)₃, O], [537: J3, C(CH₃)₃, O], [538: J4, C(CH₃)₃, O], [539: J5, C(CH₃)₃, O], [540: J6, C(CH₃)₃, O], [541: J7, C(CH₃)₃, O], [542: J8, C(CH₃)₃, O], [543: J9, C(CH₃)₃, O], [544: J10, C(CH₃)₃, O], [545: H, CF₃, O], [546: F, CF₃, O], [547: Cl, CF₃, O], [548: Br, CF₃, O], [549: CH₃, CF₃, O], [550: CN, CF₃, O], [551: J1, CF₃, O], [552: J2, CF₃, O], [553: J3, CF₃, O], [554: J4, CF₃, O], [555: J5, CF₃, O], [556: J6, CF₃, O], [557: J7, CF₃, O], [558: J8, CF₃, O], [559: J9, CF₃, O], [560: J10, CF₃, O], [561: H, CF₂CF₃, O], [562: F, CF₂CF₃, O], [563: Cl, CF₂CF₃, O], [564: Br, CF₂CF₃, O],

[565: CH₃, CF₂CF₃, O], [566: CN, CF₂CF₃, O], [567: J1, CF₂CF₃, O], [568: J2, CF₂CF₃, O], [569: J3, CF₂CF₃, O], [570: J4, CF₂CF₃, O], [571: J5, CF₂CF₃, O], [572: J6, CF₂CF₃, O], [573: J7, CF₂CF₃, O], [574: J8, CF₂CF₃, O], [575: J9, CF₂CF₃, O], [576: J10, CF₂CF₃, O], [577: H, SCF₃, O], [578: F, SCF₃, O], [579: Cl, SCF₃, O], [580: Br, SCF₃, O], [581: CH₃, SCF₃, O], [582: CN, SCF₃, O], [583: J1, SCF₃, O], [584: J2, SCF₃, O], [585: J3, SCF₃, O], [586: J4, SCF₃, O], [587: J5, SCF₃, O], [588: J6, SCF₃, O], [589: J7, SCF₃, O], [590: J8, SCF₃, O], [591: J9, SCF₃, O], [592: J10, SCF₃, O], [593: H, SOCF₃, O], [594: F, SOCF₃, O], [595: Cl, SOCF₃, O], [596: Br, SOCF₃, O], [597: CH₃, SOCF₃, O], [598: CN, SOCF₃, O], [599: J1, SOCF₃, O], [600: J2, SOCF₃, O], [601: J3, SOCF₃, O], [602: J4, SOCF₃, O], [603: J5, SOCF₃, O], [604: J6, SOCF₃, O], [605: J7, SOCF₃, O], [606: J8, SOCF₃, O], [607: J9, SOCF₃, O], [608: J10, SOCF₃, O], [609: H, SO₂CF₃, O], [610: F, SO₂CF₃, O], [611: Cl, SO₂CF₃, O], [612: Br, SO₂CF₃, O], [613: CH₃, SO₂CF₃, O], [614: CN, SO₂CF₃, O], [615: J1, SO₂CF₃, O], [616: J2, SO₂CF₃, O], [617: J3, SO₂CF₃, O], [618: J4, SO₂CF₃, O], [619: J5, SO₂CF₃, O], [620: J6, SO₂CF₃, O][621: J7, SO₂CF₃, O], [622: J8, SO₂CF₃, O], [623: J9, SO₂CF₃, O], [624: J10, SO₂CF₃, O], [625: H, CH₂C≡CH, O], [626: F, CH₂C≡CH, O][627: Cl, CH₂C≡CH, O], [628: Br, CH₂C≡CH, O], [629: CH₃, CH₂C≡CH, O], [630: CN, O], [631: J1, CH₂C≡CH, O], [632: J2, CH₂C≡CH, S], [633: J3, CH₂C≡CH, O], [634: J4, CH₂C≡CH, O], [635: J5, CH₂C≡CH, O], [636: J6, CH₂C≡CH, O], [637: J7, CH₂C≡CH, O], [638: J8, CH₂C≡CH, O], [639: J9, CH₂C≡CH, O], [640: J10, CH₂C≡CH, O], [641: H, OCH₂C≡CH, O], [642: F, OCH₂C≡CH, O], [643: Cl, OCH₂C≡CH, O], [644 Br, OCH₂C≡CH, O], [645: CH₃, OCH₂C≡CH, O], [646 CN, OCH₂C≡CH, O], [647: J1, OCH₂C≡CH, O], [648: J2, OCH₂C≡CH, O], [649: J3, OCH₂C≡CH, O], [650: J4, OCH₂C≡CH, O], [651: J5, OCH₂C≡CH, O], [652: J6, OCH₂C≡CH, O], [653: J7, OCH₂C≡CH, O], [654: J8, OCH₂C≡CH, O], [655: J9, OCH₂C≡CH, O], [656: J10, OCH₂C≡CH,O], [657H, Cl, O], [658: F, Cl, O], [659: Cl, Cl, O], [660: Br, Cl, O], [661: CH₃, Cl, O], [662: CN, Cl, O], [663: J1, Cl, O], [664: J2, Cl, O], [665: J3, Cl, O], [666: J4, Cl, O], [667: J5, Cl, O], [668: J6, Cl, O], [669: J7, Cl, O], [670: J8, Cl, O], [671: J9, Cl, O], [672: J10, Cl, O], [673: H, CN, O], [674: F, CN, O], [675: Cl, CN, O], [676: Br, CN, O], [677: CH₃, CN, O], [678: CN, CN, O], [679: J1, CN, O], [680: J2, CN, O], [681: J3, CN, O], [682: J4, CN, O], [683: J5, CN, O], [684: J6, CN, O], [685: J7, CN, O], [686: J8, CN, O], [687: J9, CN, O], [688: J10, CN, O], [689: H, C≡CH, O], [690: F, C≡CH, O], [691: Cl, C≡CH, O], [692: Br, C≡CH, O], [693: CH₃, C≡CH, O], [694: CN, C≡CH, O], [695: J1, C≡CH, O], [696: J2, C≡CH, O], [697: J3, C≡CH, O], [698: J4, C≡CH, O], [699: J5, C≡CH, O], [700: J6, C≡CH, O], [701: J7, C≡CH, O], [702: J8, C≡CH, O], [703: J9, C≡CH, O], [704: J10, C≡CH, O], [705: H, H, NC(CH₃)₃], [706: F, H, NC(CH₃)₃], [707: Cl, H, NC(CH₃)₃], [708: Br, H, NC(CH₃)₃], [709: CH₃, H, NC(CH₃)₃], [710: CN, H, NC(CH₃)₃], [711: J1, H, NC(CH₃)₃], [712: J2, H, NC(CH₃)₃], [713: J3, H, NC(CH₃)₃], [714: J4, H, NC(CH₃)₃], [715: J5, H, NC(CH₃)₃], [716: J6, H, NC(CH₃)₃], [717: J7, H, NC(CH₃)₃], [718: J8, H, NC(CH₃)₃], [719: J9, H, NC(CH₃)₃], [720: J10, H, NC(CH₃)₃], [721: H, CN, NC(CH₃)₃], [722: F, CN, NC(CH₃)₃], [723: Cl, CN, NC(CH₃)₃], [724: Br, CN, NC(CH₃)₃], [725: CH₃, CN, NC(CH₃)₃], [726: CN, CN, NC(CH₃)₃], [727: J1, CN, NC(CH₃)₃], [728: J2, CN, NC(CH₃)₃], [729: J3, CN, NC(CH₃)₃], [730: J4, CN, NC(CH₃)₃], [731: J5, CN, NC(CH₃)₃], [732: J6, CN, NC(CH₃)₃], [733: J7, CN, NC(CH₃)₃], [734: J8, CN, NC(CH₃)₃], [735: J9, CN, NC(CH₃)₃], [736: J10, CN, NC(CH₃)₃], [737: H, H, NCH₂CF₃], [738: F, H, NCH₂CF₃], [739: Cl, H, NCH₂CF₃], [740: Br, H, NCH₂CF₃], [741: CH₃, H, NCH₂CF₃], [742: CN, H, NCH₂CF₃], [743: J1, H, NCH₂CF₃], [744: J2, H, NCH₂CF₃], [745: J3, H, NCH₂CF₃], [746: J4, H, NCH₂CF₃], [747: J5, H, NCH₂CF₃], [748: J6, H, NCH₂CF₃], [749: J7, H, NCH₂CF₃], [750: J8, H, NCH₂CF₃], [751: J9, H, NCH₂CF₃], [752: J10, H, NCH₂CF₃], [753: H, CN, NCH₂CF₃], [754: F, CN, NCH₂CF₃], [755: Cl, CN, NCH₂CF₃], [756: Br, CN, NCH₂CF₃], [757: CH₃, CN, NCH₂CF₃], [758: CN, CN, NCH₂CF₃], [759: J1, CN, NCH₂CF₃], [760: J2, CN, NCH₂CF₃], [761: J3, CN, NCH₂CF₃], [762: J4, CN, NCH₂CF₃], [763: J5, CN, NCH₂CF₃], [764: J6, CN, NCH₂CF₃], [765: J7, CN, NCH₂CF₃], [766: J8, CN, NCH₂CF₃], [767: J9, CN, NCH₂CF₃], [768: J10, CN, NCH₂CF₃], [769: H, H, NCH₂C≡CH], [770: F, H, NCH₂C≡CH], [771: Cl, H, NCH₂C≡CH], [772: Br, H, NCH₂C≡CH], [773: CH₃, H, NCH₂C≡CH], [774: CN, H, NCH₂C≡CH], [775: J1, H, NCH₂C≡CH], [776: J2, H, NCH₂C≡CH], [777: J3, H, NCH₂C≡CH], [778: J4, H, NCH₂C≡CH], [779: J5, H, NCH₂C≡CH], [780: J6, H, NCH₂C≡CH], [781: J7, H, NCH₂C≡CH], [782: J8, H, NCH₂C≡CH], [783: J9, H, NCH₂C≡CH], [784: J10, H, NCH₂C≡CH], [785: H, CN, NCH₂C≡CH], [786: F, CN, NCH₂C≡CH][787: Cl, CN, NCH₂C≡CH], [788: Br, CN, NCH₂C≡CH][789: CH₃, CN, NCH₂C≡CH], [790: CN, CN, NCH₂C≡CH], [791: J1, CN, NCH₂C≡CH], [792: J2, CN, NCH₂C≡CH], [793: J3, CN, NCH₂C≡CH], [794: J4, CN, NCH₂C≡CH], [795: J5, CN, NCH₂C≡CH], [796: J6, CN, NCH₂C≡CH], [797: J7, CN, NCH₂C≡CH], [798: J8, CN, NCH₂C≡CH], [799: J9, CN, NCH₂C≡CH], [800: J10, CN, NCH₂C≡CH]

A compound represented by the fmula ($I^{64}$):

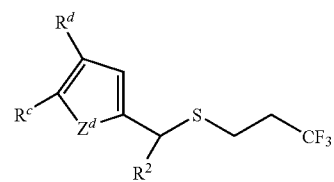

wherein $R^2$, $R^c$, $R^d$ and $Z^d$ represent any one of combinations shown below.

A compound represented by the formula ($I^{65}$):

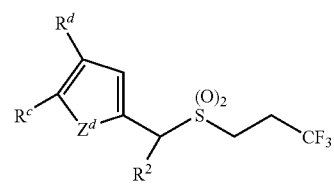

wherein $R^2$, $R^c$, $R^d$ and $Z^d$ represent any one of combinations shown below.

A compound represented by the formula ($I^{66}$):

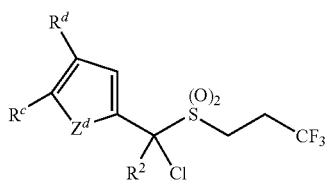

wherein $R^2$, $R^c$, $R^d$ and $Z^d$ represent any one of combinations shown below.

A compound represented by the formula ($I^{67}$):

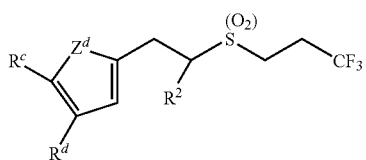

wherein $R^2$, $R^c$, $R^d$ and $Z^d$ represent any one of combinations shown below.

A compound represented by the formula ($I^{68}$):

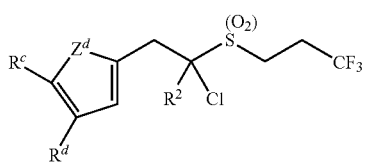

wherein $R^2$, $R^c$, $R^d$ and $Z^d$ represent any one of combinations shown below.

A compound represented by the formula ($I^{69}$):

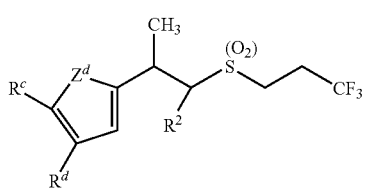

wherein $R^2$, $R^c$, $R^d$ and $Z^d$ represent any one of combinations shown below.

A compound represented by the formula ($I^{70}$):

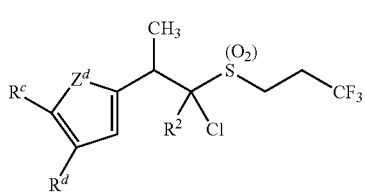

wherein $R^2$, $R^c$, $R^d$ and $Z^d$ represent any one of combinations shown below.

A compound represented by the formula ($I^{71}$):

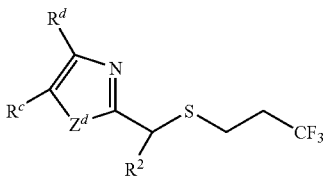

wherein $R^2$, $R^c$, $R^d$ and $Z^d$ represent any one of combinations shown below.

A compound represented by the formula ($I^{72}$):

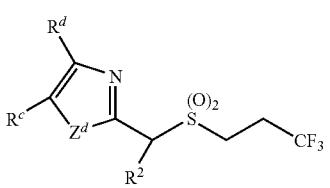

wherein $R^2$, $R^c$, $R^d$ and $Z^d$ represent any one of combinations shown below.

A compound represented by the formula ($I^{73}$):

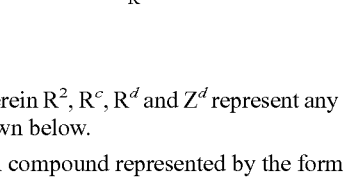

wherein $R^2$, $R^c$, $R^d$ and $Z^d$ represent any one of combinations shown below.

A compound represented by the formula ($I^{74}$):

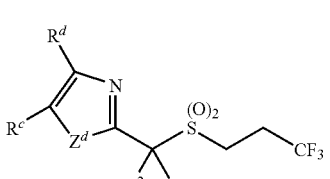

wherein $R^2$, $R^c$, $R^d$ and $Z^d$ represent any one of combinations shown below.

A compound represented by the formula ($I^{75}$):

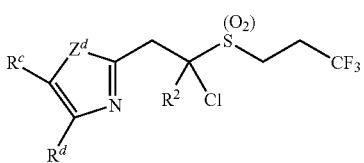

wherein $R^2$, $R^c$, $R^d$ and $Z^d$ represent any one of combinations shown below.

A compound represented by the formula ($I^{76}$):

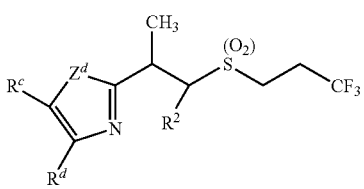

wherein $R^2$, $R^c$, $R^d$ and $Z^d$ represent any one of combinations shown below.

A compound represented by the formula ($I^{77}$):

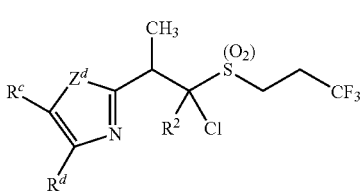

wherein $R^2$, $R^c$, $R^d$ and $Z^d$ represent any one of combinations shown below.

Combinations of $R^2$, $R^c$, $R^d$ and $Z^d$ for the compounds represented by the formulas ($I^{64}$) to ($I^{77}$) are shown below. In brackets, a combination number, a group represented by $R^2$, a group represented by $R^c$, a group represented by $R^d$, and a group represented by $Z^d$ are shown in this order. Herein, symbols J1 to J10 are as defined above.

[Combination number: $R^2$, $R^c$, $R^d$, $Z^d$]=[1: H, C(CH₃)₃, H, NH], [2: F, C(CH₃)₃, H, NH], [3: Cl, C(CH₃)₃, H, NH], [4: Br, C(CH₃)₃, H, NH], [5: CH₃, C(CH₃)₃, H, NH], [6: CN, C(CH₃)₃, H, NH], [7: J1, C(CH₃)₃, H, NH], [8: J2, C(CH₃)₃, H, NH], [9: J3, C(CH₃)₃, H, NH], [10: J4, C(CH₃)₃, H, NH], [11: J5, C(CH₃)₃, H, NH], [12: J6, C(CH₃)₃, H, NH], [13: J7, C(CH₃)₃, H, NH], [14: J8, C(CH₃)₃, H, NH], [15: J9, C(CH₃)₃, H, NH], [16: J10, C(CH₃)₃, H, NH], [17: H, CF₃, H, NH], [18: F, CF₃, H, NH], [19: Cl, CF₃, H, NH], [20: Br, CF₃, H, NH], [21: CH₃, CF₃, H, NH], [22: CN, CF₃, H, NH], [23: J1, CF₃, H, NH], [24: J2, CF₃, H, NH], [25: J3, CF₃, H, NH], [26: J4, CF₃, H, NH], [27: J5, CF₃, H, NH], [28: J6, CF₃, H, NH], [29: J7, CF₃, H, NH], [30: J8, CF₃, H, NH], [31: J9, CF₃, H, NH], [32: J10, CF₃, H, NH], [33: H, CF₂CF₃, H, NH], [34: F, CF₂CF₃, H, NH], [35: Cl, CF₂CF₃, H, NH], [36: Br, CF₂CF₃, H, NH], [37: CH₃, CF₂CF₃, H, NH][38: CN, CF₂CF₃, H, NH], [39: J₁, CF₂CF₃, H, NH], [40: J2, CF₂CF₃, H, NH], [41: J3, CF₂CF₃, H, NH], [42: J4, CF₂CF₃, H, NH], [43: J5, CF₂CF₃, H, NH], [44: J6, CF₂CF₃, H, NH], [45: J7 CF₂CF₃, NH], [46: J8, CF₂CF₃, H, NH], [47: J9 CF₂CF₃, H, NH], [48: J10, CF₂CF₃, H, NH], [49: H, SCF₃, H, NH], [50: F, SCF₃, H, NH], [51: Cl, SCF₃, H, NH], [52: Br, SCF₃, H, NH], [53: CH₃, SCF₃, H, NH], [54: CN, SCF₃, H, NH], [55: J1, SCF₃, H, NH], [56: J2, SCF₃, H, NH], [57: J3, SCF₃, H, NH], [58: J4, SCF₃, H, NH], [59: J5, SCF₃, H, NH], [60: J6, SCF₃, H, NH], [61: J7, SCF₃, H, NH], [62: J8, SCF₃, H, NH], [63: J9, SCF₃, H, NH], [64: J10, SCF₃, H, NH], [65: H, SOCF₃, H, NH], [66: F, SOCF₃, H, NH], [67: Cl, SOCF₃, H, NH], [68: Br, SOCF₃, H, NH], [69: CH₃, SOCF₃, H, NH], [70: CN, SOCF₃, H, NH], [71: J1, SOCF₃, H, NH], [72: J2, SOCF₃, H, NH], [73: J3, SOCF₃, H, NH], [74: J4, SOCF₃, H, NH], [75: J5, SOCF₃, H, NH], [76: J6, SOCF₃, H, NH], [77: J7, SOCF₃, H, NH], [78: J8, SOCF₃, H, NH], [79: J9, SOCF₃, H, NH], [80: J10, SOCF₃, H, NH], [81: H, SO2CF₃, H, NH], [82: F, SO₂CF₃, H, NH][83: Cl, SO₂CF₃, H, NH], [84: Br, SO₂CF₃, H, NH], [85: CH₃, SO₂CF₃, H, NH], [86: CN, SO₂CF₃, H, NH], [87: J1, SO₂CF₃, H, NH], [88: J2, SO₂CF₃, H, NH], [89: J3, SO₂CF₃, H, NH], [90: J4, SO₂CF₃, H, NH], [91: J5, SO₂CF₃, H, NH], [92: J6, SO₂CF₃, H, NH], [93: J7, SO₂CF₃, H, NH], [94: J8, SO₂CF₃, H, NH], [95: J9, SO₂CF₃, H, NH], [96: J10, SO₂CF₃, H, NH], [97: H, CH₂C=CH, H, NH], [98: F, CH₂C=CH, H, NH], [99: Cl, CH₂C=CH, H, NH], [100: Br, CH₂C=CH, H, NH], [101: CH₃, CH₂C=CH, H, NH], [102: CN, CH₂C=CH, H, NH], [103: J1, CH₂C=CH, H, NH], [104: J2, CH₂C=CH, H, NH], [105: J3, CH₂C=CH, H, NH], [106: J4, CH₂C=CH, H, NH], [107: J5, CH₂C=CH, H, NH], [108: J6, CH₂C=CH, H, NH], [109: J7, CH₂C=CH, H, NH], [110: J8, CH₂C=CH, H, NH], [111: J9, CH₂C=CH, H, NH], [112: J10, CH₂C=CH, H, NH], [113: H, OCH₂C=CH, H, NH], [114: F, OCH₂C=CH, H, NH], [115: Cl, OCH₂C=CH, H, NH], [116: Br, OCH₂C=CH, H, NH], [117: CH₃, OCH₂C=CH, H, NH], [118: CN, OCH₂C=CH, NH], [119: J1, OCH₂C=CH, H, NH], [120: J2, OCH₂C=CH, H, NH], [121: J3, OCH₂C=CH, H, NH][122: J4, OCH₂C=CH, H, NH], [123: J5, OCH₂C=CH, H, NH], [124: J6, OCH₂C=CH, H, NH], [125: J7, OCH₂C=CH, H, NH][126: J8, OCH₂C=CH, H, NH], [127: J9, OCH₂C=CH, H, NH], [128: J10, OCH₂C=CH, H, NH], [129: H, Cl, H, NH], [130: F, Cl, H, NH], [131: Cl, Cl, H, NH], [132: Br, Cl, H, NH], [133: CH₃, Cl, H, NH], [134: CN, Cl, H, NH], [135: J1, Cl, H, NH], [136: J2, Cl, H, NH], [137: J3, Cl, H, NH], [138: J4, Cl, H, NH], [139: J5, Cl, H, NH], [140: J6, Cl, H, NH], [141: J7, Cl, H, NH], [142: J8, Cl, H, NH], [143: J9, Cl, H, NH], [144: J10, Cl, H, NH], [145: H, C=CH, H, NH], [146: F, C=CH, H, NH], [147: Cl, C=CH, H, NH], [148: Br, C=CH, H, NH], [149: CH₃, C=CH, H, NH], [150: CN, C=CH, H, NH], [151: J1, C=CH, H, NH], [152: J2, C=CH, H, NH], [153: J3, C=CH, H, NH], [154: J4, C=CH, H, NH], [155: J5, C=CH, H, NH], [156: J6, C=CH, H, NH], [157: J7, C=CH, H, NH], [158: J8, C=CH, H, NH], [159: J9, C=CH, H, NH], [160: J10, C=CH, H, NH], [161: H, CN, H, NH], [162: F, CN, H, NH], [163: Cl, CN, H, NH], [164: Br, CN, H, NH], [165: CH₃, CN, H, NH], [166: CN, CN, H, NH], [167: J1, CN, H, NH], [168: J2, CN, H, NH], [169: J3, CN, H, NH], [170: J4, CN, H, NH], [171: J5, CN, H, NH], [172: J6, CN, H, NH], [173: J7, CN, H, NH], [174: J8, CN, H, NH], [175: J9, CN, H, NH], [176: J10, CN, H, NH], [177: H, C(CH₃)₃, CN, NH], [178: F, C(CH₃)₃, CN, NH], [179: Cl, C(CH₃)₃, CN, NH], [180: Br, C(CH₃)₃, CN, NH], [181: CH₃, C(CH₃)₃, CN, NH], [182: CN, C(CH₃)₃, CN, NH], [183: J1, C(CH₃)₃, CN, NH], [184: J2, C(CH₃)₃, CN, NH], [185: J3, C(CH₃)₃, CN, NH], [186: J4, C(CH₃)₃, CN, NH], [187: J5, C(CH₃)₃, CN, NH], [188: J6, C(CH₃)₃, CN, NH], [189: J7, C(CH₃)₃, CN, NH], [190: J8, C(CH₃)₃, CN, NH], [191: J9, C(CH₃)₃, CN, NH], [192: J10, C(CH₃)₃, CN, NH], [193: H, CF₃, CN, NH], [194:

F, CF₃, CN, NH], [195: Cl, CF₃, CN, NH], [196: Br, CF₃, CN, NH], [197: CH₃, CF₃, CN, NH], [198: CN, CF₃, CN, NH], [199: J1, CF₃, CN, NH], [200: J2, CF₃, CN, NH], [201: J3, CF₃, CN, NH], [202: J4, CF₃, CN, NH], [203: J5, CF₃, CN, NH], [204: J6, CF₃, CN, NH], [205: J7, CF₃, CN, NH], [206: J8, CF₃, CN, NH], [207: J9, CF₃, CN, NH], [208: J10, CF₃, CN, NH], [209: H, CF₂CF₃, CN, NH], [210: F, CF₂CF₃, CN, NH][211: Cl, CF₂CF₃, CN, NH], [212: Br, CF₂CF₃, CN, NH], [213: CH₃, CF₂CF₃, CN, NH], [214: CN, CF₂CF₃, CN, NH], [215: J1, CF₂CF₃, CN, NH], [216: J2, CF₂CF₃, CN, NH], [217: J3, CF₂CF₃, NH], [218: J4, CF₂CF₃, CN, NH], [219: J5, CF₂CF₃, CN, NH], [220: J6, CF₂CF₃, CN, NH], [221: J7, CF₂CF₃, CN, NH], [222: J8, CF₂CF₃, CN, NH], [223: J9, CF₂CF₃, CN, NH], [224: J10, CF₂CF₃, CN, NH], [225: H, SCF₃, CN, NH], [226: F, SCF₃, CN, NH], [227: Cl, SCF₃, CN, NH], [228: Br, SCF₃, CN, NH], [229: CH₃, SCF₃, CN, NH], [230: CN, SCF₃, CN, NH], [231: J1, SCF₃, CN, NH], [232: J2, SCF₃, CN, NH], [233: J3, SCF₃, CN, NH], [234: J4, SCF₃, CN, NH], [235: J5, SCF₃, CN, NH], [236: J6, SCF₃, CN, NH], [237: J7, SCF₃, CN, NH], [238: J8, SCF₃, CN, NH], [239: J9, SCF₃, CN, NH], [240: J10, SCF₃, CN, NH], [241: H, SOCF₃, CN, NH], [242: F, SOCF₃, CN, NH], [243: Cl, SOCF₃, CN, NH], [244: Br, SOCF₃, CN, NH], [245: CH₃, SOCF₃, CN, NH], [246: CN, SOCF₃, CN, NH], [247: J1, SOCF₃, CN, NH], [248: J2, SOCF₃, CN, NH], [249: J3, SOCF₃, CN, NH], [250: J4, SOCF₃, CN, NH], [251: J5, SOCF₃, CN, NH], [252: J6, SOCF₃, CN, NH], [253: J7, SOCF₃, CN, NH], [254: J8, SOCF₃, CN, NH], [255: J9, SOCF, CN, NH], [256: J10, SOCF₃, CN, NH], [257: H, SO2CF₃, CN, NH], [258: F, SO2CF₃, CN, NH], [259: Cl, SO2CF₃, CN, NH], [260: Br, SO2CF₃, CN, NH], [261: CH₃, SO2CF₃, CN, NH], [262: CN, SO2CF₃, CN, NH], [263: J1, SO2CF₃, CN, NH], [264: J2, SO2CF₃, CN, NH], [265: J3, SO2CF₃, CN, NH], [266: J4, SO2CF₃, CN, NH], [267: J5, SO2CF₃, CN, NH], [268: J6, SO2CF₃, CN, NH], [269: J7, SO2CF₃, CN, NH], [270: J8, SO2CF₃, CN, NH], [271: J9, SO2CF₃, CN, NH], [272: J10, SO2CF₃, CN, NH], [273: H, CH₂C≡CH, CN, NH], [274: F, CH₂C≡CH, CN, NH], [275: Cl, CH₂C≡CH, CN, NH], [276: Br, CH₂C≡CH, CN, NH], [277: CH₃, CH₂C≡CH, CN, NH], [278: CN, CH₂C≡CH, CN, NH], [279: J1, CH₂C≡CH, CN, NH], [280: J2, CH₂C≡CH, CN, NH], [281: J3, CH₂C≡CH, CN, NH], [282: J4, CH₂C≡CH, CN, NH], [283: J5, CH₂C≡CH, CN, NH], [284: J6, CH₂C≡CH, CN, NH], [285: J7, CH₂C≡CH, CN, NH], [286: J8, CH₂C≡CH, CN, NH], [287: J9, CH₂C≡CH, CN, NH], [288: J10, CH₂C≡CH, CN, NH], [289: H, OCH₂C≡CH, CN, NH], [290: F, OCH₂C≡CH, CN, NH], [291: Cl, OCH₂C≡CH, CN, NH], [292: Br, OCH₂C≡CH, CN, NH], [293: CH₃, OCH₂C≡CH, CN, NH], [294: CN, OCH₂C≡CH, CN, NH], [295: J1, OCH₂C≡CH, CN, NH], [296: J2, OCH₂C≡CH, CN, NH], [297: J3, OCH₂C≡CH, CN, NH], [298: J4, OCH₂C≡CH, CN, NH], [299: J5, OCH₂C≡CH, CN, NH], [300: J6, OCH₂C≡CH, CN, NH], [301: J7, OCH₂C≡CH, CN, NH], [302: J8, OCH₂C≡CH, CN, NH], [303: J9, OCH₂C≡CH, CN, NH], [304: J10, OCH₂C≡CH, CN, NH], [305: H, Cl, CN, NH], [306: F, Cl, CN, NH], [307: Cl, Cl, CN, NH], [308: Br, Cl, CN, NH], [309: CH₃, Cl, CN, NH], [310: CN, Cl, CN, NH], [311: J1, Cl, CN, NH], [312: J2, Cl, CN, NH], [313: J3, Cl, CN, NH], [314: J4, Cl, CN, NH], [315: J5, Cl, CN, NH], [316: J6, Cl, CN, NH], [317: J7, Cl, CN, NH], [318: J8, Cl, CN, NH], [319: J9, Cl, CN, NH], [320: J10, Cl, CN, NH], [321: H, C≡CH, CN, NH], [322: F, C≡CH, CN, NH], [323: Cl, C≡CH, CN, NH], [324: Br, C≡CH, CN, NH], [325: CH₃, C≡CH, CN, NH], [326: CN, C≡CH, CN, NH], [327: J1, C≡CH, CN, NH], [328: J2, C≡CH, CN, NH], [329: J3, C≡CH, CN, NH], [330: J4, C≡CH, CN, NH], [331: J5, C≡CH, CN, NH], [332: J6, C≡CH, CN, NH], [333: J7, C≡CH, CN, NH], [334: J8, C≡CH, CN, NH], [335: J9, C≡CH, CN, NH], [336: J10, C≡CH, CN, NH], [337: H, CN, CN, NH], [338: F, CN, CN, NH], [339: Cl, CN, CN, NH], [340: Br, CN, CN, NH], [341: CH₃, CN, CN, NH], [342: CN, CN, CN, NH], [343: J1, CN, CN, NH], [344: J2, CN, CN, NH], [345: J3, CN, CN, NH], [346: J4, CN, CN, NH], [347: J5, CN, CN, NH], [348: J6, CN, CN, NH], [349: J7, CN, CN, NH], [350: J8, CN, CN, NH], [351: J9, CN, CN, NH], [352: J10, CN, CN, NH], [353: H, C(CH₃)₃, H, NH], [354: F, C(CH₃)₃, H, NH], [355: Cl, C(CH₃)₃, H, NH], [356: Br, C(CH₃)₃, H, NH], [357: CH₃, C(CH₃)₃, H, NH], [358: CN, C(CH₃)₃, H, NH], [359: J1, C(CH₃)₃, H, NH], [360: J2, C(CH₃)₃, H, NH], [361: J3, C(CH₃)₃, H, NH], [362: J4, C(CH₃)₃, H, NH], [363: J5, C(CH₃)₃, H, NH], [364: J6, C(CH₃)₃, H, NH], [365: J7, C(CH₃)₃, H, NH], [366: J8, C(CH₃)₃, H, NH], [367: J9, C(CH₃)₃, H, NH], [368: J10, C(CH₃)₃, H, NH], [369: H, CF₃, H, NH], [370: F, CF₃, H, NH], [371: Cl, CF₃, H, NH], [372: Br, CF₃, H, NH], [373: CH₃, CF₃, H, NH], [374: CN, CF₃, H, NH], [375: J₁, CF₃, H, NH], [376: J2, CF₃, H, NH], [277: J3, CF₃, H, NH], [378: J4, CF₃, H, NH], [379: J5, CF₃, H, NH], [380: J6, CF₃, H, NH], [381: J7, CF₃, H, NH], [382: J8, CF₃, H, NH], [283: J9, CF₃, H, NH], [384: J10, CF₃, H, NH], [385: H, CF₂CF₃, H, NH], [286: F, CF₂CF₃, H, NH], [387: Cl, CF₂CF₃, H, NH], [388: Br, CF₂CF₃, H, NH], [389: CH₃, CF₂CF₃, H, NH], [390: CN, CF₂CF₃, H, NH], [391: J₁, CF₂CF₃, H, NH], [392: J2, CF₂CF₃, H, NH], [393: J3, CF₂CF₃, H, NH], [394: J4, CF₂CF₃, H, NH], [395: J5, CF₂CF₃, H, NH], [396: J6, CF₂CF₃, H, NH], [397: J7, CF₂CF₃, H, NH], [398: J8, CF₂CF₃, H, NH], [399: J9, CF₂CF₃, H, NH], [400: J10, CF₂CF₃, H, NH], [401: H, SCF₃, H, NH], [402: F, SCF₃, H, NH], [403: Cl, SCF₃, H, NH], [404: Br, SCF₃, H, NH], [405: CH₃, SCF₃, H, NH], [406: CN, SCF₃, H, NH], [407: J1, SCF₃, H, NH], [408: J2, SCF₃, H, NH], [409: J3, SCF₃, H, NH], [410: J4, SCF₃, H, NH], [411: J5, SCF₃, H, NH], [412: J6, SCF₃, H, NH], [413: J7, SCF₃, H, NH], [414: J8, SCF₃, H, NH], [415: J9, SCF₃, H, NH], [416: J10, SCF₃, H, NH], [417 SOCF₃, H, NH], [418: F, SOCF₃, H, NH], [419: Cl, SOCF₃, H, NH], [420: Br, SOCF₃, H, NH], [421: CH₃, SOCF₃, H, NH], [422: CN, SOCF₃, H, NH], [423: J1, SOCF₃, H, NH], [424: J2, SOCF₃, H, NH], [425: J3, SOCF₃, H, NH], [426: J4, SOCF₃, H, NH], [427: J5, SOCF₃, H, NH], [428: J6, SOCF₃, H, NH], [429: J7, SOCF₃, H, NH], [430: J8, SOCF₃, H, NH], [431: J9, SOCF₃, H, NH], [432: J10, SOCF₃, H, NH], [433: H, SO₂CF₃, H, NH], [434: F, SO₂CF₃, H, NH], [435: Cl, SO₂CF₃, H, NH], [436: Br, SO₂CF₃, H, NH], [437: CH₃, SO₂CF₃, H, NH], [438: CN, SO₂CF₃, H, NH], [439: J1, SO₂CF₃, H, NH], [440: J2, SO₂CF₃, H, NH], [441: J3, SO₂CF₃, H, NH], [442: J4, SO₂CF₃, H, NH], [443: J5, SO₂CF₃, H, NH], [444: J6, SO₂CF₃, H, NH], [445: J7, SO₂CF₃, H, NH], [446: J8, SO₂CF₃, H, NH], [447: J9, SO₂CF₃, H, NH], [448: J10, SO₂CF₃, H, NH], [449: H, CH₂C≡CH, H, NH], [450: F, CH₂C≡CH, H, NH], [451: Cl, CH₂C≡CH, H, NH], [452: Br, CH₂C≡CH, H, NH], [453: CH₃, CH₂C≡CH, H, NH], [454: CN, CH₂C≡CH, H, NH], [455: J1, CH₂C≡CH, H, NH], [456: J2, CH₂C≡CH, H, NH], [457: J3, CH₂C≡CH, H, NH], [458: J4, CH₂C≡CH, H, NH], [459: J5, CH₂C≡CH, H, NH], [460: J6, CH₂C≡CH, H, NH], [461: J7, CH₂C≡CH, H, NH], [462: J8, CH₂C≡CH, H, NH], [463: J9, CH₂C≡CH, H, NH], [464: J10, CH₂C≡CH, H, NH], [465: H, OCH₂C≡CH, H, NH], [466: F, OCH₂C≡CH, H, NH][467: Cl, OCH₂C≡CH, H, NH], [468: Br, OCH₂C≡CH, H, NH], [469: CH₃, OCH₂C≡CH, H, NH], [470: CN, OCH₂C≡CH, H, NH] [471: J1, OCH₂C≡CH, H, NH] [472: J2, OCH₂C≡CH, H, NH], [473: J3, OCH₂C≡CH, H, NH], [474: J4,

OCH₂C≡CH, H, NH], [475: J5, OCH₂C≡CH, H, NH], [476: J6, OCH₂C≡CH, H, NH], [477: J7, OCH₂C≡CH, H, NH], [478: J8, OCH₂C≡CH, H, NH], [479: J9, OCH₂C≡CH, H, NH], [480: J10, OCH₂C≡CH, H, NH], [481: H, Cl, H, NH], [482: F, Cl, H, NH.], [483: Cl, Cl, H, NH], [484: Br, Cl, H, NH], [485: CH₃, Cl, H, NH], [486: CN, Cl, H, NH], [487: J1, Cl, H, NH], [488: J2, Cl, H, NH], [489: J3, Cl, H, NH], [490: J4, Cl, H, NH], [491: J5, Cl, H, NH], [492: J6, Cl, H, NH], [493: J7, Cl, H, NH], [494: J8, Cl, H, NH], [495: J9, Cl, H, NH], [496: J10, Cl, H, NH], [497: H, C≡CH, H, NH], [498: F, C≡CH, H, NH], [499: Cl, C≡CH, H, NH], [500: Br, C≡CH, H, NH], [501: CH₃, C≡CH, H, NH], [502: CN, C≡CH, H, NH], [503: J1, C≡CH, H, NH], [504: J2, C≡CH, H, NH], [505: J3, C≡CH, H, NH], [506: J4, C≡CH, H, NH], [507: J5, C≡CH, H, NH], [508: J6, C≡CH, H, NH], [509: J7, C≡CH, H, NH], [510: J8, C≡CH, H, NH], [511: J9, C≡CH, H, NH], [512: J10, C≡CH, H, NH], [513: H, CN, H, NH], [514: F, CN, H, NH], [515: Cl, CN, H, NH], [516: Br, CN, H, NH], [517: CH₃, CN, H, NH], [518: CN, CN, H, NH], [519: J1, CN, H, NH], [520: J2, CN, H, NH], [521: J3, CN, H, NH], [522: J4, CN, H, NH], [523: J5, CN, H, NH], [524: J6, CN, H, NH], [525: J7, CN, H, NH], [526: J8, CN, H, NH], [527: J9, CN, H, NH], [528: J10, CN, H, NH], [529: H, C(CH₃)₃, CN, NH], [530: F, C(CH₃)₃, CN, NH], [531: Cl, C(CH₃)₃, CN, NH], [532: Br, C(CH₃)₃, CN, NH], [533: CH₃, C(CH₃)₃, CN, NH], [534: CN, C(CH₃)₃, CN, NH], [535: J1, C(CH₃)₃, CN, NH], [536: J2, C(CH₃)₃, CN, NH], [537: J3, C(CH₃)₃, CN, NH], [538: J4, C(CH₃)₃, CN, NH], [539: J5, C(CH₃)₃, CN, NH], [540: J6, C(CH₃)₃, CN, NH], [541: J7, C(CH₃)₃, CN, NH], [542: J8, C(CH₃)₃, CN, NH], [543: J9, C(CH₃)₃, CN, NH], [544: J10, C(CH₃)₃, CN, NH], [545: H, CF₃, CN, NH], [546: F, CF₃, CN, NH], [547: Cl, CF₃, CN, NH], [548: Br, CF₃, CN, NH], [549: CH₃, CF₃, CN, NH], [550: CN, CF₃, CN, NH], [551: J1, CF₃, CN, NH], [552: J2, CF₃, CN, NH], [553: J3, CF₃, CN, NH], [554: J4, CF₃, CN, NH], [555: J5, CF₃, CN, NH], [556: J6, CF₃, CN, NH], [557: J7, CF₃, CN, NH], [558: J8, CF₃, CN, NH], [559: J9, CF₃, CN, NH], [560: J10, CF₃, CN, NH], [561: H, CF₂CF₃, CN, NH], [562: F, CF₂CF₃, CN, NH], [563: Cl, CF₂CF₃, CN, NH], [564: Br, CF₂CF₃, CN, NH], [565: CH₃, CF₂CF₃, CN, NH][566: CN, CF₂CF₃, CN, NH], [567: J₁, CF₂CF₃, CN, NH][568: J2, CF₂CF₃, CN, NH], [569: J3, CF₂CF₃, CN, NH], [570: J4, CF₂CF₃, CN, NH], [571: J5, CF₂CF₃, CN, NH], [572: J6, CF₂CF₃, CN, NH], [573: J7, CF₂CF₃, CN, NH], [574: J8, CF₂CF₃, CN, NH], [575: J9, CF₂CF₃, CN, NH], [576: J10, CF₂CF₃, CN, NH], [577: H, SCF₃, CN, NH], [578: F, SCF₃, CN, NH], [579: Cl, SCF₃, CN, NH], [580: Br, SCF₃, CN, NH], [581: CH₃, SCF₃, CN, NH], [582: CN, SCF₃, CN, NH], [583: J1, SCF₃, CN, NH], [584: J2, SCF₃, CN, NH], [585: J3, SCF₃, CN, NH], [586: J4, SCF₃, CN, NH], [587: J5, SCF₃, CN, NH], [588: J6, SCF₃, CN, NH], [589: J7, SCF₃, CN, NH], [590: J8, SCF₃, CN, NH], [591: J9, SCF₃, CN, NH], [592: J10, SCF₃, CN, NH], [593: H, SOCF₃, CN, NH], [594: F, SOCF₃, CN, NH], [595: Cl, SOCF₃, CN, NH], [596: Br, SOCF₃, CN, NH], [597: CH₃, SOCF₃, CN, NH], [598: CN, SOCF₃, CN, NH], [599: J1, SOCF₃, CN, NH], [600: J2, SOCF₃, CN, NH], [601: J3, SOCF₃, CN, NH], [602: J4, SOCF₃, CN, NH], [603: J5, SOCF₃, CN, NH], [604: J6, SOCF₃, CN, NH], [605: J7, SOCF₃, CN, NH], [606: J8, SOCF₃, CN, NH], [607: J9, SOCF₃, CN, NH], [608: J10, SOCF₃, CN, NH], [609: H, SO₂CF₃, CN, NH], [610: F, SO₂CF₃, CN, NH], [611: Cl, SO₂CF₃, CN, NH], [612: Br, SO₂CF₃, CN, NH], [613: CH₃, SO₂CF₃, CN, NH], [614: CN, SO₂CF₃, CN, NH], [615: J₁, SO₂CF₃, CN, NH], [616: J2, SO₂CF₃, CN, NH], [617: J3, SO₂CF₃, CN, NH], [618: J4, SO₂CF₃, CN, NH], [619: J5, SO₂CF₃, CN, NH], [620: J6, SO₂CF₃, CN, NH], [621: J7, SO₂CF₃, CN, NH], [622: J8, SO₂CF₃, CN, NH], [623: J9, SO₂CF₃, CN, NH], [624: J10, SO₂CF₃, CN, NH][625: H, CH₂C≡CH, CN, NH], [626: F, CH₂C≡CH, CN, NH][627: Cl, CH₂C≡CH, CN, NH], [628: Br, CH₂C≡CH, CN, NH] [629: CH₃, CH₂C≡CH, CN, NH], [630: CN, CH₂C≡CH, CN, NH], [631: J₁, CH₂C≡CH, CN, NH], [632: J2, CH₂C≡CH, CN, NH], [633: J3, CH₂C≡CH, CN, NH], [634: J4, CH₂C≡CH, CN, NH], [635: J5, CH₂C≡CH, CN, NH], [636: J6, CH₂C≡CH, CN, NH], [637: J7, CH₂C≡CH, CN, NH], [638: J8, CH₂C≡CH, CN, NH], [639: J9, CH₂C≡CH, CN, NH], [640: J10, CH₂C≡CH, CN, NH] [641: H, OCH₂C≡CH, CN, NH], [642: F, OCH₂C≡CH, CN, NH][643: Cl, OCH₂C≡CH, CN, NH], [644: Br, OCH₂C≡CH, CN, NH], [645: CH₃, OCH₂C≡CH, CN, NH], [646: CN, OCH₂C≡CH, CN, NH], [647: J1, OCH₂C≡CH, CN, NH], [648: J2, OCH₂C≡CH, CN, NH], [649: J3, OCH₂C≡CH, CN, NH], [650: J4, OCH₂C≡CH, CN, NH], [651: J5, OCH₂C≡CH, CN, NH], [652: J6, OCH₂C≡CH, CN, NH], [653: J7, OCH₂C≡CH, CN, NH], [654: J8, OCH₂C≡CH, CN, NH], [655: J9, OCH₂C≡CH, CN, NH], [656: J10, OCH₂C≡CH, CN, NH], [657: H, Cl, CN, NH], [658: F, Cl, CN, NH], [659: Cl, Cl, CN, NH], [660: Br, Cl, CN, NH], [661: CH₃, Cl, CN, NH], [662: CN, Cl, CN, NH], [663: J1, Cl, CN, NH], [664: J2, Cl, CN, NH], [665: J3, Cl, CN, NH], [666: J4, Cl, CN, NH], [667: J5, Cl, CN, NH], [668: J6, Cl, CN, NH], [669: J7, Cl, CN, NH], [670: J8, Cl, CN, NH], [671: J9, Cl, CN, NH], [672: J10, Cl, CN, NH], [673: H, C≡CH, CN, NH], [674: F, C≡CH, CN, NH], [675: Cl, C≡CH, CN, NH], [676: Br, C≡CH, CN, NH], [677: CH₃, C≡CH, CN, NH], [678: CN, C≡CH, CN, NH], [679: J1, C≡CH, CN, NH], [680: J2, C≡CH, CN, NH], [681: J3, C≡CH, CN, NH], [682: J4, C≡CH, CN, NH], [683: J5, C≡CH, CN, NH], [684: J6, C≡CH, CN, NH], [685: J7, C≡CH, CN, NH], [686: J8, C≡CH, CN, NH], [687: J9, C≡CH, CN, NH], [688: J10, C≡CH, CN, NH], [689: H, C(CH₃)₃, H, NCH₃], [690: F, C(CH₃)₃, H, NCH₃], [691: Cl, C(CH₃)₃, H, NCH₃], [692: Br, C(CH₃)₃, H, NCH₃], [693: CH₃, C(CH₃)₃, H, NCH₃], [694: CN, C(CH₃)₃, H, NCH₃], [695: J1, C(CH₃)₃, H, NCH₃], [696: J2, C(CH₃)₃, H, NCH₃], [697: J3, C(CH₃)₃, H, NCH₃], [698: J4, C(CH₃)₃, H, NCH₃], [699: J5, C(CH₃)₃, H, NCH₃], [700: J6, C(CH₃)₃, H, NCH₃], [701: J7, C(CH₃)₃, H, NCH₃], [702: J8, C(CH₃)₃, H, NCH₃], [703: J9, C(CH₃)₃, H, NCH₃], [704: J10, C(CH₃)₃, H, NCH₃], [705: H, CF₃, H, NCH₃], [706: F, CF₃, H, NCH₃], [707: Cl, CF₃, H, NCH₃], [708: Br, CF₃, H, NCH₃], [709: CH₃, CF₃, H, NCH₃], [710: CN, CF₃, H, NCH₃], [711: J1, CF₃, H, NCH₃], [712: J2, CF₃, H, NCH₃], [713: J3, CF₃, H, NCH₃], [714: J4, CF₃, H, NCH₃], [715: J5, CF₃, H, NCH₃], [716: J6, CF₃, H, NCH₃], [717: J7, CF₃, H, NCH₃], [718: J8, CF₃, H, NCH₃], [719: J9, CF₃, H, NCH₃], [720: J10, CF₃, H, NCH₃], [721: H, CF₂CF₃, H, NCH₃], [722: F, CF₂CF₃, H, NCH₃], [723: Cl, CF₂CF₃, H, NCH₃], [724: Br, CF₂CF₃, H, NCH₃], [725: CH₃, CF₂CF₃, H, NCH₃], [726: CN, CF₂CF₃, H, NCH₃], [727: J1, CF₂CF₃, H, NCH₃], [728: J2, CF₂CF₃, H, NCH₃], [729: J3, CF₂CF₃, H, NCH₃], [730: J4, CF₂CF₃, H, NCH₃], [731: J5, CF₂CF₃, H, NCH₃], [732: J6, CF₂CF₃, H, NCH₃], [733: J7, CF₂CF₃, H, NCH₃], [734: J8, CF₂CF₃, H, NCH₃], [735: J9, CF₂CF₃, H, NCH₃], [736: J10, CF₂CF₃, H, NCH₃], [737: H, SCF₃, H, NCH₃], [738: F, SCF₃, H, NCH₃], [739: Cl, SCF₃, H, NCH₃], [740: Br, SCF₃, H, NCH₃], [741: CH₃, SCF₃, H, NCH₃], [742: CN, SCF₃, H, NCH₃], [743: J1, SCF₃, H, NCH₃], [744: J2, SCF₃, H, NCH₃], [745: J3, SCF₃, H, NCH₃], [746: J4, SCF₃, H, NCH₃], [747: J5, SCF₃, H, NCH₃], [748: J6, SCF₃, H, NCH₃], [749: J7, SCF₃, H, NCH₃], [750: J8, SCF₃, H, NCH₃], [751: J9, SCF₃, H, NCH₃], [752: J10, SCF₃, H, NCH₃], [753: H, SOCF₃, H, NCH₃], [754: F, SOCF₃, H, NCH₃], [755: Cl, SOCF₃, H, NCH₃], [756: Br, SOCF₃, H, NCH₃], [757: CH₃, SOCF₃, H,

NCH₃], [758: CN, SOCF₃, H, NCH₃], [759: J1, SOCF₃, H, NCH₃], [760: J2, SOCF₃, H, NCH₃], [761: J3, SOCF₃, H, NCH₃], [762: J4, SOCF₃, H, NCH₃], [763: J5, SOCF₃, H, NCH₃], [764: J6, SOCF₃, H, NCH₃], [765: J7, SOCF₃, H, NCH₃], [766: J8, SOCF₃, H, NCH₃], [767: J9, SOCF₃, H, NCH₃], [768: J10, SOCF₃, H, NCH₃], [769: H, SO₂CF₃, H, NCH₃], [770: F, SO₂CF₃, H, NCH₃], [771: Cl, SO₂CF₃, H, NCH₃], [772: Br, SO₂CF₃, H, NCH₃], [773: CH₃, SO₂CF₃, H, NCH₃], [774: CN, SO₂CF₃, H, NCH₃], [775: J1, SO₂CF₃, H, NCH₃], [776: J2, SO₂CF₃, H, NCH₃], [777: J3, SO₂CF₃, H, NCH₃], [778: J4, SO₂CF₃, H, NCH₃], [779: J5, SO₂CF₃, H, NCH₃], [780: J6, SO₂CF₃, H, NCH₃], [781: J7, SO₂CF₃, H, NCH₃], [782: J8, SO₂CF₃, H, NCH₃], [783: J9, SO₂CF₃, H, NCH₃], [784: J10, SO₂CF₃, H, NCH₃], [785: H, CH₂C≡CH, H, NCH₃], [786: F, CH₂C≡CH, H, NCH₃], [787: Cl, CH₂C≡CH, H, NCH₃], [788: Br, CH₂C≡CH, H, NCH₃], [789: CH₃, CH₂C≡CH, H, NCH₃], [790: CN, CH₂C≡CH, H, NCH₃], [791: J₁, CH₂C≡CH, H, NCH₃], [792: J2, CH₂C≡CH, H, NCH₃], [793: J3, CH₂C≡CH, H, NCH₃], [794: J4, CH₂C≡CH, H, NCH₃], [795: J5, CH₂C≡CH, H, NCH₃], [796: J6, CH₂C≡CH, H, NCH₃], [797: J7, CH₂C≡CH, H, NCH₃], [798: J8, CH₂C≡CH, H, NCH₃], [799: J9, CH₂C≡CH, H, NCH₃], [800: J10, CH₂C≡CH, H, NCH₃], [801: H, OCH₂C≡CH, H, NCH₃], [802: F, OCH₂C≡CH, H, NCH₃], [803: Cl, OCH₂C≡CH, H, NCH₃], [804: Br, OCH₂C≡CH, H, NCH₃], [805: CH₃, OCH₂C≡CH, H, NCH₃], [806: CN, OCH₂C≡CH, H, NCH₃], [807: J1, OCH₂C≡CH, H, NCH₃], [808: J2, OCH₂C≡CH, H, NCH₃], [809: J3, OCH₂C≡CH, H, NCH₃], [810: J4, OCH₂C≡CH, H, NCH₃], [811: J5, OCH₂C≡CH, H, NCH₃], [812: J6, OCH₂C≡CH, H, NCH₃], [813: J7, OCH₂C≡CH, H, NCH₃], [814: J8, OCH₂C≡CH, H, NCH₃], [815: J9, OCH₂C≡CH, H, NCH₃], [816: J10, OCH₂C≡CH, H, NCH₃], [817: H, Cl, H, NCH₃], [818: F, Cl, H, NCH₃], [819: Cl, Cl, H, NCH₃], [820: Br, Cl, H, NCH₃], [821: CH₃, Cl, H, NCH₃], [822: CN, Cl, H, NCH₃], [823: J1, Cl, H, NCH₃], [824: J2, Cl, H, NCH₃], [825: J3, Cl, H, NCH₃], [826: J4, Cl, H, NCH₃], [827: J5, Cl, H, NCH₃], [828: J6, Cl, H, NCH₃], [829: J7, Cl, H, NCH₃], [830: J8, Cl, H, NCH₃], [831: J9, Cl, H, NCH₃], [832: J10, Cl, H, NCH₃], [833: H, C≡CH, H, NCH₃], [834: F, C≡CH, H, NCH₃], [835: Cl, C≡CH, H, NCH₃], [836: Br, C≡CH, H, NCH₃], [837: CH₃, C≡CH, H, NCH₃], [838: CN, C≡CH, H, NCH₃], [839: J1, C≡CH, H, NCH₃], [840: J2, C≡CH, H, NCH₃], [841: J3, C≡CH, H, NCH₃], [842: J4, C≡CH, H, NCH₃], [843: J5, C≡CH, H, NCH₃], [844: J6, C≡CH, H, NCH₃], [845: J7, C≡CH, H, NCH₃], [846: J8, C≡CH, H, NCH₃], [847: J9, C≡CH, H, NCH₃], [848: J10, C≡CH, H, NCH₃], [849: H, CN, H, NCH₃], [850: F, CN, H, NCH₃], [851: Cl, CN, H, NCH₃], [852: Br, CN, H, NCH₃], [853: CH₃, CN, H, NCH₃], [854: CN, CN, H, NCH₃], [855: J1, CN, H, NCH₃], [856: J2, CN, H, NCH₃], [857: J3, CN, H, NCH₃], [858: J4, CN, H, NCH₃], [859: J5, CN, H, NCH₃], [860: J6, CN, H, NCH₃], [861: J7, CN, H, NCH₃], [862: J8, CN, H, NCH₃], [863: J9, CN, H, NCH₃], [864: J10, CN, H, NCH₃], [865: H, C(CH₃)₃, CN, NCH₃], [866: F, C(CH₃)₃, CN, NCH₃], [867: Cl, C(CH₃)₃, CN, NCH₃], [868: Br, C(CH₃)₃, CN, NCH₃], [869: CH₃, C(CH₃)₃, CN, NCH₃], [870: CN, C(CH₃)₃, CN, NCH₃], [871: J1, C(CH₃)₃, CN, NCH₃], [872: J2, C(CH₃)₃, CN, NCH₃], [873: J3, C(CH₃)₃, CN, NCH₃], [874: J4, C(CH₃)₃, CN, NCH₃], [875: J5, C(CH₃)₃, CN, NCH₃], [876: J6, C(CH₃)₃, CN, NCH₃], [877: J7, C(CH₃)₃, CN, NCH₃], [878: J8, C(CH₃)₃, CN, NCH₃], [879: J9, C(CH₃)₃, CN, NCH₃], [880: J10, C(CH₃)₃, CN, NCH₃], [881: H, CF₃, CN, NCH₃], [882: F, CF₃, CN, NCH₃], [883: Cl, CF₃, CN, NCH₃], [884: Br, CF₃, CN, NCH₃], [885: CH₃, CF₃, CN, NCH₃], [886: CN, CF₃, CN, NCH₃], [887: J1, CF₃, CN, NCH₃], [888: J2, CF₃, CN, NCH₃], [889: J3, CF₃, CN, NCH₃], [890: J4, CF₃, CN, NCH₃], [891: J5, CF₃, CN, NCH₃], [892: J6, CF₃, CN, NCH₃], [893: J7, CF₃, CN, NCH₃], [894: J8, CF₃, CN, NCH₃], [895: J9, CF₃, CN, NCH₃], [896: J10, CF₃, CN, NCH₃], [897: H, CF₂CF₃, CN, NCH₃], [898: F, CF₂CF₃, CN, NCH₃], [899: Cl, CF₂CF₃, CN, NCH₃], [900: Br, CF₂CF₃, CN, NCH₃], [901: CH₃, CF₂CF₃, CN, NCH₃], [902 CN, CF₂CF₃, CN, NCH₃], [903: J1, CF₂CF₃, CN, NCH₃], [904: J2, CF₂CF₃, CN, NCH₃], [905: J3, CF₂CF₃, CN, NCH₃], [906: J4, CF₂CF₃, CN, NCH₃], [907: J5, CF₂CF₃, CN, NCH₃], [908: J6, CF₂CF₃, CN, NCH₃], [909: J7, CF₂CF₃, CN, NCH₃], [910: J8, CF₂CF₃, CN, NCH₃], [911: J9, CF₂CF₃, CN, NCH₃], [912: J10, CF₂CF₃, CN, NCH₃], [913: H, SCF₃, CN, NCH₃], [914: F, SCF₃, CN, NCH₃], [915: Cl, SCF₃, CN, NCH₃], [916: Br, SCF₃, CN, NCH₃], [917: CH₃, SCF₃, CN, NCH₃], [918: CN, SCF₃, CN, NCH₃], [919: J1, SCF₃, CN, NCH₃], [920: J2, SCF₃, CN, NCH₃], [921: J3, SCF₃, CN, NCH₃], [922: J4, SCF₃, CN, NCH₃], [923: J5, SCF₃, CN, NCH₃], [924: J6, SCF₃, CN, NCH₃], [925: J7, SCF₃, CN, NCH₃], [926: J8, SCF₃, CN, NCH₃], [927: J9, SCF₃, CN, NCH₃], [928: J10, SCF₃, CN, NCH₃], [929: H, SOCF₃, CN, NCH₃], [930: F, SOCF₃, CN, NCH₃], [931: Cl, SOCF₃, CN, NCH₃], [932: Br, SOCF₃, CN, NCH₃], [933: CH₃, SOCF₃, CN, NCH₃], [934: CN, SOCF₃, CN, NCH₃], [935: J1, SOCF₃, CN, NCH₃], [936: J2, SOCF₃, CN, NCH₃], [937: J3, SOCF₃, CN, NCH₃], [938: J4, SOCF₃, CN, NCH₃], [939: J5, SOCF₃, CN, NCH₃], [940: J6, SOCF₃, CN, NCH₃], [941: J7, SOCF₃, CN, NCH₃], [942: J8, SOCF₃, CN, NCH₃], [943: J9, SOCF₃, CN, NCH₃], [944: J10, SOCF₃, CN, NCH₃], [945: H, SO₂CF₃, CN, NCH₃], [946: F, SO₂CF₃, CN, NCH₃], [947: Cl, SO₂CF₃, CN, NCH₃], [948: Br, SO₂CF₃, CN, NCH₃], [949: CH₃, SO₂CF₃, CN, NCH₃], [950: CN, SO₂CF₃, CN, NCH₃], [951: J₁, SO₂CF₃, CN, NCH₃], [952: J2, SO₂CF₃, CN, NCH₃], [953: J3, SO₂CF₃, CN, NCH₃], [954: J4, SO₂CF₃, CN, NCH₃], [955: J5, SO₂CF₃, CN, NCH₃], [956: J6, SO₂CF₃, CN, NCH₃], [957: J7, SO₂CF₃, CN, NCH₃], [958: J8 SO₂CF₃, CN, NCH₃], [959: J9, SO₂CF₃, CN, NCH₃], [960: J10, SO₂CF₃, CN, NCH₃], [961: H, CH₂C≡CH, CN, NCH₃], [962: F, CH₂C≡CH, CN, NCH₃], [963: Cl, CH₂C≡CH, CN, NCH₃], [964: Br, CH₂C≡CH, CN, NCH₃], [965: CH₃, CH₂C≡CH, CN, NCH₃], [966: CN, CH₂C≡CH, CN, NCH₃], [967: J1, CH₂C≡CH, CN, NCH₃], [968: J2, CH₂C≡CH, CN, NCH₃], [969: J3, CH₂C≡CH, CN, NCH₃], [970: J4, CH₂C≡CH, CN, NCH₃], [971: J5, CH₂C≡CH, CN, NCH₃], [972: J6, CH₂C≡CH, CN, NCH₃], [973: J7, CH₂C≡CH, CN, NCH₃], [974: J8, CH₂C≡CH, CN, NCH₃], [975: J9, CH₂C≡CH, CN, NCH₃], [976: J10, CH₂C≡CH, CN, NCH₃], [977: H, OCH₂C≡CH, CN, NCH₃], [978: F, OCH₂C≡CH, CN, NCH₃], [979: Cl, OCH₂C≡CH, CN, NCH₃], [980: Br, OCH₂C≡CH, CN, NCH₃], [981: CH₃, OCH₂C≡CH, CN, NCH₃], [982: CN, OCH₂C≡CH, CN, NCH₃], [983: J1, OCH₂C≡CH, CN, NCH₃], [984: J2, OCH₂C≡CH, CN, NCH₃], [985: J3, OCH₂C≡CH, CN, NCH₃], [986: J4, OCH₂C≡CH, CN, NCH₃], [987: J5, OCH₂C≡CH, CN, NCH₃], [988: J6, OCH₂C≡CH, CN, NCH₃], [989: J7, OCH₂C≡CH, CN, NCH₃], [990: J8, OCH₂C≡CH, CN, NCH₃], [991: J9, OCH₂C≡CH, CN, NCH₃], [992: J10, OCH₂C≡CH, CN, NCH₃], [993: H, Cl, CN, NCH₃], [994: F, Cl, CN, NCH₃], [995: Cl, Cl, CN, NCH₃], [996: Br, Cl, CN, NCH₃], [997: CH₃, Cl, CN, NCH₃], [998: CN, Cl, CN, NCH₃], [999: J1, Cl, CN, NCH₃], [1000: J2, Cl, CN, NCH₃], [1001: J3, Cl, CN, NCH₃], [1002: J4, Cl, CN, NCH₃], [1003: J5, Cl, CN, NCH₃], [1004: J6, Cl, CN, NCH₃], [1005: J7, Cl, CN, NCH₃], [1006: J8, Cl, CN, NCH₃], [1007: J9, Cl, CN, NCH₃], [1008: J10, Cl, CN, NCH₃], [1009: H, C≡CH, CN, NCH₃], [1010: F, C≡CH, CN, NCH₃],

[1011: Cl, C≡CH, CN, NCH₃], [1012: Br, CN, NCH₃], [1013: CH₃, C≡CH, CN, NCH₃], [1014: CN, C≡CH, CN, NCH₃], [1015: J1, C≡CH, CN, NCH₃], [1016: J2, C≡CH, CN, NCH₃], [1017: J3, C≡CH, CN, NCH₃], [1018: J4, C≡CH, CN, NCH₃], [1019: J5, C≡CH, CN, NCH₃], [1020: J6, C≡CH, CN, NCH₃], [1021: J7, CN, NCH₃], [1022: J8, C≡CH, CN, NCH₃], [1023: J9, C≡CH, CN, NCH₃], [1024: J10, C≡CH, CN, NCH₃], [1025: H, CN, CN, NCH₃], [1026: F, CN, CN, NCH₃], [1027: Cl, CN, CN, NCH₃], [1028: Br, CN, CN, NCH₃], [1029: CH₃, CN, CN, NCH₃], [1030: CN, CN, CN, NCH₃], [1031: J1, CN, CN, NCH₃], [1032: J2, CN, CN, NCH₃], [1033: J3, CN, CN, NCH₃], [1034: J4, CN, CN, NCH₃], [1035: J5, CN, CN, NCH₃], [1036: J6, CN, CN, NCH₃], [1037: J7, CN, CN, NCH₃], [1038: J8, CN, CN, NCH₃], [1039: J9, CN, CN, NCH₃], [1040: J10, CN, CN, NCH₃], [1041: H, C(CH₃)₃, H, NCH₃], [1042: F, C(CH₃)₃, H, NCH₃], [1043: Cl, C(CH₃)₃, H, NCH₃], [1044: Br, C(CH₃)₃, H, NCH₃], [1045: CH₃, C(CH₃)₃, H, NCH₃], [1046: CN, C(CH₃)₃, H, NCH₃], [1047: J1, C(CH₃)₃, H, NCH₃], [1048: J2, C(CH₃)₃, H, NCH₃], [1049: J3, C(CH₃)₃, H, NCH₃], [1050: J4, C(CH₃)₃, H, NCH₃], [1051: J5, C(CH₃)₃, H, NCH₃], [1052: J6, C(CH₃)₃, H, NCH₃], [1053: J7, C(CH₃)₃, H, NCH₃], [1054: J8, C(CH₃)₃, H, NCH₃], [1055: J9, C(CH₃)₃, H, NCH₃], [1056: J10, C(CH₃)₃, H, NCH₃], [1057: H, CF₃, H, NCH₃], [1058: F, CF₃, H, NCH₃], [1059: Cl, CF₃, H, NCH₃], [1060: Br, CF₃, H, NCH₃], [1061: CH₃, CF₃, H, NCH₃], [1062: CN, CF₃, H, NCH₃], [1063: J1, CF₃, H, NCH₃], [1064: J2, CF₃, H, NCH₃], [1065: J3, CF₃, H, NCH₃], [1066: J4, CF₃, H, NCH₃], [1067: J5, CF₃, H, NCH₃], [1068: J6, CF₃, H, NCH₃], [1069: J7, CF₃, H, NCH₃], [1070: J8, CF₃, H, NCH₃], [1071: J9, CF₃, H, NCH₃], [1072: J10, CF₃, H, NCH₃], [1073: H, CF₂CF₃, H, NCH₃], [1074: F, CF₂CF₃, H, NCH₃], [1075: Cl, CF₂CF₃, H, NCH₃], [1076: Br, CF₂CF₃, H, NCH₃], [1077: CH₃, CF₂CF₃, H, NCH₃], [1078: CN, CF₂CF₃, H, NCH₃], [1079: J1, CF₂CF₃, H, NCH₃], [1080: J2, CF₂CF₃, H, NCH₃], [1081: J3, CF₂CF₃, H, NCH₃], [1082: J4, CF₂CF₃, H, NCH₃], [1083: J5, CF₂CF₃, H, NCH₃], [1084: J6, CF₂CF₃, H, NCH₃], [1085: J7, CF₂CF₃, H, NCH₃], [1086: J8, CF₂CF₃, H, NCH₃], [1087: J9, CF₂CF₃, H, NCH₃], [1088: J10, CF₂CF₃, H, NCH₃], [1089: H, SCF₃, H, NCH₃], [1090: F, SCF₃, H, NCH₃], [1091: Cl, SCF₃, H, NCH₃], [1092: Br, SCF₃, H, NCH₃], [1093: CH₃, SCF₃, H, NCH₃], [1094: CN, SCF₃, H, NCH₃], [1095: J1, SCF₃, H, NCH₃], [1096: J2, SCF₃, H, NCH₃], [1097: J3, SCF₃, H, NCH₃], [1098: J4, SCF₃, H, NCH₃], [1099: J5, SCF₃, H, NCH₃], [1100: J6, SCF₃, H, NCH₃], [1101: J7, SCF₃, H, NCH₃], [1102: J8, SCF₃, H, NCH₃], [1103: J9, SCF₃, H, NCH₃], [1104: J10, SCF₃, H, NCH₃], [1105: H, SOCF₃, H, NCH₃], [1106: F, SOCF₃, H, NCH₃], [1107: Cl, SOCF₃, H, NCH₃], [1108: Br, SOCF₃, H, NCH₃], [1109: CH₃, SOCF₃, H, NCH₃], [1110: CN, SOCF₃, H, NCH₃], [1111: J1, SOCF₃, H, NCH₃], [1112: J2, SOCF₃, H, NCH₃], [1113: J3, SOCF₃, H, NCH₃], [1114: J4, SOCF₃, H, NCH₃], [1115: J5, SOCF₃, H, NCH₃], [1116: J6, SOCF₃, H, NCH₃], [1117: J7, SOCF₃, H, NCH₃], [1118: J8, SOCF₃, H, NCH₃], [1119: J9, SOCF₃, H, NCH₃], [1120: J10, SOCF₃, H, NCH₃], [1121: H, SO2CF₃, H, NCH₃], [1122: F, SO2CF₃, H, NCH₃], [1123: Cl, SO2CF₃, H, NCH₃], [1124: Br, SO2CF₃, H, NCH₃], [1125: CH₃, SO2CF₃, H, NCH₃], [1126: CN, SO2CF₃, H, NCH₃], [1127: J1, SO2CF₃, H, NCH₃], [1128: J2, SO2CF₃, H, NCH₃], [1129: J3, SO2CF₃, H, NCH₃], [1130: J4, SO2CF₃, H, NCH₃], [1131: J5, SO2CF₃, H, NCH₃], [1132: J6, SO2CF₃, H, NCH₃], [1133: J7, SO2CF₃, H, NCH₃], [1134: J8, SO2CF₃, H, NCH₃], [1135: J9, SO2CF₃, H, NCH₃], [1136: J10, SO2CF₃, H, NCH₃], [1137: H, CH₂C≡CH, H, NCH₃], [1138: F, CH₂C≡CH, H, NCH₃], [1139: Cl, CH₂C≡CH, H, NCH₃], [1140: Br, CH₂C≡CH, H, NCH₃], [1141: CH₃, CH₂C≡CH, H, NCH₃], [1142: CN, CH₂C≡CH, H, NCH₃], [1143: J1, CH₂C≡CH, H, NCH₃], [1144: J2, CH₂C≡CH, H, NCH₃], [1145: J3, CH₂C≡CH, H, NCH₃], [1146: J4, CH₂C≡CH, H, NCH₃], [1147: J5, CH₂C≡CH, H, NCH₃], [1148: J6, CH₂C≡CH, H, NCH₃], [1149: J7, CH₂C≡CH, H, NCH₃], [1150: J8, CH₂C≡CH, H, NCH₃], [1151: J9, CH₂C≡CH, H, NCH₃], [1152: J10, CH₂C≡CH, H, NCH₃], [1153: H, OCH₂C≡CH, H, NCH₃], [1154: F OCH₂C H, NCH₃], [1155: Cl, OCH₂C≡CH, H, NCH₃], [1156: Br, OCH₂C≡CH, H, NCH₃], [1157: CH₃, OCH₂C≡CH, H, NCH₃], [1158: CN, OCH₂C≡CH, H, NCH₃], [1159: J1, OCH₂C≡CH, H, NCH₃], [1160: J2, OCH₂C≡CH, H, NCH₃], [1161: J3, OCH₂C≡CH, H, NCH₃], [1162: J4, OCH₂C≡CH, H, NCH₃], [1163: J5, OCH₂C≡CH, H, NCH₃], [1164: J6, OCH₂C≡CH, H, NCH₃], [1165: J7, OCH₂C≡CH, H, NCH₃], [1166: J8, OCH₂C≡CH, H, NCH₃], [1167: J9, OCH₂C≡CH, H, NCH₃], [1168: J10 OCH₂C≡CH H, NCH₃], [1169: H Cl, H, NCH₃], [1170: F, Cl, H, NCH₃], [1171: Cl, Cl, H, NCH₃], [1172: Br, Cl, H, NCH₃], [1173: CH₃, Cl, H, NCH₃], [1174: CN, Cl, H, NCH₃], [1175: J1, Cl, H, NCH₃], [1176: J2, Cl, H, NCH₃], [1177: J3, Cl, H, NCH₃], [1178: J4, Cl, H, NCH₃], [1179: J5, Cl, H, NCH₃], [1180: J6, Cl, H, NCH₃], [1181: J7, Cl, H, NCH₃], [1182: J8, Cl, H, NCH₃], [1183: J9, Cl, H, NCH₃], [1184: J10, Cl, H, NCH₃], [1185: H, C≡CH, H, NCH₃], [1186: F, C≡CH, H, NCH₃], [1187: Cl, C≡CH, H, NCH₃], [1188: Br, H, NCH₃], [1189: CH₃, C≡CH, H, NCH₃], [1190: CN, C≡CH, H, NCH₃], [1191: J1, C≡CH, H, NCH₃], [1192: J2, C≡CH, H, NCH₃], [1195: J3, C≡CH, H, NCH₃], [1194: J4, C≡CH, H, NCH₃], [1195: J5, C≡CH, H, NCH₃], [1196: J6, C≡CH, H, NCH₃], [1197: J7, C≡CH, H, NCH₃], [1198: J8, C≡CH, H, NCH₃], [1199: J9, C≡CH, H, NCH₃], [1200: J10, C≡CH, H, NCH₃], [1201: H, CN, H, NCH₃], [1202: F, CN, H, NCH₃], [1203: Cl, CN, H, NCH₃], [1204: Br, CN, H, NCH₃], [1205: CH₃, CN, H, NCH₃], [1206: CN, CN, H, NCH₃], [1207: J1, CN, H, NCH₃], [1208: J2, CN, H, NCH₃], [1209: J3, CN, H, NCH₃], [1210: J4, CN, H, NCH₃], [1211: J5, CN, H, NCH₃], [1212: J6, CN, H, NCH₃], [1213: J7, CN, H, NCH₃], [1214: J8, CN, H, NCH₃], [1215: J9, CN, H, NCH₃], [1216: J10, CN, H, NCH₃], [1217: H, C(CH₃)₃, CN, NCH₃], [1218: F, C(CH₃)₃, CN, NCH₃], [1219: Cl, C(CH₃)₃, CN, NCH₃], [1220: Br, C(CH₃)₃, CN, NCH₃], [1221: CH₃, C(CH₃)₃, CN, NCH₃], [1222: CN, C(CH₃)₃, CN, NCH₃], [1223: J1, C(CH₃)₃, CN, NCH₃], [1224: J2, C(CH₃)₃, CN, NCH₃], [1225: J3, C(CH₃)₃, CN, NCH₃], [1226: J4, C(CH₃)₃, CN, NCH₃], [1227: J5, C(CH₃)₃, CN, NCH₃], [1228: J6, C(CH₃)₃, CN, NCH₃], [1229: J7, C(CH₃)₃, CN, NCH₃], [1230: J8, C(CH₃)₃, CN, NCH₃], [1231: J9, C(CH₃)₃, CN, NCH₃], [1232: J10, C(CH₃)₃, CN, NCH₃], [1233: H, CF₃, CN, NCH₃], [1234: F, CF₃, CN, NCH₃], [1235: Cl, CF₃, CN, NCH₃], [1236: Br, CF₃, CN, NCH₃], [1237: CH₃, CF₃, CN, NCH₃], [1238: CN, CF₃, CN, NCH₃], [1239: J₁, CF₃, CN, NCH₃], [1240: J2, CF₃, CN, NCH₃], [1241: J3, CF₃, CN, NCH₃], [1242: J4, CF₃, CN, NCH₃], [1243: J5, CF₃, CN, NCH₃], [1244: J6, CF₃, CN, NCH₃], [1245: J7, CF₃, CN, NCH₃], [1246: J8, CF₃, CN, NCH₃], [1247: J9, CF₃, CN, NCH₃], [1248: J10, CF₃, CN, NCH₃], [1249: H, CF₂CF₃, CN, NCH₃], [1250: F, CF₂CF₃, CN, NCH₃], [1251: Cl, CF₂CF₃, CN, NCH₃], [1252: Br, CF₂CF₃, CN, NCH₃], [1253: CH₃ CF₂CF₃, CN, NCH₃], [1254: CN, CF₂CF₃, CN, NCH₃], [1255 CF₂CF₃, CN, NCH₃], [1256: J2, CF₂CF₃, CN, NCH₃], [1257: J3, CF₂CF₃, CN, NCH₃], [1258: J4, CF₂CF₃, CN, NCH₃], [1259: J5, CF₂CF₃, CN, NCH₃], [1260: J6, CF₂CF₃, CN, NCH₃], [1261: J7, CF₂CF₃, CN, NCH₃], [1262: J8, CF₂CF₃, CN, NCH₃], [1263: J9, CF₂CF₃, CN, NCH₃], [1264: J10, CF₂CF₃, CN, NCH₃], [1265: H, SCF₃, CN, NCH₃], [1266: F, SCF₃, CN, NCH₃], [1267: Cl, SCF₃, CN, NCH₃],

[1268: Br, SCF₃, CN, NCH₃], [1269: CH₃, SCF₃, CN, NCH₃], [1270: CN, SCF₃, CN, NCH₃], [1271: J1, SCF₃, CN, NCH₃], [1272: J2, SCF₃, CN, NCH₃], [1273: J3, SCF₃, CN, NCH₃], [1274: J4, SCF₃, CN, NCH₃], [1275: J5, SCF₃, CN, NCH₃], [1276: J6, SCF₃, CN, NCH₃], [1277: J7, SCF₃, CN, NCH₃], [1278: J8, SCF₃, CN, NCH₃], [1279: J9, SCF₃, CN, NCH₃], [1280: J10, SCF₃, CN, NCH₃], [1281: H, SOCF₃, CN, NCH₃], [1282: F, SOCF₃, CN, NCH₃], [1283: Cl, SOCF₃, CN, NCH₃], [1284: Br, SOCF₃, CN, NCH₃], [1285: CH₃, SOCF₃, CN, NCH₃], [1286: CN, SOCF₃, CN, NCH₃], [1287: J1, SOCF₃, CN, NCH₃], [1288: J2, SOCF₃, CN, NCH₃], [1289: J3, SOCF₃, CN, NCH₃], [1290: J4, SOCF₃, CN, NCH₃], [1291: J5, SOCF₃, CN, NCH₃], [1292: J6, SOCF₃, CN, NCH₃], [1293: J7, SOCF₃, CN, NCH₃], [1294: J8, SOCF₃, CN, NCH₃], [1295: J9, SOCF₃, CN, NCH₃], [1296: J10, SOCF₃, CN, NCH₃], [1297: H, SO2CF₃, CN, NCH₃], [1298: F, SO2CF₃, CN, NCH₃], [1299: Cl, SO2CF₃, CN, NCH₃], [1300: Br, SO2CF₃, CN, NCH₃], [1301: CH₃, SO2CF₃, CN, NCH₃], [1302: CN, SO2CF₃, CN, NCH₃], [1303: J1, SO2CF₃, CN, NCH₃], [1304: J2, SO2CF₃, CN, NCH₃], [1305: J3, SO2CF₃, CN, NCH₃], [1306: J4, SO2CF₃, CN, NCH₃], [1307: J5, SO2CF₃, CN, NCH₃], [1308: J6, SO2CF₃, CN, NCH₃], [1309: J7, SO2CF₃, CN, NCH₃], [1310: J8, SO2CF₃, CN, NCH₃], [1311: J9, SO2CF₃, CN, NCH₃], [1312: J10, SO2CF₃, CN, NCH₃], [1313: H, CH₂C≡CH, CN, NCH₃], [1314: F, CH₂C≡CH, CN, NCH₃], [1315: Cl, CH₂C≡CH, CN, NCH₃], [1316: Br, CH₂C≡CH, CN, NCH₃], [1317: CH₃, CH₂C≡CH, CN, NCH₃], [1318: CN, CH₂C≡CH, CN, NCH₃], [1319: J1, CH₂C≡CH, CN, NCH₃], [1320: J2, CH₂C≡CH, CN, NCH₃], [1321: J3, CH₂C≡CH, CN, NCH₃], [1322: J4, CH₂C≡CH, CN, NCH₃], [1323: J5, CH₂C≡CH, CN, NCH₃], [1324: J6, CH₂C≡CH, CN, NCH₃], [1325: J7, CH₂C≡CH, CN, NCH₃], [1326: J8, CH₂C≡CH, CN, NCH₃], [1327: J9, CH₂C≡CH, CN, NCH₃], [1328: J10, CH₂C≡CH, CN, NCH₃], [1329: H, OCH₂C≡CH, CN, NCH₃], [1330: F, OCH₂C≡CH, CN, NCH₃], [1331: Cl, OCH₂C≡CH, CN, NCH₃], [1332: Br, OCH₂C≡CH, CN, NCH₃], [1333: CH₃, OCH₂C≡CH, CN, NCH₃], [1334: CN, OCH₂C≡CH, CN, NCH₃], [1335: J1, OCH₂C≡CH, CN, NCH₃], [1336: J2, OCH₂C≡CH, CN, NCH₃], [1337: J3, OCH₂C≡CH, CN, NCH₃], [1338: J4, OCH₂C≡CH, CN, NCH₃], [1339: J5, OCH₂C≡CH, CN, NCH₃]. [1340: J6, OCH₂C≡CH, CN, NCH₃], [1341: J7, OCH₂C≡CH, CN, NCH₃], [1342: J8, OCH₂C≡CH, CN, NCH₃], [1343: J9, OCH₂C≡CH, CN, NCH₃], [1344: J10, OCH₂C≡CH, CN, NCH₃], [1345: H, Cl, CN, NCH₃], [1346: F, Cl, CN, NCH₃], [1347: Cl, Cl, CN, NCH₃], [1348: Br, Cl, CN, NCH₃], [1349: CH₃, Cl, CN, NCH₃], [1350: CN, Cl, CN, NCH₃], [1351: J1, Cl, CN, NCH₃], [1352: J2, Cl, CN, NCH₃], [1353: J3, Cl, CN, NCH₃], [1354: J4, Cl, CN, NCH₃], [1355: J5, Cl, CN, NCH₃], [1356: J6, Cl, CN, NCH₃], [1357: J7, Cl, CN, NCH₃], [1358: J8, Cl, CN, NCH₃], [1359: J9, Cl, CN, NCH₃], [1360: J10, Cl, CN, NCH₃], [1361: H, C≡CH, CN, NCH₃], [1362: F, C≡CH, CN, NCH₃], [1363: Cl, C≡CH, CN, NCH₃], [1364: Br, C≡CH, CN, NCH₃], [1365: CH₃, C≡CH, CN, NCH₃], [1366: CN, C≡CH, CN, NCH₃], [1367: J1, C≡CH, CN, NCH₃], [1368: J2, C≡CH, CN, NCH₃], [1369: J3, C≡CH, CN, NCH₃], [1370: J4, C≡CH, CN, NCH₃], [1371: J5, C≡CH, CN, NCH₃], [1372: J6, C≡CH, CN, NCH₃], [1373: J7, C≡CH, CN, NCH₃], [1374: J8, C≡CH, CN, NCH₃], [1375: J9, C≡CH, CN, NCH₃], [1376: J10, C≡CH, CN, NCH₃], [1377: H, C(CH₃)₃, H, S], [1378: F, C(CH₃)₃, H, S], [1379: Cl, C(CH₃)₃, H, S], [1380: Br, C(CH₃)₃, H, S], [1381: CH₃, C(CH₃)₃, H, S], [1382: CN, C(CH₃)₃, H, S], [1383: J1, C(CH₃)₃, H, S], [1384: J2, C(CH₃)₃, H, S], [1385: J3, C(CH₃)₃, H, S], [1386: J4, C(CH₃)₃, H, S], [1387: J5, C(CH₃)₃, H, S], [1388: J6, C(CH₃)₃, H, S], [1389: J7, C(CH₃)₃, H, S], [1390: J8, C(CH₃)₃, H, S], [1391: J9, C(CH₃)₃, H, S], [1392: J10, C(CH₃)₃, H, S], [1393: H, CF₃, H, S], [1394: F, CF₃, H, S], [1395: Cl, CF₃, H, S], [1396: Br, CF₃, H, S], [1397: CH₃, CF₃, H, S], [1398: CN, CF₃, H, S], [1399: J1, CF₃, H, S], [1400: J2, CF₃, H, S], [1401: J3, CF₃, H, S], [1402: J4, CF₃, H, S], [1403: J5, CF₃, H, S], [1404: J6, CF₃, H, S], [1405: J7, CF₃, H, S], [1406: J8, CF₃, H, S], [1407: J9, CF₃, H, S], [1408: J10, CF₃, H, S], [1409: H, CF₂CF₃, H, S], [1410: F, CF₂CF₃, H, S], [1411: Cl, CF₂CF₃, H, S], [1412: Br, CF₂CF₃, H, S], [1413: CH₃, CF₂CF₃, H, S], [1414: CN, CF₂CF₃, H, S], [1415: J1, CF₂CF₃, H, S], [1416: J2, CF₂CF₃, H, S], [1417: J3, CF₂CF₃, H, S], [1418: J4, CF₂CF₃, H, S], [1419: J5, CF₂CF₃, H, S], [1420: J6, CF₂CF₃, H, S], [1421: J7, CF₂CF₃, H, S], [1422: J8, CF₂CF₃, H, S], [1423: J9, CF₂CF₃, H, S], [1424: J10, CF₂CF₃, H, S], [1425: H, SCF₃, H, S], [1426: F, SCF₃, H, S], [1427: Cl, SCF₃, H, S], [1428: Br, SCF₃, H, S], [1429: CH₃, SCF₃, H, S], [1430: CN, SCF₃, H, S], [1431: J1, SCF₃, H, S], [1432: J2, SCF₃, H, S], [1433: J3, SCF₃, H, S], [1434: J4, SCF₃, H, S], [1435: J5, SCF₃, H, S], [1436: J6, SCF₃, H, S], [1437: j7, SCF₃, H, S], [1438: J8, SCF₃, H, S], [1439: J9, SCF₃, H, S], [1440: J10, SCF₃, H, S], [1441: H, SOCF₃, H, S], [1442: F, SOCF₃, H, S], [1443: Cl, SOCF₃, H, S], [1444: Br, SOCF₃, H, S], [1445: CH₃, SOCF₃, H, S], [1446: CN, SOCF₃, H, S], [1447: J1, SOCF₃, H, S], [1448: J2, SOCF₃, H, S], [1449: J3, SOCF₃, H, S], [1450: J4, SOCF₃, H, S], [1451: J5, SOCF₃, H, S], [1452: J6, SOCF₃, H, S], [1453: J7, SOCF₃, H, S], [1454: J8, SOCF₃, H, S], [1455: J9, SOCF₃, H, S], [1456: J10, SOCF₃, H, S], [1457: H, SO2CF₃, H, S], [1458: F, SO2CF₃, H, S], [1459: Cl, SO2CF₃, H, S], [1460: Br, SO2CF₃, H, S], [1461: CH₃, SO2CF₃, H, S], [1462: CN, SO2CF₃, H, S], [1463: J1, SO2CF₃, H, S], [1464: J2, SO2CF₃, H, S], [1465: J3, SO2CF₃, H, S], [1466: J4, SO2CF₃, H, S], [1467: J5, SO2CF₃, H, S], [1468: J6, SO2CF₃, H, S], [1469: J7, SO2CF₃, H, S], [1470: J8, SO2CF₃, H, S][1471: J9, SO2CF₃, H, S], [1472: J10, SO2CF₃, H, S], [1473: H, CH₂C≡CH, H, S], [1474: F, CH₂C≡CH, H, S][1475: Cl, CH₂C≡CH, H, S], [1476: Br, CH₂C≡CH, H, S], [1477: CH₃, CH₂C≡CH, H, S], [1478: CN, CH₂C≡CH, H, S], [1479: J1, CH₂C≡CH, H, S], [1480: J2, CH₂C≡CH, H, S], [1481: J3, CH₂C≡CH, H, S], [1482: J4, CH₂C≡CH, H, S], [1483: J5, CH₂C≡CH, H, S], [1484: J6, CH₂C≡CH, H, S], [1485: J7, CH₂C≡CH, H, S], [1486: J8, CH₂C≡CH, H, S], [1487: J9, CH₂C≡CH, H, S], [1488: J10, CH₂C≡CH, H, S], [1489: H, OCH₂C≡CH, H, S], [1490: F, OCH₂C≡CH, H, S], [1491: Cl, OCH₂C≡CH, H, S], [1492: Br, OCH₂C≡CH, H, S], [1493: CH₃, OCH₂C≡CH, H, S], [1494: CN, OCH₂C≡CH, H, S], [1495: J1, OCH₂C≡CH, H, S], [1496: J2, OCH₂C≡CH, H, S], [1497: J3, OCH₂C≡CH, H, S], [1498: J4, OCH₂C≡CH, H, S], [1499: J5, OCH₂C≡CH, H, S], [1500: J6, OCH₂C≡CH, H, S], [1501: J7, OCH₂C≡CH, H, S], [1502: J8, OCH₂C≡CH, H, S], [1503: J9, OCH₂C≡CH, H, S], [1504: J10, OCH₂C≡CH, H, S], [1505: H, Cl, H, S], [1506: F, Cl, H, S], [1507: Cl, Cl, H, S], [1508: Br, Cl, H, S], [1509: CH₃, Cl, H, S], [1510: CN, Cl, H, S], [1511: J1, Cl, H, S], [1512: J2, Cl, H, S], [1513: J3, Cl, H, S], [1514: J4, Cl, H, S], [1515: J5, Cl, H, S], [1516: J6, Cl, H, S], [1517: J7, Cl, H, S], [1518: J8, Cl, H, S], [1519: J9, Cl, H, S], [1520: J10, Cl, H, S], [1521: H, C≡CH, H, S], [1522: F, C≡CH, H, S], [1523: Cl, C≡CH, H, S], [1524: Br, C≡CH, H, S], [1525: CH₃, C≡CH, H, S], [1526: CN, C≡CH, H, S], [1527: J1, C≡CH, H, S], [1528: J2, C≡CH, H, S], [1529: J3, C≡CH, H, S], [1530: J4, C≡CH, H, S], [1531: J5, C≡CH, H, S], [1532: J6, C≡CH, H, S], [1533: J7, C≡CH, H, S], [1534: J8, C≡CH, H, S], [1535: J9, C≡CH, H, S], [1536: J10, C≡CH, H, S], [1537: H, CN, H, S], [1538: F, CN, H, S], [1539: Cl, CN, H, S],

[1540: Br, CN, H, S], [1541: CH₃, CN, H, S], [1542: CN, CN, H, S], [1543: J1, CN, H, S], [1544: J2, CN, H, S], [1545: J3, CN, H, S], [1546: J4, CN, H, S], [1547: J5, CN, H, S], [1548: J6, CN, H, S], [1549: J7, CN, H, S], [1550: J8, CN, H, S], [1551: J9, CN, H, S], [1552: J10, CN, H, S], [1553: H, C(CH₃)₃, CN, S], [1554: F, C(CH₃)₃, CN, S], [1555: Cl, C(CH₃)₃, CN, S], [1556: Br, C(CH₃)₃, CN, S], [1557: CH₃, C(CH₃)₃, CN, S], [1558: CN, C(CH₃)₃, CN, S], [1559: J1, C(CH₃)₃, CN, S], [1560: J2, C(CH₃)₃, CN, S], [1561: J3, C(CH₃)₃, CN, S], [1562: J4, C(CH₃)₃, CN, S], [1563: J5, C(CH₃)₃, CN, S], [1564: J6, C(CH₃)₃, CN, S], [1565: J7, C(CH₃)₃, CN, S], [1566: J8, C(CH₃)₃, CN, S], [1567: J9, C(CH₃)₃, CN, S], [1568: J10, C(CH₃)₃, CN, S], [1569: H, CF₃, CN, S], [1570: F, CF₃, CN, S], [1571: Cl, CF₃, CN, S], [1572: Br, CF₃, CN, S], [1573: CH₃, CF₃, CN, S], [1574: CN, CF₃, CN, S], [1575: J1, CF₃, CN, S], [1576: J2, CF₃, CN, S], [1577: J3, CF₃, CN, S], [1578: J4, CF₃, CN, S], [1579: J5, CF₃, CN, S], [1580: J6, CF₃, CN, S], [1581: J7, CF₃, CN, S], [1582: J8, CF₃, CN, S], [1583: J9, CF₃, CN, S], [1584: J10, CF₃, CN, S], [1585: H, CF₂CF₃, CN, S], [1586: F, CF₂CF₃, CN, S], [1587: Cl, CF₂CF₃, CN, S], [1588: Br, CF₂CF₃, CN, S], [1589: CH₃, CF₂CF₃, CN, S], [1590: CN, CF₂CF₃, CN, S], [1591: J1, CF₂CF₃, CN, S], [1592: J2, CF₂CF₃, CN, S], [1593: J3, CF₂CF₃, CN, S], [1594: J4, CF₂CF₃, CN, S], [1595: J5, CF₂CF₃, CN, S], [1596: J6, CF₂CF₃, CN, S], [1597: J7, CF₂CF₃, CN, S], [1598: J8, CF₂CF₃, CN, S], [1599: J9, CF₂CF₃, CN, S], [1600: J10, CF₂CF₃, CN, S], [1601: H, SCF₃, CN, S], [1602: F, SCF₃, CN, S], [1603: Cl, SCF₃, CN, S], [1604: Br, SCF₃, CN, S], [1605: CH₃, SCF₃, CN, S], [1606: CN, SCF₃, CN, S], [1607: J1, SCF₃, CN, S], [1608: J2, SCF₃, CN, S], [1609: J3, SCF₃, CN, S], [1610: J4, SCF₃, CN, S], [1611: J5, SCF₃, CN, S], [1612: J6, SCF₃, CN, S], [1613: J7, SCF₃, CN, S], [1614: J8, SCF₃, CN, S], [1615: J9, SCF₃, CN, S], [1616: J10, SCF₃, CN, S], [1617: H, SOCF₃, CN, S], [1618: F, SOCF₃, CN, S], [1619: Cl, SOCF₃, CN, S], [1620: Br, SOCF₃, CN, S], [1621: CH₃, SOCF₃, CN, S], [1622: CN, SOCF₃, CN, S], [1623: J1, SOCF₃, CN, S], [1624: J2, SOCF₃, CN, S], [1625: J3, SOCF₃, CN, S], [1626: J4, SOCF₃, CN, S], [1627: J5, SOCF₃, CN, S], [1628: J6, SOCF₃, CN, S], [1629: J7, SOCF₃, CN, S], [1630: J8, SOCF₃, CN, S], [1631: J9, SOCF₃, CN, S], [1632: J10, SOCF₃, CN, S], [1633: H, SO₂CF₃, CN, S], [1634: F, SO₂CF₃, CN, S], [1635: Cl, SO₂CF₃, CN, S], [1636: Br, SO₂CF₃, CN, S], [1637: CH₃, SO₂CF₃, CN, S], [1638: CN, SO₂CF₃, CN, S], [1639: J1, SO₂CF₃, CN, S], [1640: J2, SO₂CF₃, CN, S], [1641: J3, SO₂CF₃, CN, S], [1642: J4, SO₂CF₃, CN, S], [1643: J5, SO₂CF₃, CN, S], [1644: J6, SO₂CF₃, CN, S], [1645: J7, SO₂CF₃, CN, S], [1646: J8, SO₂CF₃, CN, S], [1647: J9, SO₂CF₃, CN, S], [1648: J10, SO₂CF₃, CN, S], [1649: H, CH₂C≡CH, CN, S], [1650: F, CH₂C≡CH, CN, S], [1651: Cl, CH₂C≡CH, CN, S], [1652: Br, CH₂C≡CH, S][1653: CH₃, CH₂C≡CH, CN, S], [1654: CN, CH₂C≡CH, CN, S], [1655: J1, CH₂C≡CH, CN, S], [1656: J2, CH₂C≡CH, CN, S], [1657: J3, CH₂C≡CH, CN, S], [1658: J4, CH₂C≡CH, CN, S], [1659: J5, CH₂C≡CH, CN, S], [1660: J6, CH₂C≡CH, CN, S], [1661: J7, CH₂C≡CH, CN, S], [1662: J8, CH₂C≡CH, CN, S], [1663: J9, CH₂C≡CH, CN, S], [1664: J10, CH₂C≡CH, CN, S], [1665: H, OCH₂C≡CH, CN, S], [1666: F, OCH₂C≡CH, CN, S], [1667: Cl, OCH₂C≡CH, CN, S], [1668: Br, OCH₂C≡CH, CN, S], [1669: CH₃, OCH₂C≡CH, CN, S], [1670: CN, OCH₂C≡CH, CN, S], [1671: J1, OCH₂C≡CH, CN, S], [1672: J2, OCH₂C≡CH, CN, S], [1673: J3, OCH₂C≡CH, CN, S], [1674: J4, OCH₂C≡CH, CN, S], [1675: J5, OCH₂C≡CH, CN, S], [1676: J6, OCH₂C≡CH, CN, S], [1677: J7, OCH₂C≡CH, CN, S], [1678: J8, OCH₂C≡CH, CN, S], [1679: J9, OCH₂C≡CH, CN, S], [1680: J10, OCH₂C≡CH, CN, S], [1681: H, Cl, CN, S], [1682: F, Cl, CN, S], [1683: Cl, Cl, CN, S], [1684: Br, Cl, CN, S], [1685: CH₃, Cl, CN, S], [1686: CN, Cl, CN, S], [1687: J1, Cl, CN, S], [1688: J2, Cl, CN, S], [1689: J3, Cl, CN, S], [1690: J4, Cl, CN, S], [1691: J5, Cl, CN, S], [1692: J6, Cl, CN, S], [1693: J7, Cl, CN, S], [1694: J8, Cl, CN, S], [1695: J9, Cl, CN, S], [1696: J10, Cl, CN, S], [1697: H, C≡CH, CN, S], [1698: F, C≡CH, CN, S], [1699: Cl, C≡CH, CN, S], [1700: Br, C≡CH, CN, S], [1701: CH₃, C≡CH, CN, S], [1702: CN, C≡CH, CN, S], [1703: J1, C≡CH, CN, S], [1704: J2, C≡CH, CN, S], [1705: J3, C≡CH, CN, S], [1706: J4, C≡CH, CN, S], [1707: J5, C≡CH, CN, S], [1708: J6, C≡CH, CN, S], [1709: J7, C≡CH, CN, S], [1710: J8, C≡CH, CN, S], [1711: J9, C≡CH, CN, S], [1712: J10, C≡CH, CN, S], [1713: H, CN, CN, S], [1714: F, CN, CN, S], [1715: Cl, CN, CN, S], [1716: Br, CN, CN, S], [1717: CH₃, CN, CN, S], [1718: CN, CN, CN, S], [1719: J1, CN, CN, S], [1720: J2, CN, CN, S], [1721: J3, CN, CN, S], [1722: J4, CN, CN, S], [1723: J5, CN, CN, S], [1724: J6, CN, CN, S], [1725: J7, CN, CN, S], [1726: J8, CN, CN, S], [1727: J9, CN, CN, S], [1728: J10, CN, CN, S], [1729: H, C(CH₃)₃, H, S], [1730: F, C(CH₃)₃, H, S], [1731: Cl, C(CH₃)₃, H, S], [1732: Br, C(CH₃)₃, H, S], [1733: CH₃, C(CH₃)₃, H, S], [1734: CN, C(CH₃)₃, H, S], [1735: J1, C(CH₃)₃, H, S], [1736: J2, C(CH₃)₃, H, S], [1737: J3, C(CH₃)₃, H, S], [1738: J4, C(CH₃)₃, H, S], [1739: J5, C(CH₃)₃, H, S], [1740: J6, C(CH₃)₃, H, S], [1741: J7, C(CH₃)₃, H, S], [1742: J8, C(CH₃)₃, H, S], [1743: J9, C(CH₃)₃, H, S], [1744: J10, C(CH₃)₃, H, S], [1745: H, CF₃, H, S], [1746: F, CF₃, H, S], [1747: Cl, CF₃, H, S], [1748: Br, CF₃, H, S], [1749: CH₃, CF₃, H, S], [1750: CN, CF₃, H, S], [1751: J1, CF₃, H, S], [1752: J2, CF₃, H, S], [1753: J3, CF₃, H, S], [1754: J4, CF₃, H, S], [1755: J5, CF₃, H, S], [1756: J6, CF₃, H, S], [1757: J7, CF₃, H, S], [1758: J8, CF₃, H, S], [1759: J9, CF₃, H, S], [1760: J10, CF₃, H, S], [1761: H, CF₂CF₃, H, S], [1762: F, CF₂CF₃, H, S], [1763: Cl, CF₂CF₃, H, S], [1764: Br, CF₂CF₃, H, S], [1765: CH₃, CF₂CF₃, H, S], [1766: CN, CF₂CF₃, H, S][1767: J1, CF₂CF₃, H, S], [1768: J2, CF₂CF₃, H, S], [1769: J3, CF₂CF₃, H, S], [1770: J4, CF₂CF₃, H, S], [1771: J5, CF₂CF₃, H, S], [1772: J6, CF₂CF₃, H, S], [1773: J7, CF₂CF₃, H, S], [1774: J8, CF₂CF₃, H, S], [1775: J9, CF₂CF₃, H, S], [1776: J10, CF₂CF₃, S], [1777: H, SCF₃, H, S], [1778: F, SCF₃, H, S], [1779: Cl, SCF₃, H, S], [1780: Br, SCF₃, H, S], [1781: CH₃, SCF₃, H, S], [1782: CN, SCF₃, H, S], [1783: J1, SCF₃, H, S], [1784: J2, SCF₃, H, S], [1785: J3, SCF₃, H, S], [1786: J4, SCF₃, H, S], [1787: J5, SCF₃, H, S], [1788: J6, SCF₃, H, S], [1789: J7, SCF₃, H, S], [1790: J8, SCF₃, H, S], [1791: J9, SCF₃, H, S], [1792: J10, SCF₃, H, S], [1793: H, SOCF₃, H, S], [1794: F, SOCF₃, H, S], [1795: Cl, SOCF₃, H, S], [1796: Br, SOCF₃, H, S], [1797: CH₃, SOCF₃, H, S], [1798: CN, SOCF₃, H, S], [1799: J1, SOCF₃, H, S], [1800: J2, SOCF₃, H, S], [1801: J3, SOCF₃, H, S], [1802: J4, SOCF₃, H, S], [1803: J5, SOCF₃, H, S], [1804: J6, SOCF₃, H, S], [1805: J7, SOCF₃, H, S], [1806: J8, SOCF₃, H, S], [1807: J9, SOCF₃, H, S], [1808: J10, SOCF₃, H, S], [1809: H, SO₂CF₃, H, S], [1810: F, SO₂CF₃, H, S], [1811: Cl, SO₂CF₃, H, S], [1812: Br, SO₂CF₃, H, S], [1813: CH₃, SO₂CF₃, H, S], [1814: CN, SO₂CF₃, H, S], [1815: J1, SO₂CF₃, S], [1816: J2, SO₂CF₃, H, S][1817: J3, SO₂CF₃, S], [1818: J4, SO₂CF₃, H, S], [1819: J5, SO₂CF₃, H, S], [1820: J6, SO₂CF₃, S], [1821: J7, SO₂CF₃, S], [1822: J8, SO₂CF₃, S], [1823: J9, SO₂CF₃, H, S], [1824: J10, SO₂CF₃, S], [1825: H, CH₂C≡CH, H, S], [1826: F, CH₂C≡CH, H, S], [1827: Cl, CH₂C≡CH, H, S], [1828: Br, CH₂C≡CH, S], [1829: CH₃, CH₂C≡CH, H, S], [1830: CN, CH₂C≡CH, H, S], [1831: J1, CH₂C≡CH, H, S], [1832: J2, CH₂C≡CH, H, S], [1833: J3, CH₂C≡CH, H, S], [1834: J4, CH₂C≡CH, H, S], [1835: J5, CH₂C≡CH, H, S], [1836: J6, CH₂C≡CH, H, S], [1837: J7, CH₂C≡CH, H, S], [1838: J8, CH₂C≡CH, H,

S], [1839: J9, CH₂C≡CH, H, S], [1840: J10, CH₂C≡CH, H, S], [1841: H, OCH₂C≡CH, H, S], [1842: F, OCH₂C≡CH, H, S], [1843: Cl, OCH₂C≡CH, H, S], [1844: Br, OCH₂C≡CH, H, S], [1845: CH₃, OCH₂C≡CH, H, S], [1846: CN, OCH₂C≡CH, H, S], [1847: J1, OCH₂C≡CH, H, S], [1848: J2, OCH₂C≡CH, H, S], [1849: J3, OCH₂C≡CH, H, S], [1850: J4, OCH₂C≡CH, H, S], [1851: J5, OCH₂C≡CH, H, S], [1852: J6, OCH₂C≡CH, H, S], [1853: J7, OCH₂C≡CH, H, S], [1854: J8, OCH₂C≡CH, H, S], [1855: J9, OCH₂C≡CH, H, S], [1856: J10, OCH₂C≡CH, H, S], [1857: H, Cl, H, S], [1858: F, Cl, H, S], [1859: Cl, Cl, H, S], [1860: Br, Cl, H, S], [1861: CH₃, Cl, H, S], [1862: CN, Cl, H, S], [1863: J1, Cl, H, S], [1864: J2, Cl, H, S], [1865: J3, Cl, H, S], [1866: J4, Cl, H, S], [1867: J5, Cl, H, S], [1868: J6, Cl, H, S], [1869: J7, Cl, H, S], [1870: J8, Cl, H, S], [1871: J9, Cl, H, S], [1872: J10, Cl, H, S], [1873: H, C≡CH, H, S], [1874: F, C≡CH, H, S], [1875: Cl, C≡CH, H, S], [1876: Br, C≡CH, H, S], [1877: CH₃, C≡CH, H, S], [1878: CN, C≡CH, H, S], [1879: J1, C≡CH, H, S], [1880: J2, C≡CH, H, S], [1881: J3, C≡CH, H, S], [1882: J4, C≡CH, H, S], [1883: J5, C≡CH, H, S], [1884: J6, C≡CH, H, S], [1885: J7, C≡CH, H, S], [1886: J8, C≡CH, H, S], [1887: J9, C≡CH, H, S], [1888: J10, C≡CH, H, S], [1889: H, CN, H, S], [1890: F, CN, H, S], [1891: Cl, CN, H, S], [1892: Br, CN, H, S], [1893: CH₃, CN, H, S], [1894: CN, CN, H, S], [1895: J1, CN, H, S], [1896: J2, CN, H, S], [1897: J3, CN, H, S], [1898: J4, CN, H, S], [1899: J5, CN, H, S], [1900: J6, CN, H, S], [1901: J7, CN, H, S], [1902: J8, CN, H, S], [1903: J9, CN, H, S], [1904: J10, CN, H, S], [1905: H, C(CH₃)₃, CN, S], [1906: F, C(CH₃)₃, CN, S], [1907: Cl, C(CH₃)₃, CN, S], [1908: Br, C(CH₃)₃, CN, S], [1909: CH₃, C(CH₃)₃, CN, S], [1910: CN, C(CH₃)₃, CN, S], [1911: J1, C(CH₃)₃, CN, S], [1912: J2, C(CH₃)₃, CN, S], [1913: J3, C(CH₃)₃, CN, S], [1914: J4, C(CH₃)₃, CN, S], [1915: J5, C(CH₃)₃, CN, S], [1916: J6, C(CH₃)₃, CN, S], [1917: J7, C(CH₃)₃, CN, S], [1918: J8, C(CH₃)₃, CN, S], [1919: J9, C(CH₃)₃, CN, S], [1920: J10, C(CH₃)₃, CN, S], [1921: H, CF₃, CN, S], [1922: F, CF₃, CN, S], [1923: Cl, CF₃, CN, S], [1924: Br, CF₃, CN, S], [1925: CH₃, CF₃, CN, S], [1926: CN, CF₃, CN, S], [1927: J1, CF₃, CN, S], [1928: J2, CF₃, CN, S], [1929: J3, CF₃, CN, S], [1930: J4, CF₃, CN, S], [1931: J5, CF₃, CN, S], [1932: J6, CF₃, CN, S], [1933: J7, CF₃, CN, S], [1934: J8, CF₃, CN, S], [1935: J9, CF₃, CN, S], [1936: J10, CF₃, CN, S], [1937: H, CF₂CF₃, CN, S], [1938: F, CF₂CF₃, CN, S], [1939: Cl, CF₂CF₃, CN, S], [1940: Br, CF₂CF₃, CN, S], [1941: CH₃, CF₂CF₃, CN, S], [1942: CN, CF₂CF₃, CN, S], [1943: J1, CF₂CF₃, CN, S], [1944: J2, CF₂CF₃, CN, S], [1945: J3, CF₂CF₃, CN, S], [1946: J4, CF₂CF₃, CN, S], [1947: J5, CF₂CF₃, CN, S], [1948: J6, CF₂CF₃, CN, S], [1949: J7, CF₂CF₃, CN, S], [1950: J8, CF₂CF₃, CN, S], [1951: J9, CF₂CF₃, CN, S], [1952: J10, CF₂CF₃, CN, S], [1953: H, SCF₃, CN, S], [1954: F, SCF₃, CN, S], [1955: Cl, SCF₃, CN, S], [1956: Br, SCF₃, CN, S], [1957: CH₃, SCF₃, CN, S], [1958: CN, SCF₃, CN, S], [1959: J1, SCF₃, CN, S], [1960: J2, SCF₃, CN, S], [1961: J3, SCF₃, CN, S], [1962: J4, SCF₃, CN, S], [1963: J5, SCF₃, CN, S], [1964: J6, SCF₃, CN, S], [1965: J7, SCF₃, CN, S], [1966: J8, SCF₃, CN, S], [1967: J9, SCF₃, CN, S], [1968: J10, SCF₃, CN, S], [1969: H, SOCF₃, CN, S], [1970: F, SOCF₃, CN, S], [1971: Cl, SOCF₃, CN, S], [1972: Br, SOCF₃, CN, S], [1973: CH₃, SOCF₃, CN, S], [1974: CN, SOCF₃, CN, S], [1975: J1, SOCF₃, CN, S], [1976: J2, SOCF₃, CN, S], [1977: J3, SOCF₃, CN, S], [1978: J4, SOCF₃, CN, S], [1979: J5, SOCF₃, CN, S], [1980: J6, SOCF₃, CN, S], [1981: J7, SOCF₃, CN, S], [1982: J8, SOCF₃, CN, S], [1983: J9, SOCF₃, CN, S], [1984: J10, SOCF₃, CN, S], [1985: H, SO2CF₃, CN, S], [1986: F, SO2CF₃, CN, S], [1987: Cl, SO2CF₃, CN, S], [1988: Br, SO2CF₃, CN, S], [1989: CH₃, SO2CF₃, CN, S], [1990: CN, SO2CF₃, CN, S], [1991: J1, SO2CF₃, CN, S], [1992: J2, SO2CF₃, CN, S], [1993: J3, SO2CF₃, CN, S], [1994: J4, SO2CF₃, CN, S], [1995: J5, SO2CF₃, CN, S], [1996: J6, SO2CF₃, CN, S], [1997: J7, SO2CF₃, CN, S], [1998: J8, SO2CF₃, CN, S], [1999: J9, SO2CF₃, CN, S], [2000: J10, SO2CF₃, CN, S], [2001: H, CH₂C≡CH, CN, S], [2002: F, CH₂C≡CH, CN, S], [2003: Cl, CH₂C≡CH, CN, S], [2004: Br, CH₂C≡CH, CN, S], [2005: CH₃, CH₂C≡CH, CN, S], [2006: CN, CH₂C≡CH, CN, S], [2007: J1, CH₂C≡CH, CN, S], [2008: J2, CH₂C≡CH, CN, S], [2009: J3, CH₂C≡CH, CN, S], [2010: J4, CH₂C≡CH, CN, S], [2011: J5, CH₂C≡CH, CN, S], [2012: J6, CH₂C≡CH, CN, S], [2013: J7, CH₂C≡CH, CN, S], [2014: J8, CH₂C≡CH, CN, S], [2015: J9, CH₂C≡CH, CN, S], [2016: J10, CH₂C≡CH, CN, S], [2017: H, OCH₂C≡CH, CN, S], [2018: F, OCH₂C≡CH, CN, S], [2019: Cl, OCH₂C≡CH, CN, S], [2020: Br, OCH₂C≡CH, CN, S], [2021: CH₃, OCH₂C≡CH, CN, S], [2022: CN, OCH₂C≡CH, CN, S], [2023: J1, OCH₂C≡CH, CN, S], [2024: J2, OCH₂C≡CH, CN, S], [2025: J3, OCH₂C≡CH, CN, S], [2026: J4, OCH₂C≡CH, CN, S], [2027: J5, OCH₂C≡CH, CN, S], [2028: J6, OCH₂C≡CH, CN, S], [2029: J7, OCH₂C≡CH, CN, S], [2030: J8, OCH₂C≡CH, CN, S], [2031: J9, OCH₂C≡CH, CN, S], [2032: J10, OCH₂C≡CH, CN, S], [2033: H, Cl, CN, S], [2034: F, Cl, CN, S], [2035: Cl, Cl, CN, S], [2036: Br, Cl, CN, S], [2037: CH₃, Cl, CN, S], [2038: CN, Cl, CN, S], [2039: J1, Cl, CN, S], [2040: J2, Cl, CN, S], [2041: J3, Cl, CN, S], [2042: J4, Cl, CN, S], [2043: J5, Cl, CN, S], [2044: J6, Cl, CN, S], [2045: J7, Cl, CN, S], [2046: J8, Cl, CN, S], [2047: J9, Cl, CN, S], [2048: J10, Cl, CN, S], [2049: H, C≡CH, CN, S], [2050: F, C≡CH, CN, S], [2051: Cl, C≡CH, CN, S], [2052: Br, C≡CH, CN, S], [2053: CH₃, C≡CH, CN, S], [2054: CN, C≡CH, CN, S], [2055: J1, C≡CH, CN, S], [2056: J2, C≡CH, CN, S], [2057: J3, C≡CH, CN, S], [2058: J4, C≡CH, CN, S], [2059: J5, C≡CH, CN, S], [2060: J6, C≡CH, CN, S], [2061: J7, C≡CH, CN, S], [2062: J8, C≡CH, CN, S], [2063: J9, C≡CH, CN, S], [2064: J10, C≡CH, CN, S], [2065: H, C(CH₃)₃, H, O], [2066: F, C(CH₃)₃, H, O], [2067: Cl, C(CH₃)₃, H, O], [2068: Br, C(CH₃)₃, H, O], [2069: CH₃, C(CH₃)₃, H, O], [2070: CN, C(CH₃)₃, H, O], [2071: J1, C(CH₃)₃, H, O], [2072: J2, C(CH₃)₃, H, O], [2073: J3, C(CH₃)₃, H, O], [2074: J4, C(CH₃)₃, H, O], [2075: J5, C(CH₃)₃, H, O], [2076: J6, C(CH₃)₃, H, O], [2077: J7, C(CH₃)₃, H, O], [2078: J8, C(CH₃)₃, H, O], [2079: J9, C(CH₃)₃, H, O], [2080: J10, C(CH₃)₃, H, O], [2081: H, CF₃, H, O], [2082: F, CF₃, H, O], [2083: Cl, CF₃, H, O], [2084: Br, CF₃, H, O], [2085: CH₃, CF₃, H, O], [2086: CN, CF₃, H, O], [2087: J1, CF₃, H, O], [2088: J2, CF₃, H, O], [2089: J3, CF₃, H, O], [2090: J4, CF₃, H, O], [2091: J5, CF₃, H, O], [2092: J6, CF₃, H, O], [2093: J7, CF₃, H, O], [2094: J8, CF₃, H, O], [2095: J9, CF₃, H, O], [2096: J10, CF₃, H, O], [2097: H, CF₂CF₃, H, O], [2098: F, CF₂CF₃, H, O], [2099: Cl, CF₂CF₃, H, O], [2100: Br, CF₂CF₃, H, O], [2101: CH₃, CF₂CF₃, H, O], [2102: CN, CF₂CF₃, H, O], [2103: J1, CF₂CF₃, H, O], [2104: J2, CF₂CF₃, H, O], [2105: J3, CF₂CF₃, H, O], [2106: J4, CF₂CF₃, H, O], [2107: J5, CF₂CF₃, H, O], [2108: J6, CF₂CF₃, H, O], [2109: J7, CF₂CF₃, H, O], [2110: J8, CF₂CF₃, H, O], [2111: J9, CF₂CF₃, H, O], [2112: J10, CF₂CF₃, H, O], [2113: H, SCF₃, H, O], [2114: F, SCF₃, H, O], [2115: Cl, SCF₃, H, O], [2116: Br, SCF₃, H, O], [2117: CH₃, SCF₃, H, O], [2118: CN, SCF₃, H, O], [2119: J1, SCF₃, H, O], [2120: J2, SCF₃, H, O], [2121: J3, SCF₃, H, O], [2122: J4, SCF₃, H, O], [2123: J5, SCF₃, H, O], [2124: J6, SCF₃, H, O], [2125: J7, SCF₃, H, O], [2126: J8, SCF₃, H, O], [2127: J9, SCF₃, H, O], [2128: J10, SCF₃, H, O], [2129: H, SOCF₃, H, O], [2130: F, SOCF₃, H, O], [2131: Cl, SOCF₃, H, O], [2132: Br, SOCF₃, H, O], [2133: CH₃, SOCF₃, H, O], [2134: CN, SOCF₃, H, O], [2135:

J1, SOCF$_3$, H, O], [2136: J2, SOCF$_3$, H, O], [2137: J3, SOCF$_3$, H, O], [2138: J4, SOCF$_3$, H, O], [2139: J5, SOCF$_3$, H, O], [2140: J6, SOCF$_3$, H, O], [2141: J7, SOCF$_3$, H, O], [2142: J8, SOCF$_3$, H, O], [2143: J9, SOCF$_3$, H, O], [2144: J10, SOCF$_3$, H, O], [2145: H, SO2CF$_3$, H, O], [2146: F, SO2CF$_3$, H, O], [2147: Cl, SO2CF$_3$, H, O], [2148: Br, SO2CF$_3$, H, O], [2149: CH$_3$, SO2CF$_3$, H, O], [2150: CN, SO2CF$_3$, H, O], [2151: J1, SO2CF$_3$, H, O], [2152: J2, SO2CF$_3$, H, O], [2153: J3, SO2CF$_3$, H, O], [2154: J4, SO2CF$_3$, H, O], [2155: J5, SO2CF$_3$, H, O], [2156: J6, SO2CF$_3$, H, O], [2157: J7, SO2CF$_3$, H, O], [2158: J8, SO2CF$_3$, H, O], [2159: J9, SO2CF$_3$, H, O], [2160: J10, SO2CF$_3$, H, O], [2161: H, CH$_2$C≡CH, H, O], [2162: F, CH$_2$C≡CH, H, O], [2163: Cl, CH$_2$C≡CH, H, O], [2164: Br, CH$_2$C≡CH, H, O], [2165: CH$_3$, CH$_2$C≡CH, H, O], [2166: CN, CH$_2$C≡CH, H, O], [2167: J1, CH$_2$C≡CH, H, O], [2168: J2, CH$_2$C≡CH, H, O], [2169: J3, CH$_2$C≡CH, H, O], [2170: J4, CH$_2$C≡CH, H, O], [2171: J5, CH$_2$C≡CH, H, O], [2172: J6, CH$_2$C≡CH, H, O], [2173: J7, CH$_2$C≡CH, H, O], [2174: J8, CH$_2$C≡CH, H, O], [2175: J9, CH$_2$C≡CH, H, O], [2176: J10, CH$_2$C≡CH, H, O], [2177: H, OCH$_2$C≡CH, H, O], [2178: F, OCH$_2$C≡CH, H, O], [2179: Cl, OCH$_2$C≡CH, H, O], [2180: Br, OCH$_2$C≡CH, H, O], [2181: CH$_3$, OCH$_2$C≡CH, H, O], [2182: CN, OCH$_2$C≡CH, H, O], [2183: J1, OCH$_2$C≡CH, H, O], [2184: J2, OCH$_2$C≡CH, H, O], [2185: J3, OCH$_2$C≡CH, H, O], [2186: J4, OCH$_2$C≡CH, H, O], [2187: J5, OCH$_2$C≡CH, H, O], [2188: J6, OCH$_2$C≡CH, H, O], [2189: J7, OCH$_2$C≡CH, H, O], [2190: J8, OCH$_2$C≡CH, H, O], [2191: J9, OCH$_2$C≡CH, H, O], [2192: J10, OCH$_2$C≡CH, H, O], [2193: H, Cl, H, O], [2194: F, Cl, H, O], [2195: Cl, Cl, H, O], [2196: Br, Cl, H, O], [2197: CH$_3$, Cl, H, O], [2198: CN, Cl, H, O], [2199: J1, Cl, H, O], [2200: J2, Cl, H, O], [2201: J3, Cl, H, O], [2202: J4, Cl, H, O], [2203: J5, Cl, H, O], [2204: J6, Cl, H, O], [2205: J7, Cl, H, O], [2206: J8, Cl, H, O], [2207: J9, Cl, H, O], [2208: J10, Cl, H, O], [2209: H, C≡CH, H, O], [2210: F, C≡CH, H, O], [2211: Cl, C≡CH, H, O], [2212: Br, C≡CH, H, O], [2213: CH$_3$, C≡CH, H, O], [2214: CN, C≡CH, H, O], [2215: J1, C≡CH, H, O], [2216: J2, C≡CH, H, O], [2217: J3, C≡CH, H, O], [2218: J4, C≡CH, H, O], [2219: J5, C≡CH, H, O], [2220: J6, C≡CH, H, O], [2221: J7, C≡CH, H, O], [2222: J8, C≡CH, H, O], [2223: J9, C≡CH, H, O], [2224: J10, C≡CH, H, O], [2225: H, CN, H, O], [2226: F, CN, H, O], [2227: Cl, CN, H, O], [2228: Br, CN, H, O], [2229: CH$_3$, CN, H, O], [2230: CN, CN, H, O], [2231: J1, CN, H, O], [2232: J2, CN, H, O], [2233: J3, CN, H, O], [2234: J4, CN, H, O], [2235: J5, CN, H, O], [2236: J6, CN, H, O], [2237: J7, CN, H, O], [2238: J8, CN, H, O], [2239: J9, CN, H, O], [2240: J10, CN, H, O], [2241: H, C(CH$_3$)$_3$, CN, O], [2242: F, C(CH$_3$)$_3$, CN, O], [2243: Cl, C(CH$_3$)$_3$, CN, O], [2244: Br, C(CH$_3$)$_3$, CN, O], [2245: CH$_3$, C(CH$_3$)$_3$, CN, O], [2246: CN, C(CH$_3$)$_3$, CN, O], [2247: J1, C(CH$_3$)$_3$, CN, O], [2248: J2, C(CH$_3$)$_3$, CN, O], [2249: J3, C(CH$_3$)$_3$, CN, O], [2250: J4, C(CH$_3$)$_3$, CN, O], [2251: J5, C(CH$_3$)$_3$, CN, O], [2252: J6, C(CH$_3$)$_3$, CN, O], [2253: J7, C(CH$_3$)$_3$, CN, O], [2254: J8, C(CH$_3$)$_3$, CN, O], [2255: J9, C(CH$_3$)$_3$, CN, O], [2256: J10, C(CH$_3$)$_3$, CN, O], [2257: H, CF$_3$, CN, O], [2258: F, CF$_3$, CN, O], [2259: Cl, CF$_3$, CN, O], [2260: Br, CF$_3$, CN, O], [2261: CH$_3$, CF$_3$, CN, O], [2262: CN, CF$_3$, CN, O], [2263: J1, CF$_3$, CN, O], [2264: J2, CF$_3$, CN, O], [2265: J3, CF$_3$, CN, O], [2266: J4, CF$_3$, CN, O], [2267: J5, CF$_3$, CN, O], [2268: J6, CF$_3$, CN, O], [2269: J7, CF$_3$, CN, O], [2270: J8, CF$_3$, CN, O], [2271: J9, CF$_3$, CN, O], [2272: J10, CF$_3$, CN, O], [2273: H, CF$_2$CF$_3$, CN, O], [2274: F, CF$_2$CF$_3$, CN, O], [2275: Cl, CF$_2$CF$_3$, CN, O], [2276: Br, CF$_2$CF$_3$, CN, O], [2277: CH$_3$, CF$_2$CF$_3$, CN, O], [2278: CN, CF$_2$CF$_3$, CN, O], [2279: J$_1$, CF$_2$CF$_3$, CN, O], [2280: J2, CF$_2$CF$_3$, CN, O], [2281: J3, CF$_2$CF$_3$, CN, O], [2282: J4, CF$_2$CF$_3$, CN, O], [2283: J5, CF$_2$CF$_3$, CN, O], [2284: J6, CF$_2$CF$_3$, CN, O], [2285: J7, CF$_2$CF$_3$, CN, O], [2286: J8, CF$_2$CF$_3$, CN, O], [2287: J9, CF$_2$CF$_3$, CN, O], [2288: J10, CF$_2$CF$_3$, CN, O], [2289: H, SCF$_3$, CN, O], [2290: F, SCF$_3$, CN, O], [2291: Cl, SCF$_3$, CN, O], [2292: Br, SCF$_3$, CN, O], [2293: CH$_3$, SCF$_3$, CN, O], [2294: CN, SCF$_3$, CN, O], [2295: J1, SCF$_3$, CN, O], [2296: J2, SCF$_3$, CN, O], [2297: J3, SCF$_3$, CN, O], [2298: J4, SCF$_3$, CN, O], [2299: J5, SCF$_3$, CN, O], [2300: J6, SCF$_3$, CN, O], [2301: J7, SCF$_3$, CN, O], [2302: J8, SCF$_3$, CN, O], [2303: J9, SCF$_3$, CN, O], [2304: J10, SCF$_3$, CN, O], [2305: H, SOCF$_3$, CN, O], [2306: F, SOCF$_3$, CN, O], [2307: Cl, SOCF$_3$, CN, O], [2308: Br, SOCF$_3$, CN, O], [2309: CH$_3$, SOCF$_3$, CN, O], [2310: CN, SOCF$_3$, CN, O], [2311: J1, SOCF$_3$, CN, O], [2312: J2, SOCF$_3$, CN, O], [2313: J3, SOCF$_3$, CN, O], [2314: J4, SOCF$_3$, CN, O], [2315: J5, SOCF$_3$, CN, O], [2316: J6, SOCF$_3$, CN, O], [2317: J7, SOCF$_3$, CN, O], [2318: J8, SOCF$_3$, CN, O], [2319: J9, SOCF$_3$, CN, O], [2320: J10, SOCF$_3$, CN, O], [2321: H, SO$_2$CF$_3$, CN, O], [2322: F, SO$_2$CF$_3$, CN, O][2323: Cl, SO$_2$CF$_3$, CN, O], [2324: Br, SO$_2$CF$_3$, CN, O][2325: CH$_3$, SO$_2$CF$_3$, CN, O], [2326: CN, SO$_2$CF$_3$, CN, O], [2327: J$_1$, SO$_2$CF$_3$, CN, O], [2328: J2, SO$_2$CF$_3$, CN, O], [2329: J3, SO$_2$CF$_3$, CN, O], [2330: J4, SO$_2$CF$_3$, CN, O][2331: J5, SO$_2$CF$_3$, CN, O], [2332: J6, SO$_2$CF$_3$, CN, O][2333: J7, SO$_2$CF$_3$, CN, O], [2334: J8, SO$_2$CF$_3$, CN, O], [2335: J9, SO$_2$CF$_3$, CN, O], [2336: J10, SO$_2$CF$_3$, CN, O], [2337: H, CH$_2$C≡CH, CN, O], [2338: F, CH$_2$C≡CH, CN, O], [2339: Cl, CH$_2$C≡CH, CN, O], [2340: Br, CH$_2$C≡CH, CN, O][2341: CH$_3$, CH$_2$C≡CH, CN, O], [2342: CN, CH$_2$C≡CH, CN, O], [2343: J1, CH$_2$C≡CH, CN, O], [2344: J2, CH$_2$C≡CH, CN, O], [2345: J3, CH$_2$C≡CH, CN, O], [2346: J4, CH$_2$C≡CH, CN, O], [2347: J5, CH$_2$C≡CH, CN, O], [2348: J6, CH$_2$C≡CH, CN, O], [2349: J7, CH$_2$C≡CH, CN, O], [2350: J8, CH$_2$C≡CH, CN, O], [2351: J9, CH$_2$C≡CH, CN, O], [2352: J10, CH$_2$C≡CH, CN, O], [2353: H, OCH$_2$C≡CH, CN, O], [2354: F, OCH$_2$C≡CH, CN, O], [2355: Cl, OCH$_2$C≡CH, CN, O], [2356: Br, OCH$_2$C≡CH, CN, O], [2357: CH$_3$, OCH$_2$C≡CH, CN, O], [2358: CN, OCH$_2$C≡CH, CN, O], [2359: J1, OCH$_2$C≡CH, CN, O], [2360: J2, OCH$_2$C≡CH, CN, O], [2361: J3, OCH$_2$C≡CH, CN, O], [2362: J4, OCH$_2$C≡CH, CN, O], [2363: J5, OCH$_2$C≡CH, CN, O], [2364: J6, OCH$_2$C≡CH, CN, O], [2365: J7, OCH$_2$C≡CH, CN, O], [2366: J8, OCH$_2$C≡CH, CN, O], [2367: J9, OCH$_2$C≡CH, CN, O], [2368: J10, OCH$_2$C≡CH, CN, O], [2369: H, Cl, CN, O], [2370: F, Cl, CN, O], [2371: Cl, Cl, CN, O], [2372: Br, Cl, CN, O], [2373: CH$_3$, Cl, CN, O], [2374: CN, Cl, CN, O], [2375: J1, Cl, CN, O], [2376: J2, Cl, CN, O], [2377: J3, Cl, CN, O], [2378: J4, Cl, CN, O], [2379: J5, Cl, CN, O], [2380: J6, Cl, CN, O], [2381: J7, Cl, CN, O], [2382: J8, Cl, CN, O], [2383: J9, Cl, CN, O], [2384: J10, Cl, CN, O], [2385: H, C≡CH, CN, O], [2386: F, C≡CH, CN, O], [2387: Cl, C≡CH, CN, O], [2388: Br, C≡CH, CN, O], [2389: CH$_3$, C≡CH, CN, O], [2390: CN, C≡CH, CN, O], [2391: J1, C≡CH, CN, O], [2392: J2, C≡CH, CN, O], [2393: J3, C≡CH, CN, O], [2394: J4, C≡CH, CN, O], [2395: J5, C≡CH, CN, O], [2396: J6, C≡CH, CN, O], [2397: J7, C≡CH, CN, O], [2398: J8, C≡CH, CN, O], [2399: J9, C≡CH, CN, O], [2400: J10, C≡CH, CN, O], [2401: H, CN, CN, O], [2402: F, CN, CN, O], [2403: Cl, CN, CN, O], [2404: Br, CN, CN, O], [2405: CH$_3$, CN, CN, O], [2406: CN, CN, CN, O], [2407: J1, CN, CN, O], [2408: J2, CN, CN, O], [2409: J3, CN, CN, O], [2410: J4, CN, CN, O], [2411: J5, CN, CN, O], [2412: J6, CN, CN, O], [2413: J7, CN, CN, O], [2414: J8, CN, CN, O], [2415: J9, CN, CN, O], [2416: J10, CN, CN, O], [2417: H, C(CH$_3$)$_3$, H, O], [2418: F, C(CH$_3$)$_3$, H, O], [2419: Cl, C(CH$_3$)$_3$, H, O], [2420: Br, C(CH$_3$)$_3$, H, O],

[2421: CH₃, C(CH₃)₃, H, O], [2422: CN, C(CH₃)₃, H, O], [2423: J1, C(CH₃)₃, H, O], [2424: J2, C(CH₃)₃, H, O], [2425: J3, C(CH₃)₃, H, O], [2426: J4, C(CH₃)₃, H, O], [2427: J5, C(CH₃)₃, H, O], [2428: J6, C(CH₃)₃, H, O], [2429: J7, C(CH₃)₃, H, O], [2430: J8, C(CH₃)₃, H, O], [2431: J9, C(CH₃)₃, H, O], [2432: J10, C(CH₃)₃, H, O], [2433: H, CF₃, H, O], [2434: F, CF₃, H, O], [2435: Cl, CF₃, H, O], [2436: Br, CF₃, H, O], [2437: CH₃, CF₃, H, O], [2438: CN, CF₃, H, O], [2439: J1, CF₃, H, O], [2440: J2, CF₃, H, O], [2441: J3, CF₃, H, O], [2442: J4, CF₃, H, O], [2443: J5, CF₃, H, O], [2444: J6, CF₃, H, O], [2445: J7, CF₃, H, O], [2446: J8, CF₃, H, O], [2447: J9, CF₃, H, O], [2448: J10, CF₃, H, O], [2449: H, CF₂CF₃, H, O], [2450: F, CF₂CF₃, H, O], [2451: Cl, CF₂CF₃, H, O], [2452: Br, CF₂CF₃, H, O], [2453: CH₃, CF₂CF₃, H, O], [2454: CN, CF₂CF₃, H, O], [2455: J1, CF₂CF₃, H, O], [2456: J2, CF₂CF₃, H, O], [2457: J3, CF₂CF₃, H, O], [2458: J4, CF₂CF₃, H, O], [2459: J5, CF₂CF₃, H, O], [2460: J6, CF₂CF₃, H, O], [2461: J7, CF₂CF₃, H, O], [2462: J8, CF₂CF₃, H, O], [2463: J9, CF₂CF₃, H, O], [2464: J10, CF₂CF₃, H, O], [2465: H, SCF₃, H, O], [2466: F, SCF₃, H, O], [2467: Cl, SCF₃, H, O], [2468: Br, SCF₃, H, O], [2469: CH₃, SCF₃, H, O], [2470: CN, SCF₃, H, O], [2471: J1, SCF₃, H, O], [2472: J2, SCF₃, H, O], [2473: J3, SCF₃, H, O], [2474: J4, SCF₃, H, O], [2475: J5, SCF₃, H, O], [2476: J6, SCF₃, H, O], [2477: J7, SCF₃, H, O], [2478: J8, SCF₃, H, O], [2479: J9, SCF₃, H, O], [2480: J10, SCF₃, H, O], [2481: H, SOCF₃, H, O], [2482: F, SOCF₃, H, O], [2483: Cl, SOCF₃, H, O], [2484: Br, SOCF₃, H, O], [2485: CH₃, SOCF₃, H, O], [2486: CN, SOCF₃, H, O], [2487: J1, SOCF₃, H, O], [2488: J2, SOCF₃, H, O], [2489: J3, SOCF₃, H, O], [2490: J4, SOCF₃, H, O], [2491: J5, SOCF₃, H, O], [2492: J6, SOCF₃, H, O], [2493: J7, SOCF₃, H, O], [2494: J8, SOCF₃, H, O], [2495: J9, SOCF₃, H, O], [2496: J10, SOCF₃, H, O], [2497: H, SO₂CF₃, H, O], [2498: F, SO₂CF₃, H, O], [2499: Cl, SO₂CF₃, H, O], [2500: Br, SO₂CF₃, H, O][2501: CH₃, SO₂CF₃, H, O], [2502: CN, SO₂CF₃, H, O], [2503: J1, SO₂CF₃, H, O], [2504: J2, SO₂CF₃, H, O], [2505: J3, SO₂CF₃, H, O], [2506: J4, SO₂CF₃, H, O], [2507: J5, SO₂CF₃, H, O], [2508: J6, SO₂CF₃, H, O], [2509: J7, SO₂CF₃, H, O], [2510: J8, SO₂CF₃, H, O], [2511: J9, SO₂CF₃, H, O], [2512: J10, SO₂CF₃, H, O], [2513: H, CH₂C=CH, H, O], [2514: F, CH₂C=CH, H, O], [2515: Cl, CH₂C=CH, H, O], [2516: Br, CH₂C=CH, H, O], [2517: CH₃, CH₂C=CH, H, O], [2518: CN, CH₂C=CH, H, O], [2519: J1, CH₂C=CH, H, O], [2520: J2, CH₂C=CH, H, O], [2521: J3, CH₂C=CH, H, O], [2522: J4, CH₂C=CH, H, O], [2523: J5, CH₂C=CH, H, O], [2524: J6, CH₂C=CH, H, O], [2525: J7, CH₂C=CH, H, O], [2526: J8, CH₂C=CH, H, O], [2527: J9, CH₂C=CH, H, O], [2528: J10, CH₂C=CH, H, O], [2529: H, OCH₂C=CH, H, O], [2530: F, OCH₂C=CH, H, O], [2531: J1, OCH₂C=CH, H, O], [2532: Br, OCH₂C=CH, H, O], [2533: CH₃, OCH₂C=CH, H, O], [2534: CN, OCH₂C=CH, H, O], [2535: J1, OCH₂C=CH, H, O], [2536: J2, OCH₂C=CH, H, O], [2537: J3, OCH₂C=CH, H, O], [2538: J4, OCH₂C=CH, H, O], [2539: J5, OCH₂C=CH, H, O], [2540: J6, OCH₂C=CH, H, O], [2541: J7, OCH₂C=CH, H, O], [2542: J8, OCH₂C=CH, H, O], [2543: J9, OCH₂C=CH, H, O], [2544: J10, OCH₂C=CH, H, O], [2545: H, Cl, H, O], [2546: F, Cl, H, O], [2547: Cl, Cl, H, O], [2548: Br, Cl, H, O], [2549: CH₃, Cl, H, O], [2550: CN, Cl, H, O], [2551: J1, Cl, H, O], [2552: J2, Cl, H, O], [2553: J3, Cl, H, O], [2554: J4, Cl, H, O], [2555: J5, Cl, H, O], [2556: J6, Cl, H, O], [2557: J7, Cl, H, O], [2558: J8, Cl, H, O], [2559: J9, Cl, H, O], [2560: J10, Cl, H, O], [2561: H, C=CH, H, O], [2562: F, C=CH, H, O], [2563: Cl, C=CH, H, O], [2564: Br, C=CH, H, O], [2565: CH₃, C=CH, H, O], [2566: CN, C=CH, H, O], [2567: J1, C=CH, H, O], [2568: J2, C=CH, H, O], [2569: J3, C=CH, H, O], [2570: J4, C=CH, H, O], [2571: J5, C=CH, H, O], [2572: J6, C=CH, H, O], [2573: J7, C=CH, H, O], [2574: J8, C=CH, H, O], [2575: J9, C=CH, H, O], [2576: J10, H, O], [2577: H, CN, H, O], [2578: F, CN, H, O], [2579: Cl, CN, H, O], [2580: Br, CN, H, O], [2581: CH₃, CN, H, O], [2582: CN, CN, H, O], [2583: J1, CN, H, O], [2584: J2, CN, H, O], [2585: J3, CN, H, O], [2586: J4, CN, H, O], [2587: J5, CN, H, O], [2588: J6, CN, H, O], [2589: J7, CN, H, O], [2590: J8, CN, H, O], [2591: J9, CN, H, O], [2592: J10, CN, H, O], [2593: H, C(CH₃)₃, CN, O], [2594: F, C(CH₃)₃, CN, O], [2595: Cl, C(CH₃)₃, CN, O], [2596: Br, C(CH₃)₃, CN, O], [2597: CH₃, C(CH₃)₃, CN, O], [2598: CN, C(CH₃)₃, CN, O], [2599: J1, C(CH₃)₃, CN, O], [2600: J2, C(CH₃)₃, CN, O], [2601: J3, C(CH₃)₃, CN, O], [2602: J4, C(CH₃)₃, CN, O], [2603: J5, C(CH₃)₃, CN, O], [2604: J6, C(CH₃)₃, CN, O], [2605: J7, C(CH₃)₃, CN, O], [2606: J8, C(CH₃)₃, CN, O], [2607: J9, C(CH₃)₃, CN, O], [2608: J10, C(CH₃)₃, CN, O], [2609: H, CF₃, CN, O], [2610: F, CF₃, CN, O], [2611: Cl, CF₃, CN, O], [2612: Br, CF₃, CN, O], [2613: CH₃, CF₃, CN, O], [2614: CN, CF₃, CN, O], [2615: J1, CF₃, CN, O], [2616: J2, CF₃, CN, O], [2617: J3, CF₃, CN, O], [2618: J4, CF₃, CN, O], [2619: J5, CF₃, CN, O], [2620: J6, CF₃, CN, O], [2621: J7, CF₃, CN, O], [2622: J8, CF₃, CN, O], [2623: J9, CF₃, CN, O], [2624: J10, CF₃, CN, O], [2625: H, CF₂CF₃, CN, O], [2626: F, CF₂CF₃, CN, O], [2627: Cl, CF₂CF₃, CN, O], [2628: Br, CF₂CF₃, CN, O], [2629: CH₃, CF₂CF₃, CN, O][2630: CN, CF₂CF₃, CN, O], [2631: J1, CF₂CF₃, CN, O], [2632: J2, CF₂CF₃, CN, O], [2633: J3, CF₂CF₃, CN, O], [2634: J4, CF₂CF₃, CN, O], [2635: J5, CF₂CF₃, CN, O], [2636: J6, CF₂CF₃, CN, O], [2637: J7, CF₂CF₃, CN, O], [2638: J8, CF₂CF₃, CN, O], [2639: J9, CF₂CF₃, CN, O], [2640: J10, CF₂CF₃, CN, O], [2641: H, SCF₃, CN, O], [2642: F, SCF₃, CN, O], [2643: Cl, SCF₃, CN, O], [2644: Br, SCF₃, CN, O], [2645: CH₃, SCF₃, CN, O], [2646: CN, SCF₃, CN, O], [2647: J1, SCF₃, CN, O], [2648: J2, SCF₃, CN, O], [2649: J3, SCF₃, CN, O], [2650: J4, SCF₃, CN, O], [2651: J5, SCF₃, CN, O], [2652: J6, SCF₃, CN, O], [2653: J7, SCF₃, CN, O], [2654: J8, SCF₃, CN, O], [2655: J9, SCF₃, CN, O], [2656: J10, SCF₃, CN, O], [2657: H, SOCF₃, CN, O], [2658: F, SOCF₃, CN, O], [2659: Cl, SOCF₃, CN, O], [2660: Br, SOCF₃, CN, O], [2661: CH₃, SOCF₃, CN, O], [2662: CN, SOCF₃, CN, O], [2663: J1, SOCF₃, CN, O], [2664: J2, SOCF₃, CN, O], [2665: J3, SOCF₃, CN, O], [2666: J4, SOCF₃, CN, O], [2667: J5, SOCF₃, CN, O], [2668: J6, SOCF₃, CN, O], [2669: J7, SOCF₃, CN, O], [2670: J8, SOCF₃, CN, O], [2671: J9, SOCF₃, CN, O], [2672: J10, SOCF₃, CN, O], [2673: H, SO₂CF₃, CN, O], [2674: F, SO₂CF₃, CN, O], [2675: Cl, SO₂CF₃, CN, O], [2676: Br, SO₂CF₃, CN, O], [2677: CH₃, SO₂CF₃, CN, O], [2678: CN, SO₂CF₃, CN, O], [2679: J₁, SO₂CF₃, CN, O], [2680: J2, SO₂CF₃, CN, O], [2681: J3, SO₂CF₃, CN, O], [2682: J4, SO₂CF₃, CN, O], [2683: J5, SO₂CF₃, CN, O], [2684: J6, SO₂CF₃, CN, O], [2685: J7, SO₂CF₃, CN, O], [2686: J8, SO₂CF₃, CN, O], [2687: J9, SO₂CF₃, CN, O], [2688: J10, SO₂CF₃, CN, O], [2689: H, CH₂C=CH, CN, O], [2690: F, CH₂C=CH, CN, O], [2691: Cl, CH₂C=CH, CN, O], [2692: Br, CH₂C=CH, CN, O], [2693: CH₃, CH₂C=CH, CN, O], [2694: CN, CH₂C=CH, CN, O], [2695: J1, CH₂C=CH, CN, O], [2696: J2, CH₂C=CH, CN, O], [2697: J3, CH₂C=CH, CN, O], [2698: J4, CH₂C=CH, CN, O], [2699: J5, CH₂C=CH, CN, O], [2700: J6, CH₂C=CH, CN, O], [2701: J7, CH₂C=CH, CN, O], [2702: J8, CH₂C=CH, CN, O], [2703: J9, CH₂C=CH, CN, O], [2704: J10, CH₂C=CH, CN, O], [2705: H, OCH₂C=CH, CN, O], [2706: F, OCH₂C=CH, CN, O], [2707: Cl, OCH₂C=CH, CN, O], [2708: Br, OCH₂C=CH, CN, O][2709: CH₃, OCH₂C=CH, CN, O], [2710: CN, OCH₂C=CH, CN, O], [2711: J1, OCH₂C=CH, CN, O], [2712: J2, OCH₂C=CH, CN, O], [2713: J3,

OCH$_2$C≡CH, CN, O], [2714: J4, OCH$_2$C≡CH, CN, O], [2715: J5, OCH$_2$C≡CH, CN, O], [2716: J6, OCH$_2$C≡CH, CN, O], [2717: J7, OCH$_2$C≡CH, CN, O], [2718: J8, OCH$_2$C≡CH, CN, O], [2719: J9, OCH$_2$C≡CH, CN, O], [2720: J10, OCH$_2$C≡CH, CN, O], [2721: H, Cl, CN, O], [2722: F, Cl, CN, O], [2723: Cl, Cl, CN, O], [2724: Br, Cl, CN, O], [2725: CH$_3$, Cl, CN, O], [2726: CN, Cl, CN, O], [2727: J1, Cl, CN, O], [2728: J2, Cl, CN, O], [2729: J3, Cl, CN, O], [2730: J4, Cl, CN, O], [2731: J5, Cl, CN, O], [2732: J6, Cl, CN, O], [2733: J7, Cl, CN, O], [2734: J8, Cl, CN, O], [2735: J9, Cl, CN, O], [2736: J10, Cl, CN, O], [2737: H, C≡CH, CN, O], [2738: F, C≡CH, CN, O], [2739: Cl, CN, O], [2740: Br, C≡CH, CN, O], [2741: CH$_3$, C≡CH, CN, O], [2742: CN, C≡CH, CN, O], [2743: J1, C≡CH, CN, O], [2744: J2, C≡CH, CN, O], [2745: J3, C≡CH, CN, O], [2746: J4, C≡CH, CN, O], [2747: J5, C≡CH, CN, O], [2748: J6, C≡CH, CN, O], [2749: J7, C≡CH, CN, O], [2750: J8, C≡CH, CN, O], [2751: J9, C≡CH, CN, O], [2752: J10, C≡CH, CN, O].

A compound represented by the formula ($I^{78}$):

$$(I^{78})$$

wherein $R^2$ and $R^e$ represent any one of combinations shown below.

A compound represented by the formula ($I^{79}$):

$$(I^{79})$$

wherein $R^2$ and $R^e$ represent any one of combinations shown below.

A compound represented by the formula ($I^{80}$):

$$(I^{80})$$

wherein $R^2$ and $R^e$ represent any one of combinations shown below.

A compound represented by the formula ($I^{81}$):

$$(I^{81})$$

wherein $R^2$ and $R^e$ represent any one of combinations shown below.

A compound represented by the formula ($I^{82}$):

$$(I^{82})$$

wherein $R^2$ and $R^e$ represent any one of combinations shown below.

A compound represented by the formula ($I^{83}$):

$$(I^{83})$$

wherein $R^2$ and $R^e$ represent any one of combinations shown below.

A compound represented by the formula ($I^{84}$):

$$(I^{84})$$

wherein $R^2$ and $R^e$ represent any one of combinations shown below.

A compound represented by the formula ($I^{85}$):

$$(I^{85})$$

wherein $R^2$ and $R^e$ represent any one of combinations shown below.

A compound represented by the formula ($I^{86}$):

$$(I^{86})$$

wherein $R^2$ and $R^e$ represent any one of combinations shown below.

A compound represented by the formula ($I^{87}$):

($I^{87}$)

wherein $R^2$ and $R^e$ represent any one of combinations shown below.

A compound represented by the formula ($I^{88}$):

($I^{88}$)

wherein $R^2$ and $R^e$ represent any one of combinations shown below.

A compound represented by the formula ($I^{89}$):

($I^{89}$)

wherein $R^2$ and $R^e$ represent any one of combinations shown below.

A compound represented by the formula ($I^{90}$):

($I^{90}$)

wherein $R^2$ and $R^e$ represent any one of combinations shown below.

A compound represented by the formula ($I^{91}$):

($I^{91}$)

wherein $R^2$ and $R^e$ represent any one of combinations shown below.

A compound represented by the formula ($I^{92}$):

($I^{92}$)

wherein $R^2$ and $R^e$ represent any one of combinations shown below.

A compound represented by the formula ($I^{93}$):

($I^{93}$)

wherein $R^2$ and $R^e$ represent any one of combinations shown below.

A compound represented by the formula ($I^{94}$):

($I^{94}$)

wherein $R^2$ and $R^e$ represent any one of combinations shown below.

A compound represented by the formula ($I^{95}$):

($I^{95}$)

wherein $R^2$ and $R^e$ represent any one of combinations shown below.

A compound represented by the formula ($I^{96}$):

($I^{96}$)

wherein $R^2$ and $R^e$ represent any one of combinations shown below.

A compound represented by the formula ($I^{97}$):

$$I^{97}$$

wherein $R^2$ and $R^e$ represent any one of combinations shown below.

A compound represented by the formula ($I^{98}$):

$$I^{98}$$

wherein $R^2$ and $R^e$ represent any one of combinations shown below.

A compound represented by the formula ($I^{99}$):

$$I^{99}$$

wherein $R^2$ and $R^e$ represent any one of combinations shown below.

A compound represented by the formula ($I^{100}$):

$$I^{100}$$

wherein $R^2$ and $R^e$ represent any one of combinations shown below.

A compound represented by the formula ($I^{101}$):

$$I^{101}$$

wherein $R^2$ and $R^e$ represent any one of combinations shown below.

A compound represented by the formula ($I^{102}$):

$$I^{102}$$

wherein $R^2$ and $R^e$ represent any one of combinations shown below.

A compound represented by the formula ($I^{103}$):

$$I^{103}$$

wherein $R^2$ and $R^e$ represent any one of combinations shown below.

A compound represented by the formula ($I^{104}$):

$$I^{104}$$

wherein $R^2$ and $R^e$ represent any one of combinations shown below.

A compound represented by the formula ($I^{105}$):

$$I^{105}$$

wherein $R^2$ and $R^e$ represent any one of combinations shown below.

A compound represented by the formula ($I^{106}$):

$$I^{106}$$

wherein $R^2$ and $R^e$ represent any one of combinations shown below.

A compound represented by the formula ($I^{107}$):

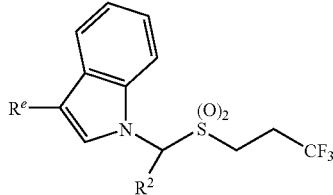

wherein $R^2$ and $R^e$ represent any one of combinations shown below.

A compound represented by the formula ($I^{108}$):

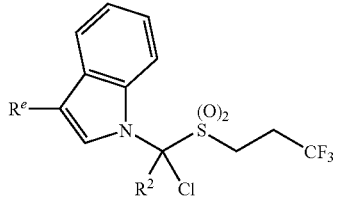

wherein $R^2$ and $R^e$ represent any one of combinations shown below.

A compound represented by the formula ($I^{109}$):

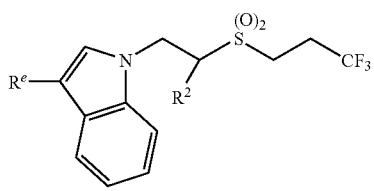

wherein $R^2$ and $R^e$ represent any one of combinations shown below.

A compound represented by the formula ($I^{110}$):

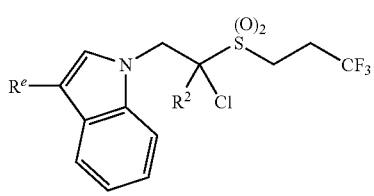

wherein $R^2$ and $R^e$ represent any one of combinations shown below.

A compound represented by the formula ($I^{111}$):

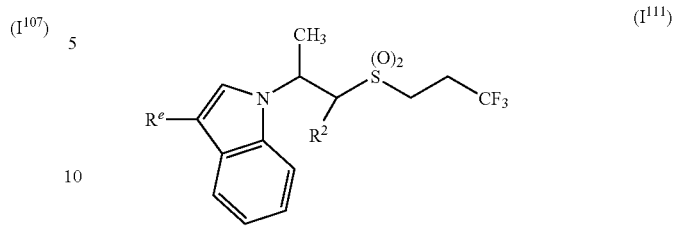

wherein $R^2$ and $R^e$ represent any one of combinations shown below.

A compound represented by the formula ($I^{112}$):

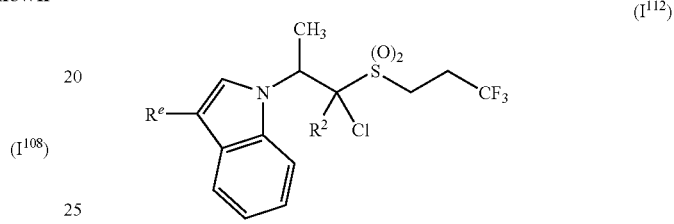

wherein $R^2$ and $R^e$ represent any one of combinations shown below.

Combinations of $R^2$ and $R^e$ for the compounds represented by the formulas ($I^{78}$) to ($I^{112}$) are shown below. In brackets, a combination number, a group represented by $R^2$ and a group represented by $R^e$ are shown in this order. Herein, symbols J1 to J10 are as defined above.

[Combination number: $R^2$, $R^e$]=[1: H, C(CH$_3$)$_3$], [2: F, C(CH$_3$)$_3$], [3: Cl, C(CH$_3$)$_3$], [4: Br, C(CH$_3$)$_3$], [5: CH$_3$, C(CH$_3$)$_3$], [6: CN, C(CH$_3$)$_3$], [7: J1, C(CH$_3$)$_3$], [8: J2, C(CH$_3$)$_3$], [9: J3, C(CH$_3$)$_3$], [10: J4, C(CH$_3$)$_3$], [11: J5, C(CH$_3$)$_3$], [12: J6C(CH$_3$)$_3$], [13: J7, C(CH$_3$)$_3$], [14: J8, C(CH$_3$)$_3$], [15: J9, C(CH$_3$)$_3$], [16: J10, C(CH$_3$)$_3$], [17: H, CF$_3$], [18: F, CF$_3$], [19: Cl, CF$_3$], [20: Br, CF$_3$], [21: CH$_3$, CF$_3$], [22: CN, CF$_3$], [23: J1, CF$_3$], [24: J2, CF$_3$], [25: J3, CF$_3$], [26: J4, CF$_3$], [27: J5, CF$_3$], [28: J6, CF$_3$], [29: J7, CF$_3$], [30: J8, CF$_3$], [31: J9, CF$_3$], [32: J10, CF$_3$], [33: H, CF$_2$CF$_3$], [34: F, CF$_2$CF$_3$], [35: Cl, CF$_2$CF$_3$], [36: Br, CF$_2$CF$_3$], [37: CH$_3$, CF$_2$CF$_3$], [38: CN, CF$_2$CF$_3$], [39: J$_1$, CF$_2$CF$_3$], [40: J2, CF$_2$CF$_3$], [41: J3, CF$_2$CF$_3$], [42: J4, CF$_2$CF$_3$], [43: J5, CF$_2$CF$_3$], [44: J6, CF$_2$CF$_3$], [45: J7, CF$_2$CF$_3$], [46: J8, CF$_2$CF$_3$], [47: J9, CF$_2$CF$_3$], [48: J10, CF$_2$CF$_3$], [49: H, SCF$_3$], [50: F, SCF$_3$], [51: Cl, SCF$_3$], [52: Br, SCF$_3$], [53: CH$_3$, SCF$_3$], [54: CN, SCF$_3$], [55: J1, SCF$_3$], [56: J2, SCF$_3$], [57: J3, SCF$_3$], [58: J4, SCF$_3$], [59: J5, SCF$_3$], [60: J6, SCF$_3$], [61: J7, SCF$_3$], [62: J8, SCF$_3$], [63: J9, SCF$_3$], [64: J10, SCF$_3$], [65: H, SOCF$_3$], [66: F, SOCF$_3$], [67: Cl, SOCF$_3$], [68: Br, SOCF$_3$], [69: CH$_3$, SOCF$_3$], [70: CN, SOCF$_3$], [71: J1, SOCF$_3$], [72: J2, SOCF$_3$], [73: J3, SOCF$_3$], [74: J4, SOCF$_3$], [75: J5, SOCF$_3$], [76: J6, SOCF$_3$], [77: J7, SOCF$_3$], [78: J8, SOCF$_3$], [79: J9, SOCF$_3$], [80: J10, SOCF$_3$], [81: H, SO$_2$CF$_3$], [82: F, SO$_2$CF$_3$], [83: Cl, SO$_2$CF$_3$], [84: Br, SO$_2$CF$_3$], [85: CH$_3$, SO$_2$CF$_3$], [86: CN, SO$_2$CF$_3$], [87: J1, SO$_2$CF$_3$], [88: J2, SO$_2$CF$_3$], [89: J3, SO$_2$CF$_3$], [90: J4, SO$_2$CF$_3$], [91: J5, SO$_2$CF$_3$], [92: J6, SO$_2$CF$_3$], [93: J7, SO$_2$CF$_3$], [94: J8, SO$_2$CF$_3$], [95: J9, SO$_2$CF$_3$], [96: J10, SO$_2$CF$_3$], [97: H, CH$_2$C≡CH], [98: F, CH$_2$C≡CH], [99: Cl, CH$_2$C≡CH], [100: Br, CH$_2$C≡CH], [101: CH$_3$, CH$_2$C≡CH], [102CN, CH$_2$C≡CH], [103: J1, CH$_2$C≡CH], [104: J2, CH$_2$C≡CH], [105: J3, CH$_2$C≡CH], [106: J4, CH$_2$C≡CH], [107: J5, CH$_2$C≡CH], [108: J6, CH$_2$C≡CH], [109: J7 CH$_2$C≡C H], [110: J8, CH$_2$C≡CH],

[111: J9, CH₂C=CH], [112: J10, CH₂C=CH], [113: H, OCH₂C=CH], [114: F, OCH₂C=CH], [115: Cl, OCH₂C=CH], [116: Br, OCH₂C=CH], [117: CH₃, OCH₂C=CH], [118: CN, OCH₂C=CH], [119: J1, OCH₂C=CH], [120: J2, OCH₂C=CH], [121: J3, OCH₂C=CH], [122: J4, OCH₂C=CH], [123: J5, OCH₂C=CH], [124: J6, OCH₂C=CH], [125: J7, OCH₂C=CH], [126: J8, OCH₂C=CH], [127: J9, OCH₂C=CH], [128: J10, OCH₂C=CH], [129: H, Cl], [130: F, Cl], [131: Cl, Cl], [132: Br, Cl], [133: CH₃, Cl], [134: CN, Cl], [135: J1, Cl], [136: J2, Cl], [137: J3, Cl], [138: J4, Cl], [139: J5, Cl], [140: J6, Cl], [141: J7, Cl], [142: J8, Cl], [143: J9, Cl], [144: J10, Cl], [145: H, CN], [146: F, CN], [147: Cl, CN], [148: Br, CN], [149: CH₃, CN], [150: CN, CN], [151: J1, CN], [152: J2, CN], [153: J3, CN], [154: J4, CN], [155: J5, CN], [156: J6, CN], [157: J7, CN], [158: J8, CN], [159: J9, CN], [160: J10, CN], [161: H, C=CH], [162: F, C=CH], [163: Cl, C=CH], [164: Br, C=CH], [165: CH₃, C=CH], [166: CN, C=CH], [167: J1, C=CH], [168: J2, C=CH], [169: J3, C=CH], [170: J4, C=CH], [171: J5, C=CH], [172: J6, C=CH], [173: J7, C=CH], [174: J8, C=CH], [175: J9, C=CH], [176: J10, C=CH].

A compound represented by the formula ($I^{113}$):

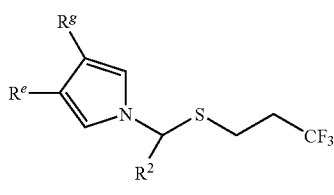

wherein $R^2$, $R^f$ and $R^g$ represent any one of combinations shown below.

A compound represented by the formula ($I^{114}$):

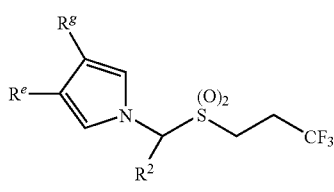

wherein $R^2$, $R^f$ and $R^g$ represent any one of combinations shown below.

A compound represented by the formula ($I^{115}$):

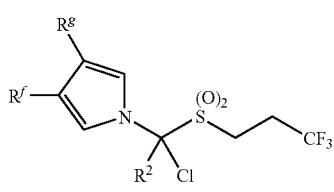

wherein $R^2$, $R^f$ and $R^g$ represent any one of combinations shown below.

A compound represented by the formula ($I^{116}$):

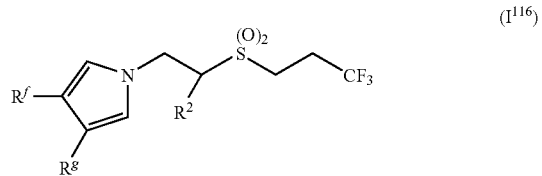

wherein $R^2$, $R^f$ and $R^g$ represent any one of combinations shown below.

A compound represented by the formula ($I^{117}$):

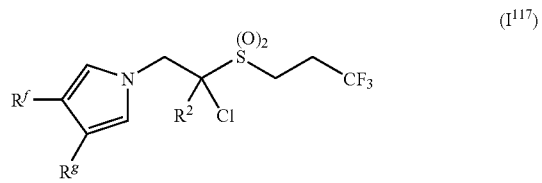

wherein $R^2$, $R^f$ and $R^g$ represent any one of combinations shown below.

A compound represented by the formula ($I^{118}$):

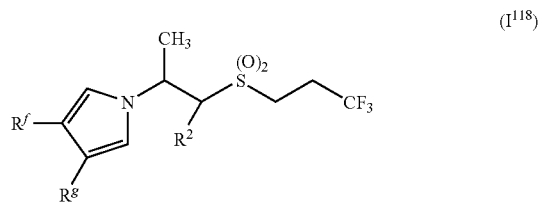

wherein $R^2$, $R^f$ and $R^g$ represent any one of combinations shown below.

A compound represented by the formula ($I^{119}$):

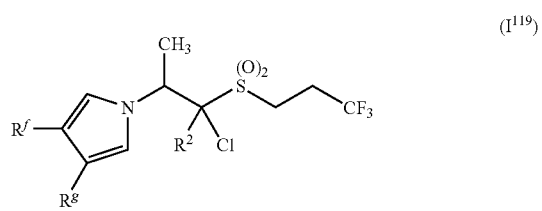

wherein $R^2$, $R^f$ and $R^g$ represent any one of combinations shown below.

A compound represented by the formula ($I^{120}$):

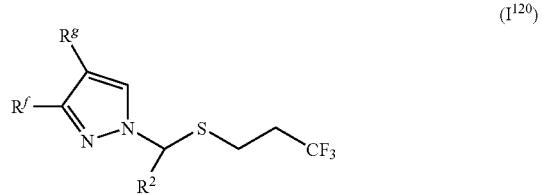

wherein $R^2$, $R^f$ and $R^g$ represent any one of combinations shown below.

A compound represented by the formula ($I^{121}$):

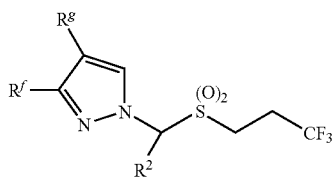

wherein $R^2$, $R^f$ and $R^g$ represent any one of combinations shown below.

A compound represented by the formula ($I^{122}$):

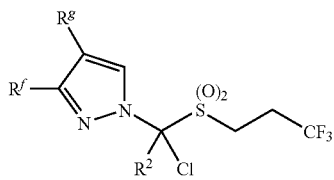

wherein $R^2$, $R^f$ and $R^g$ represent any one of combinations shown below.

A compound represented by the formula ($I^{122}$):

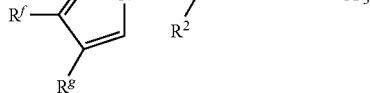

wherein $R^2$, $R^f$ and $R^g$ represent any one of combinations shown below.

A compound represented by the formula ($I^{124}$):

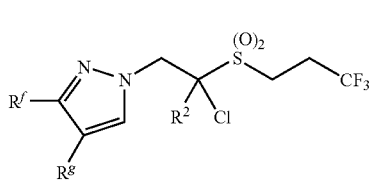

wherein $R^2$, $R^f$ and $R^g$ represent any one of combinations shown below.

A compound represented by the formula ($I^{125}$):

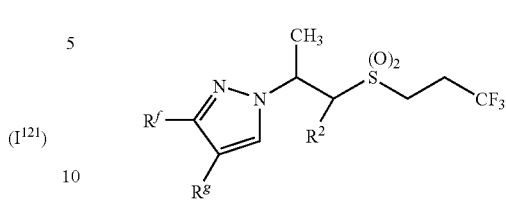

wherein $R^2$, $R^f$ and $R^g$ represent any one of combinations shown below.

A compound represented by the formula ($I^{126}$):

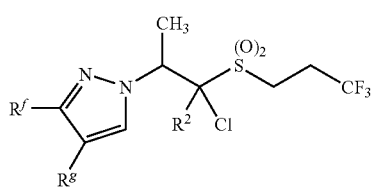

wherein $R^2$, $R^f$ and $R^g$ represent any one of combinations shown below.

Combinations of $R^2$, $R^f$ and $R^g$ for the compounds represented by the formulas ($I^{113}$) to ($I^{126}$) are shown below. In brackets, a combination number, a group represented by $R^2$, a group represented by $R^f$, and a group represented by $R^g$ are shown in this order. Herein, symbols J1 to J10 are as defined above.

[Combination number: $R^2$, $R^f$, $R^g$]=[1: H, C(CH$_3$)$_3$, H], [2: F, C(CH$_3$)$_3$, H], [3: Cl, C(CH$_3$)$_3$, H], [4: Br, C(CH$_3$)$_3$, H], [5: CH$_3$, C(CH$_3$)$_3$, H], [6: CN, C(CH$_3$)$_3$, H], [7: J1, C(CH$_3$)$_3$, H], [8: J2, C(CH$_3$)$_3$, H], [9: J3, C(CH$_3$)$_3$, H], [10: J4, C(CH$_3$)$_3$, H], [11: J5, C(CH$_3$)$_3$, H], [12: J6, C(CH$_3$)$_3$, H], [13: J7, C(CH$_3$)$_3$, H], [14: J8, C(CH$_3$)$_3$, H], [15: J9, C(CH$_3$)$_3$, H], [16: J10, C(CH$_3$)$_3$, H], [17: H, CF$_3$, H], [18: F, CF$_3$, H], [19: Cl, CF$_3$, H], [20: Br, CF$_3$, H], [21: CH$_3$, CF$_3$, H], [22: CN, CF$_3$, H], [23: J1, CF$_3$, H], [24: J2, CF$_3$, H], [25: J3, CF$_3$, H], [26: J4, CF$_3$, H], [27: J5, CF$_3$, H], [28: J6, CF$_3$, H], [29: J7, CF$_3$, H], [30: J8, CF$_3$, H], [31: J9, CF$_3$, H], [32: J10, CF$_3$, H], [33: H, CF$_2$CF$_3$, H], [34: F, CF$_2$CF$_3$, H], [35: Cl, CF$_2$CF$_3$, H], [36: Br, CF$_2$CF$_3$, H], [37: CH$_3$, CF$_2$CF$_3$, H], [38: CN, CF$_2$CF$_3$, H], [39: J1, CF$_2$CF$_3$, H], [40: J2, CF$_2$CF$_3$, H], [41: J3, CF$_2$CF$_3$, H], [42: J4, CF$_2$CF$_3$, H], [43: J5, CF$_2$CF$_3$, H], [44: J6, CF$_2$CF$_3$, H], [45: J7, CF$_2$CF$_3$, H], [46: J8, CF$_2$CF$_3$, H], [47: J9, CF$_2$CF$_3$, H], [48: J10, CF$_2$CF$_3$, H], [49: H, SCF$_3$, E1], [50: F, SCF$_3$, H], [51: Cl, SCF$_3$, H], [52: Br, SCF$_3$, H], [53: CH$_3$, SCF$_3$, H], [54: CN, SCF$_3$, H], [55: J1, SCF$_3$, H], [56: J2, SCF$_3$, H], [57: J3, SCF$_3$, H], [58: J4, SCF$_3$, H], [59: J5, SCF$_3$, H], [60: J6, SCF$_3$, H], [61: J7, SCF$_3$, H], [62: J8, SCF$_3$, H], [63: J9, SCF$_3$, H], [64: J10, SCF$_3$, H], [65: H, SOCF$_3$, H], [66: F, SOCF$_3$, H], [67: Cl, SOCF$_3$, H], [68: Br, SOCF$_3$, H], [69: CH$_3$, SOCF$_3$, H], [70: CN, SOCF$_3$, H], [71: J1, SOCF$_3$, H], [72: J2, SOCF$_3$, H], [73: J3, SOCF$_3$, H], [74: J4, SOCF$_3$, H], [75: J5, SOCF$_3$, H], [76: J6, SOCF$_3$, H], [77: J7, SOCF$_3$, H], [78: J8, SOCF$_3$, H], [79: J9, SOCF$_3$, H], [80: J10, SOCF$_3$, H], [81: H, SO$_2$CF$_3$, H], [82: F, SO$_2$CF$_3$, H], [83: Cl, SO$_2$CF$_3$, H], [84: Br, SO$_2$CF$_3$, H], [85: CH$_3$, SO$_2$CF$_3$, H], [86: CN, SO$_2$CF$_3$, H], [87: J$_1$, SO$_2$CF$_3$], [88: J2, SO$_2$CF$_3$, H], [89: J3, SO$_2$CF$_3$, H], [90: J4, SO$_2$CF$_3$, H], [91: J5, SO$_2$CF$_3$, H], [92: J6, SO$_2$CF$_3$, H], [93: J7, SO$_2$CF$_3$, H], [94: J8, SO$_2$CF$_3$, H], [95: J9, SO$_2$CF$_3$, H], [96: J10, SO$_2$CF$_3$, H], [97: H, CH$_2$C≡CH, H], [98: F, CH$_2$C≡CH, H], [99: Cl, CH$_2$C≡CH, H], [100: Br, CH$_2$C≡CH, H], [101: CH$_3$, CH₂C=CH, H], [102: CN, CH₂C=CH, H], [103: J1, CH₂C=CH, H], [104: J2, CH₂C=CH, H], [105: J3, CH₂C=CH, H], [106: J4, CH₂C=CH, H], [107: J5, CH₂C=CH, H], [108: J6, CH₂C=CH, H], [109: J7, CH₂C=CH, H], [110: J8, CH₂C=CH, H], [111: J9, CH₂C=CH, H], [112: J10, CH₂C=CH, H], [113: H, OCH₂C=CH, H], [114: F, OCH₂C=CH, H], [115: Cl, OCH₂C=CH, H], [116: Br, OCH₂C=CH, H], [117: CH₃, OCH₂C=CH, H], [118: CN, OCH₂C=CH, H], [119: J1, OCH₂C=CH, H], [120: J2, OCH₂C=CH, H], [121: J3, OCH₂C=CH, H], [122: J4, OCH₂C=CH, H], [123: J5, OCH₂C=CH, H], [124: J6, OCH₂C=CH, H], [125: J7, OCH₂C=CH, H], [126: J8, OCH₂C=CH, H], [127: J9, OCH₂C=CH, H], [128: J10, OCH₂C=CH, H], [129: H, Cl, H], [130: F, Cl, H], [131: Cl, Cl, H], [132: Br, Cl, H], [133: CH₃, Cl, H], [134: CN, Cl, H], [135: J1, Cl, H], [136: J2, Cl, H], [137: J3, Cl, H], [138: J4, Cl, H], [139: J5, Cl, H], [140: J6, Cl, H], [141: J7, Cl, H], [142: J8, Cl, H], [143: J9, Cl, H], [144: J10, Cl, H], [145: H, C=CH, H], [146: F, C=CH, H], [147: Cl, C=CH, H], [148: Br, C=CH, H], [149: CH₃, C=CH, H], [150: CN, C=CH, H], [151: J1, C=CH, H], [152: J2, C=CH, H], [153: J3, C=CH, H], [154: J4, C=CH, H], [155: J5, C=CH, H], [156: J6, C=CH, H], [157: J7, C=CH, H], [158: J8, C=CH, H], [159: J9, C=CH, H], [160: J10, C=CH, H], [161: H, CN, H], [162: F, CN, H], [163: Cl, CN, H], [164: Br, CN, H], [165: CH₃, CN, H], [166: CN, CN, H], [167: J1, CN, H], [168: J2, CN, H], [169: J3, CN, H], [170: J4, CN, H], [171: J5, CN, H], [172: J6, CN, H], [173: J7, CN, H], [174: J8, CN, H], [175: J9, CN, H], [176: J10, CN, H], [177: H, C(CH₃)₃, CN], [178: F, C(CH₃)₃, CN], [179: Cl, C(CH₃)₃, CN], [180: Br, C(CH₃)₃, CN], [181: CH₃, C(CH₃)₃, CN], [182: CN, C(CH₃)₃, CN], [183: J1, C(CH₃)₃, CN], [184: J2, C(CH₃)₃, CN], [185: J3, C(CH₃)₃, CN], [186: J4, C(CH₃)₃, CN], [187: J5, C(CH₃)₃, CN], [188: J6, C(CH₃)₃, CN], [189: J7, C(CH₃)₃, CN], [190: J8, C(CH₃)₃, CN], [191: J9, C(CH₃)₃, CN], [192: J10, C(CH₃)₃, CN], [193: H, CF₃, CN], [194: F, CF₃, CN], [195: Cl, CF₃, CN], [196: Br, CF₃, CN], [197: CH₃, CF₃, CN], [198: CN, CF₃, CN], [199: J1, CF₃, CN], [200: J2, CF₃, CN], [201: J3, CF₃, CN], [202: J4, CF₃, CN], [203: J5, CF₃, CN], [204: J6, CF₃, CN], [205: J7, CF₃, CN], [206: J8, CF₃, CN], [207: J9, CF₃, CN], [208: J10, CF₃, CN], [209: H, CF₂CF₃, CN], [210: F, CF₂CF₃, CN], [211: Cl, CF₂CF₃, CN], [212: Br, CF₂CF₃, CN], [213: CH₃, CF₂CF₃, CN], [214: CN, CF₂CF₃, CN], [215: J1, CF₂CF₃, CN], [216: J2, CF₂CF₃, CN], [217: J3, CF₂CF₃, CN], [218: J4, CF₂CF₃, CN], [219: J5, CF₂CF₃, CN], [220: J6, CF₂CF₃, CN], [221: J7, CF₂CF₃, CN], [222: J8, CF₂CF₃, CN], [223: J9, CF₂CF₃, CN], [224: J10, CF₂CF₃, CN], [225: H, SCF₃, CN], [226: F, SCF₃, CN], [227: Cl, SCF₃, CN], [228: Br, SCF₃, CN], [229: CH₃, SCF₃, CN], [230: CN, SCF₃, CN], [231: J1, SCF₃, CN], [232: J2, SCF₃, CN], [233: J3, SCF₃, CN], [234: J4, SCF₃, CN], [235: J5, SCF₃, CN], [236: J6, SCF₃, CN], [237: J7, SCF₃, CN], [238: J8, SCF₃, CN], [239: J9, SCF₃, CN], [240: J10, SCF₃, CN], [241: H, SOCF₃, CN], [242: F, SOCF₃, CN], [243: Cl, SOCF₃, CN], [244: Br, SOCF₃, CN], [245: CH₃, SOCF₃, CN], [246: CN, SOCF₃, CN], [247: J1, SOCF₃, CN], [248: J2, SOCF₃, CN], [249: J3, SOCF₃, CN], [250: J4, SOCF₃, CN], [251: J5, SOCF₃, CN], [252: J6, SOCF₃, CN], [253: J7, SOCF₃, CN], [254: J8, SOCF₃, CN], [255: J9, SOCF₃, CN], [256: J10, SOCF₃, CN], [257: H, SO₂CF₃, CN], [258: F, SO₂CF₃, CN], [259: Cl, SO₂CF₃, CN], [260: Br, SO₂CF₃, CN], [261: CH₃, SO₂CF₃, CN], [262: CN, SO₂CF₃, CN][263: J1, SO₂CF₃, CN], [264: J2, SO₂CF₃, CN], [265: J3, SO₂CF₃, CN], [266: J4, SO₂CF₃, CN], [267: J5, SO₂CF₃, CN], [268: J6, SO₂CF₃, CN][269: J7, SO₂CF₃, CN], [270: J8, SO₂CF₃, CN][271: J9, SO₂CF₃, CN][272: J10, SO₂CF₃, CN], [273: H, CH₂C=CH, CN], [274: F, CH₂C=CH, CN], [275: Cl, CH₂C=CH, CN], [276: Br, CH₂C=CH, CN], [277: CH₃, CH₂C=CH, CN], [278: CN, CH₂C=CH, CN], [279: J1, CH₂C=CH, CN], [280: J2, CH₂C=CH₂CN], [281: J3, CH₂C=CH, CN], [282: J4, CH₂C=CH, CN], [283: J5, CH₂C=CH, CN], [284: J6, CH₂C=CH, CN], [285: J7, CH₂C=CH, CN], [286: J8, CH₂C=CH, CN], [287: J9, CH₂C=CH, CN], [288: J10, CH₂C=CH, CN], [289: H, OCH₂C=CH, CN], [290: F, OCH₂C=CH, CN], [291: Cl, OCH₂C=CH, CN], [292: Br, OCH₂C=CH, CN], [293: CH₃, OCH₂C=CH, CN], [294: CN, OCH₂C=CH, CN], [295: J1, OCH₂C=CH, CN], [296: J2, OCH₂C=CH, CN], [297: J3, OCH₂C=CH, CN], [298: J4, OCH₂C=CH, CN], [299: J5, OCH₂C=CH, CN], [300: J6, OCH₂C=CH, CN], [301: J7, OCH₂C=CH, CN], [302: J8, OCH₂C=CH, CN], [303: J9, OCH₂C=CH, CN], [304: J10, OCH₂C=CH, CN], [305: H, Cl, CN], [306: F, Cl, CN], [307: Cl, Cl, CN], [308: Br, Cl, CN], [309: CH₃, Cl, CN], [310: CN, Cl, CN], [311: J1, Cl, CN], [312: J2, Cl, CN], [313: J3, Cl, CN], [314: J4, Cl, CN], [315: J5, Cl, CN], [316: J6, Cl, CN], [317: J7, Cl, CN], [318: J8, Cl, CN], [319: J9, Cl, CN], [320: J10, Cl, CN], [321: H, C=CH, CN], [322: F, C=CH, CN], [323: Cl, C=CH, CN], [324: Br, C=CH, CN], [325: CH₃, C=CH, CN], [326: CN, C=CH, CN], [327: J1, C=CH, CN], [328: J2, C=CH, CN], [329: J3, C=CH, CN], [330: J4, C=CH, CN], [331: J5, C=CH, CN], [332: J6, C=CH, CN], [333: J7, C=CH, CN], [334: J8, C=CH, CN], [335: J9, C=CH, CN], [336: J10, C=CH, CN], [337: H, CN, CN], [338: F, CN, CN], [339: Cl, CN, CN], [340: Br, CN, CN], [341: CH₃, CN, CN], [342: CN, CN, CN], [343: J1, CN, CN], [344: J2, CN, CN], [345: J3, CN, CN], [346: J4, CN, CN], [347: J5, CN, CN], [348: J6, CN, CN], [349: J7, CN, CN], [350: J8, CN, CN], [251: J9, CN, CN], [352: J10, CN, CN], [353: H, H, C(CH₃)₃], [354: F, H, C(CH₃)₃], [355: Cl, H, C(CH₃)₃], [356: Br, H, C(CH₃)₃], [357: CH₃, H, C(CH₃)₃], [358: CN, H, C(CH₃)₃], [359: J1, H, C(CH₃)₃], [360: J2, H, C(CH₃)₃], [361: J3, H, C(CH₃)₃], [362: J4, H, C(CH₃)₃], [363: J5, H, C(CH₃)₃], [364: J6, H, C(CH₃)₃], [365: J7, H, C(CH₃)₃], [366: J8, H, C(CH₃)₃], [367: J9, H, C(CH₃)₃], [368: J10, H, C(CH₃)₃], [369: H, H, CF₃], [370: F, H, CF₃], [371: Cl, H, CF₃], [372: Br, H, CF₃], [373: CH₃, H, CF₃], [374: CN, H, CF₃], [375: J1, H, CF₃], [376: J2, H, CF₃], [377: J3, H, CF₃], [378: J4, H, CF₃], [379: J5, H, CF₃], [380: J6, H, CF₃], [381: J7, H, CF₃], [382: J8, H, CF₃], [383: J9, H, CF₃], [384: J10, H, CF₃], [385: H, H, CF₂CF₃], [386: F, H, CF₂CF₃], [387: Cl, H, CF₂CF₃], [388: Br, H, CF₂CF₃], [389: CH₃, H, CF₂CF₃], [390: CN, H, CF₂CF₃], [391: J1, H, CF₂CF₃], [392: J2, H, CF₂CF₃], [393: J3, H, CF₂CF₃], [394: J4, H, CF₂CF₃], [395: J5, H, CF₂CF₃], [396: J6, H, CF₂CF₃], [397: J7, H, CF₂CF₃], [398: J8, H, CF₂CF₃], [399: J9, H, CF₂CF₃], [400: J10, H, CF₂CF₃], [401: H, H, SCF₃], [402: F, H, SCF₃], [403: Cl, H, SCF₃], [404: Br, H, SCF₃], [405: CH₃, H, SCF₃], [406: CN, H, SCF₃], [407: J1, H, SCF₃], [408: J2, H, SCF₃], [409: J3, H, SCF₃], [410: J4, H, SCF₃], [411: J5, H, SCF₃], [412: J6, H, SCF₃], [413: J7, H, SCF₃], [414: J8, H, SCF₃], [415: J9, H, SCF₃], [416: J10, H, SCF₃], [417: H, H, SOCF₃], [418: F, H, SOCF₃], [419: Cl, H, SOCF₃], [420: Br, H, SOCF₃], [421: CH₃, H, SOCF₃], [422: CN, H, SOCF₃], [423: J1, H, SOCF₃], [424: J2, H, SOCF₃], [425: J3, H, SOCF₃], [426: J4, H, SOCF₃], [427: J5, H, SOCF₃], [428: J6, H, SOCF₃], [429: J7, H, SOCF₃], [430: J8, H, SOCF₃], [431: J9, H, SOCF₃], [432: J10, H, SOCF₃], [433: H, H, SO₂CF₃], [434: F, H, SO₂CF₃], [435: Cl, H, SO₂CF₃], [436: Br, H, SO₂CF₃], [437: CH₃, H, SO₂CF₃], [438: CN, H, SO₂CF₃], [439: J1, H, SO₂CF₃], [440: J2, H, SO₂CF₃], [441: J3, H, SO₂CF₃], [442: J4, H, SO₂CF₃], [443: J5, H, SO₂CF₃], [444: J6, H, SO₂CF₃], [445: J7, H, SO₂CF₃], [446: J8, H, SO₂CF₃], [447: J9, H, SO₂CF₃], [448: J10, H, SO₂CF₃], [449: H, H, CH₂C=CH], [450: F, H, CH₂C=CH][451: Cl, H, CH₂C≡CH], [452: Br, H, CH₂C≡CH], [453: CH₃, H, CH₂C≡CH], [454: CN, H, CH₂C≡CH], [455: J1, H, CH₂C≡CH], [456: J2, H, CH₂C≡CH], [457: J3, H, CH₂C≡CH], [458: J4, H, CH₂C≡CH], [459: J5, H, CH₂C≡CH], [460: J6, H, CH₂C≡CH], [461: J7, H, CH₂C≡CH], [462: J8, H, CH₂C≡CH], [463: J9, H, CH₂C≡CH], [464: J10, H, CH₂C≡CH], [465: H, H, OCH₂C≡CH], [466: F, H, OCH₂C≡CH], [467: Cl, H, OCH₂C≡CH], [468: Br, H, OCH₂C≡CH][469: CH₃, H, OCH₂C≡CH], [470: CN, H, OCH₂C≡CH], [471: J1, H, OCH₂C≡CH], [472: J2, H, OCH₂C≡CH], [473: J3, H, OCH₂C≡CH], [474: J4, H, OCH₂C≡CH], [475: J5, H, OCH₂C≡CH], [476: J6, H, OCH₂C≡CH], [477: J7, H, OCH₂C≡CH], [478: J8, H, OCH₂C≡CH], [479: J9, H, OCH₂C≡CH], [480: J10, H, OCH₂C≡CH], [481: H, H, Cl], [482: F, H, Cl], [483: Cl, H, Cl], [484: Br, H, Cl], [485: CH₃, H, Cl], [486: CN, H, Cl], [487: J1, H, Cl], [488: J2, H, Cl], [489: J3, H, Cl], [490: J4, H, Cl], [491: J5, H, Cl], [492: J6, H, Cl], [493: J7, H, Cl], [494: J8, H, Cl], [495: J9, H, Cl], [496: J10, H, Cl], [497: H, H, C≡CH], [498: F, H, C≡CH], [499: Cl, H, C≡CH], [500: Br, H, C≡CH], [501: CH₃, H, C≡CH], [502: CN, H, C≡CH], [503: J1, H, C≡CH], [504: J2, H, C≡CH], [505: J3, H, C≡CH], [506: J4, H, C≡CH], [507: J5, H, C≡CH], [508: J6, H, C≡CH], [509: J7, H, C≡CH], [510: J8, H, C≡CH], [511: J9, H, C≡CH], [512: J10, H, C≡CH], [513: H, H, CN], [514: F, H, CN], [515: Cl, H, CN], [516: Br, H, CN], [517: CH₃, H, CN], [518: CN, H, CN], [519: J1, H, CN], [520: J2, H, CN], [521: J3, H, CN], [522: J4, H, CN], [523: J5, H, CN], [524: J6, H, CN], [525: J7, H, CN], [526: J8, H, CN], [527: J9, H, CN], [528: J10, H, CN], [529: H, CN, C(CH₃)₃], [530: F, CN, C(CH₃)₃], [531: Cl, CN, C(CH₃)₃], [532: Br, CN, C(CH₃)₃], [533: CH₃, CN, C(CH₃)₃], [534: CN, CN, C(CH₃)₃], [535: J1, CN, C(CH₃)₃], [536: J2, CN, C(CH₃)₃], [537: J3, CN, C(CH₃)₃], [538: J4, CN, C(CH₃)₃], [539: J5, CN, C(CH₃)₃], [540: J6, CN, C(CH₃)₃], [541: J7, CN, C(CH₃)₃], [542: J8, CN, C(CH₃)₃], [543: J9, CN, C(CH₃)₃], [544: J10, CN, C(CH₃)₃], [545: H, CN, CF₃], [546: F, CN, CF₃], [547: Cl, CN, CF₃], [548: Br, CN, CF₃], [549: CH₃, CN, CF₃], [550: CN, CN, CF₃], [551: J1, CN, CF₃], [552: J2, CN, CF₃], [553: J3, CN, CF₃], [554: J4, CN, CF₃], [555: J5, CN, CF₃], [556: J6, CN, CF₃], [557: J7, CN, CF₃], [558: J8, CN, CF₃], [559: J9, CN, CF₃], [560: J10, CN, CF₃], [561: H, CN, CF₂CF₃], [562: F, CN, CF₂CF₃], [563: Cl, CN, CF₂CF₃], [564: Br, CN, CF₂CF₃], [565: CH₃, CN, CF₂CF₃], [566: CN, CN, CF₂CF₃], [567: J1, CF₂CF₃], [568: J2, CN, CF₂CF₃], [569: J3, CN, CF₂CF₃], [570: J4, CN, CF₂CF₃], [571: J5, CN, CF₂CF₃], [572: J6, CN, CF₂CF₃], [573: J7, CN, CF₂CF₃], [574: J8, CN, CF₂CF₃], [575: J9, CN, CF₂CF₃], [576: J10, CN, CF₂CF₃], [577: H, CN, SCF₃], [578: F, CN, SCF₃], [579: Cl, CN, SCF₃], [580: Br, CN, SCF₃], [581: CH₃, CN, SCF₃], [582: CN, CN, SCF₃], [583: J1, CN, SCF₃], [584: J2, CN, SCF₃], [585: J3, CN, SCF₃], [586: J4, CN, SCF₃], [587: J5, CN, SCF₃], [588: J6, CN, SCF₃], [589: J7, CN, SCF₃], [590: J8, CN, SCF₃], [591: J9, CN, SCF₃], [592: J10, CN, SCF₃], [593 CN, SOCF₃], [594: F, CN, SOCF₃], [595: Cl, CN, SOCF₃], [596: Br, CN, SOCF₃], [597: CH₃, CN, SOCF₃], [598: CN, CN, SOCF₃], [599: J1, CN, SOCF₃], [600: J2, CN, SOCF₃], [601: J3, CN, SOCF₃], [602: J4, CN, SOCF₃], [603: J5, CN, SOCF₃], [604: J6, CN, SOCF₃], [605: J7, CN, SOCF₃], [606: J8, CN, SOCF₃], [607: J9, CN, SOCF₃], [608: J10, CN, SOCF₃], [609: H, CN, SO₂CF₃], [610: F, CN, SO₂CF₃], [611: Cl, CN, SO₂CF₃], [612: Br, CN, SO₂CF₃], [613: CH₃, CN, SO₂CF₃], [614: CN, CN, SO₂CF₃], [615: J1, CN, SO₂CF₃], [616: J2, CN, SO₂CF₃], [617: J3, CN, SO₂CF₃], [618: J4, CN, SO₂CF₃], [619: J5, CN, SO₂CF₃], [620: J6, CN, SO₂CF₃], [621: J7, CN, SO₂CF₃], [622: J8, CN, SO₂CF₃], [623: J9, CN, SO₂CF₃], [624: J10, CN, SO₂CF₃], [625: H, CN, CH₂C≡CH], [626: F, CN, CH₂C≡CH], [627: Cl, CN, CH₂C≡CH], [628: Br, CN, CH₂C≡CH], [629: CH₃, CN, CH₂C≡CH], [630: CN, CN, CH₂C≡CH], [631: J1, CN, CH₂C≡CH], [632: J2, CN, CH₂C≡CH], [633: J3, CN, CH₂C≡CH], [634: J4, CN, CH₂C≡CH], [635: J5, CN, CH₂C≡CH], [636: J6, CN, CH₂C≡CH], [637: J7, CN, CH₂C≡CH], [638: J8, CN, CH₂C≡CH], [639: J9, CN, CH₂C≡CH], [640: J10, CN, CH₂C≡CH], [641: H, CN, OCH₂C≡CH], [642: F, CN, OCH₂C≡CH], [643: Cl, CN, OCH₂C≡CH], [644: Br, CN, OCH₂C≡CH], [645: CH₃, CN, OCH₂C≡CH], [646: CN, CN, OCH₂C≡CH], [647: J1, CN, OCH₂C≡CH], [648: J2, CN, OCH₂C≡CH], [649: J3, CN, OCH₂C≡CH], [650: J4, CN, OCH₂C≡CH], [651: J5, CN, OCH₂C≡CH], [652: J6, CN, OCH₂C≡CH], [653: J7, CN, OCH₂C≡CH], [654: J8, CN, OCH₂C≡CH], [655: J9, CN, OCH₂C≡CH], [656: J10, CN, OCH₂C≡CH], [657: H, CN, Cl], [658: F, CN, Cl], [659: Cl, CN, Cl], [660: Br, CN, Cl], [661: CH₃, CN, Cl], [662: CN, CN, Cl], [663: J1, CN, Cl], [664: J2, CN, Cl], [665: J3, CN, Cl], [666: J4, CN, Cl], [667: J5, CN, Cl], [668: J6, CN, Cl], [669: J7, CN, Cl], [670: J8, CN, Cl], [671: J9, CN, Cl], [672: J10, CN, Cl], [673: H, CN, C≡CH], [674: F, CN, C≡CH], [675: Cl, CN, C≡CH], [676: Br, CN, C≡CH], [677: CH₃, CN, C≡CH], [678: CN, CN, C≡CH], [679: J1, CN, C≡CH], [680: J2, CN, C≡CH], [681: J3, CN, C≡CH], [682: J4, CN, C≡CH], [683: J5, CN, C≡CH], [684: J6, CN, C≡CH], [685: J7, CN, C≡CH], [686: J8, CN, C≡CH], [687: J9, CN, C≡CH], [688: J10, CN, C≡CH].

A compound represented by the formula ($I^{127}$):

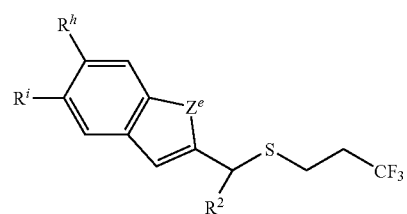

wherein $R^2$, $R^h$, $R^i$ and $Z^e$ represent any one of combinations shown below.

A compound represented by the formula ($I^{128}$):

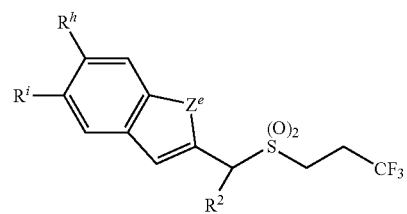

wherein $R^2$, $R^h$, $R^i$ and $Z^e$ represent any one of combinations shown below.

A compound represented by the formula ($I^{129}$):

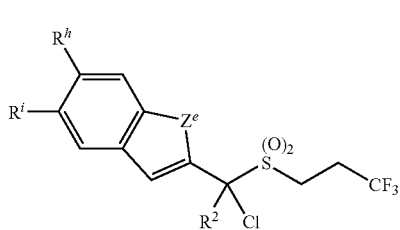

($I^{129}$)

wherein $R^2$, $R^h$, $R^i$ and $Z^e$ represent any one of combinations shown below.

A compound represented by the formula ($I^{130}$):

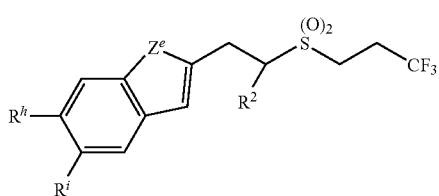

($I^{130}$)

wherein $R^2$, $R^h$, $R^i$ and $Z^e$ represent any one of combinations shown below.

A compound represented by the formula ($I^{131}$):

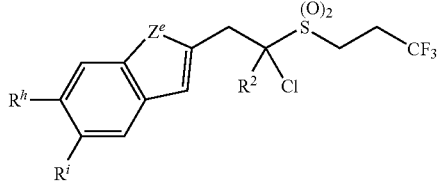

($I^{131}$)

wherein $R^2$, $R^h$, $R^i$ and $Z^e$ represent any one of combinations shown below.

A compound represented by the formula ($I^{132}$):

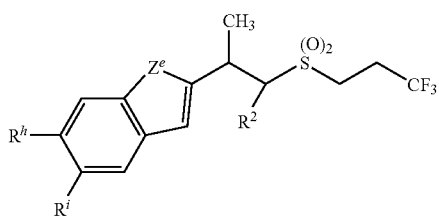

($I^{132}$)

wherein $R^2$, $R^h$, $R^i$ and $Z^e$ represent any one of combinations shown below.

A compound represented by the formula ($I^{133}$):

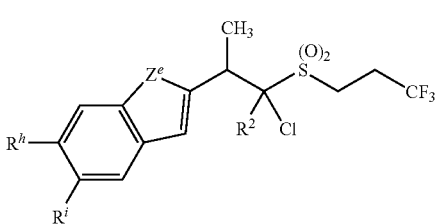

($I^{133}$)

wherein $R^2$, $R^h$, $R^i$ and $Z^e$ represent any one of combinations shown below.

A compound represented by the formula ($I^{134}$):

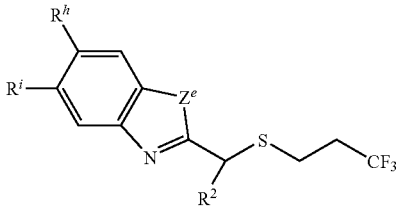

($I^{134}$)

wherein $R^2$, $R^h$, $R^i$ and $Z^e$ represent any one of combinations shown below.

A compound represented by the formula ($I^{135}$):

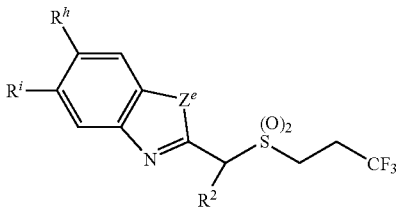

($I^{135}$)

wherein $R^2$, $R^h$, $R^i$ and $Z^e$ represent any one of combinations shown below.

A compound represented by the formula ($I^{136}$):

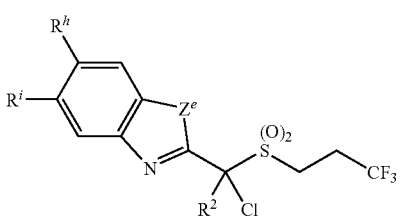

($I^{136}$)

wherein $R^2$, $R^h$, $R^i$ and $Z^e$ represent any one of combinations shown below.

A compound represented by the formula ($I^{137}$):

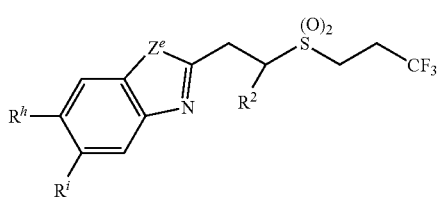

wherein $R^2$, $R^h$, $R^i$ and $Z^e$ represent any one of combinations shown below.

A compound represented by the formula ($I^{138}$):

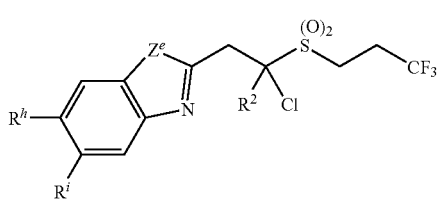

wherein $R^2$, $R^h$, $R^i$ and $Z^e$ represent any one of combinations shown below.

A compound represented by the formula ($I^{139}$):

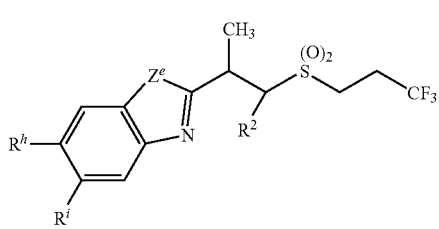

wherein $R^2$, $R^h$, $R^i$ and $Z^e$ represent any one of combinations shown below.

A compound represented by the formula ($I^{140}$):

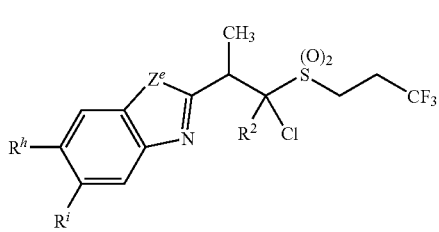

wherein $R^2$, $R^h$, $R^i$ and $Z^e$ represent any one of combinations shown below.

Combinations of $R^2$, $R^h$, $R^i$ and $Z^e$ for the compounds represented by the formulas ($I^{127}$) to ($I^{140}$) are shown below. In branckets, a combination number, a group represented by $R^2$, a group represented by $R^h$, a group represented by $R^i$, and a group represented by $Z^e$ are shown in this order. Herein, symbols J1 to J10 are as defined above.

[Combination number: $R^2$, $R^h$, $R^i$, $Z^e$]=[1: H, H, H, NH], [2: F, H, H, NH], [3: Cl, H, H, NH], [4: Br, H, H, NH], [5: CH₃, H, H, NH], [6: CN, H, H, NH], [7: J1, H, H, NH], [8: J2, H, H, NH], [9: J3, H, H, NH], [10: J4, H, H, NH], [11: J5, H, H, NH], [12: J6, H, H, NH], [13: J7, H, H, NH], [14: J8, H, H, NH], [15: J9, H, H, NH], [16: J10, H, H, NH], [17: H, CN, H, NH], [18: F, CN, H, NH], [19: Cl, CN, H, NH], [20: Br, CN, H, NH], [21: CH₃, CN, H, NH], [22: CN, CN, H, NH], [23: J1, CN, H, NH], [24: J2, CN, H, NH], [25: J3, CN, H, NH], [26: J4, CN, H, NH], [27: J5, CN, H, NH], [28: J6, CN, H, NH], [29: J7, CN, H, NH], [30: J8, CN, H, NH], [31: J9, CN, H, NH], [32: J10, CN, H, NH], [33: H, Cl, H, NH], [34: F, Cl, H, NH], [35: Cl, Cl, H, NH], [36: Br, Cl, H, NH], [37: CH₃, Cl, H, NH], [38: CN, Cl, H, NH], [39: J1, Cl, H, NH], [40: J2, Cl, H, NH], [41: J3, Cl, H, NH], [42: J4, Cl, H, NH], [43: J5, Cl, H, NH], [44: J6, Cl, H, NH], [45: J7, Cl, H, NH], [46: J8, Cl, H, NH], [47: J9, Cl, H, NH], [48: J10, Cl, H, NH], [49: H, H, CN, NH], [50: F, H, CN, NH], [51: Cl, H, CN, NH], [52: Br, H, CN, NH], [53: CH₃, H, CN, NH], [54: CN, H, CN, NH], [55: J1, H, CN, NH], [56: J2, H, CN, NH], [57: J3, H, CN, NH], [58: J4, H, CN, NH], [59: J5, H, CN, NH], [60: J6, H, CN, NH], [61: J7, H, CN, NH], [62: J8, H, CN, NH], [63: J9, H, CN, NH], [64: J10, H, CN, NH], [65: H, CN, CN, NH], [66: F, CN, CN, NH], [67: Cl, CN, CN, NH], [68: Br, CN, CN, NH], [69: CH₃, CN, CN, NH], [70: CN, CN, CN, NH], [71: J1, CN, CN, NH], [72: J2, CN, CN, NH], [73: J3, CN, CN, NH], [74: J4, CN, CN, NH], [75: J5, CN, CN, NH], [76: J6, CN, CN, NH], [77: J7, CN, CN, NH], [78: J8, CN, CN, NH], [79: J9, CN, CN, NH], [80: J10, CN, CN, NH], [81: H, Cl, CN, NH], [82: F, Cl, CN, NH], [83: Cl, Cl, CN, NH], [84: Br, Cl, CN, NH], [85: CH₃, Cl, CN, NH], [86: CN, Cl, CN, NH], [87: J1, Cl, CN, NH], [88: J2, Cl, CN, NH], [89: J3, Cl, CN, NH], [90: J4, Cl, CN, NH], [91: J5, Cl, CN, NH], [92: J6, Cl, CN, NH], [93: J7, Cl, CN, NH], [94: J8, Cl, CN, NH], [95: J9, Cl, CN, NH], [96: J10, Cl, CN, NH], [97: H, H, Cl, NH], [98: F, H, Cl, NH], [99: Cl, H, Cl, NH], [100: Br, H, Cl, NH], [101: CH₃, H, Cl, NH], [102: CN, H, Cl, NH], [103: J1, H, Cl, NH], [104: J2, H, Cl, NH], [105: J3, H, Cl, NH], [106: J4, H, Cl, NH], [107: J5, H, Cl, NH], [108: J6, H, Cl, NH], [109: J7, H, Cl, NH], [110: J8, H, Cl, NH], [111: J9, H, Cl, NH], [112: J10, H, Cl, NH], [113: H, CN, Cl, NH], [114: F, CN, Cl, NH], [115: Cl, CN, Cl, NH], [116: Br, CN, Cl, NH], [117: CH₃, CN, Cl, NH], [118: CN, CN, Cl, NH], [119: J1, CN, Cl, NH], [120: J2, CN, Cl, NH], [121: J3, CN, Cl, NH], [122: J4, CN, Cl, NH], [123: J5, CN, Cl, NH], [124: J6, CN, Cl, NH], [125: J7, CN, Cl, NH], [126: J8, CN, Cl, NH], [127: J9, CN, Cl, NH], [128: J10, CN, Cl, NH], [129: H, Cl, Cl, NH], [130: F, Cl, Cl, NH], [131: Cl, Cl, Cl, NH], [132: Br, Cl, Cl, NH], [133: CH₃, Cl, Cl, NH], [134: CN, Cl, Cl, NH], [135: J1, Cl, Cl, NH], [136: J2, Cl, Cl, NH], [137: J3, Cl, Cl, NH], [138: J4, Cl, Cl, NH], [139: J5, Cl, Cl, NH], [140: J6, Cl, Cl, NH], [141: J7, Cl, Cl, NH], [142: J8, Cl, Cl, NH], [143: J9, Cl, Cl, NH], [144: J10, Cl, Cl, NH], [145: H, H, H, NCH₃], [146: F, H, H, NCH₃], [147: Cl, H, H, NCH₃], [148: Br, H, H, NCH₃], [149: CH₃, H, H, NCH₃], [150: CN, H, H, NCH₃], [151: J1, H, H, NCH₃], [152: J2, H, H, NCH₃], [153: J3, H, H, NCH₃], [154: J4, H, H, NCH₃], [155: J5, H, H, NCH₃], [156: J6, H, H, NCH₃], [157: J7, H, H, NCH₃], [158: J8, H, H, NCH₃], [159: J9, H, H, NCH₃], [160: J10, H, H, NCH₃], [161: H, CN, H, NCH₃], [162: F, CN, H, NCH₃], [163: Cl, CN, H, NCH₃], [164: Br, CN, H, NCH₃], [165: CH₃, CN, H, NCH₃], [166: CN, CN, H, NCH₃], [167: J1, CN, H, NCH₃], [168: J2, CN, H, NCH₃], [169: J3, CN, H, NCH₃], [170: J4, CN, H, NCH₃], [171: J5, CN, H, NCH₃], [172: J6, CN, H, NCH₃], [173: J7, CN, H, NCH₃], [174: J8, CN, H, NCH₃], [175: J9, CN, H, NCH₃], [176: J10, CN, H, NCH₃], [177: H, Cl, H, NCH₃], [178: F, Cl, H, NCH₃], [179: Cl, Cl, H, NCH₃], [180: Br, Cl, H, NCH₃], [181: CH₃, Cl, H, NCH₃], [182: CN, Cl, H, NCH₃], [183: J1, Cl, H, NCH₃], [184: J2, Cl, H, NCH₃], [185: J3, Cl, H, NCH₃], [186: J4, Cl, H, NCH₃], [187: J5, Cl, H, NCH₃], [188: J6, Cl, H, NCH₃], [189: J7, Cl, H, NCH₃], [190: J8, Cl, H, NCH₃], [191: J9, Cl, H, NCH₃], [192: J10, Cl, H, NCH₃], [193: H, H, CN, NCH₃], [194: F, H, CN, NCH₃], [195: Cl, H, CN, NCH₃], [196: Br, H, CN, NCH₃], [197: CH₃, H, CN, NCH₃], [198: CN, H, CN, NCH₃], [199: J1, H, CN, NCH₃], [200: J2, H, CN, NCH₃], [201: J3, H, CN, NCH₃], [202: J4, H, CN, NCH₃], [203: J5, H, CN, NCH₃], [204: J6, H, CN, NCH₃], [205: J7, H, CN, NCH₃], [206: J8, H, CN, NCH₃], [207: J9, H, CN, NCH₃], [208: J10, H, CN, NCH₃], [209: H, CN, CN, NCH₃], [210: F, CN, CN, NCH₃], [211: Cl, CN, CN, NCH₃], [212: Br, CN, CN, NCH₃], [213: CH₃, CN, CN, NCH₃], [214: CN, CN, CN, NCH₃], [215: J1, CN, CN, NCH₃], [216: J2, CN, CN, NCH₃], [217: J3, CN, CN, NCH₃], [218: J4, CN, CN, NCH₃], [219: J5, CN, CN, NCH₃], [220: J6, CN, CN, NCH₃], [221: J7, CN, CN, NCH₃], [222: J8, CN, CN, NCH₃], [223: J9, CN, CN, NCH₃], [224: J10, CN, CN, NCH₃], [225: H, Cl, CN, NCH₃], [226: F, Cl, CN, NCH₃], [227: Cl, Cl, CN, NCH₃], [228: Br, Cl, CN, NCH₃], [229: CH₃, Cl, CN, NCH₃], [230: CN, Cl, CN, NCH₃], [231: J1, Cl, CN, NCH₃], [232: J2, Cl, CN, NCH₃], [233: J3, Cl, CN, NCH₃], [234: J4, Cl, CN, NCH₃], [235: J5, Cl, CN, NCH₃], [236: J6, Cl, CN, NCH₃], [237: J7, Cl, CN, NCH₃], [238: J8, Cl, CN, NCH₃], [239: J9, Cl, CN, NCH₃], [240: J10, Cl, CN, NCH₃], [241: H, H, Cl, NCH₃], [242: F, H, Cl, NCH₃], [243: Cl, H, Cl, NCH₃], [244: Br, H, Cl, NCH₃], [245: CH₃, H, Cl, NCH₃], [246: CN, H, Cl, NCH₃], [247: J1, H, Cl, NCH₃], [248: J2, H, Cl, NCH₃], [249: J3, H, Cl, NCH₃], [250: J4, H, Cl, NCH₃], [251: J5, H, Cl, NCH₃], [252: J6, H, Cl, NCH₃], [253: J7, H, Cl, NCH₃], [254: J8, H, Cl, NCH₃], [255: J9, H, Cl, NCH₃], [256: J10, H, Cl, NCH₃], [257: H, CN, Cl, NCH₃], [258: F, CN, Cl, NCH₃], [259: Cl, CN, Cl, NCH₃], [260: Br, CN, Cl, NCH₃], [261: CH₃, CN, Cl, NCH₃], [262: CN, CN, Cl, NCH₃], [263: J1, CN, Cl, NCH₃], [264: J2, CN, Cl, NCH₃], [265: J3, CN, Cl, NCH₃], [266: J4, CN, Cl, NCH₃], [267: J5, CN, Cl, NCH₃], [268: J6, CN, Cl, NCH₃], [269: J7, CN, Cl, NCH₃], [270: J8, CN, Cl, NCH₃], [271: J9, CN, Cl, NCH₃], [272: J10, CN, Cl, NCH₃], [273: H, Cl, Cl, NCH₃], [274: F, Cl, Cl, NCH₃], [275: Cl, Cl, Cl, NCH₃], [276: Br, Cl, Cl, NCH₃], [277: CH₃, Cl, Cl, NCH₃], [278: CN, Cl, Cl, NCH₃], [279: J1, Cl, Cl, NCH₃], [280: J2, Cl, Cl, NCH₃], [281: J3, Cl, Cl, NCH₃], [282: J4, Cl, Cl, NCH₃], [283: J5, Cl, Cl, NCH₃], [284: J6, Cl, Cl, NCH₃], [285: J7, Cl, Cl, NCH₃], [286: J8, Cl, Cl, NCH₃], [287: J9, Cl, Cl, NCH₃], [288: J10, Cl, Cl, NCH₃], [289: H, H, H, S], [290: F, H, H, S], [291: Cl, H, H, S], [292: Br, H, H, S], [293: CH₃, H, H, S], [294: CN, H, H, S], [295: J1, H, H, S], [296: J2, H, H, S], [297: J3, H, H, S], [298: J4, H, H, S], [299: J5, H, H, S], [300: J6, H, H, S], [301: J7, H, H, S], [302: J8, H, H, S], [303: J9, H, H, S], [304: J10, H, H, S], [305: H, CN, H, S], [306: F, CN, H, S], [307: Cl, CN, H, S], [308: Br, CN, H, S], [309: CH₃, CN, H, S], [310: CN, CN, H, S], [311: J1, CN, H, S], [312: J2, CN, H, S], [313: J3, CN, H, S], [314: J4, CN, H, S], [315: J5, CN, H, S], [316: J6, CN, H, S], [317: J7, CN, H, S], [318: J8, CN, H, S], [319: J9, CN, H, S], [320: J10, CN, H, S], [321: H, Cl, H, S], [322: F, Cl, H, S], [323: Cl, Cl, H, S], [324: Br, Cl, H, S], [325: CH₃, Cl, H, S], [326: CN, Cl, H, S], [327: J1, Cl, H, S], [328: J2, Cl, H, S], [329: J3, Cl, H, S], [330: J4, Cl, H, S], [331: J5, Cl, H, S], [332: J6, Cl, H, S], [333: J7, Cl, H, S], [334: J8, Cl, H, S], [335: J9, Cl, H, S], [336: J10, Cl, H, S], [337: H, H, CN, S], [338: F, H, CN, S], [339: Cl, H, CN, S], [340: Br, H, CN, S], [341: CH₃, H, CN, S], [342: CN, H, CN, S], [343: J1, H, CN, S], [344: J2, H, CN, S], [345: J3, H, CN, S], [346: J4, H, CN, S], [347: J5, H, CN, S], [348: J6, H, CN, S], [349: J7, H, CN, S], [350: J8, H, CN, S], [351: J9, H, CN, S], [352: J10, H, CN, S], [353: H, CN, CN, S], [354: F, CN, CN, S], [355: Cl, CN, CN, S], [356: Br, CN, CN, S], [357: CH₃, CN, CN, S], [358: CN, CN, CN, S], [359: J1, CN, CN, S], [360: J2, CN, CN, S], [361: J3, CN, CN, S], [362: J4, CN, CN, S], [363: J5, CN, CN, S], [364: J6, CN, CN, S], [365: J7, CN, CN, S], [366: J8, CN, CN, S], [367: J9, CN, CN, S], [368: J10, CN, CN, S], [369: H, Cl, CN, S], [370: F, Cl, CN, S], [371: Cl, Cl, CN, S], [372: Br, Cl, CN, S], [373: CH₃, Cl, CN, S], [374: CN, Cl, CN, S], [375: J1, Cl, CN, S], [376: J2, Cl, CN, S], [377: J3, Cl, CN, S], [378: J4, Cl, CN, S], [379: J5, Cl, CN, S], [380: J6, Cl, CN, S], [381: J7, Cl, CN, S], [382: J8, Cl, CN, S], [383: J9, Cl, CN, S], [384: J10, Cl, CN, S], [385: H, H, Cl, S], [386: F, H, Cl, S], [387: Cl, H, Cl, S], [388: Br, H, Cl, S], [389: CH₃, H, Cl, S], [390: CN, H, Cl, S], [391: J1, H, Cl, S], [392: J2, H, Cl, S], [393: J3, H, Cl, S], [394: J4, H, Cl, S], [395: J5, H, Cl, S], [396: J6, H, Cl, S], [397: J7, H, Cl, S], [398: J8, H, Cl, S], [399: J9, H, Cl, S], [400: J10, H, Cl, S], [401: H, CN, Cl, S], [402: F, CN, Cl, S], [403: Cl, CN, Cl, S], [404: Br, CN, Cl, S], [405: CH₃, CN, Cl, S], [406: CN, CN, Cl, S], [407: J1, CN, Cl, S], [408: J2, CN, Cl, S], [409: J3, CN, Cl, S], [410: J4, CN, Cl, S], [411: J5, CN, Cl, S], [412: J6, CN, Cl, S], [413: J7, CN, Cl, S], [414: J8, CN, Cl, S], [415: J9, CN, Cl, S], [416: J10, CN, Cl, S], [417: H, Cl, Cl, S], [418: F, Cl, Cl, S], [419: Cl, Cl, Cl, S], [420: Br, Cl, Cl, S], [421: CH₃, Cl, Cl, S], [422: CN, Cl, Cl, S], [423: J1, Cl, Cl, S], [424: J2, Cl, Cl, S], [425: J3, Cl, Cl, S], [426: J4, Cl, Cl, S], [427: J5, Cl, Cl, S], [428: J6, Cl, Cl, S], [429: J7, Cl, Cl, S], [430: J8, Cl, Cl, S], [431: J9, Cl, Cl, S], [432: J10, Cl, Cl, S], [433: H, H, H, O], [434: F, H, H, O], [435: Cl, H, H, O], [436: Br, H, H, O], [437: CH₃, H, H, O], [438: CN, H, H, O], [439: J1, H, H, O], [440: J2, H, H, O], [441: J3, H, H, O], [442: J4, H, H, O], [443: J5, H, H, O], [444: J6, H, H, O], [445: J7, H, H, O], [446: J8, H, H, O], [447: J9, H, H, O], [448: J10, H, H, O], [449: H, CN, H, O], [450: F, CN, H, O], [451: Cl, CN, H, O], [452: Br, CN, H, O], [453: CH₃, CN, H, O], [454: CN, CN, H, O], [455: J1, CN, H, O], [456: J2, CN, H, O], [457: J3, CN, H, O], [458: J4, CN, H, O], [459: J5, CN, H, O], [460: J6, CN, H, O], [461: J7, CN, H, O], [462: J8, CN, H, O], [463: J9, CN, H, O], [464: J10, CN, H, O], [465: H, Cl, H, O], [466: F, Cl, H, O], [467: Cl, Cl, H, O], [468: Br, Cl, H, O], [469: CH₃, Cl, H, O], [470: CN, Cl, H, O], [471: J1, Cl, H, O], [472: J2, Cl, H, O], [473: J3, Cl, H, O], [474: J4, Cl, H, O], [475: J5, Cl, H, O], [476: J6, Cl, H, O], [477: J7, Cl, H, O], [478: J8, Cl, H, O], [479: J9, Cl, H, O], [480: J10, Cl, H, O], [481: H, H, CN, O], [482: F, H, CN, O], [483: Cl, H, CN, O], [484: Br, H, CN, O], [485: CH₃, H, CN, O], [486: CN, H, CN, O], [487: J1, H, CN, O], [488: J2, H, CN, O], [489: J3, H, CN, O], [490: J4, H, CN, O], [491: J5, H, CN, O], [492: J6, H, CN, O], [493: J7, H, CN, O], [494: J8, H, CN, O], [495: J9, H, CN, O], [496: J10, H, CN, O], [497: H, CN, CN, O], [498: F, CN, CN, O], [499: Cl, CN, CN, O], [500: Br, CN, CN, O], [501: CH₃, CN, CN, O], [502: CN, CN, CN, O], [503: J1, CN, CN, O], [504: J2, CN, CN, O], [505: J3, CN, CN, O], [506: J4, CN, CN, O], [507: J5, CN, CN, O], [508: J6, CN, CN, O], [509: J7, CN, CN, O], [510: J8, CN, CN, O], [511: J9, CN, CN, O], [512: J10, CN, CN, O], [513: H, Cl, CN, O], [514: F, Cl, CN, O], [515: Cl, Cl, CN, O], [516: Br, Cl, CN, O], [517: CH₃, Cl, CN, O], [518: CN, Cl, CN, O], [519: J1, Cl, CN, O], [520: J2, Cl, CN, O], [521: J3, Cl, CN, O], [522: J4, Cl, CN, O], [523: J5, Cl, CN, O], [524: J6, Cl, CN, O], [525: J7, Cl, CN, O], [526: J8, Cl, CN, O], [527: J9, Cl, CN, O], [528: J10, Cl, CN, O], [529: H, H, Cl, O], [530: F, H, Cl, O], [531: Cl, H, Cl, O], [532: Br, H, Cl, O], [533: CH₃, H, Cl, O], [534: CN, H, Cl, O], [535: J1, H, Cl, O], [536: J2, H, Cl, O], [537: J3, H, Cl, O], [538: J4, H, Cl, O], [539: J5, H, Cl, O], [540: J6, H, Cl, O], [541: J7, H, Cl, O], [542: J8, H, Cl, O], [543: J9, H, Cl, O], [544: J10, H, Cl, O], [545: H, CN, Cl, O], [546: F, CN, Cl, O], [547: Cl, CN, Cl, O], [548: Br, CN, Cl, O], [549: CH₃, CN, Cl, O], [550: CN, CN, Cl, O], [551: J1, CN, Cl, O], [552: J2, CN, Cl, O], [553: J3, CN, Cl, O], [554: J4, CN, Cl, O], [555: J5, CN, Cl, O], [556: J6, CN, Cl, O], [557: J7, CN, Cl, O], [558: J8, CN, Cl, O],

[559: J9, CN, Cl, O], [560: J10, CN, Cl, O], [561: H, Cl, Cl, O], [562: F, Cl, Cl, O], [563: Cl, Cl, Cl, O], [564: Br, Cl, Cl, O], [565: $CH_3$, Cl, Cl, O], [566: CN, Cl, Cl, O], [567: J1, Cl, Cl, O], [568: J2, Cl, Cl, O], [569: J3, Cl, Cl, O], [570: J4, Cl, Cl, O], [571: J5, Cl, Cl, O], [572: J6, Cl, Cl, O], [573: J7, Cl, Cl, O], [574: J8, Cl, Cl, O], [575: J9, Cl, Cl, O], [576: J10, Cl, Cl, O].

A compound represented by the formula ($I^{141}$):

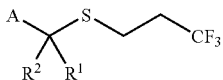

wherein $R^1$, $R^2$ and A represent any one of combinations shown below.

A compound represented by the formula ($I^{142}$):

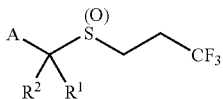

wherein $R^1$, $R^2$ and A represent any one of combinations shown below.

A compound represented by the formula ($I^{143}$):

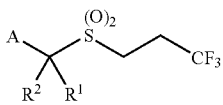

wherein $R^1$, $R^2$ and A represent any one of combinations shown below.

A compound represented by the formula ($I^{144}$):

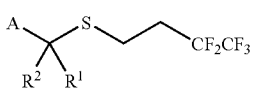

wherein $R^1$, $R^2$ and A represent any one of combinations shown below.

A compound represented by the formula ($I^{145}$):

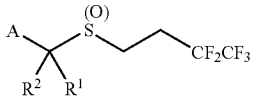

wherein $R^1$, $R^2$ and A represent any one of combinations shown below.

A compound represented by the formula ($I^{146}$):

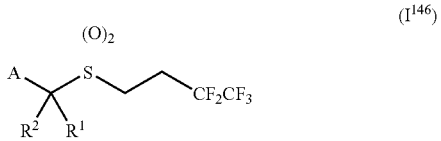

wherein $R^1$, $R^2$ and A represent any one of combinations shown below.

A compound represented by the formula ($I^{147}$):

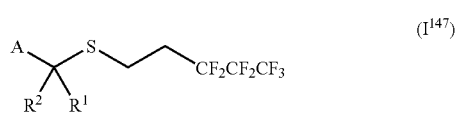

wherein $R^1$, $R^2$ and A represent any one of combinations shown below.

A compound represented by the formula ($I^{148}$):

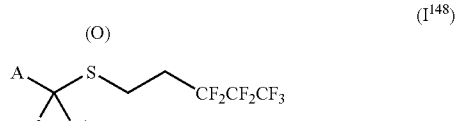

wherein $R^1$, $R^2$ and A represent any one of combinations shown below.

A compound represented by the formula ($I^{149}$):

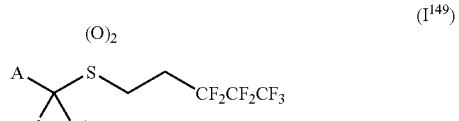

wherein $R^1$, $R^2$ and A represent any one of combinations shown below.

A compound represented by the formula ($I^{150}$):

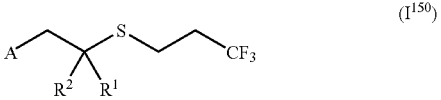

wherein $R^1$, $R^2$ and A represent any one of combinations shown below.

A compound represented by the formula ($I^{151}$):

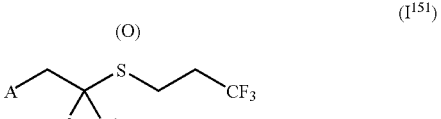

wherein $R^1$, $R^2$ and A represent any one of combinations shown below.

A compound represented by the formula (I$^{152}$):

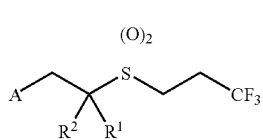
(I$^{152}$)

wherein R$^1$, R$^2$ and A represent any one of combinations shown below.

A compound represented by the formula (I$^{153}$):

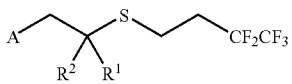
(I$^{153}$)

wherein R$^1$, R$^2$ and A represent any one of combinations shown below.

A compound represented by the formula (I$^{154}$):

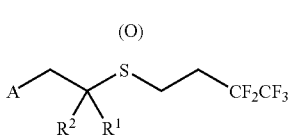
(I$^{154}$)

wherein R$^1$, R$^2$ and A represent any one of combinations shown below.

A compound represented by the formula (I$^{155}$):

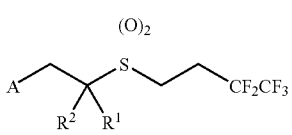
(I$^{155}$)

wherein R$^1$, R$^2$ and A represent any one of combinations shown below.

A compound represented by the formula (I$^{156}$):

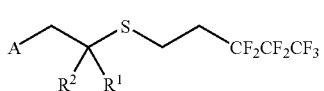
(I$^{156}$)

wherein R$^1$, R$^2$ and A represent any one of combinations shown below.

A compound represented by the formula (I$^{157}$):

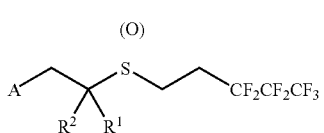
(I$^{157}$)

wherein R$^1$, R$^2$ and A represent any one of combinations shown below.

A compound represented by thb formula (I$^{158}$):

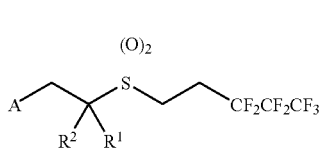
(I$^{158}$)

wherein R$^1$, R$^2$ and A represent any one of combinations shown below.

A compound represented by the formula (I$^{159}$):

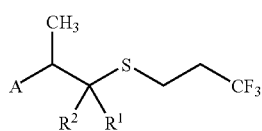
(I$^{159}$)

wherein R$^1$, R$^2$ and A represent any one of combinations shown below.

A compound represented by the formula (I$^{160}$):

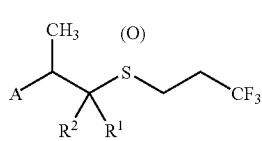
(I$^{160}$)

wherein R$^1$, R$^2$ and A represent any one of combinations shown below.

A compound represented by the formula (I$^{161}$):

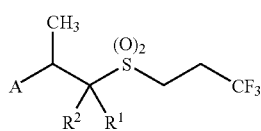
(I$^{161}$)

wherein R$^1$, R$^2$ and A represent any one of combinations shown below.

A compound represented by the formula (I$^{162}$):

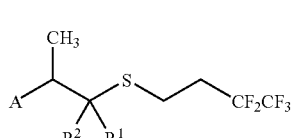
(I$^{162}$)

wherein R$^1$, R$^2$ and A represent any one of combinations shown below.

A compound represented by the formula ($I^{163}$):

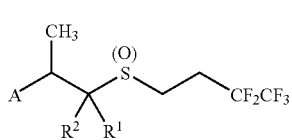

wherein $R^1$, $R^2$ and A represent any one of combinations shown below.

A compound represented by the formula ($I^{164}$):

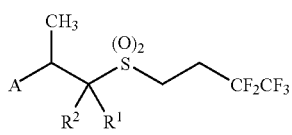

wherein $R^1$, $R^2$ and A represent any one of combinations shown below.

A compound represented by the formula ($I^{165}$):

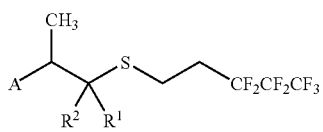

wherein $R^1$, $R^2$ and A represent any one of combinations shown below.

A compound represented by the formula ($I^{166}$):

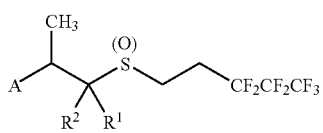

wherein $R^1$, $R^2$ and A represent any one of combinations shown below.

A compound represented by the formula ($I^{167}$):

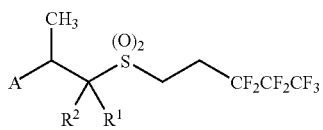

wherein $R^1$, $R^2$ and A represent any one of combinations shown below.

A compound represented by the formula ($I^{168}$):

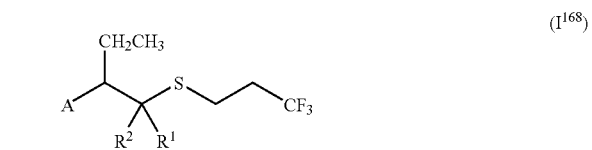

wherein $R^1$, $R^2$ and A represent any one of combinations shown below.

A compound represented by the formula ($I^{169}$):

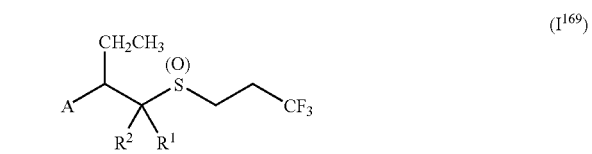

wherein $R^1$, $R^2$ and A represent any one of combinations shown below.

A compound represented by the formula ($I^{170}$):

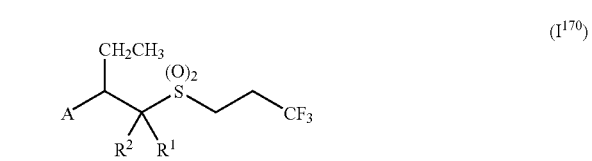

wherein $R^1$, $R^2$ and A represent any one of combinations shown below.

A compound represented by the formula ($I^{171}$):

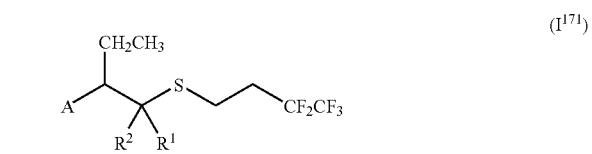

wherein $R^1$, $R^2$ and A represent any one of combinations shown below.

A compound represented by the formula ($I^{172}$):

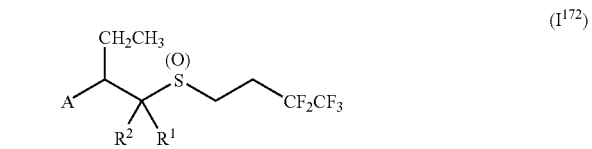

wherein $R^1$, $R^2$ and A represent any one of combinations shown below.

A compound represented by the formula (I¹⁷³):

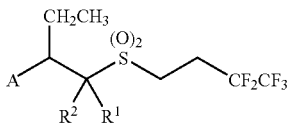
(I¹⁷³)

wherein R¹, R² and A represent any one of combinations shown below.

A compound represented by the formula (I¹⁷⁴):

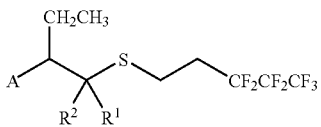
(I¹⁷⁴)

wherein R¹, R² and A represent any one of combinations shown below.

A compound represented by the formula (I¹⁷⁵):

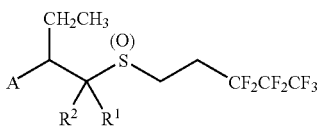
(I¹⁷⁵)

wherein R¹, R² and A represent any one of combinations shown below.

A compound represented by the formula (I¹⁷⁶):

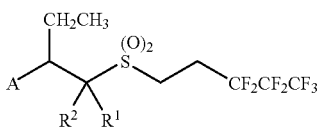
(I¹⁷⁶)

wherein R¹, R² and A represent any one of combinations shown below.

A compound represented by the formula (I¹⁷⁷):

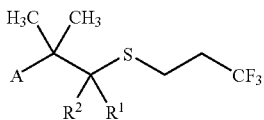
(I¹⁷⁷)

wherein R¹, R² and A represent any one of combinations shown below.

A compound represented by the formula (I¹⁷⁸):

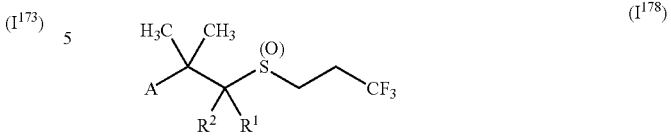
(I¹⁷⁸)

wherein R¹, R² and A represent any one of combinations shown below.

A compound represented by the formula (I¹⁷⁹):

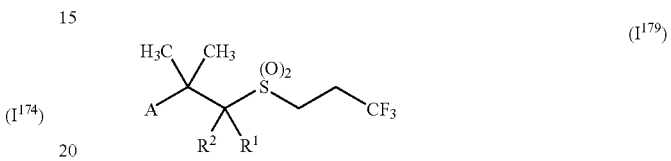
(I¹⁷⁹)

wherein R¹, R² and A represent any one of combinations shown below.

A compound represented by the formula (I¹⁸⁰):

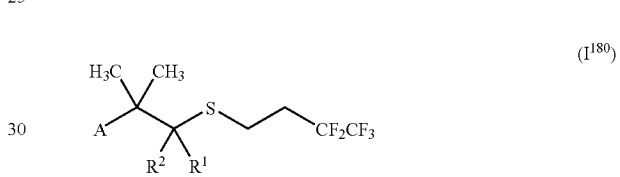
(I¹⁸⁰)

wherein R¹, R² and A represent any one of combinations shown below.

A compound represented by the formula (I¹⁸¹):

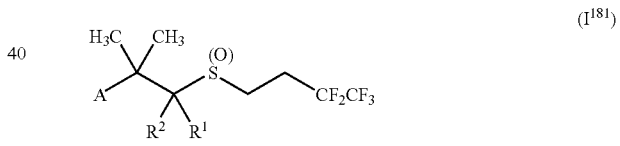
(I¹⁸¹)

wherein R¹, R² and A represent any one of combinations shown below.

A compound represented by the formula (I¹⁸²):

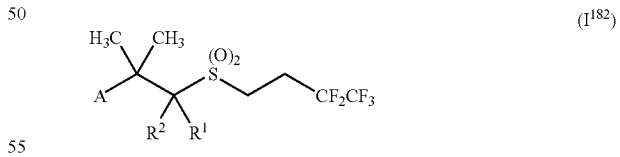
(I¹⁸²)

wherein R¹, R² and A represent any one of combinations shown below.

A compound represented by the formula (I¹⁸³):

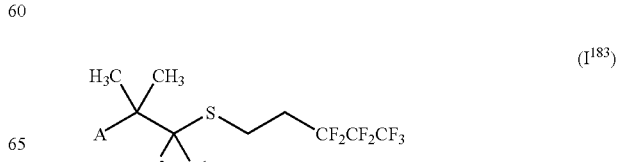
(I¹⁸³)

wherein $R^1$, $R^2$ and A represent any one of combinations shown below.

A compound represented by the formula ($I^{184}$):

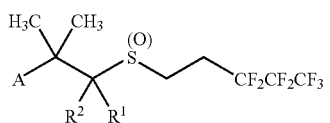

(I$^{184}$)

wherein $R^1$, $R^2$ and A represent any one of combinations shown below.

A compound represented by the formula ($I^{185}$):

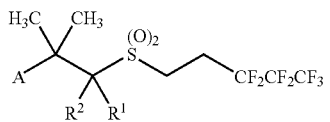

(I$^{185}$)

wherein $R^1$, $R^2$ and A represent any one of combinations shown below.

Combinations of $R^1$, $R^2$ and A for the compounds represented by the formulas ($I^{141}$) to ($I^{185}$) are shown below. In branckets, a combination number, a group represented by $R^1$, a group represented by $R^2$, and a group represented by A are shown in this order. Herein, symbols J1 to J10 are as defined above. Symbols A1 to A41 represent the following 5-membered aromatic heterocyclic groups.

A1
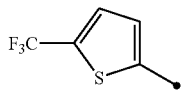

A2
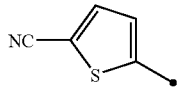

A3
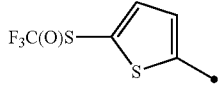

A4
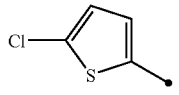

A5
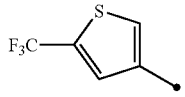

A6
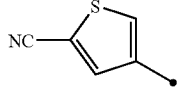

A7
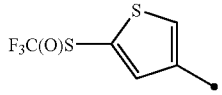

A8
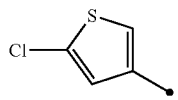

A9
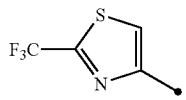

A10
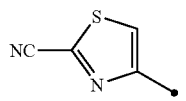

A11
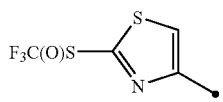

A12
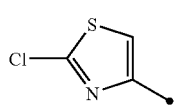

A13
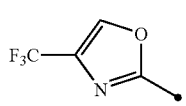

A14
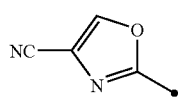

A15
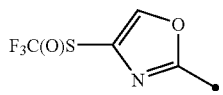

A16
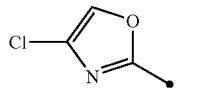

A17
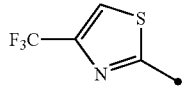

A18
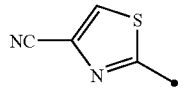

A19
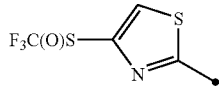

A20
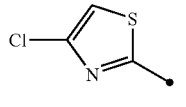

A21
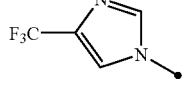

A22
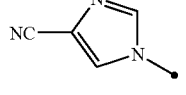

-continued

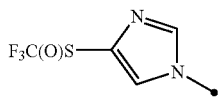

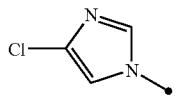

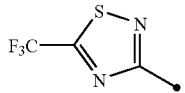

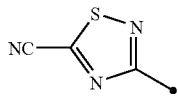

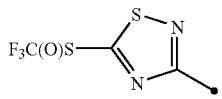

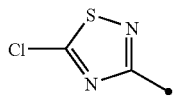

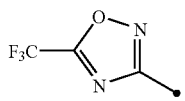

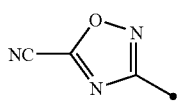

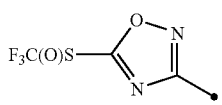

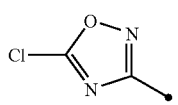

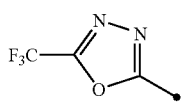

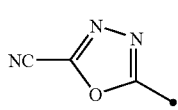

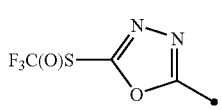

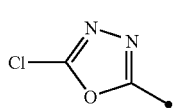

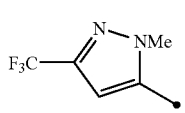

-continued

A23 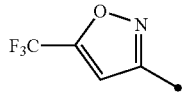

A24 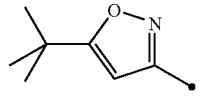

A25 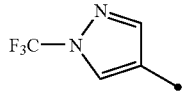

A26 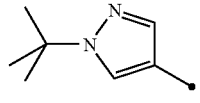

A27
A28
A29
A30
A31
A32
A33
A34
A35
A36
A37
A38
A39
A40
A41

[Combination number: $R^1$, $R^2$, A]=[1: F, F, A1], [2: Br, F, A1], [3: $CH_3$, F, A1], [4: CN, F, A1], [5: J1, F, A1], [6: J2, F, A1], [7: J3, F, A1], [8: J4, F, A1], [9: J5, F, A1], [10: J6, F, A1], [11: J7, F, A1], [12: J8, F, A1], [13: J9, F, A1], [14: J10, F, A1], [15: F, Br, A1], [16: Br, Br, A1], [17: $CH_3$, Br, A1], [18: CN, Br, A1], [19: J1, Br, A1], [20: J2, Br, A1], [21: J3, Br, A1], [22: J4, Br, A1], [23: J5, Br, A1], [24: J6, Br, A1], [25: J7, Br, A1], [26: J8, Br, A1], [27: J9, Br, A1], [28: J10, Br, A1], [29: F, $CH_3$, A1], [30: Br, $CH_3$, A1], [31: $CH_3$, $CH_3$, A1], [32: CN, $CH_3$, A1], [33: J1, $CH_3$, A1], [34: J2, $CH_3$, A1], [35: J3, $CH_3$, A1], [36: J4, $CH_3$, A1], [37: J5, $CH_3$, A1], [38: J6, $CH_3$, A1], [39: J7, $CH_3$, A1], [40: J8, $CH_3$, A1], [41: J9, $CH_3$, A1], [42: J10, $CH_3$, A1], [43: F, $CH_2CH_3$, A1], [44: Br, $CH_2CH_3$, A1], [45: $CH_3$, $CH_2CH_3$, A1], [46: CN, $CH_2CH_3$, A1], [47: J1, $CH_2CH_3$, A1], [48: J2, $CH_2CH_3$, A1], [49: J3, $CH_2CH_3$, A1], [50: J4, $CH_2CH_3$, A1], [51: J5, $CH_2CH_3$, A1], [52: J6, $CH_2CH_3$, A1], [53: J7, $CH_2CH_3$, A1], [54: J8, $CH_2CH_3$, A1], [55: J9, $CH_2CH_3$, A1], [56: J10, $CH_2CH_3$, A1], [57: F, F, A2], [58: Br, F, A2], [59: $CH_3$, F, A2], [60: CN, F, A2], [61: J1, F, A2], [62: J2, F, A2], [63: J3, F, A2], [64: J4, F, A2], [65: J5, F, A2], [66: J6, F, A2], [67: J7, F, A2], [68: J8, F, A2], [69: J9, F, A2], [70: J10, F, A2], [71: F, Br, A2], [72: Br, Br, A2], [73: $CH_3$, Br, A2], [74: CN, Br, A2], [75: J1, Br, A2], [76: J2, Br, A2], [77: J3, Br, A2], [78: J4, Br, A2], [79: J5, Br, A2], [80: J6, Br, A2], [81: J7, Br, A2], [82: J8, Br, A2], [83: J9, Br, A2], [84: J10, Br, A2], [85: F, $CH_3$, A2], [86: Br, $CH_3$, A2], [87: $CH_3$, $CH_3$, A2], [88: CN, $CH_3$, A2], [89: J1, $CH_3$, A2], [90: J2, $CH_3$, A2], [91: J3, $CH_3$, A2], [92: J4, $CH_3$, A2], [93: J5, $CH_3$, A2], [94: J6, $CH_3$, A2], [95: J7, $CH_3$, A2], [96: J8, $CH_3$, A2], [97: J9, $CH_3$, A2], [98: J10, $CH_3$, A2], [99: F, $CH_2CH_3$, A2], [100: Br, $CH_2CH_3$, A2], [101: $CH_3$, $CH_2CH_3$, A2], [102: CN, $CH_2CH_3$, A2], [103: J1, $CH_2CH_3$, A2], [104: J2, $CH_2CH_3$, A2], [105: J3, $CH_2CH_3$, A2], [106: J4, $CH_2CH_3$, A2], [107: J5, $CH_2CH_3$, A2], [108: J6, $CH_2CH_3$, A2], [109: J7, $CH_2CH_3$, A2], [110: J8, $CH_2CH_3$, A2], [111: J9, $CH_2CH_3$, A2], [112: J10, $CH_2CH_3$, A2], [113: F, F, A3], [114: Br, F, A3], [115: $CH_3$, F, A3], [116: CN, F, A3], [117: J1, F, A3], [118: J2, F, A3], [119: J3, F, A3], [120: J4, F, A3], [121: J5, F, A3], [122: J6, F, A3], [123: J7, F, A3], [124: J8, F, A3], [125: J9, F, A3], [126: J10, F, A3], [127: F, Br, A3], [128: Br, Br, A3], [129: $CH_3$, Br, A3], [130: CN, Br, A3], [131: J1, Br, A3], [132: J2, Br, A3], [133: J3, Br, A3], [134: J4, Br, A3], [135: J5, Br, A3], [136: J6, Br, A3], [137: J7, Br, A3], [138: J8, Br, A3], [139: J9, Br, A3], [140: J10, Br, A3], [141: F, $CH_3$, A3], [142: Br, $CH_3$, A3], [143: $CH_3$, $CH_3$, A3], [144: CN, $CH_3$, A3], [145: J1, $CH_3$, A3], [146: J2, $CH_3$, A3], [147: J3, $CH_3$, A3], [148: J4, $CH_3$, A3], [149: J5, $CH_3$, A3], [150: J6, $CH_3$, A3], [151: J7, CH₃, A3], [152: J8, CH₃, A3], [153: J9, CH₃, A3], [154: J10, CH₃, A3], [155: F, CH₂CH₃, A3], [156: Br, CH₂CH₃, A3], [157: CH₃, CH₂CH₃, A3], [158: CN, CH₂CH₃, A3], [159: J1, CH₂CH₃, A3], [160: J2, CH₂CH₃, A3], [161: J3, CH₂CH₃, A3], [162: J4, CH₂CH₃, A3], [163: J5, CH₂CH₃, A3], [164: J6, CH₂CH₃, A3], [165: J7, CH₂CH₃, A3], [166: J8, CH₂CH₃, A3], [167: J9, CH₂CH₃, A3], [168: J10, CH₂CH₃, A3], [169: F, F, A4], [170: Br, F, A4], [171: CH₃, F, A4], [172: CN, F, A4], [173: J1, F, A4], [174: J2, F, A4], [175: J3, F, A4], [176: J4, F, A4], [177: J5, F, A4], [178: J6, F, A4], [179: J7, F, A4], [180: J8, F, A4], [181: J9, F, A4], [182: J10, F, A4], [183: F, Br, A4], [184: Br, Br, A4], [185: CH₃, Br, A4], [186: CN, Br, A4], [187: J1, Br, A4], [188: J2, Br, A4], [189: J3, Br, A4], [190: J4, Br, A4], [191: J5, Br, A4], [192: J6, Br, A4], [193: J7, Br, A4], [194: J8, Br, A4], [195: J9, Br, A4], [196: J10, Br, A4], [197: F, CH₃, A4], [198: Br, CH₃, A4], [199: CH₃, CH₃, A4], [200: CN, CH₃, A4], [201: J1, CH₃, A4], [202: J2, CH₃, A4], [203: J3, CH₃, A4], [204: J4, CH₃, A4], [205: J5, CH₃, A4], [206: J6, CH₃, A4], [207: J7, CH₃, A4], [208: J8, CH₃, A4], [209: J9, CH₃, A4], [210: J10, CH₃, A4], [211: F, CH₂CH₃, A4], [212: Br, CH₂CH₃, A4], [213: CH₃, CH₂CH₃, A4], [214: CN, CH₂CH₃, A4], [215: J1, CH₂CH₃, A4], [216: J2, CH₂CH₃, A4], [217: J3, CH₂CH₃, A4], [218: J4, CH₂CH₃, A4], [219: J5, CH₂CH₃, A4], [220: J6, CH₂CH₃, A4], [221: J7, CH₂CH₃, A4], [222: J8, CH₂CH₃, A4], [223: J9, CH₂CH₃, A4], [224: J10, CH₂CH₃, A4], [225: F, F, A5], [226: Br, F, A5], [227: CH₃, F, A5], [228: CN, F, A5], [229: J1, F, A5], [230: J2, F, A5], [231: J3, F, A5], [232: J4, F, A5], [233: J5, F, A5], [234: J6, F, A5], [235: J7, F, A5], [236: J8, F, A5], [237: J9, F, A5], [238: J10, F, A5], [239: F, Br, A5], [240: Br, Br, A5], [241: CH₃, Br, A5], [242: CN, Br, A5], [243: J1, Br, A5], [244: J2, Br, A5], [245: J3, Br, A5], [246: J4, Br, A5], [247: J5, Br, A5], [248: J6, Br, A5], [249: J7, Br, A5], [250: J8, Br, A5], [251: J9, Br, A5], [252: J10, Br, A5], [253: F, CH₃, A5], [254: Br, CH₃, A5], [255: CH₃, CH₃, A5], [256: CN, CH₃, A5], [257: J1, CH₃, A5], [258: J2, CH₃, A5], [259: J3, CH₃, A5], [260: J4, CH₃, A5], [261: CH₃, A5], [262: J6, CH₃, A5], [263: J7, CH₃, A5], [264: J8, CH₃, A5], [265: J9, CH₃, A5], [266: J10, CH₃, A5], [267: F, CH₂CH₃, A5], [268: Br, CH₂CH₃, A5], [269: CH₃, CH₂CH₃, A5], [270: CN, CH₂CH₃, A5], [271: J1, CH₂CH₃, A5], [272: J2, CH₂CH₃, A5], [273: J3, CH₂CH₃, A5], [274: J4, CH₂CH₃, A5], [275: J5, CH₂CH₃, A5], [276: J6, CH₂CH₃, A5], [277: J7, CH₂CH₃, A5], [278: J8, CH₂CH₃, A5], [279: J9, CH₂CH₃, A5], [280: J10, CH₂CH₃, A5], [281: F, F, A6], [282: Br, F, A6], [283: CH₃, F, A6], [284: CN, F, A6], [285: J1, F, A6], [286: J2, F, A6], [287: J3, F, A6], [288: J4, F, A6], [289: J5, F, A6], [290: J6, F, A6], [291: J7, F, A6], [292: J8, F, A6], [293: J9, F, A6], [294: J10, F, A6], [295: F, Br, A6], [296: Br, Br, A6], [297: CH₃, Br, A6], [298: CN, Br, A6], [299: J1, Br, A6], [300: J2, Br, A6], [301: J3, Br, A6], [302: J4, Br, A6], [303: J5, Br, A6], [304: J6, Br, A6], [305: J7, Br, A6], [306: J8, Br, A6], [307: J9, Br, A6], [308: J10, Br, A6], [309: F, CH₃, A6], [310: Br, CH₃, A6], [311: CH₃, CH₃, A6], [312: CN, CH₃, A6], [313: J1, CH₃, A6], [314: J2, CH₃, A6], [315: J3, CH₃, A6], [316: J4, CH₃, A6], [317: CH₃, A6], [318: J6, CH₃, A6], [319: J7, CH₃, A6], [320: J8, CH₃, A6], [321: J9, CH₃, A6], [322: J10, CH₃, A6], [323: F, CH₂CH₃, A6], [324: Br, CH₂CH₃, A6], [325: CH₃, CH₂CH₃, A6], [326: CN, CH₂CH₃, A6], [327: J1, CH₂CH₃, A6], [328: J2, CH₂CH₃, A6], [329: J3, CH₂CH₃, A6], [330: J4, CH₂CH₃, A6], [331: J5, CH₂CH₃, A6], [332: J6, CH₂CH₃, A6], [333: J7, CH₂CH₃, A6], [334: J8, CH₂CH₃, A6], [335: J9, CH₂CH₃, A6], [336: J10, CH₂CH₃, A6], [337: F, F, A7], [338: Br, F, A7], [339: CH₃, F, A7], [340: CN, F, A7], [341: J1, F, A7], [342: J2, F, A7], [343: J3, F, A7], [344: J4, F, A7], [345: J5, F, A7], [346: J6, F, A7], [347: J7, F, A7], [348: J8, F, A7], [349: J9, F, A7], [350: J10, F, A7], [351: F, Br, A7], [352: Br, Br, A7], [353: CH₃, Br, A7], [354: CN, Br, A7], [355: J1, Br, A7], [356: J2, Br, A7], [357: J3, Br, A7], [358: J4, Br, A7], [359: J5, Br, A7], [360: J6, Br, A7], [361: J7, Br, A7], [362: J8, Br, A7], [363: J9, Br, A7], [364: J10, Br, A7], [365: F, CH₃, A7], [366: Br, CH₃, A7], [367: CH₃, CH₃, A7], [368: CN, CH₃, A7], [369: J1, CH₃, A7], [370: J2, CH₃, A7], [371: J3, CH₃, A7], [372: J4, CH₃, A7], [373: J5, CH₃, A7], [374: J6, CH₃, A7], [375: J7, CH₃, A7], [376: J8, CH₃, A7], [377: J9, CH₃, A7], [378: J10, CH₃, A7], [379: F, CH₂CH₃, A7], [380: Br, CH₂CH₃, A7], [381: CH₃, CH₂CH₃, A7], [382: CN, CH₂CH₃, A7], [383: J1, CH₂CH₃, A7], [384: J2, CH₂CH₃, A7], [385: J3, CH₂CH₃, A7], [386: J4, CH₂CH₃, A7], [387: J5, CH₂CH₃, A7], [388: J6, CH₂CH₃, A7], [389: J7, CH₂CH₃, A7], [390: J8, CH₂CH₃, A7], [391: J9, CH₂CH₃, A7], [392: J10, CH₂CH₃, A7], [393: F, F, A8], [394: Br, F, A8], [395: CH₃, F, A8], [396: CN, F, A8], [397: J1, F, A8], [398: J2, F, A8], [399: J3, F, A8], [400: J4, F, A8], [401: J5, F, A8], [402: J6, F, A8], [403: J7, F, A8], [404: J8, F, A8], [405: J9, F, A8], [406: J10, F, A8], [407: F, Br, A8], [408: Br, Br, A8], [409: CH₃, Br, A8], [410: CN, Br, A8], [411: J1, Br, A8], [412: J2, Br, A8], [413: J3, Br, A8], [414: J4, Br, A8], [415: J5, Br, A8], [416: J6, Br, A8], [417: J7, Br, A8], [418: J8, Br, A8], [419: J9, Br, A8], [420: J10, Br, A6], [421: F, CH₃, A8], [422: Br, CH₃, A8], [423: CH₃, CH₃, A8], [424: CN, CH₃, A8], [425: J1, CH₃, A8], [426: J2, CH₃, A8], [427: J3, CH₃, A8], [428: J4, CH₃, A8], [429: J5, CH₃, A8], [430: J6, CH₃, A8], [431: J7, CH₃, A8], [432: J8, CH₃, A8], [433: J9, CH₃, A8], [434: J10, CH₃, A8], [435: F, CH₂CH₃, A8], [436: Br, CH₂CH₃, A8], [437: CH₃, CH₂CH₃, A8], [438: CN, CH₂CH₃, A8], [439: J1, CH₂CH₃, A8], [440: J2, CH₂CH₃, A8], [441: J3, CH₂CH₃, A8], [442: J4, CH₂CH₃, A8], [443: J5, CH₂CH₃, A8], [444: J6, CH₂CH₃, A8], [445: J7, CH₂CH₃, A8], [446: J8, CH₂CH₃, A8], [447: J9, CH₂CH₃, A8], [448: J10, CH₂CH₃, A8], [449: F, F, A9], [450: Br, F, A9], [451: CH₃, F, A9], [452: CN, F, A9], [453: J1, F, A9], [454: J2, F, A9], [455: J3, F, A9], [456: J4, F, A9], [457: J5, F, A9], [458: J6, F, A9], [459: J7, F, A9], [460: J8, F, A9], [461: J9, F, A9], [462: J10, F, A9], [463: F, Br, A9], [464: Br, Br, A9], [465: CH₃, Br, A9], [466: CN, Br, A9], [467: J1, Br, A9], [468: J2, Br, A9], [469: J3, Br, A9], [470: J4, Br, A9], [471: J5, Br, A9], [472: J6, Br, A9], [473: J7, Br, A9], [474: J8, Br, A9], [475: J9, Br, A9], [476: J10, Br, A9], [477: F, CH₃, A9], [478: Br, CH₃, A9], [479: CH₃, CH₃, A9], [480: CN, CH₃, A9], [481: J1, CH₃, A9], [482: J2, CH₃, A9], [483: J3, CH₃, A9], [484: J4, CH₃, A9], [485: J5, CH₃, A9], [486: J6, CH₃, A9], [487: J7, CH₃, A9], [488: J8, CH₃, A9], [489: J9, CH₃, A9], [490: J10, CH₃, A9], [491: F, CH₂CH₃, A9], [492: Br, CH₂CH₃, A9], [493: CH₃, CH₂CH₃, A9], [494: CN, CH₂CH₃, A9], [495: J1, CH₂CH₃, A9], [496: J2, CH₂CH₃, A9], [497: J3, CH₂CH₃, A9], [498: J4, CH₂CH₃, A9], [499: J5, CH₂CH₃, A9], [500: J6, CH₂CH₃, A9], [501: J7, CH₂CH₃, A9], [502: J8, CH₂CH₃, A9], [503: J9, CH₂CH₃, A9]. [504: J10, CH₂CH₃, A9], [505: F, F, A10], [506: Br, F, A10], [507: CH₃, F, A10], [508: CN, F, A10], [509: J1, F, A10], [510: J2, F, A10], [511: J3, F, A10], [512: J4, F, A10], [513: J5, F, A10], [514: J6, F, A10], [515: J7, F, A10], [516: J8, F, A10], [517: J9, F, A10], [518: J10, F, A10], [519: F, Br, A10], [520: Br, Br, A10], [521: CH₃, Br, A10], [522: CN, Br, A10], [523: J1, Br, A10], [524: J2, Br, A10], [525: J3, Br, A10], [526: J4, Br, A10], [527: J5, Br, A10], [528: J6, Br, A10], [529: J7, Br, A10], [530: J8, Br, A10], [531: J9, Br, A10], [532: J10, Br, A10], [533: F, CH₃, A10], [534: Br, CH₃, A10], [535: CH₃, CH₃, A10], [536: CN, CH₃, A10], [537: J1, CH₃, A10], [538: J2, CH₃, A10], [539: J3, CH₃, A10], [540: J4, CH₃, A10], [541: J5, CH₃, A10], [542: J6, CH₃, A10], [543: J7, CH₃, A10], [544: J8, CH₃, A10], [545: J9, CH₃, A10], [546: J10, CH₃, A10], [547: F, CH₂CH₃, A10], [548: Br, CH₂CH₃, A10], [549: CH₃, CH₂CH₃, A10], [55⁰: CN, CH₂CH₃, A10], [551: J1, CH₂CH₃, A10], [552: J2, CH₂CH₃, A10], [553: J3, CH₂CH₃, A10], [554: J4, CH₂CH₃, A10], [555: J5, CH₂CH₃, A10], [556: J6, CH₂CH₃, A10], [557: J7, CH₂CH₃, A10], [558: J8, CH₂CH₃, A10], [559: J9, CH₂CH₃, A10], [560: J10, CH₂CH₃, A10], [561: F, F, A11], [562: Br, F, A11], [563: CH₃, F, A11], [564: CN, F, A11], [565: J1, F, A11], [566: J2, F, A11], [567: J3, F, A11], [568: J4, F, A11], [569: J5, F, A11], [570: J6, F, A11], [571: J7, F, A11], [572: J8, F, A11], [573: J9, F, A11], [574: J10, F, A11], [575: F, Br, A11], [576: Br, Br, A11], [577: CH₃, Br, A11], [578: CN, Br, A11], [579: J1, Br, A11], [580: J2, Br, A11], [581: J3, Br, A11], [582: J4, Br, A11], [583: J5, Br, A11], [584: J6, Br, A11], [585: J7, Br, A11], [586: J8, Br, A11], [587: J9, Br, A11], [588: J10, Br, A11], [589: F, CH₃, A11], [590: Br, CH₃, A11], [591: CH₃, CH₃, A11], [592: CN, CH₃, A11], [593: J1, CH₃, A11], [594: J2, CH₃, A11], [595: J3, CH₃, A11], [596: J4, CH₃, A11], [597: J5, CH₃, A11], [598: J6, CH₃, A11], [599: J7, CH₃, A11], [600: J8, CH₃, A11], [601: J9, CH₃, A11], [602: J10, CH₃, A11], [603: F, CH₂CH₃, A11], [604: Br, CH₂CH₃, A11], [605: CH₃, CH₂CH₃, A11], [606: CN, CH₂CH₃, A11], [607: J1, CH₂CH₃, A11], [608: J2, CH₂CH₃, A11], [609: J3, CH₂CH₃, A11], [610: J4, CH₂CH₃, A11], [611: J5, CH₂CH₃, A11], [612: J6, CH₂CH₃, A11], [613: J7, CH₂CH₃, A11], [614: J8, CH₂CH₃, A11], [615: J9, CH₂CH₃, A11], [616: J10, CH₂CH₃, A11], [617: F, F, A12], [618: Br, F, A12], [619: CH₃, F, A12], [620: CN, F, A12], [621: J1, F, A12], [622: J2, F, A12], [623: J3, F, A12], [624: J4, F, A12], [625: J5, F, A12], [626: J6, F, A12], [627: J7, F, A12], [628: J8, F, A12], [629: J9, F, A12], [630: J10, F, A12], [631: F, Br, A12], [632: Br, Br, A12], [633: CH₃, Br, A12], [634: CN, Br, A12], [635: J1, Br, A12], [636: J2, Br, A12], [637: J3, Br, A12], [638: J4, Br, A12], [639: J5, Br, A12], [640: J6, Br, A12], [641: J7, Br, A12], [642: J8, Br, A12], [643: J9, Br, A12], [644: J10, Br, A12], [645: F, CH₃, A12], [646: Br, CH₃, A12], [647: CH₃, CH₃, A12], [648: CN, CH₃, A12], [649: J1, CH₃, A12], [650: J2, CH₃, A12], [651: J3, CH₃, A12], [652: J4, CH₃, A12], [653: J5, CH₃, A12], [654: J6, CH₃, A12], [655: J7, CH₃, A12], [656: J8, CH₃, A12], [657: J9, CH₃, A12], [658: J10, CH₃, A12], [659: F, CH₂CH₃, A12], [660: Br, CH₂CH₃, A12], [661: CH₃, CH₂CH₃, A12], [662: CN, CH₂CH₃, A12], [663: J1, CH₂CH₃, A12], [664: J2, CH₂CH₃, A12], [665: J3, CH₂CH₃, A12], [666: J4, CH₂CH₃, A12], [667: J5, CH₂CH₃, A12], [668: J6, CH₂CH₃, A12], [669: J7, CH₂CH₃, A12], [670: J8, CH₂CH₃, A12], [671: J9, CH₂CH₃, A12], [672: J10, CH₂CH₃, A12], [673: F, F, A13], [674: Br, F, A13], [675: CH₃, F, A13], [676: CN, F, A13], [677: J1, F, A13], [678: J2, F, A13], [679: J3, F, A13], [680: J4, F, A13], [681: J5, F, A13], [682: J6, F, A13], [683: J7, F, A13], [684: J8, F, A13], [685: J9, F, A13], [686: J10, F, A13], [687: F, Br, A13], [688: Br, Br, A13], [689: CH₃, Br, A13], [690: CN, Br, A13], [691: J1, Br, A13], [692: J2, Br, A13], [693: J3, Br, A13], [694: J4, Br, A13], [695: J5, Br, A13], [696: J6, Br, A13], [697: J7, Br, A13], [698: J8, Br, A13], [699: J9, Br, A13], [700: J10, Br, A13], [701: F, CH₃, A13], [702: Br, CH₃, A13], [703: CH₃, CH₃, A13], [704: CN, CH₃, A13], [705: J1, CH₃, A13], [706: J2, CH₃, A13], [707: J3, CH₃, A13], [708: J4, CH₃, A13], [709: J5, CH₃, A13], [710: J6, CH₃, A13], [711: J7, CH₃, A13], [712: J8, CH₃, A13], [713: J9, CH₃, A13], [714: J10, CH₃, A13], [715: F, CH₂CH₃, A13], [716: Br, CH₂CH₃, A13], [717: CH₃, CH₂CH₃, A13], [718: CN, CH₂CH₃, A13], [719: J1, CH₂CH₃, A13], [720: J2, CH₂CH₃, A13], [721: J3, CH₂CH₃, A13], [722: J4, CH₂CH₃, A13], [723: J5, CH₂CH₃, A13], [724: J6, CH₂CH₃, A13], [725: J7, CH₂CH₃, A13], [726: J8, CH₂CH₃, A13], [727: J9, CH₂CH₃, A13], [728: J10, CH₂CH₃, A13], [729: F, F, A14], [730: Br, F, A14], [731: CH₃, F, A14], [732: CN, F, A14], [733: J1, F, A14], [734: J2, F, A14], [735: J3, F, A14], [736: J4, F, A14], [737: J5, F, A14], [738: J6, F, A14], [739: J7, F, A14], [740: J8, F, A14], [741: J9, F, A14], [742: J10, F, A14], [743: F, Br, A14], [744: Br, Br, A14], [745: CH₃, Br, A14], [746: CN, Br, A14], [747: J1, Br, A14], [748: J2, Br, A14], [749: J3, Br, A14], [750: J4, Br, A14], [751: J5, Br, A14], [752: J6, Br, A14], [753: J7, Br, A14], [754: J8, Br, A14], [755: J9, Br, A14], [756: J10, Br, A14], [757: F, CH₃, A14], [758: Br, CH₃, A14], [759: CH₃, CH₃, A14], [760: CN, CH₃, A14], [761: J1, CH₃, A14], [762: J2, CH₃, A14], [763: J3, CH₃, A14], [764: J4, CH₃, A14], [765: J5, CH₃, A14], [766: J6, CH₃, A14], [767: J7, CH₃, A14], [768: J8, CH₃, A14], [769: J9, CH₃, A14], [770: J10, CH₃, A14], [771: F, CH₂CH₃, A14], [772: Br, CH₂CH₃, A14], [773: CH₃, CH₂CH₃, A14], [774: CN, CH₂CH₃, A14], [775: J1, CH₂CH₃, A14], [776: J2, CH₂CH₃, A14], [777: J3, CH₂CH₃, A14], [778: J4, CH₂CH₃, A14], [779: J5, CH₂CH₃, A14], [780: J6, CH₂CH₃, A14], [781: J7, CH₂CH₃, A14], [782: J8, CH₂CH₃, A14], [783: J9, CH₂CH₃, A14], [784: J10, CH₂CH₃, A14], [785: F, F, A15], [786: Br, F, A15], [787: CH₃, F, A15], [788: CN, F, A15], [789: J1, F, A15], [790: J2, F, A15], [791: J3, F, A15], [792: J4, F, A15], [793: J5, F, A15], [794: J6, F, A15], [795: J7, F, A15], [796: J8, F, A15], [797: J9, F, A15], [798: J10, F, A15], [799: F, Br, A15], [800: Br, Br, A15], [801: CH₃, Br, A15], [802: CN, Br, A15], [803: J1, Br, A15], [804: J2, Br, A15], [805: J3, Br, A15], [806: J4, Br, A15], [807: J5, Br, A15], [808: J6, Br, A15], [809: J7, Br, A15], [810: J8, Br, A15], [811: J9, Br, A15], [812: J10, Br, A15], [813: F, CH₃, A15], [814: Br, CH₃, A15], [815: CH₃, CH₃, A15], [816: CN, CH₃, A15], [817: J1, CH₃, A15], [818: J2, CH₃, A15], [819: J3, CH₃, A15], [820: J4, CH₃, A15], [821: J5, CH₃, A15], [822: J6, CH₃, A15], [823: J7, CH₃, A15], [824: J8, CH₃, A15], [825: J9, CH₃, A15], [826: J10, CH₃, A15], [827: F, CH₂CH₃, A15], [828: Br, CH₂CH₃, A15], [829: CH₃, CH₂CH₃, A15], [830: CN, CH₂CH₃, A15], [831: J1, CH₂CH₃, A15], [832: J2, CH₂CH₃, A15], [833: J3, CH₂CH₃, A15], [834: J4, CH₂CH₃, A15], [835: J5, CH₂CH₃, A15], [836: J6, CH₂CH₃, A15], [837: J7, CH₂CH₃, A15], [838: J8, CH₂CH₃, A15], [839: J9, CH₂CH₃, A15], [840: J10, CH₂CH₃, A15], [841: F, F, A16], [842: Br, F, A16], [843: CH₃, F, A16], [844: CN, F, A16], [845: J1, F, A16], [846: J2, F, A16], [847: J3, F, A16], [848: J4, F, A16], [849: J5, F, A16], [850: J6, F, A16], [851: J7, F, A16], [852: J8, F, A16], [853: J9, F, A16], [854: J10, F, A16], [855: F, Br, A16], [856: Br, Br, A16], [857: CH₃, Br, A16], [858: CN, Br, A16], [859: J1, Br, A16], [860: J2, Br, A16], [861: J3, Br, A16], [862: J4, Br, A16], [863: J5, Br, A16], [864: J6, Br, A16], [865: J7, Br, A16], [866: J8, Br, A16], [867: J9, Br, A16], [868: J10, Br, A16], [869: F, CH₃, A16], [870: Br, CH₃, A16], [871: CH₃, CH₃, A16], [872: CN, CH₃, A16], [873: J1, CH₃, A16], [874: J2, CH₃, A16], [875: J3, CH₃, A16], [876: J4, CH₃, A16], [877: J5, CH₃, A16], [878: J6, CH₃, A16], [879: J7, CH₃, A16], [880: J8, CH₃, A16], [881: J9, CH₃, A16], [882: J10, CH₃, A16], [883: F, CH₂CH₃, A16], [884: Br, CH₂CH₃, A16], [885: CH₃, CH₂CH₃, A16], [886: CN, CH₂CH₃, A16], [887: J1, CH₂CH₃, A16], [888: J2, CH₂CH₃, A16], [889: J3, CH₂CH₃, A16], [890: J4, CH₂CH₃, A16], [891: J5, CH₂CH₃, A16], [892: J6, CH₂CH₃, A16], [893: J7, CH₂CH₃, A16], [894: J8, CH₂CH₃, A16], [895: J9, CH₂CH₃, A16], [896: J10, CH₂CH₃, A16], [897: F, F, A17], [898: Br, F, A17], [899: CH₃, F, A17], [900: CN, F, A17], [901: J1, F, A17], [902: J2, F, A17], [903: J3, F, A17], [904: J4, F, A17], [905: J5, F, A17], [906: J6, F, A17], [907: J7, F, A17], [908: J8, F, A17], [909: J9, F, A17], [910: J10, F, A17], [911: F, Br, A17], [912: Br, Br, A17], [913: CH₃, Br, A17], [914: CN, Br, A17], [915: J1, Br, A17], [916: J2, Br, A17], [917: J3, Br, A17], [918: J4, Br, A17], [919: J5, Br, A17], [920: J6, Br, A17], [921: J7, Br, A17], [922: J8, Br, A17], [923: J9, Br, A17], [924: J10, Br, A17], [925: F, CH₃, A17], [926: Br, CH₃, A17], [927: CH₃, CH₃, A17], [928: CN, CH₃, A17], [929: J1, CH₃, A17], [930: J2, CH₃, A17], [931: J3, CH₃, A17], [932: J4, CH₃, A17], [933: J5, CH₃, A17], [934: J6, CH₃, A17], [935: J7, CH₃, A17], [936: J8, CH₃, A17], [937: J9, CH₃, A17], [938: J10, CH₃, A17], [939: F, CH₂CH₃, A17], [940: Br, CH₂CH₃, A17], [941: CH₃, CH₂CH₃, A17], [942: CN, CH₂CH₃, A17], [943: J1, CH₂CH₃, A17], [944: J2, CH₂CH₃, A17], [945: J3, CH₂CH₃, A17], [946: J4, CH₂CH₃, A17], [947: J5, CH₂CH₃, A17], [948: J6, CH₂CH₃, A17], [949: J7, CH₂CH₃, A17], [950: J8, CH₂CH₃, A17], [951: J9, CH₂CH₃, A17], [952: J10, CH₂CH₃, A17], [953: F, F, A18], [954: Br, F, A18], [955: CH₃, F, A18], [956: CN, F, A18], [957: J1, F, A18], [958: J2, F, A18], [959: J3, F, A18], [960: J4, F, A18], [961: J5, F, A18], [962: J6, F, A18], [963: J7, F, A18], [964: J8, F, A18], [965: J9, F, A18], [966: J10, F, A18], [967: F, Br, A18], [968: Br, Br, A18], [969: CH₃, Br, A18], [970: CN, Br, A18], [971: J1, Br, A18], [972: J2, Br, A18], [973: J3, Br, A18], [974: J4, Br, A18], [975: J5, Br, A18], [976: J6, Br, A18], [977: J7, Br, A18], [978: J8, Br, A18], [979: J9, Br, A18], [980: J10, Br, A18], [981: F, CH₃, A18], [982: Br, CH₃, A18], [983: CH₃, CH₃, A18], [984: CN, CH₃, A18], [985: J1, CH₃, A18], [986: J2, CH₃, A18], [987: J3, CH₃, A18], [988: J4, CH₃, A18], [989: J5, CH₃, A18], [990: J6, CH₃, A18], [991: J7, CH₃, A18], [992: J8, CH₃, A18], [993: J9, CH₃, A18], [994: J10, CH₃, A18], [995: F, CH₂CH₃, A18], [996: Br, CH₂CH₃, A18], [997: CH₃, CH₂CH₃, A18], [998: CN, CH₂CH₃, A18], [999: J1, CH₂CH₃, A18], [1000: J2, CH₂CH₃, A18], [1001: J3, CH₂CH₃, A18], [1002: J4, CH₂CH₃, A18], [1003: J5, CH₂CH₃, A18], [1004: J6, CH₂CH₃, A18], [1005: J7, CH₂CH₃, A18], [1006: J8, CH₂CH₃, A18], [1007: J9, CH₂CH₃, A18], [1008: J10, CH₂CH₃, A18], [1009: F, F, A19], [1010: Br, F, A19], [1011: CH₃, F, A19], [1012: CN, F, A19], [1013: J1, F, A19], [1014: J2, F, A19], [1015: J3, F, A19], [1016: J4, F, A19], [1017: J5, F, A19], [1018: J6, F, A19], [1019: J7, F, A19], [1020: J8, F, A19], [1021: J9, F, A19], [1022: J10, F, A19], [1023: F, Br, A19], [1024: Br, Br, A19], [1025: CH₃, Br, A19], [1026: CN, Br, A19], [1027: J1, Br, A19], [1028: J2, Br, A19], [1029: J3, Br, A19], [1030: J4, Br, A19], [1031: J5, Br, A19], [1032: J6, Br, A19], [1033: J7, Br, A19], [1034: J8, Br, A19], [1035: J9, Br, A19], [1036: J10, Br, A19], [1037: F, CH₃, A19], [1038: Br, CH₃, A19], [1039: CH₃, CH₃, A19], [1040: CN, CH₃, A19], [1041: J1, CH₃, A19], [1042: J2, CH₃, A19], [1043: J3, CH₃, A19], [1044: J4, CH₃, A19], [1045: J5, CH₃, A19], [1046: J6, CH₃, A19], [1047: J7, CH₃, A19], [1048: J8, CH₃, A19], [1049: J9, CH₃, A19], [1050: J10, CH₃, A19], [1051: F, CH₂CH₃, A19], [1052: Br, CH₂CH₃, A19], [1053: CH₃, CH₂CH₃, A19], [1054: CN, CH₂CH₃, A19], [1055: J1, CH₂CH₃, A19], [1056: J2, CH₂CH₃, A19], [1057: J3, CH₂CH₃, A19], [1058: J4, CH₂CH₃, A19], [1059: J5, CH₂CH₃, A19], [1060: J6, CH₂CH₃, A19], [1061: J7, CH₂CH₃, A19], [1062: J8, CH₂CH₃, A19], [1063: J9, CH₂CH₃, A19], [1064: J10, CH₂CH₃, A19], [1065: F, F, A20], [1066: Br, F, A20], [1067: CH₃, F, A20], [1068: CN, F, A20], [1069: J1, F, A20], [1070: J2, F, A20], [1071: J3, F, A20], [1072: J4, F, A20], [1073: J5, F, A20], [1074: J6, F, A20], [1075: J7, F, A20], [1076: J8, F, A20], [1077: J9, F, A20], [1078: J10, F, A20], [1079: F, Br, A20], [1080: Br, Br, A20], [1081: CH₃, Br, A20], [1082: CN, Br, A20], [1083: J1, Br, A20], [1084: J2, Br, A20], [1085: J3, Br, A20], [1086: J4, Br, A20], [1087: J5, Br, A20], [1088: J6, Br, A20], [1089: J7, Br, A20], [1090: J8, Br, A20], [1091: J9, Br, A20], [1092: J10, Br, A20], [1093: F, CH₃, A20], [1094: Br, CH₃, A20], [1095: CH₃, CH₃, A20], [1096: CN, CH₃, A20], [1097: J1, CH₃, A20], [1098: J2, CH₃, A20], [1099: J3, CH₃, A20], [1100: J4, CH₃, A20], [1101: J5, CH₃, A20], [1102: J6, CH₃, A20], [1103: J7, CH₃, A20], [1104: J8, CH₃, A20], [1105: J9, CH₃, A20], [1106: J10, CH₃, A20], [1107: F, CH₂CH₃, A20], [1108: Br, CH₂CH₃, A20], [1109: CH₃, CH₂CH₃, A20], [1110: CN, CH₂CH₃, A20], [1111: J1, CH₂CH₃, A20], [1112: J2, CH₂CH₃, A20], [1113: J3, CH₂CH₃, A20], [1114: J4, CH₂CH₃, A20], [1115: J5, CH₂CH₃, A20], [1116: J6, CH₂CH₃, A20], [1117: J7, CH₂CH₃, A20], [1118: J8, CH₂CH₃, A20], [1119: J9, CH₂CH₃, A20], [1120: J10, CH₂CH₃, A20], [1121: F, F, A21], [1122: Br, F, A21], [1123: CH₃, F, A21], [1124: CN, F, A21], [1125: J1, F, A21], [1126: J2, F, A21], [1127: J3, F, A21], [1128: J4, F, A21], [1129: J5, F, A21], [1130: J6, F, A21], [1131: J7, F, A21], [1132: J8, F, A21], [1133: J9, F, A21], [1134: J10, F, A21], [1135: F, Br, A21], [1136: Br, Br, A21], [1137: CH₃, Br, A21], [1138: CN, Br, A21], [1139: J1, Br, A21], [1140: J2, Br, A21], [1141: J3, Br, A21], [1142: J4, Br, A21], [1143: J5, Br, A21], [1144: J6, Br, A21], [1145: J7, Br, A21], [1146: J8, Br, A21], [1147: J9, Br, A21], [1148: J10, Br, A21], [1149: F, CH₃, A21], [1150: Br, CH₃, A21], [1151: CH₃, CH₃, A21], [1152: CN, CH₃, A21], [1153: J1, CH₃, A21], [1154: J2, CH₃, A21], [1155: J3, CH₃, A21], [1156: J4, CH₃, A21], [1157: J5, CH₃, A21], [1158: J6, CH₃, A21], [1159: J7, CH₃, A21], [1160: J8, CH₃, A21], [1161: J9, CH₃, A21], [1162: J10, CH₃, A21], [1163: F, CH₂CH₃, A21], [1164: Br, CH₂CH₃, A21], [1165: CH₃, CH₂CH₃, A21], [1166: CN, CH₂CH₃, A21], [1167: J1, CH₂CH₃, A21], [1168: J2, CH₂CH₃, A21], [1169: J3, CH₂CH₃, A21], [1170: J4, CH₂CH₃, A21], [1171: J5, CH₂CH₃, A21], [1172: J6, CH₂CH₃, A21], [1173: J7, CH₂CH₃, A21], [1174: J8, CH₂CH₃, A21], [1175: J9, CH₂CH₃, A21], [1176: J10, CH₂CH₃, A21], [1177: F, F, A22], [1178: Br, F, A22], [1179: CH₃, F, A22], [1180: CN, F, A22], [1181: J1, F, A22], [1182: J2, F, A22], [1183: J3, F, A22], [1184: J4, F, A22], [1185: J5, F, A22], [1186: J6, F, A22], [1187: J7, F, A22], [1188: J8, F, A22], [1189: J9, F, A22], [1190: J10, F, A22], [1191: F, Br, A22], [1192: Br, Br, A22], [1193: CH₃, Br, A22], [1194: CN, Br, A22], [1195: J1, Br, A22], [1196: J2, Br, A22], [1197: J3, Br, A22], [1198: J4, Br, A22], [1199: J5, Br, A22], [1200: J6, Br, A22], [1201: J7, Br, A22], [1202: J8, Br, A22], [1203: J9, Br, A22], [1204: J10, Br, A22], [1205: F, CH₃, A22], [1206: Br, CH₃, A22], [1207: CH₃, CH₂, A22], [1208: CN, CH₃, A22], [1209: J1, CH₃, A22], [1210: J2, CH₃, A22], [1211: J3, CH₃, A22], [1212: J4, CH₃, A22], [1213: J5, CH₃, A22], [1214: J6, CH₃, A22], [1215: J7, CH₃, A22], [1216: J8, CH₃, A22], [1217: J9, CH₃, A22], [1218: J10, CH₃, A22], [1219: F, CH₂CH₃, A22], [1220: Br, CH₂CH₃, A22], [1221: CH₃, CH₂CH₃, A22], [1222: CN, CH₂CH₃, A22], [1223: J1, CH₂CH₃, A22], [1224: J2, CH₂CH₃, A22], [1225: J3, CH₂CH₃, A22], [1226: J4, CH₂CH₃, A22], [1227: J5, CH₂CH₃, A22], [1228: J6, CH₂CH₃, A22], [1229: J7, CH₂CH₃, A22], [1230: J8, CH₂CH₃, A22], [1231: J9, CH₂CH₃, A22], [1232: J10, CH₂CH₃, A22], [1233: F, F, A23], [1234: Br, F, A23], [1235: CH₃, F, A23], [1236: CN, F, A23], [1237: J1, F, A23], [1238: J2, F, A23], [1239: J3, F, A23], [1240: J4, F, A23], [1241: J5, F, A23], [1242: J6, F, A23], [1243: J7, F, A23], [1244: J8, F, A23], [1245: J9, F, A23], [1246: J10, F, A23], [1247: F, Br, A23], [1248: Br, Br, A23], [1249: CH₃, Br, A23], [1250: CN, Br, A23], [1251: J1, Br, A23], [1252: J2, Br, A23], [1253: J3, Br, A23], [1254: J4, Br, A23], [1255: J5, Br, A23], [1256: J6, Br, A23], [1257: J7, Br, A23], [1258: J8, Br, A23], [1259: J9, Br, A23], [1260: J10, Br, A23], [1261: F, CH₂, A23], [1262: Br, CH₃, A23], [1263: CH₃, CH₃, A23], [1264: CN, CH₃, A23], [1265: J1, CH₃, A23], [1266: J2, CH₃, A23], [1267: J3, CH₃, A23], [1268: J4, CH₃, A23], [1269: J5, CH₃, A23], [1270: J6, CH₃, A23], [1271: J7, CH₃, A23], [1272: J8, CH₃, A23], [1273: J9, CH₃, A23], [1274: J10, CH₃, A23], [1275: F, CH₂CH₃, A23], [1276: Br, CH₂CH₃, A23], [1277: CH₃, CH₂CH₃, A23], [1278: CN, CH₂CH₃, A23], [1279: J1, CH₂CH₃, A23], [1280:

J2, CH₂CH₃, A23], [1281: J3, CH₂CH₃, A23], [1282: J4, CH₂CH₃, A23], [1283: J5, CH₂CH₃, A23], [1284: J6, CH₂CH₃, A23], [1285: J7, CH₂CH₃, A23], [1286: J8, CH₂CH₃, A23], [1287: J9, CH₂CH₃, A23], [1288: J10, CH₂CH₃, A23], [1289: F, F, A24], [1290: Br, F, A24], [1291: CH₃, F, A24], [1292: CN, F, A24], [1293: J1, F, A24], [1294: J2, F, A24], [1295: J3, F, A24], [1296: J4, F, A24], [1297: J5, F, A24], [1298: J6, F, A24], [1299: J7, F, A24], [1300: J8, F, A24], [1301: J9, F, A24], [1302: J10, F, A24], [1303: F, Br, A24], [1304: Br, Br, A24], [1305: CH₃, Br, A24], [1306: CN, Br, A24], [1307: J1, Br, A24], [1308: J2, Br, A24], [1309: J3, Br, A24], [1310: J4, Br, A24], [1311: J5, Br, A24], [1312: J6, Br, A24], [1313: J7, Br, A24], [1314: J8, Br, A24], [1315: J9, Br, A24], [1316: J10, Br, A24], [1317: F, CH₃, A24], [1318: Br, CH₃, A24], [1319: CH₃, CH₃, A24], [1320: CN, CH₃, A24], [1321: J1, CH₃, A24], [1322: J2, CH₃, A24], [1323: J3, CH₃, A24], [1324: J4, CH₃, A24], [1325: J5, CH₃, A24], [1326: J6, CH₃, A24], [1327: J7, CH₃, A24], [1328: J8, CH₃, A24], [1329: J9, CH₃, A24], [1330: J10, CH₃, A24], [1331: F, CH₂CH₃, A24], [1332: Br, CH₂CH₃, A24], [1333: CH₃, CH₂CH₃, A24], [1334: CN, CH₂CH₃, A24], [1335: J1, CH₂CH₃, A24], [1336: J2, CH₂CH₃, A24], [1337: J3, CH₂CH₃, A24], [1338: J4, CH₂CH₃, A24], [1339: J5, CH₂CH₃, A24], [1340: J6, CH₂CH₃, A24], [1341: J7, CH₂CH₃, A24], [1342: J8, CH₂CH₃, A24], [1343: J9, CH₂CH₃, A24], [1344: J10, CH₂CH₃, A24], [1345: F, F, A25], [1346: Br, F, A25], [1347: CH₃, F, A25], [1348: CN, F, A25], [1349: J1, F, A25], [1350: J2, F, A25], [1351: J3, F, A25], [1352: J4, F, A25], [1353: J5, F, A25], [1354: J6, F, A25], [1355: J7, F, A25], [1356: J8, F, A25], [1357: J9, F, A25], [1358: J10, F, A25], [1359: F, Br, A25], [1360: Br, Br, A25], [1361: CH₃, Br, A25], [1362: CN, Br, A25], [1363: J1, Br, A25], [1364: J2, Br, A25], [1365: J3, Br, A25], [1366: J4, Br, A25], [1367: J5, Br, A25], [1368: J6, Br, A25], [1369: J7, Br, A25], [1370: J8, Br, A25], [1371: J9, Br, A25], [1372: J10, Br, A25], [1373: F, CH₃, A25], [1374: Br, CH₃, A25], [1375: CH₃, CH₃, A25], [1376: CN, CH₃, A25], [1377: J1, CH₃, A25], [1378: J2, CH₃, A25], [1379: J3, CH₃, A25], [1380: J4, CH₃, A25], [1381: J5, CH₃, A25], [1382: J6, CH₃, A25], [1383: J7, CH₃, A25], [1384: J8, CH₃, A25], [1385: J9, CH₃, A25], [1386: J10, CH₃, A25], [1387: F, CH₂CH₃, A25], [1388: Br, CH₂CH₃, A25], [1389: CH₃, CH₂CH₃, A25], [1390: CN, CH₂CH₃, A25], [1391: J1, CH₂CH₃, A25], [1392: J2, CH₂CH₃, A25], [1393: J3, CH₂CH₃, A25], [1394: J4, CH₂CH₃, A25], [1395: J5, CH₂CH₃, A25], [1396: J6, CH₂CH₃, A25], [1397: J7, CH₂CH₃, A25], [1398: J8, CH₂CH₃, A25], [1399: J9, CH₂CH₃, A25], [1400: J10, CH₂CH₃, A25], [1401: F, F, A26], [1402: Br, F, A26], [1403: CH₃, F, A26], [1404: CN, F, A26], [1405: J1, F, A26], [1406: J2, F, A26], [1407: J3, F, A26], [1408: J4, F, A26], [1409: J5, F, A26], [1410: J6, F, A26], [1411: J7, F, A26], [1412: J8, F, A26], [1413: J9, F, A26], [1414: J10, F, A26], [1415: F, Br, A26], [1416: Br, Br, A26], [1417: CH₃, Br, A26], [1418: CN, Br, A26], [1419: J1, Br, A26], [1420: J2, Br, A26], [1421: J3, Br, A26], [1422: J4, Br, A26], [1423: J5, Br, A26], [1424: J6, Br, A26], [1425: J7, Br, A26], [1426: J8, Br, A26], [1427: J9, Br, A26], [1428: J10, Br, A26], [1429: F, CH₃, A26], [1430: Br, CH₃, A26], [1431: CH₃, CH₃, A26], [1432: CN, CH₃, A26], [1433: J1, CH₃, A26], [1434: J2, CH₃, A26], [1435: J3, CH₃, A26], [1436: J4, CH₃, A26], [1437: J5, CH₃, A26], [1438: J6, CH₃, A26], [1439: J7, CH₃, A26], [1440: J8, CH₃, A26], [1441: J9, CH₃, A26], [1442: J10, CH₃, A26], [1443: F, CH₂CH₃, A26], [1444: Br, CH₂CH₃, A26], [1445: CH₃, CH₂CH₃, A26], [1446: CN, CH₂CH₃, A26], [1447: J1, CH₂CH₃, A26], [1448: J2, CH₂CH₃, A26], [1449: J3, CH₂CH₃, A26], [1450: J4, CH₂CH₃, A26], [1451: J5, CH₂CH₃, A26], [1452: J6, CH₂CH₃, A26], [1453: J7, CH₂CH₃, A26], [1454: J8, CH₂CH₃, A26], [1455: J9, CH₂CH₃, A26], [1456: J10, CH₂CH₃, A26], [1457: F, F, A27], [1458: Br, F, A27], [1459: CH₃, F, A27], [1460: CN, F, A27], [1461: J1, F, A27], [1462: J2, F, A27], [1463: J3, F, A27], [1464: J4, F, A27], [1465: J5, F, A27], [1466: J6, F, A27], [1467: J7, F, A27], [1468: J8, F, A27], [1469: J9, F, A27], [1470: J10, F, A27], [1471: F, Br, A27], [1472: Br, Br, A27], [1473: CH₃, Br, A27], [1474: CN, Br, A27], [1475: J1, Br, A27], [1476: J2, Br, A27], [1477: J3, Br, A27], [1478: J4, Br, A27], [1479: J5, Br, A27], [1480: J6, Br, A27], [1481: J7, Br, A27], [1482: J8, Br, A27], [1483: J9, Br, A27], [1484: J10, Br, A27], [1485: F, CH₃, A27], [1486: Br, CH₃, A27], [1487: CH₃, CH₃, A27], [1488: CN, CH₃, A27], [1489: J1, CH₃, A27], [1490: J2, CH₃, A27], [1491: J3, CH₃, A27], [1492: J4, CH₃, A27], [1493: J5, CH₃, A27], [1494: J6, CH₃, A27], [1495: J7, CH₃, A27], [1496: J8, CH₃, A27], [1497: J9, CH₃, A27], [1498: J10, CH₃, A27], [1499: F, CH₂CH₃, A27], [1500: Br, CH₂CH₃, A27], [1501: CH₃, CH₂CH₃, A27], [1502: CN, CH₂CH₃, A27], [1503: J1, CH₂CH₃, A27], [1504: J2, CH₂CH₃, A27], [1505: J3, CH₂CH₃, A27], [1506: J4, CH₂CH₃, A27], [1507: J5, CH₂CH₃, A27], [1508: J6, CH₂CH₃, A27], [1509: J7, CH₂CH₃, A27], [1510: J8, CH₂CH₃, A27], [1511: J9, CH₂CH₃, A27], [1512: J10, CH₂CH₃, A27], [1513: F, F, A28], [1514: Br, F, A28], [1515: CH₃, F, A28], [1516: CN, F, A28], [1517: J1, F, A28], [1518: J2, F, A28], [1519: J3, F, A28], [1520: J4, F, A28], [1521: J5, F, A28], [1522: J6, F, A28], [1523: J7, F, A28], [1524: J8, F, A28], [1525: J9, F, A28], [1526: J10, F, A28], [1527: F, Br, A28], [1528: Br, Br, A28], [1529: CH₃, Br, A28], [1530: CN, Br, A28], [1531: J1, Br, A28], [1532: J2, Br, A28], [1533: J3, Br, A28], [1534: J4, Br, A28], [1535: J5, Br, A28], [1536: J6, Br, A28], [1537: J7, Br, A28], [1538: J8, Br, A28], [1539: J9, Br, A28], [1540: J10, Br, A28], [1541: F, CH₃, A28], [1542: Br, CH₃, A28], [1543: CH₃, CH₃, A28], [1544: CN, CH₃, A28], [1545: J1, CH₃, A28], [1546: J2, CH₃, A28], [1547: J3, CH₃, A28], [1548: J4, CH₃, A28], [1549: J5, CH₃, A28], [1550: J6, CH₃, A28], [1551: J7, CH₃, A28], [1552: J8, CH₃, A28], [1553: J9, CH₃, A28], [1554: J10, CH₃, A28], [1555: F, CH₂CH₃, A28], [1556: Br, CH₂CH₃, A28], [1557: CH₃, CH₂CH₃, A28], [1558: CN, CH₂CH₃, A28], [1559: J1, CH₂CH₃, A28], [1560: J2, CH₂CH₃, A28], [1561: J3, CH₂CH₃, A28], [1562: J4, CH₂CH₃, A28], [1563: J5, CH₂CH₃, A28], [1564: J6, CH₂CH₃, A28], [1565: J7, CH₂CH₃, A28], [1566: J8, CH₂CH₃, A28], [1567: J9, CH₂CH₃, A28], [1568: J10, CH₂CH₃, A28], [1569: F, F, A29], [1570: Br, F, A29], [1571: CH₃, F, A29], [1572: CN, F, A29], [1573: J1, F, A29], [1574: J2, F, A29], [1575: J3, F, A29], [1576: J4, F, A29], [1577: J5, F, A29], [1578: J6, F, A29], [1579: J7, F, A29], [1580: J8, F, A29], [1581: J9, F, A29], [1582: J10, F, A29], [1583: F, Br, A29], [1584: Br, Br, A29], [1585: CH₃, Br, A29], [1586: CN, Br, A29], [1587: J1, Br, A29], [1588: J2, Br, A29], [1589: J3, Br, A29], [1590: J4, Br, A29], [1591: J5, Br, A29], [1592: J6, Br, A29], [1593: J7, Br, A29], [1594: J8, Br, A29], [1595: J9, Br, A29], [1596: J10, Br, A29], [1597: F, CH₃, A29], [1598: Br, CH₃, A29], [1599: CH₃, CH₃, A29], [1600: CN, CH₃, A29], [1601: J1, CH₃, A29], [1602: J2, CH₃, A29], [1603: J3, CH₃, A29], [1604: J4, CH₃, A29], [1605: J5, CH₃, A29], [1606: J6, CH₃, A29], [1607: J7, CH₃, A29], [1608: J8, CH₃, A29], [1609: J9, CH₃, A29], [1610: J10, CH₃, A29], [1611: F, CH₂CH₃, A29], [1612: Br, CH₂CH₃, A29], [1613: CH₃, CH₂CH₃, A29], [1614: CN, CH₂CH₃, A29], [1615: J1, CH₂CH₃, A29], [1616: J2, CH₂CH₃, A29], [1617: J3, CH₂CH₃, A29], [1618: J4, CH₂CH₃, A29], [1619: J5, CH₂CH₃, A29], [1620: J6, CH₂CH₃, A29], [1621: J7, CH₂CH₃, A29], [1622: J8, CH₂CH₃, A29], [1623: J9, CH₂CH₃, A29], [1624: J10, CH₂CH₃, A29], [1625: F, F, A30], [1626: Br, F, A30], [1627:

CH₃, F, A30], [1628: CN, F, A30], [1629: J1, F, A30], [1630: J2, F, A30], [1631: J3, F, A30], [1632: J4, F, A30], [1633: J5, F, A30], [1634: J6, F, A30], [1635: J7, F, A30], [1636: J8, F, A30], [1637: J9, F, A30], [1638: J10, F, A30], [1639: F, Br, A30], [1640: Br, Br, A30], [1641: CH₃, Br, A30], [1642: CN, Br, A30], [1643: J1, Br, A30], [1644: J2, Br, A30], [1645: J3, Br, A30], [1646: J4, Br, A30], [1647: J5, Br, A30], [1648: J6, Br, A30], [1649: J7, Br, A30], [1650: J8, Br, A30], [1651: J9, Br, A30], [1652: J10, Br, A30], [1653: F, CH₃, A30], [1654: Br, CH₃, A30], [1655: CH₃, CH₃, A30], [1656: CN, CH₃, A30], [1657: J1, CH₃, A30], [1658: J2, CH₃, A30], [1659: J3, CH₃, A30], [1660: J4, CH₃, A30], [1661: J5, CH₃, A30], [1662: J6, CH₃, A30], [1663: J7, CH₃, A30], [1664: J8, CH₃, A30], [1665: J9, CH₃, A30], [1666: J10, CH₃, A30], [1667: F, CH₂CH₃, A30], [1668: Br, CH₂CH₃, A30], [1669: CH₃, CH₂CH₃, A30], [1670: CN, CH₂CH₃, A30], [1671: J1, CH₂CH₃, A30], [1672: J2, CH₂CH₃, A30], [1673: J3, CH₂CH₃, A30], [1674: J4, CH₂CH₃, A30], [1675: J5, CH₂CH₃, A30], [1676: J6, CH₂CH₃, A30], [1677: J7, CH₂CH₃, A30], [1678: J8, CH₂CH₃, A30], [1679: J9, CH₂CH₃, A30], [1680: J10, CH₂CH₃, A30], [1681: F, F, A31], [1682: Br, F, A31], [1683: CH₃, F, A31], [1684: CN, F, A31], [1685: J1, F, A31], [1686: J2, F, A31], [1687: J3, F, A31], [1688: J4, F, A31], [1689: J5, F, A31], [1690: J6, F, A31], [1691: J7, F, A31], [1692: J8, F, A31], [1693: J9, F, A31], [1694: J10, F, A31], [1695: F, Br, A31], [1696: Br, Br, A31], [1697: CH₃, Br, A31], [1698: CN, Br, A31], [1699: J1, Br, A31], [1700: J2, Br, A31], [1701: J3, Br, A31], [1702: J4, Br, A31], [1703: J5, Br, A31], [1704: J6, Br, A31], [1705: J7, Br, A31], [1706: J8, Br, A31], [1707: J9, Br, A31], [1708: J10, Br, A31], [1709: F, CH₃, A31], [1710: Br, CH₃, A31], [1711: CH₃, CH₃, A31], [1712: CN, CH₃, A31], [1713: J1, CH₃, A31], [1714: J2, CH₃, A31], [1715: J3, CH₃, A31], [1716: J4, CH₃, A31], [1717: J5, CH₃, A31], [1718: J6, CH₃, A31], [1719: J7, CH₃, A31], [1720: J8, CH₃, A31], [1721: J9, CH₃, A31], [1722: J10, CH₃, A31], [1723: F, CH₂CH₃, A31], [1724: Br, CH₂CH₃, A31], [1725: CH₃, CH₂CH₃, A31], [1726: CN, CH₂CH₃, A31], [1727: J1, CH₂CH₃, A31], [1728: J2, CH₂CH₃, A31], [1729: J3, CH₂CH₃, A31], [1730: J4, CH₂CH₃, A31], [1731: J5, CH₂CH₃, A31], [1732: J6, CH₂CH₃, A31], [1733: J7, CH₂CH₃, A31], [1734: J8, CH₂CH₃, A31], [1735: J9, CH₂CH₃, A31], [1736: J10, CH₂CH₃, A31], [1737: F, F, A32], [1738: Br, F, A32], [1739: CH₃, F, A32], [1740: CN, F, A32], [1741: J1, F, A32], [1742: J2, F, A32], [1743: J3, F, A32], [1744: J4, F, A32], [1745: J5, F, A32], [1746: J6, F, A32], [1747: J7, F, A32], [1748: J8, F, A32], [1749: J9, F, A32], [1750: J10, F, A32], [1751: F, Br, A32], [1752: Br, Br, A32], [1753: CH₃, Br, A32], [1754: CN, Br, A32], [1755: J1, Br, A32], [1756: J2, Br, A32], [1757: J3, Br, A32], [1758: J4, Br, A32], [1759: J5, Br, A32], [1760: J6, Br, A32], [1761: J7, Br, A32], [1762: J8, Br, A32], [1763: J9, Br, A32], [1764: J10, Br, A32], [1765: F, CH₃, A32], [1766: Br, CH₃, A32], [1767: CH₃, CH₃, A32], [1768: CN, CH₃, A32], [1769: J1, CH₃, A32], [1770: J2, CH₃, A32], [1771: J3, CH₃, A32], [1772: J4, CH₃, A32], [1773: J5, CH₃, A32], [1774: J6, CH₃, A32], [1775: J7, CH₃, A32], [1776: J8, CH₃, A32], [1777: J9, CH₃, A32], [1778: J10, CH₃, A32], [1779: F, CH₂CH₃, A32], [1780: Br, CH₂CH₃, A32], [1781: CH₃, CH₂CH₃, A32], [1782: CN, CH₂CH₃, A32], [1783: J1, CH₂CH₃, A32], [1784: J2, CH₂CH₃, A32], [1785: J3, CH₂CH₃, A32], [1786: J4, CH₂CH₃, A32], [1787: J5, CH₂CH₃, A32], [1788: J6, CH₂CH₃, A32], [1789: J7, CH₂CH₃, A32], [1790: J8, CH₂CH₃, A32], [1791: J9, CH₂CH₃, A32], [1792: J10, CH₂CH₃, A32], [1793: F, F, A33], [1794: Br, F, A33], [1795: CH₃, F, A33], [1796: CN, F, A33], [1797: J1, F, A33], [1798: J2, F, A33], [1799: J3, F, A33], [1800: J4, F, A33], [1801: J5, F, A33], [1802: J6, F, A33], [1803: J7, F, A33], [1804: J8, F, A33], [1805: J9, F, A33], [1806: J10, F, A33], [1807: F, Br, A33], [1808: Br, Br, A33], [1809: CH₃, Br, A33], [1810: CN, Br, A33], [1811: J1, Br, A33], [1812: J2, Br, A33], [1813: J3, Br, A33], [1814: J4, Br, A33], [1815: J5, Br, A33], [1816: J6, Br, A33], [1817: J7, Br, A33], [1818: J8, Br, A33], [1819: J9, Br, A33], [1820: J10, Br, A33], [1821: F, CH₃, A33], [1822: Br, CH₃, A33], [1823: CH₃, CH₃, A33], [1824: CN, CH₃, A33], [1825: J1, CH₃, A33], [1826: J2, CH₃, A33], [1827: J3, CH₃, A33], [1828: J4, CH₃, A33], [1829: J5, CH₃, A33], [1830: J6, CH₃, A33], [1831: J7, CH₃, A33], [1832: J8, CH₃, A33], [1833: J9, CH₃, A33], [1834: J10, CH₃, A33], [1835: F, CH₂CH₃, A33], [1836: Br, CH₂CH₃, A33], [1837: CH₃, CH₂CH₃, A33], [1838: CN, CH₂CH₃, A33], [1839: J1, CH₂CH₃, A33], [1840: J2, CH₂CH₃, A33], [1841: J3, CH₂CH₃, A33], [1842: J4, CH₂CH₃, A33], [1843: J5, CH₂CH₃, A33], [1844: J6, CH₂CH₃, A33], [1845: J7, CH₂CH₃, A33], [1846: J8, CH₂CH₃, A33], [1847: J9, CH₂CH₃, A33], [1848: J10, CH₂CH₃, A33], [1849: F, F, A34], [1850: Br, F, A34], [1851: CH₃, F, A34], [1852: CN, F, A34], [1853: J1, F, A34], [1854: J2, F, A34], [1855: J3, F, A34], [1856: J4, F, A34], [1857: J5, F, A34], [1858: J6, F, A34], [1859: J7, F, A34], [1860: J8, F, A34], [1861: J9, F, A34], [1862: J10, F, A34], [1863: F, Br, A34], [1864: Br, Br, A34], [1865: CH₃, Br, A34], [1866: CN, Br, A34], [1867: J1, Br, A34], [1868: J2, Br, A34], [1869: J3, Br, A34], [1870: J4, Br, A34], [1871: J5, Br, A34], [1872: J6, Br, A34], [1873: J7, Br, A34], [1874: J8, Br, A34], [1875: J9, Br, A34], [1876: J10, Br, A34], [1877: F, CH₃, A34], [1878: Br, CH₃, A34], [1879: CH₃, CH₃, A34], [1880: CN, CH₃, A34], [1881: J1, CH₃, A34], [1882: J2, CH₃, A34], [1883: J3, CH₃, A34], [1884: J4, CH₃, A34], [1885: J5, CH₃, A34], [1886: J6, CH₃, A34], [1887: J7, CH₃, A34], [1888: J8, CH₃, A34], [1889: J9, CH₃, A34], [1890: J10, CH₃, A34], [1891: F, CH₂CH₃, A34], [1892: Br, CH₂CH₃, A34], [1893: CH₃, CH₂CH₃, A34], [1894: CN, CH₂CH₃, A34], [1895: J1, CH₂CH₃, A34], [1896: J2, CH₂CH₃, A34], [1897: J3, CH₂CH₃, A34], [1898: J4, CH₂CH₃, A34], [1899: J5, CH₂CH₃, A34], [1900: J6, CH₂CH₃, A34], [1901: J7, CH₂CH₃, A34], [1902: J8, CH₂CH₃, A34], [1903: J9, CH₂CH₃, A34], [1904: J10, CH₂CH₃, A34], [1905: F, F, A35], [1906: Br, F, A35], [1907: CH₃, F, A35], [1908: CN, F, A35], [1909: J1, F, A35], [1910: J2, F, A35], [1911: J3, F, A35], [1912: J4, F, A35], [1913: J5, F, A35], [1914: J6, F, A35], [1915: J7, F, A35], [1916: J8, F, A35], [1917: J9, F, A35], [1918: J10, F, A35], [1919: F, Br, A35], [1920: Br, Br, A35], [1921: CH₃, Br, A35], [1922: CN, Br, A35], [1923: J1, Br, A35], [1924: J2, Br, A35], [1925: J3, Br, A35], [1926: J4, Br, A35], [1927: J5, Br, A35], [1928: J6, Br, A35], [1929: J7, Br, A35], [1930: J8, Br, A35], [1931: J9, Br, A35], [1932: J10, Br, A35], [1933: F, CH₃, A35], [1934: Br, CH₃, A35], [1935: CH₃, CH₃, A35], [1936: CN, CH₃, A35], [1937: J1, CH₃, A35], [1938: J2, CH₃, A35], [1939: J3, CH₃, A35], [1940: J4, CH₃, A35], [1941: J5, CH₃, A35], [1942: J6, CH₃, A35], [1943: J7, CH₃, A35], [1944: J8, CH₃, A35], [1945: J9, CH₃, A35], [1946: J10, CH₃, A35], [1947: F, CH₂CH₃, A35], [1948: Br, CH₂CH₃, A35], [1949: CH₃, CH₂CH₃, A35], [1950: CN, CH₂CH₃, A35], [1951: J1, CH₂CH₃, A35], [1952: J2, CH₂CH₃, A35], [1953: J3, CH₂CH₃, A35], [1954: J4, CH₂CH₃, A35], [1955: J5, CH₂CH₃, A35], [1956: J6, CH₂CH₃, A35], [1957: J7, CH₂CH₃, A35], [1958: J8, CH₂CH₃, A35], [1959: J9, CH₂CH₃, A35], [1960: J10, CH₂CH₃, A35], [1961: F, F, A36], [1962: Br, F, A36], [1963: CH₃, F, A36], [1964: CN, F, A36], [1965: J1, F, A36], [1966: J2, F, A36], [1967: J3, F, A36], [1968: J4, F, A36], [1969: J5, F, A36], [1970: J6, F, A36], [1971: J7, F, A36], [1972: J8, F, A36], [1973: J9, F, A36], [1974: J10, F, A36], [1975: F, Br, A36], [1976: Br, Br, A36], [1977: CH₃, Br, A36], [1978: CN,

Br, A36], [1979: J1, Br, A36], [1980: J2, Br, A36], [1981: J3, Br, A36], [1982: J4, Br, A36], [1983: J5, Br, A36], [1984: J6, Br, A36], [1985: J7, Br, A36], [1986: J8, Br, A36], [1987: J9, Br, A36], [1988: J10, Br, A36], [1989: F, $CH_3$, A36], [1990: Br, $CH_3$, A36], [1991: $CH_3$, $CH_3$, A36], [1992: CN, $CH_3$, A36], [1993: J1, $CH_3$, A36], [1994: J2, $CH_3$, A36], [1995: J3, $CH_3$, A36], [1996: J4, $CH_3$, A36], [1997: J5, $CH_3$, A36], [1998: J6, $CH_3$, A36], [1999: J7, $CH_3$, A36], [2000: J8, $CH_3$, A36], [2001: J9, $CH_3$, A36], [2002: J10, $CH_3$, A36], [2003: F, $CH_2CH_3$, A36], [2004: Br, $CH_2CH_3$, A36], [2005: $CH_3$, $CH_2CH_3$, A36], [2006: CN, $CH_2CH_3$, A36], [2007: J1, $CH_2CH_3$, A36], [2008: J2, $CH_2CH_3$, A36], [2009: J3, $CH_2CH_3$, A36], [2010: J4, $CH_2CH_3$, A36], [2011: J5, $CH_2CH_3$, A36], [2012: J6, $CH_2CH_3$, A36], [2013: J7, $CH_2CH_3$, A36], [2014: J8, $CH_2CH_3$, A36], [2015: J9, $CH_2CH_3$, A36], [2016: J10, $CH_2CH_3$, A36], [2017: F, F, A37], [2018: Br, F, A37], [2019: $CH_3$, F, A37], [2020: CN, F, A37], [2021: J1, F, A37], [2022: J2, F, A37], [2023: J3, F, A37], [2024: J4, F, A37], [2025: J5, F, A37], [2026: J6, F, A37], [2027: J7, F, A37], [2028: J8, F, A37], [2029: J9, F, A37], [2030: J10, F, A37], [2031: F, Br, A37], [2032: Br, Br, A37], [2033: $CH_3$, Br, A37], [2034: CN, Br, A37], [2035: J1, Br, A37], [2036: J2, Br, A37], [2037: J3, Br, A37], [2038: J4, Br, A37], [2039: J5, Br, A37], [2040: J6, Br, A37], [2041: J7, Br, A37], [2042: J8, Br, A37], [2043: J9, Br, A37], [2044: J10, Br, A37], [2045: F, $CH_3$, A37], [2046: Br, $CH_3$, A37], [2047: $CH_3$, $CH_3$, A37], [2048: CN, $CH_3$, A37], [2049: J1, $CH_3$, A37], [2050: J2, $CH_3$, A37], [2051: J3, $CH_3$, A37], [2052: J4, $CH_3$, A37], [2053: J5, $CH_3$, A37], [2054: J6, $CH_3$, A37], [2055: J7, $CH_3$, A37], [2056: J8, $CH_3$, A37], [2057: J9, $CH_3$, A37], [2058: J10, $CH_3$, A37], [2059: F, $CH_2CH_3$, A37], [2060: Br, $CH_2CH_3$, A37], [2061: $CH_3$, $CH_2CH_3$, A37], [2062: CN, $CH_2CH_3$, A37], [2063: J1, $CH_2CH_3$, A37], [2064: J2, $CH_2CH_3$, A37], [2065: J3, $CH_2CH_3$, A37], [2066: J4, $CH_2CH_3$, A37], [2067: J5, $CH_2CH_3$, A37], [2068: J6, $CH_2CH_3$, A37], [2069: J7, $CH_2CH_3$, A37], [2070: J8, $CH_2CH_3$, A37], [2071: J9, $CH_2CH_3$, A37], [2072: J10, $CH_2CH_3$, A37], [2073: F, F, A38], [2074: Br, F, A38], [2075: $CH_3$, F, A38], [2076: CN, F, A38], [2077: J1, F, A38], [2078: J2, F, A38], [2079: J3, F, A38], [2080: J4, F, A38], [2081: J5, F, A38], [2082: J6, F, A38], [2083: J7, F, A38], [2084: J8, F, A38], [2085: J9, F, A38], [2086: J10, F, A38], [2087: F, Br, A38], [2088: Br, Br, A38], [2089: $CH_3$, Br, A38], [2090: CN, Br, A38], [2091: J1, Br, A38], [2092: J2, Br, A38], [2093: J3, Br, A38], [2094: J4, Br, A38], [2095: J5, Br, A38], [2096: J6, Br, A38], [2097: J7, Br, A38], [2098: J8, Br, A38], [2099: J9, Br, A38], [2100: J10, Br, A38], [2101: F, $CH_3$, A38], [2102: Br, $CH_3$, A38], [2103: $CH_3$, $CH_3$, A38], [2104: CN, $CH_3$, A38], [2105: J1, $CH_3$, A38], [2106: J2, $CH_3$, A38], [2107: J3, $CH_3$, A38], [2108: J4, $CH_3$, A38], [2109: J5, $CH_3$, A38], [2110: J6, $CH_3$, A38], [2111: J7, $CH_3$, A38], [2112: J8, $CH_3$, A38], [2113: J9, $CH_3$, A38], [2114: J10, $CH_3$, A38], [2115: F, $CH_2CH_3$, A38], [2116: Br, $CH_2CH_3$, A38], [2117: $CH_3$, $CH_2CH_3$, A38], [2118: CN, $CH_2CH_3$, A38], [2119: J1, $CH_2CH_3$, A38], [2120: J2, $CH_2CH_3$, A38], [2121: J3, $CH_2CH_3$, A38], [2122: J4, $CH_2CH_3$, A38], [2123: J5, $CH_2CH_3$, A38], [2124: J6, $CH_2CH_3$, A38], [2125: J7, $CH_2CH_3$, A38], [2126: J8, $CH_2CH_3$, A38], [2127: J9, $CH_2CH_3$, A38], [2128: J10, $CH_2CH_3$, A38], [2129: F, F, A39], [2130: Br, F, A39], [2131: $CH_3$, F, A39], [2132: CN, F, A39], [2133: J1, F, A39], [2134: J2, F, A39], [2135: J3, F, A39], [2136: J4, F, A39], [2137: J5, F, A39], [2138: J6, F, A39], [2139: J7, F, A39], [2140: J8, F, A39], [2141: J9, F, A39], [2142: J10, F, A39], [2143: F, Br, A39], [2144: Br, Br, A39], [2145: $CH_3$, Br, A39], [2146: CN, Br, A39], [2147: J1, Br, A39], [2148: J2, Br, A39], [2149: J3, Br, A39], [2150: J4, Br, A39], [2151: J5, Br, A39], [2152: J6, Br, A39], [2153: J7, Br, A39], [2154: J8, Br, A39], [2155: J9, Br, A39], [2156: J10, Br, A39], [2157: F, $CH_3$, A39], [2158: Br, $CH_3$, A39], [2159: $CH_3$, $CH_3$, A39], [2160: CN, $CH_3$, A39], [2161: J1, $CH_3$, A39], [2162: J2, $CH_3$, A39], [2163: J3, $CH_3$, A39], [2164: J4, $CH_3$, A39], [2165: J5, $CH_3$, A39], [2166: J6, $CH_3$, A39], [2167: J7, $CH_3$, A39], [2168: J8, $CH_3$, A39], [2169: J9, $CH_3$, A39], [2170: J10, $CH_3$, A39], [2171: F, $CH_2CH_3$, A39], [2172: Br, $CH_2CH_3$, A39], [2173: $CH_3$, $CH_2CH_3$, A39], [2174: CN, $CH_2CH_3$, A39], [2175: J1, $CH_2CH_3$, A39], [2176: J2, $CH_2CH_3$, A39], [2177: J3, $CH_2CH_3$, A39], [2178: J4, $CH_2CH_3$, A39], [2179: J5, $CH_2CH_3$, A39], [2180: J6, $CH_2CH_3$, A39], [2181: J7, $CH_2CH_3$, A39], [2182: J8, $CH_2CH_3$, A39], [2183: J9, $CH_2CH_3$, A39], [2184: J10, $CH_2CH_3$, A39], [2185: F, F, A40], [2186: Br, F, A40], [2187: $CH_3$, F, A40], [2188: CN, F, A40], [2189: J1, F, A40], [2190: J2, F, A40], [2191: J3, F, A40], [2192: J4, F, A40], [2193: J5, F, A40], [2194: J6, F, A40], [2195: J7, F, A40], [2196: J8, F, A40], [2197: J9, F, A40], [2198: J10, F, A40], [2199: F, Br, A40], [2200: Br, Br, A40], [2201: $CH_3$, Br, A40], [2202: CN, Br, A40], [2203: J1, Br, A40], [2204: J2, Br, A40], [2205: J3, Br, A40], [2206: J4, Br, A40], [2207: J5, Br, A40], [2208: J6, Br, A40], [2209: J7, Br, A40], [2210: J8, Br, A40], [2211: J9, Br, A40], [2212: J10, Br, A40], [2213: F, $CH_3$, A40], [2214: Br, $CH_3$, A40], [2215: $CH_3$, $CH_3$, A40], [2216: CN, $CH_3$, A40], [2217: J1, $CH_3$, A40], [2218: J2, $CH_3$, A40], [2219: J3, $CH_3$, A40], [2220: J4, $CH_3$, A40], [2221: J5, $CH_3$, A40], [2222: J6, $CH_3$, A40], [2223: J7, $CH_3$, A40], [2224: J8, $CH_3$, A40], [2225: J9, $CH_3$, A40], [2226: J10, $CH_3$, A40], [2227: F, $CH_2CH_3$, A40], [2228: Br, $CH_2CH_3$, A40], [2229: $CH_3$, $CH_2CH_3$, A40], [2230: CN, $CH_2CH_3$, A40], [2231: J1, $CH_2CH_3$, A40], [2232: J2, $CH_2CH_3$, A40], [2233: J3, $CH_2CH_3$, A40], [2234: J4, $CH_2CH_3$, A40], [2235: J5, $CH_2CH_3$, A40], [2236: J6, $CH_2CH_3$, A40], [2237: J7, $CH_2CH_3$, A40], [2238: J8, $CH_2CH_3$, A40], [2239: J9, $CH_2CH_3$, A40], [2240: J10, $CH_2CH_3$, A40], [2241: F, F, A41], [2242: Br, F, A41], [2243: $CH_3$, F, A41], [2244: CN, F, A41], [2245: J1, F, A41], [2246: J2, F, A41], [2247: J3, F, A41], [2248: J4, F, A41], [2249: J5, F, A41], [2250: J6, F, A41], [2251: J7, F, A41], [2252: J8, F, A41], [2253: J9, F, A41], [2254: J10, F, A41], [2255: F, Br, A41], [2256: Br, Br, A41], [2257: $CH_3$, Br, A41], [2258: CN, Br, A41], [2259: J1, Br, A41], [2260: J2, Br, A41], [2261: J3, Br, A41], [2262: J4, Br, A41], [2263: J5, Br, A41], [2264: J6, Br, A41], [2265: J7, Br, A41], [2266: J8, Br, A41], [2267: J9, Br, A41], [2268: J10, Br, A41], [2269: F, $CH_3$, A41], [2270: Br, $CH_3$, A41], [2271: $CH_3$, $CH_3$, A41], [2272: CN, $CH_3$, A41], [2273: J1, $CH_3$, A41], [2274: J2, $CH_3$, A41], [2275: J3, $CH_3$, A41], [2276: J4, $CH_3$, A41], [2277: J5, $CH_3$, A41], [2278: J6, $CH_3$, A41], [2279: J7, $CH_3$, A41], [2280: J8, $CH_3$, A41], [2281: J9, $CH_3$, A41], [2282: J10, $CH_3$, A41], [2283: F, $CH_2CH_3$, A41], [2284: Br, $CH_2CH_3$, A41], [2285: $CH_3$, $CH_2CH_3$, A41], [2286: CN, $CH_2CH_3$, A41], [2287: J1, $CH_2CH_3$, A41], [2288: J2, $CH_2CH_3$, A41], [2289: J3, $CH_2CH_3$, A41], [2290: J4, $CH_2CH_3$, A41], [2291: J5, $CH_2CH_3$, A41], [2292: J6, $CH_2CH_3$, A41], [2293: J7, $CH_2CH_3$, A41], [2294: J8, $CH_2CH_3$, A41], [2295: J9, $CH_2CH_3$, A41], [2296: J10, $CH_2CH_3$, A41].

Next, Formulation Examples are shown. The term "part(s)" means part(s) by weight. The compounds of the present invention are represented by the compound numbers as described above.

Formulation Example 1

Nine parts of any one of the present compounds (1) to (5) is dissolved in 37.5 parts of xylene and 37.5 parts of dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 2

Five parts of the present compound (1) and 4 parts of a compound selected from the following group [A], are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

The group [A]:

aluminum phosphide, butathiofos, cadusafos, chlorethoxyfos, chlorfenvinphos, chlorpyrifos, chlorpyrifos-methyl, cyanophos (CYAP), diazinon, DCIP (dichlorodiisopropyl ether), dichlofenthion (ECP), dichlorvos (DDVP), dimethoate, dimethylvinphos, disulfoton, EPN, ethion, ethoprophos, etrimfos, fenthion (MPP), fenitrothion (MEP), fosthiazate, formothion, hydrogen phosphide, isofenphos, isoxathion, malathion, mesulfenfos, methidathion (DMTP), monocrotophos, naled (BRP), oxydeprofos (ESP), parathion, phosalone, phosmet (PMP), pirimiphos-methyl, pyridafenthion, quinalphos, phenthoate (PAP), profenofos, propaphos, prothiofos, pyraclorfos, salithion, sulprofos, tebupirimfos, temephos, tetrachlorvinphos, terbufos, thiometon, trichlorphon (DEP), vamidothion, phorate, cadusafos;

alanycarb, bendiocarb, benfuracarb, BPMC, carbaryl, carbofuran, carbosulfan, cloethocarb, ethiofencarb, fenobucarb, fenothiocarb, fenoxycarb, furathiocarb, isoprocarb (MIPC), metolcarb, methomyl, methiocarb, NAC, oxamyl, pirimicarb, propoxur (PHC), XMC, thiodicarb, xylylcarb, aldicarb;

acrinathrin, allethrin, benfluthrin, beta-cyfluthrin, bifenthrin, cycloprothrin, cyfluthrin, cyhalothrin, empenthrin, deltamethrin, esfenvalerate, ethofenprox, fenvalerate, flucythrinate, flufenoprox, flumethrin, fluvalinate, halfenprox, imiprothrin, prallethrin, pyrethrins, resmethrin, sigma-cypermethrin, silafluofen, tefluthrin, tralomethrin, transfluthrin, tetramethrin, lambda-cyhalothrin, gamma-cyhalothrin, furamethrin, tau-fluvalinate, 2,3,5,6-tetrafluoro-4-methylbenzyl 2,2-dimethyl-3-(1-propenyl)cyclopropanecarboxylate, 2,3,5,6-tetrafluoro-4-(methoxymethyl)benzyl 2,2-dimethyl-3-(2-methyl-1-propenyl)cyclopropanecarboxylate, 2,3,5,6-tetrafluoro-4-(methoxymethyl)benzyl 2,2-dimethyl-3-(2-cyano-1-propenyl)cyclopropanecarboxylate, 2,3,5,6-tetrafluoro-4-(methoxymethyl)benzyl 2,2,3,3-tetramethylcyclopropanecarboxylate; cartap, bensultap, thiocyclam, monosultap, bisultap; imidacloprid, nitenpyram, acetamiprid, thiamethoxam, thiacloprid;

chlorfluazuron, bistrifluoron, diafenthiuron, diflubenzuron, fluazuron, flucycloxuron, flufenoxuron, hexaflumuron, lufenuron, novaluron, noviflumuron, teflubenzuron, triflumuron, triazuron;

acetoprole, fipronil, vaniliprole, pyriprole, pyrafluprole, and the like;

chromafenozide, halofenozide, methoxyfenozide, tebufenozide;

aldrin, dieldrin, dienochlor, endosulfan, methoxychlor; nicotine sulfate;

avermectin-B, bromopropylate, buprofezin, chlorphenapyr, cyromazine, D-D (1,3-dichloropropene), emamectin-benzoate, fenazaquin, flupyrazofos, hydroprene, methoprene, indoxacarb, metoxadiazone, milbemycin-A, pymetrozine, pyridalyl, spinosad, sulfluramid, tolfenpyrad, triazamate, flubendiamide, lepimectin, arsenic acid, benclothiaz, calcium cyanamide, calcium polysulfide, chlordane, DDT, DSP, flufenerim, flonicamid, flurimfen, formetanate, metham-ammonium, metham-sodium, methyl bromide, potassium oleate, protrifenbute, spiromesifen, sulfur, metaflumizone, spirotetramat, pyrifluquinazone, chlorantraniliprole, tralopyril, a compound represented by the following formula (A):

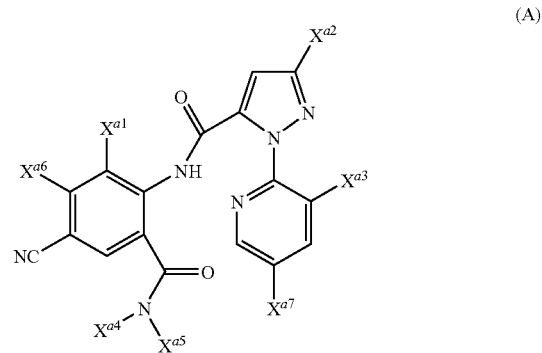

wherein $X^{a1}$ represents methyl, chlorine, bromine or fluorine, $X^{a2}$ represents fluorine, chlorine, bromine, C1-C4 haloalkyl or C1-C4 haloalkoxy, $X^{a3}$ represents fluorine, chlorine or bromine, $X^{a4}$ represents optionally substituted C1-C4 alkyl, optionally substituted C3-C4 alkenyl, optionally substituted C3-C4 alkynyl, optionally substituted C3-C5 cycloalkyl or hydrogen, $X^{a5}$ represents hydrogen or methyl, $X^{a6}$ represents hydrogen, fluorine or chlorine, and $X^{a7}$ represents hydrogen, fluorine or chlorine;

a compound represented by the following formula (B):

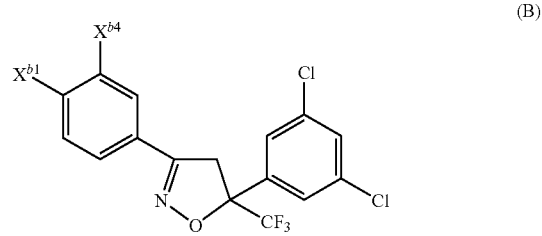

wherein $X^{bi}$ represents $X^{b2}$—NH—C(=O), $X^{b2}$—C(=O)—NH—CH$_2$, $X^{b3}$—S(O), optionally substituted pyrrol-1-yl, optionally substituted imidazol-1-yl, optionally substituted pyrazol-1-yl, or optionally substituted 1,2,4-triazol-1-yl, $X^{b2}$ represents optionally substituted C1-C4 haloalkyl such as 2,2,2-trifluoroethyl or optionally substituted C3-C6 cycloalkyl such as cyclopropyl, $X^{b3}$ represents optionally substituted C1-C4 alkyl such as methyl, and $X^{b4}$ represents hydrogen, chlorine, cyano or methyl;

a compound represented by the following formula (C):

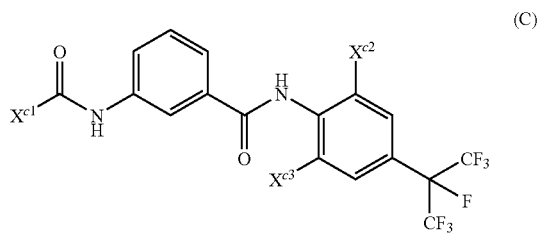

wherein $X^{c1}$ represents optionally substituted C1-C4 alkyl such as 3,3,3-trifluoropropyl, optionally substituted C1-C4 alkoxy such as 2,2,2-trichloroethoxy or optionally substituted phenyl such as 4-cyanophenyl or optionally substituted pyridyl such as 2-chloro-3-pyridyl, $X^{c2}$ represents methyl or trifluoromethylthio, and $X^{c3}$ represents methyl or halogen; acequinocyl, amitraz, benzoximate, bifenate, bromopropylate, chinomethionat, chlorobenzilate, CPCBS (chlorfenson), clofentezine, cyflumetofen, kelthane (dicofol), fenbutatin oxide, fenothiocarb, fenpyroximate, fluacrypyrim, fluproxyfen, hexythiazox, propargite (BPPS), pyridaben, pyrimidifen, tebufenpyrad, tetradifon, spirodiclofen, spiromesifen, spirotetramat, amidoflumet, and cyenopyrafen.

Formulation Example 3

Five parts of the present compound (2) and 4 parts of a compound selected from the group [A], are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 4

Five parts of the present compound (3) and 4 parts of a compound selected from the group [A], are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 5

Five parts of the present compound (4) and 4 parts of a compound selected from the group [A], are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 6

Five parts of the present compound (5) and 4 parts of a compound selected from the group [A], are dissolved in 37.5 parts of xylene and 37.5 parts of N,N-dimethylformamide. Thereto 10 parts of polyoxyethylene styryl phenyl ether and 6 parts of calcium dodecylbenzenesulfonate are added and mixed by stirring thoroughly to obtain an emulsifiable concentrate.

Formulation Example 7

Five parts of SORPOL 5060 (registered trade name for TOHO Chemical Industry Co., LTD.) is added to 40 parts of any one of the present compounds (1) to (5) and mixed thoroughly. The mixture was mixed with 32 parts of CARPLEX #80 (registered trade name for Shionogi & Co., Ltd., synthetic hydrous silicon oxide fine powder) and 23 parts of 300 mesh diatomaceous earth using a juice mixer to obtain a wettable powder.

Formulation Example 8

Three parts of any one of the present compounds (1) to (5), 5 parts of synthetic hydrous silicon oxide fine powder, 5 parts of sodium dodecylbenzenesulfonate, 30 parts of bentonite and 57 parts of clay are mixed by stirring thoroughly. To this mixture an appropriate amount of water is added. The mixture is further stirred, granulated with a granulator, and then air-dried to obtain a granule.

Formulation Example 9

Four point five parts of any one of the present compounds (1) to (5), 1 part of synthetic hydrous silicon oxide fine powder, 1 part of Dorires B (manufactured by Sankyo) as a flocculant, and 7 parts of clay are mixed thoroughly using a mortar, and then mixed by stirring using a juice mixer. To the resultant mixture 86.5 parts of cut clay is added and mixed by stirring thoroughly to obtain a dust.

Formulation Example 10

Ten parts of any one of the present compounds (1) to (5), 35 parts of white carbon containing 50% by weight of polyoxyethylene alkylether sulfate ammonium salt, and 55 parts of water are mixed and then finely-divided by a wet grinding method to obtain a formulation.

Formulation Example 11

Zero point five part of any one of the present compounds (1) to (5) is dissolved in 10 parts of dichloromethane. This solution is mixed with 89.5 parts of Isopar M (isoparaffin: registered trade name for Exxon Chemical) to obtain an oil solution.

Formulation Example 12

Zero point one part of any one of the present compounds (1) to (5) and 49.9 parts of NEO-THIOZOL (Chuo Kasei Co., Ltd.) are placed in an aerosol can. An aerosol valve is fitted to the can. The can is charged with 25 parts of dimethyl ether and 25 parts of LPG, and then shaken. An actuator is fitted to the can to obtain an oily aerosol.

Formulation Example 13

Zero point six parts of any one of the present compounds (1) to (5), 0.01 part of BHT, 5 parts of xylene, 3.39 parts of a deodorized kerosine and 1 part of an emulsifying agent [Atmos 300 (registered trade name for Atmos Chemical Ltd.)], are mixed to obtain a solution. An aerosol container is charged with the obtained solution and 50 parts of distilled water. A valve part is attached to the container and the container is then charged with 40 parts of a propellant (LPG) through the valve under increased pressure to obtain an aqueous aerosol.

Formulation Example 14

Five parts of any one of the present compounds (1) to (5) is dissolved in 80 parts of diethylene glycol monoethyl ether. Thereto 15 parts of propylene carbonate is mixed to obtain a spot-on liquid formulation.

Formulation Example 15

Ten parts of any one of the present compounds (1) to (5) is dissolved in 70 parts of diethylene glycol monoethyl ether. Thereto 20 parts of 2-octyldodecanol is mixed to obtain a pour-on liquid formulation.

Formulation Example 16

To 0.5 parts of any one of the present compounds (1) to (5) are added 60 parts of NIKKOL TEALS-42 (a 42% aqueous solution of triethanolamine lauryl sulfate, Nikko Chemicals) and 20 parts of propylene glycol. The mixture is stirred well to obtain a homogeneous solution. Thereto 19.5 parts of water is added and mixed by stirring thoroughly to obtain a homogeneous shampoo formulation.

Formulation Example 17

A porous ceramic plate with a length of 4.0 cm, a width of 0.4 cm and a thickness of 1.2 cm is impregnated with a solution of 0.1 g of any one of the present compounds (1) to (5) in 2 ml of propylene glycol to obtain a heating-type smoking agent.

Formulation Example 18

Five parts of any one of the present compounds (1) to (5) and 95 parts of an ethylene-methyl methacrylate copolymer (the proportion of methyl methacrylate in the copolymer: 10% by weight, ACRYFT WD301, Sumitomo Chemical) are melted and kneaded in a sealed pressure kneader (Moriyama Manufacturing Co., Ltd.). The obtained kneaded product is extruded through a molding die using an extruder to obtain a molded bar with a length of 15 cm and a diameter of 3 mm.

Formulation Example 19

Five parts of any one of the present compounds (1) to (5) and 95 parts of a flexible polyvinyl chloride resin are melted and kneaded in a sealed pressure kneader (Moriyama Manufacturing Co., Ltd.). The obtained kneaded product is extruded through a molding die using an extruder to obtain a molded bar with a length of 15 cm and a diameter of 3 mm.

Next, effectiveness of the compound of the present invention as an active ingredient of a pesticidal composition is shown by Test Examples.

Test Example 1

A formulation of any one of the present compounds (2) to (5) obtained according to Formulation Example 10 was diluted so that the active ingredient concentration was 500 ppm to obtain a test solution.

At the same time, 50 g of culture soil, Bonsol No. 2 (manufactured by Sumitomo Chemical Co., Ltd.) was put into a polyethylene cup, and 10 to 15 seeds of rice were planted therein. The rice plants were grown until the second foliage leaf was developed, and then cut so as to have the same height of 5 cm. The test solution was sprayed on the rice paints in an amount of 20 ml/cup. After the test solution sprayed on the rice plants was dried, the rice plants were placed in a plastic cup for the purpose of preventing test worms from escaping. Thirty first-instar larvae of brown rice planthopper were released into the cup, and the cup was sealed with a lid. Then the cup was placed in a greenhouse at 25° C. for 6 days. Then, the number of parasitic brown rice planthoppers on the rice plants was examined.

As a result, on the plants treated with any one of the present compounds (2) to (5), the number of the parasitic pests was 3 or smaller.

Test Example 2

A formulation of any one of the present compounds (1) to (5) obtained according to Formulation Example 10 was diluted so that the active ingredient concentration was 55.6 ppm to obtain a test solution.

At the same time, 50 g of culture soil, Bonsol No. 2 (manufactured by Sumitomo Chemical Co., Ltd.) was put into a polyethylene cup with five holes 5 mm in diameter at the bottom, and 10 to 15 seeds of rice were planted therein. The rice plants were grown until the second foliage leaf was developed, and then treated with 45 ml of the test solution by allowing the plants to absorb the test solution from the bottom of the cup. The rice plants were placed in a greenhouse at 25° C. for 6 days and then cut into the same height of 5 cm. Thirty first-instar larvae of brown rice planthopper were released on the rice plants, which were left at 25° C. for 6 days. Then, the number of parasitic brown rice planthoppers on the rice plants was examined.

As a result, on the plants treated with any one of the present compounds (1) to (5), the number of the parasitic pests was 3 or smaller.

Test Example 3

A formulation of any one of the present compounds (2), (3) and (4) obtained according to Formulation Example 10 was diluted with water so that the active ingredient concentration was 500 ppm to obtain a test solution.

A filter paper having a diameter of 5.5 cm was spread on the bottom of a polyethylene cup having a diameter of 5.5 cm and 0.7 ml of the test solution was added dropwise onto the filter paper. As a bait 30 mg of sucrose was uniformly placed on the filter paper. Into the polyethylene cup, 10 female imagoes of *Musca domestica* were released and the cup was sealed with a lid. After 24 hours, the number of surviving *Musca domestica* was examined and the death rate of the pest was calculated.

As a result, the treatment with any one of the present compounds (2), (3) and (4) showed a pest death rate of 90% or more.

Test Example 4

A formulation of any one of the present compounds (2), (3) and (4) obtained according to Formulation Example 10 was diluted with water so that the active ingredient concentration was 500 ppm to obtain a test solution.

A filter paper having a diameter of 5.5 cm was spread on the bottom of a polyethylene cup having a diameter of 5.5 cm and 0.7 ml of the test solution was added dropwise onto the filter paper. As a bait 30 mg of sucrose was uniformly placed on the filter paper. Into the polyethylene cup, 2 male imagoes of Blattalla germanica were released and the cup was sealed with a lid. After 6 days, the number of surviving Blattalla germanica was examined and the death rate of the pest was calculated.

As a result, the treatment with any one of the present compounds (2), (3) and 4 showed a pest death rate of 100%.

Test Example 5

A formulation of any one of the present compounds (1), (2) and (3) obtained according to Formulation Example 10 was diluted with water so that the active ingredient concentration was 500 ppm to obtain a test solution.

To 100 mL of ion-exchanged water, 0.7 ml of the test solution was added (active ingredient concentration: 3.5 ppm). Into the solution, 20 last-instar larvae of *Culex pipiens pallens* were released. One day after, the number of surviving *Culex pipiens pallens* was examined and the death rate of the pest was calculated.

As a result, the treatment with any one of the present compounds (1), (2) and (3) showed a pest death rate of 95% or more.

Industrial Applicability

The compound of the present invention is useful as an active ingredient for a pesticidal composition.

The invention claimed is:
1. A fluorine-containing organosulfur compound represented by the formula (I):

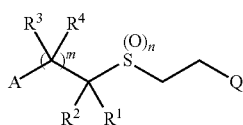

wherein m represents 0 or 1; n represents 0, 1 or 2;

A represents a pyrazolyl group optionally substituted with a group selected from the group E1, an isoxazolyl group optionally substituted with a group selected from the group E1, an isothiazolyl group optionally substituted with a group selected from the group E1, an imidazolyl group optionally substituted with a group selected from the group E1, an oxazolyl group optionally substituted with a group selected from the group E1 or a thiazolyl group optionally substituted with a group selected from the group E1;

$R^1$ and $R^3$ are the same as or different from each other, and represent a C1-C4 chain hydrocarbon group optionally substituted with one or more halogen atoms, —C(=G)$R^5$, a cyano group, a halogen atom, or a hydrogen atom;

$R^2$ and $R^4$ are the same as or different from each other, and represent a C1-C4 chain hydrocarbon group optionally substituted with one or more halogen atoms, a halogen atom, or a hydrogen atom;

Q represents a C1-C5 haloalkyl group containing at least one fluorine atom, or a fluorine atom;

G represents an oxygen atom or a sulfur atom;

$R^5$ represents a C1-C4 alkyl group optionally substituted with one or more halogen atoms, a hydroxyl group, a C1-C4 alkoxy group optionally substituted with one or more halogen atoms, a C3-C6 alkenyloxy group optionally substituted with one or more halogen atoms, a C3-C6 alkynyloxy group optionally substituted with one or more halogen atoms, an amino group, a C1-C4 alkylamino group optionally substituted with one or more halogen atoms, a di(C1-C4 alkyl)amino group optionally substituted with one or more halogen atoms, a C2-C5 cyclic amino group, or a hydrogen atom;

the group E1 is a group of monovalent substituents consisting of —$OR^6$, —$SR^6$, —$S(=O)R^6$, —$S(=O)_2R^6$, —$C(=O)R^7$, —$OC(=O)R^8$, a halogen atom, a cyano group, a nitro group, a hydroxyl group, a C1-C6 chain hydrocarbon group optionally substituted with a group of the group L, and a C3-C6 cycloalkyl group optionally substituted with one or more halogen atoms;

$R^6$ represents a C1-C4 chain hydrocarbon group optionally substituted with a halogen atom or a C3-C6 cycloalkyl group optionally substituted with one or more halogen atoms;

$R^7$ represents a hydroxyl group, a C1-C4 alkoxy group optionally substituted with one or more halogen atoms, a C3-C6 alkenyloxy group optionally substituted with one or more halogen atoms, a C3-C6 alkynyloxy group optionally substituted with one or more halogen atoms, an amino group, a C1-C4 alkylamino group optionally substituted with one or more halogen atoms, a di(C1-C4 alkyl)amino group optionally substituted with one or more halogen atoms, a C2-C5 cyclic amino group, a C1-C4 alkyl group optionally substituted with one or more halogen atoms, or a hydrogen atom;

$R^8$ represents a C1-C4 alkoxy group optionally substituted with one or more halogen atoms, a C3-C6 alkenyloxy group optionally substituted with one or more halogen atoms, a C3-C6 alkynyloxy group optionally substituted with one or more halogen atoms, an amino group, a C1-C4 alkylamino group optionally substituted with one or more halogen atoms, a di(C1-C4 alkyl)amino group optionally substituted with one or more halogen atoms, a C2-C5 cyclic amino group, a C1-C4 alkyl group optionally substituted with one or more halogen atoms, or a hydrogen atom; and the group L is a group of monovalent substituents consisting of —$OR^6$, —$SR^6$, —$S(=O)R^6$, —$S(=O)_2R^6$, —$C(=O)R^7$, —$OC(=O)R^8$, a cyano group, a nitro group, and a halogen atom.

2. The fluorine-containing organosulfur compound according to claim 1, wherein m is 0.

3. The fluorine-containing organosulfur compound according to claim 1, wherein m is 1.

4. The fluorine-containing organosulfur compound according to claim 1, wherein n is 0.

5. The fluorine-containing organosulfur compound according to claim 1, wherein n is 1 or 2.

6. A fluorine-containing organosulfur compound represented by the formula (I):

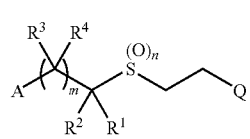

wherein m represents 0 or 1; n represents 0, 1 or 2;

A represents a pyrazolyl group optionally substituted with the group E3, an isoxazolyl group optionally substituted with a group selected from the group E3, an isothiazolyl group optionally substituted with a group selected from the group E3, an imidazolyl group optionally substituted with a group selected from the group E3, an oxazolyl group optionally substituted with a group selected from the group E3, or a thiazolyl group optionally substituted with a group selected from the group E3, and the group E3 is a group of monovalent substituents consisting of a halogen atom, a tert-butyl group, a trifluoromethyl group, a pentafluoroethyl group, an ethynyl group, a propargyl group, a propargyloxy group, a cyano group, a trifluoromethylthio group, a trifluoromethanesulfinyl group and a trifluoromethanesulfonyl group;

$R^1$ and $R^3$ are the same as or different from each other, and represent a C1-C4 chain hydrocarbon group optionally substituted with one or more halogen atoms, —C(=G)$R^5$, a cyano group, a halogen atom, or a hydrogen atom;

$R^2$ and $R^4$ are the same as or different from each other, and represent a C1-C4 chain hydrocarbon group optionally substituted with one or more halogen atoms, a halogen atom, or a hydrogen atom;

Q represents a C1-C5 haloalkyl group containing at least one fluorine atom, or a fluorine atom;

G represents an oxygen atom or a sulfur atom; and $R^5$ represents a C1-C4 alkyl group optionally substituted with one or more halogen atoms, a hydroxyl group, a C1-C4 alkoxy group optionally substituted with one or more halogen atoms, a C3-C6 alkenyloxy group optionally substituted with one or more halogen atoms, a C3-C6 alkynyloxy group optionally substituted with one or more halogen atoms, an amino group, a C1-C4 alkylamino group optionally substituted with one or more halogen atoms, a di(C1-C4 alkyl)amino group optionally substituted with one or more halogen atoms, a C2-C5 cyclic amino group, or a hydrogen atom.

7. A pesticidal composition which comprises the fluorine-containing organosulfur compound according to claim 1 as an active ingredient.

8. A method of controlling an arthropod pest which comprises applying an effective amount of the fluorine-containing organosulfur compound according to claim 1 to the arthropod pest or a place where the arthropod pest inhabits.

* * * * *